United States Patent
Gosselin et al.

(10) Patent No.: US 10,513,534 B2
(45) Date of Patent: Dec. 24, 2019

(54) 2'-CHLORO NUCLEOSIDE ANALOGS FOR HCV INFECTION

(71) Applicants: IDENIX PHARMACEUTICALS LLC, Cambridge, MA (US); Centre National De La Recherche Scientifique, Paris (FR); UNIVERSITE DE MONTPELLIER, Montpellier (FR)

(72) Inventors: Gilles Gosselin, Montpellier (FR); Christophe Claude Parsy, Jacou (FR); Francois-Rene Alexandre, Montpellier (FR); Houcine Rahali, Saint Laurent des Arbres (FR); Jean-Francois Griffon, Teyran (FR); Dominique Surleraux, Wauthier-Braine (BE); Cyril B. Dousson, Canet (FR); Claire Pierra, Montarnaud (FR); Adel M. Moussa, Burlington, MA (US); Benjamin Alexander Mayes, Boston, MA (US); Alistair James Stewart, Lincoln, MA (US)

(73) Assignees: IDENIX PHARMACEUTICALS LLC, Cambridge, MA (US); CENTRE NATIONAL DE LA RECHERCHE SCIENTIFIQUE, Paris (FR); UNIVERSITE DE MONTPELLIER, Montpellier (FR)

( * ) Notice: Subject to any disclaimer, the term of this patent is extended or adjusted under 35 U.S.C. 154(b) by 489 days.

(21) Appl. No.: 14/047,862

(22) Filed: Oct. 7, 2013

(65) Prior Publication Data
US 2014/0099283 A1  Apr. 10, 2014

Related U.S. Application Data

(60) Provisional application No. 61/711,131, filed on Oct. 8, 2012, provisional application No. 61/807,249, filed on Apr. 1, 2013.

(51) Int. Cl.
| | |
|---|---|
| C07H 19/06 | (2006.01) |
| C07H 19/073 | (2006.01) |
| C07H 19/10 | (2006.01) |
| C07H 19/11 | (2006.01) |
| C07H 19/16 | (2006.01) |
| C07H 19/173 | (2006.01) |
| C07H 19/20 | (2006.01) |
| C07H 19/213 | (2006.01) |
| A61K 31/7072 | (2006.01) |
| A61K 45/06 | (2006.01) |
| A61K 38/21 | (2006.01) |
| A61K 31/7076 | (2006.01) |
| C07H 19/14 | (2006.01) |

(Continued)

(52) U.S. Cl.
CPC ........... *C07H 19/10* (2013.01); *A61K 31/403* (2013.01); *A61K 31/497* (2013.01); *A61K 31/706* (2013.01); *A61K 31/708* (2013.01); *A61K 31/7064* (2013.01); *A61K 31/7068* (2013.01); *A61K 31/7072* (2013.01); *A61K 31/7076* (2013.01); *A61K 31/7105* (2013.01); *A61K 38/212* (2013.01); *A61K 45/06* (2013.01); *C07H 19/06* (2013.01); *C07H 19/11* (2013.01); *C07H 19/12* (2013.01); *C07H 19/14* (2013.01); *C07H 19/16* (2013.01); *C07H 19/20* (2013.01); *C07H 19/213* (2013.01); *C07H 19/23* (2013.01)

(58) Field of Classification Search
None
See application file for complete search history.

(56) References Cited

U.S. PATENT DOCUMENTS

| | | |
|---|---|---|
| 3,480,613 A | 11/1969 | Walton et al. |
| 4,808,614 A | 2/1989 | Hertel |

(Continued)

FOREIGN PATENT DOCUMENTS

| | | |
|---|---|---|
| CN | 1133642 C | 1/2004 |
| CN | 103848876 A | 6/2014 |

(Continued)

OTHER PUBLICATIONS

U.S. Appl. No. 11/005,443, filed Dec. 6, 2004, LaColla et al.

(Continued)

*Primary Examiner* — Traviss C McIntosh, III
(74) *Attorney, Agent, or Firm* — Squire Patton Boggs (US) LLP

(57) ABSTRACT

Provided herein are compounds, compositions and methods for the treatment of Flaviviridae infections, including HCV infections. In certain embodiments, compounds and compositions of nucleoside derivatives are disclosed, which can be administered either alone or in combination with other anti-viral agents. In certain embodiments, the compounds are 2'-chloro nucleosides according to Formula 2001:

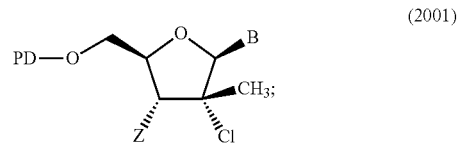

(2001)

or a pharmaceutically acceptable salt, solvate, stereoisomeric form, tautomeric form or polymorphic form thereof, wherein B, Z and PD are as described herein.

60 Claims, No Drawings

(51) Int. Cl.
    *A61K 31/7064* (2006.01)
    *C07H 19/12* (2006.01)
    *A61K 31/706* (2006.01)
    *A61K 31/7068* (2006.01)
    *A61K 31/708* (2006.01)
    *A61K 31/403* (2006.01)
    *A61K 31/497* (2006.01)
    *A61K 31/7105* (2006.01)
    *C07H 19/23* (2006.01)

(56) References Cited

U.S. PATENT DOCUMENTS

| | | | |
|---|---|---|---|
| 6,174,868 | B1 | 1/2001 | Anderson et al. |
| 6,284,458 | B1 | 9/2001 | Anderson et al. |
| 6,348,587 | B1 | 2/2002 | Schinazi et al. |
| 6,391,542 | B1 | 5/2002 | Anderson et al. |
| 6,423,489 | B1 | 7/2002 | Anderson et al. |
| 6,433,159 | B1 | 8/2002 | Anderson |
| 6,455,513 | B1 | 9/2002 | McGuigan et al. |
| 6,566,365 | B1 | 5/2003 | Storer |
| 6,573,247 | B1 | 6/2003 | McGuigan et al. |
| 6,608,191 | B1 | 8/2003 | Anderson et al. |
| 6,638,919 | B2 | 10/2003 | McGuigan et al. |
| 6,660,721 | B2 | 12/2003 | Devos et al. |
| 6,777,395 | B2 | 8/2004 | Bhat et al. |
| 6,784,161 | B2 | 8/2004 | Ismaili et al. |
| 6,784,166 | B2 | 8/2004 | Devos et al. |
| 6,812,219 | B2 | 11/2004 | LaColla et al. |
| 6,833,361 | B2 | 12/2004 | Hong et al. |
| 6,846,810 | B2 | 1/2005 | Martin et al. |
| 6,911,424 | B2 | 6/2005 | Schinazi et al. |
| 6,914,054 | B2 | 7/2005 | Sommadossi et al. |
| 6,927,291 | B2 | 8/2005 | Jin et al. |
| 6,995,146 | B2 | 2/2006 | Anderson et al. |
| 7,018,989 | B2 | 3/2006 | McGuigan et al. |
| 7,019,135 | B2 | 3/2006 | McGuigan et al. |
| 7,094,770 | B2 | 8/2006 | Watanabe et al. |
| 7,105,493 | B2 | 9/2006 | Sommadossi et al. |
| 7,105,499 | B2 | 9/2006 | Carroll et al. |
| 7,115,590 | B1 | 10/2006 | Daluge et al. |
| 7,125,855 | B2 | 10/2006 | Bhat et al. |
| 7,138,376 | B2 | 11/2006 | Gosselin et al. |
| 7,148,206 | B2 | 12/2006 | Sommadossi et al. |
| 7,157,441 | B2 | 1/2007 | Sommadossi et al. |
| 7,163,929 | B2 | 1/2007 | Sommadossi et al. |
| 7,169,766 | B2 | 1/2007 | Sommadossi et al. |
| 7,192,936 | B2 | 3/2007 | LaColla et al. |
| 7,202,224 | B2 | 4/2007 | Eldrup et al. |
| 7,285,658 | B2 | 10/2007 | Cook et al. |
| 7,300,924 | B2 | 11/2007 | Boojamra et al. |
| 7,307,065 | B2 | 12/2007 | Schinazi et al. |
| 7,323,449 | B2 | 1/2008 | Olsen et al. |
| 7,323,453 | B2 | 1/2008 | Olsen et al. |
| 7,339,054 | B2 | 3/2008 | Xu et al. |
| 7,365,057 | B2 | 4/2008 | LaColla et al. |
| 7,378,402 | B2 | 5/2008 | Martin et al. |
| 7,384,924 | B2 | 6/2008 | LaColla et al. |
| 7,405,204 | B2 * | 7/2008 | Roberts .............. A61K 31/7076 514/42 |
| 7,429,572 | B2 | 9/2008 | Clark |
| 7,452,901 | B2 | 11/2008 | Boojamra et al. |
| 7,456,155 | B2 | 11/2008 | Sommadossi et al. |
| 7,524,825 | B2 | 4/2009 | Keicher et al. |
| 7,534,767 | B2 | 5/2009 | Butora et al. |
| 7,547,704 | B2 | 6/2009 | LaColla et al. |
| 7,582,618 | B2 | 9/2009 | Sommadossi et al. |
| 7,598,230 | B2 | 10/2009 | Cook et al. |
| 7,598,373 | B2 | 10/2009 | Storer et al. |
| 7,608,597 | B2 | 10/2009 | Sommadossi et al. |
| 7,608,599 | B2 | 10/2009 | Klumpp et al. |
| 7,608,600 | B2 | 10/2009 | Storer et al. |
| 7,608,601 | B2 | 10/2009 | Devos et al. |
| 7,625,875 | B2 | 12/2009 | Gosselin et al. |
| 7,632,821 | B2 | 12/2009 | Butora et al. |
| 7,632,940 | B2 | 12/2009 | Harrington et al. |
| 7,635,689 | B2 | 12/2009 | LaColla et al. |
| 7,645,745 | B2 | 1/2010 | Sarma |
| 7,645,747 | B2 | 1/2010 | Boojamra et al. |
| 7,662,798 | B2 | 2/2010 | LaColla et al. |
| 7,666,856 | B2 | 2/2010 | Johansson et al. |
| 7,754,699 | B2 | 7/2010 | Chun et al. |
| 7,772,208 | B2 | 8/2010 | Schinazi et al. |
| 7,781,576 | B2 | 8/2010 | Mayes et al. |
| 7,807,653 | B2 | 10/2010 | Cook et al. |
| 7,820,631 | B2 | 10/2010 | McGuigan et al. |
| 7,824,851 | B2 | 11/2010 | Sommadossi et al. |
| 7,842,672 | B2 | 11/2010 | Boojamra et al. |
| 7,871,991 | B2 | 1/2011 | Boojamra et al. |
| 7,879,815 | B2 | 2/2011 | MacCoss et al. |
| 7,902,202 | B2 | 3/2011 | Sommadossi et al. |
| 7,915,232 | B2 | 3/2011 | Martin et al. |
| 7,951,787 | B2 | 5/2011 | McGuigan |
| 7,951,788 | B2 | 5/2011 | Cheng |
| 7,951,789 | B2 | 5/2011 | Sommadossi et al. |
| 7,964,580 | B2 | 6/2011 | Sofia et al. |
| 7,973,013 | B2 | 7/2011 | Cho et al. |
| 8,008,264 | B2 | 8/2011 | Butler et al. |
| 8,012,941 | B2 | 9/2011 | Cho et al. |
| 8,012,942 | B2 | 9/2011 | Butler et al. |
| 8,022,083 | B2 | 9/2011 | Boojamra et al. |
| 8,071,567 | B2 | 12/2011 | Devos et al. |
| 8,076,310 | B2 | 12/2011 | Herdewijn et al. |
| 8,119,607 | B2 | 2/2012 | Francom et al. |
| 8,119,779 | B2 | 2/2012 | McGuigan et al. |
| 8,148,349 | B2 | 4/2012 | Meppen et al. |
| 8,168,583 | B2 | 5/2012 | Schinazi et al. |
| 8,173,621 | B2 | 5/2012 | Du et al. |
| 8,183,216 | B2 | 5/2012 | Di Francesco et al. |
| 8,236,779 | B2 | 8/2012 | Ma et al. |
| 8,299,038 | B2 | 10/2012 | Sommadossi et al. |
| 8,318,682 | B2 | 11/2012 | Butler et al. |
| 8,318,701 | B2 | 11/2012 | Boojamra et al. |
| 8,324,179 | B2 | 12/2012 | Chen et al. |
| 8,329,926 | B2 | 12/2012 | Boojamra et al. |
| 8,334,270 | B2 | 12/2012 | Sofia et al. |
| 8,399,428 | B2 | 3/2013 | Wagner |
| 8,404,651 | B2 | 3/2013 | Iyer et al. |
| 8,415,308 | B2 | 4/2013 | Cho et al. |
| 8,415,322 | B2 | 4/2013 | Clark |
| 8,455,451 | B2 | 6/2013 | Cho et al. |
| 8,481,712 | B2 | 7/2013 | Bhat et al. |
| 8,481,713 | B2 | 7/2013 | Wang et al. |
| 8,507,460 | B2 | 8/2013 | Surleraux et al. |
| 8,551,973 | B2 | 10/2013 | Bao et al. |
| 8,552,021 | B2 | 10/2013 | Jonckers et al. |
| 8,563,530 | B2 | 10/2013 | Chang et al. |
| 8,569,478 | B2 | 10/2013 | Du et al. |
| 8,575,119 | B2 | 11/2013 | Wang et al. |
| 8,580,268 | B2 | 11/2013 | Debelak et al. |
| 8,580,765 | B2 | 11/2013 | Sofia et al. |
| 8,609,627 | B2 | 12/2013 | Cho et al. |
| 8,618,076 | B2 | 12/2013 | Ross et al. |
| 8,637,475 | B1 | 1/2014 | Storer et al. |
| 8,642,756 | B2 | 2/2014 | Ross et al. |
| 8,658,616 | B2 | 2/2014 | McGuigan et al. |
| 8,680,071 | B2 | 3/2014 | Surleraux et al. |
| 8,691,788 | B2 | 4/2014 | Sommadossi et al. |
| 8,716,262 | B2 | 5/2014 | Sofia et al. |
| 8,716,263 | B2 | 5/2014 | Chun et al. |
| 8,728,725 | B2 | 5/2014 | Paul et al. |
| 8,735,372 | B2 | 5/2014 | Du et al. |
| 8,759,318 | B2 | 6/2014 | Chamberlain et al. |
| 8,759,510 | B2 | 6/2014 | Du et al. |
| 8,765,710 | B2 | 7/2014 | Sofia et al. |
| 8,765,935 | B2 | 7/2014 | Wagner |
| 8,772,474 | B2 | 7/2014 | Beigelman et al. |
| 8,802,840 | B2 | 8/2014 | Francom et al. |
| 8,816,074 | B2 | 8/2014 | Chu et al. |
| 8,841,275 | B2 | 9/2014 | Du et al. |
| 8,859,756 | B2 | 10/2014 | Ross et al. |
| 8,871,737 | B2 | 10/2014 | Smith et al. |
| 8,877,731 | B2 | 11/2014 | Beigelman et al. |
| 8,877,733 | B2 | 11/2014 | Cho et al. |

(56) References Cited

U.S. PATENT DOCUMENTS

| | | |
|---|---|---|
| 8,889,159 B2 | 11/2014 | Cleary et al. |
| 8,906,880 B2 * | 12/2014 | Du .................... A61K 31/706 514/51 |
| 8,946,244 B2 | 2/2015 | Chu et al. |
| 8,951,985 B2 | 2/2015 | Surleraux et al. |
| 8,957,046 B2 | 2/2015 | Du et al. |
| 8,962,580 B2 | 2/2015 | Manoharan et al. |
| 9,006,209 B2 | 4/2015 | Jonckers et al. |
| 9,012,428 B2 | 4/2015 | Jonckers et al. |
| 9,060,971 B2 | 6/2015 | Or et al. |
| 9,061,041 B2 * | 6/2015 | Girijavallabhan ...................... A61K 31/7042 |
| 9,085,573 B2 | 7/2015 | Du et al. |
| 9,085,599 B2 | 7/2015 | Or et al. |
| 9,090,642 B2 | 7/2015 | Cho et al. |
| 9,095,599 B2 | 8/2015 | Chang et al. |
| 9,108,999 B2 | 8/2015 | Zhang et al. |
| 9,109,001 B2 | 8/2015 | Parsy et al. |
| 9,150,603 B2 | 10/2015 | Girijavallabhan et al. |
| 9,156,872 B2 | 10/2015 | Girijavallabhan et al. |
| 9,156,874 B2 | 10/2015 | Chang et al. |
| 9,187,515 B2 | 11/2015 | Mayes et al. |
| 9,192,621 B2 | 11/2015 | Mayes et al. |
| 9,211,300 B2 | 12/2015 | Mayes et al. |
| 9,242,988 B2 | 1/2016 | Girijavallabhan et al. |
| 9,243,025 B2 | 1/2016 | Surleraux |
| 9,296,778 B2 | 3/2016 | Parsy et al. |
| 9,309,275 B2 | 4/2016 | Stewart et al. |
| 2003/0008841 A1 | 1/2003 | Devos et al. |
| 2003/0087873 A1 | 5/2003 | Stuyver et al. |
| 2004/0006002 A1 | 1/2004 | Sommadossi et al. |
| 2004/0014108 A1 | 1/2004 | Eldrup et al. |
| 2004/0110718 A1 | 6/2004 | Devos et al. |
| 2004/0121980 A1 | 6/2004 | Martin et al. |
| 2004/0229840 A1 | 11/2004 | Bhat et al. |
| 2004/0266723 A1 | 12/2004 | Otto et al. |
| 2005/0009737 A1 | 1/2005 | Clark |
| 2005/0009775 A1 | 1/2005 | Howes et al. |
| 2005/0038240 A1 | 2/2005 | Connolly et al. |
| 2005/0124532 A1 | 6/2005 | Sommadossi et al. |
| 2006/0040890 A1 | 2/2006 | Martin et al. |
| 2006/0040944 A1 | 2/2006 | Gosselin et al. |
| 2006/0234962 A1 | 10/2006 | Olsen et al. |
| 2006/0264389 A1 | 11/2006 | Bhat et al. |
| 2007/0004669 A1 | 1/2007 | Carroll et al. |
| 2007/0027065 A1 | 2/2007 | LaColla et al. |
| 2007/0027104 A1 | 2/2007 | LaColla et al. |
| 2007/0032449 A1 | 2/2007 | LaColla et al. |
| 2007/0037735 A1 | 2/2007 | Gosselin et al. |
| 2007/0042990 A1 | 2/2007 | Gosselin et al. |
| 2007/0060503 A1 | 3/2007 | Gosselin et al. |
| 2007/0060504 A1 | 3/2007 | Gosselin et al. |
| 2007/0060505 A1 | 3/2007 | Gosselin et al. |
| 2007/0060541 A1 | 3/2007 | Gosselin et al. |
| 2007/0265222 A1 | 11/2007 | MacCoss et al. |
| 2008/0070861 A1 | 3/2008 | Clark |
| 2008/0139802 A1 | 6/2008 | Axt et al. |
| 2008/0253995 A1 | 10/2008 | Clark |
| 2008/0261913 A1 | 10/2008 | Sommadossi et al. |
| 2008/0280842 A1 | 11/2008 | MacCoss et al. |
| 2008/0286230 A1 | 11/2008 | Sommadossi et al. |
| 2009/0004135 A1 | 1/2009 | Clark |
| 2009/0036666 A1 | 2/2009 | Clark |
| 2009/0048189 A1 | 2/2009 | Keicher et al. |
| 2009/0118223 A1 | 5/2009 | Erion et al. |
| 2009/0169504 A1 | 7/2009 | Sommadossi et al. |
| 2009/0176732 A1 | 7/2009 | Beigelman et al. |
| 2009/0238790 A2 | 9/2009 | Sommadossi et al. |
| 2009/0306007 A1 | 12/2009 | Wagner |
| 2009/0318380 A1 | 12/2009 | Sofia et al. |
| 2010/0003217 A1 | 1/2010 | Cretton-Scott et al. |
| 2010/0056468 A1 | 3/2010 | Kotra et al. |
| 2010/0077085 A1 | 3/2010 | Cohen |
| 2010/0081628 A1 | 4/2010 | Du et al. |
| 2010/0240604 A1 | 9/2010 | Beigelman et al. |
| 2010/0249068 A1 | 9/2010 | Beigelman et al. |
| 2010/0279969 A1 | 11/2010 | Schinazi et al. |
| 2010/0279973 A1 | 11/2010 | Chun et al. |
| 2010/0279974 A1 | 11/2010 | Pierra et al. |
| 2010/0286083 A1 | 11/2010 | Bao et al. |
| 2010/0297079 A1 | 11/2010 | Almond et al. |
| 2010/0298257 A1 | 11/2010 | Ross et al. |
| 2010/0316594 A1 | 12/2010 | Sommadossi et al. |
| 2011/0015146 A1 | 1/2011 | Sofia et al. |
| 2011/0021454 A1 | 1/2011 | Du et al. |
| 2011/0124592 A1 | 5/2011 | McGuigan et al. |
| 2011/0217261 A1 | 9/2011 | Or et al. |
| 2011/0243886 A1 | 10/2011 | Surleraux et al. |
| 2011/0244027 A1 | 10/2011 | Chu et al. |
| 2011/0245484 A1 | 10/2011 | Ross et al. |
| 2011/0251152 A1 | 10/2011 | Ross et al. |
| 2011/0257121 A1 | 10/2011 | Chang et al. |
| 2011/0269707 A1 | 11/2011 | Stuyver et al. |
| 2011/0286962 A1 | 11/2011 | Sommadossi et al. |
| 2011/0306541 A1 | 12/2011 | Delaney, IV et al. |
| 2011/0306573 A1 | 12/2011 | Avolio et al. |
| 2012/0010164 A1 | 1/2012 | Surnma et al. |
| 2012/0034184 A1 | 2/2012 | Devos et al. |
| 2012/0040924 A1 | 2/2012 | Cho et al. |
| 2012/0052046 A1 | 3/2012 | Chamberlain et al. |
| 2012/0070411 A1 | 3/2012 | Beigelman et al. |
| 2012/0107274 A1 | 5/2012 | Clarke et al. |
| 2012/0165286 A1 | 6/2012 | Beigelman et al. |
| 2012/0245335 A1 | 9/2012 | Clark |
| 2013/0017171 A1 | 1/2013 | Sommadossi et al. |
| 2013/0064794 A1 | 3/2013 | Surleraux et al. |
| 2013/0149283 A1 | 6/2013 | Sommadossi et al. |
| 2013/0244968 A1 | 9/2013 | Jonckers et al. |
| 2013/0273005 A1 | 10/2013 | Delaney et al. |
| 2013/0315862 A1 | 11/2013 | Sommadossi et al. |
| 2013/0315868 A1 | 11/2013 | Mayes et al. |
| 2013/0330297 A1 | 12/2013 | Storer et al. |
| 2014/0099283 A1 | 4/2014 | Gosselin et al. |
| 2014/0112886 A1 | 4/2014 | Moussa et al. |
| 2014/0112887 A1 | 4/2014 | Mayes et al. |
| 2014/0113880 A1 | 4/2014 | Storer et al. |
| 2014/0128339 A1 | 5/2014 | Girijavallabhan et al. |
| 2014/0140951 A1 | 5/2014 | Moussa et al. |
| 2014/0140952 A1 | 5/2014 | Moussa et al. |
| 2014/0140955 A1 | 5/2014 | McGuigan et al. |
| 2014/0205566 A1 | 7/2014 | Liao et al. |
| 2014/0212382 A1 | 7/2014 | Schinazi et al. |
| 2014/0221304 A1 | 8/2014 | Verma et al. |
| 2014/0235567 A1 | 8/2014 | Verma et al. |
| 2014/0248242 A1 | 9/2014 | Dousson et al. |
| 2014/0271547 A1 | 9/2014 | Dukhan et al. |
| 2014/0315850 A1 | 10/2014 | Huang et al. |
| 2014/0356325 A1 | 12/2014 | Zhi et al. |
| 2014/0364446 A1 | 12/2014 | Dukhan et al. |
| 2014/0369959 A1 | 12/2014 | Smith et al. |
| 2015/0037282 A1 | 2/2015 | Mayes et al. |
| 2015/0231166 A1 | 8/2015 | Du et al. |
| 2016/0002281 A1 | 1/2016 | Mayes et al. |
| 2016/0031927 A1 | 2/2016 | Ivachtchenko |
| 2016/0045526 A1 | 2/2016 | Girijavallabhan et al. |
| 2016/0082030 A1 | 3/2016 | Mayes et al. |
| 2016/0083413 A1 | 3/2016 | Gosselin et al. |

FOREIGN PATENT DOCUMENTS

| | | |
|---|---|---|
| CN | 103848877 A | 6/2014 |
| GB | 2316425 A | 9/1984 |
| WO | WO 1993/017651 A3 | 9/1993 |
| WO | WO 2002/057287 A2 | 7/2002 |
| WO | WO 2003/105770 A2 | 12/2003 |
| WO | WO 2005/020884 A2 | 3/2005 |
| WO | WO 2005/020885 A2 | 3/2005 |
| WO | WO 2007/027248 A2 | 3/2007 |
| WO | WO 2011/150288 A1 | 12/2011 |
| WO | WO 2012/048013 A2 | 4/2012 |
| WO | WO 2012/092484 A2 | 7/2012 |
| WO | WO 2012/142075 A1 | 10/2012 |
| WO | WO 2012/142085 A1 | 10/2012 |
| WO | WO 2012/142093 A2 | 10/2012 |

(56) References Cited

FOREIGN PATENT DOCUMENTS

| | | |
|---|---|---|
| WO | WO 2012/158811 A2 | 11/2012 |
| WO | WO 2013/009735 A1 | 1/2013 |
| WO | WO 2013/009737 A1 | 1/2013 |
| WO | WO 2013/013009 A2 | 1/2013 |
| WO | WO 2013/084165 A1 | 6/2013 |
| WO | WO 2013/092447 A1 | 6/2013 |
| WO | WO 2013/106344 A1 | 7/2013 |
| WO | WO 2014/124430 A1 | 8/2014 |
| WO | WO 2014/204831 A1 | 12/2014 |
| WO | WO 2015/061683 A1 | 4/2015 |
| WO | WO 2015/066370 A1 | 5/2015 |
| WO | WO 2015/077360 A2 | 5/2015 |
| WO | WO 2015/081133 A2 | 6/2015 |
| WO | WO 2015/081297 A1 | 6/2015 |
| WO | WO 2015/095305 A1 | 6/2015 |
| WO | WO 2015/095419 A1 | 6/2015 |
| WO | WO 2015/134780 A1 | 9/2015 |
| WO | WO 2015/161137 A1 | 10/2015 |

OTHER PUBLICATIONS

U.S. Appl. No. 14/146,520, filed Jan. 2, 2014, Storer et al.
International Search Report and Written Opinion in PCT/US2013/063731, dated Nov. 13, 2013, 12 pages.
Congiatu et al., Novel Potential Anticancer Naphthyl Phosphoramidates of BVdU: Separation of Diastereoisomers and Assignment of the Absolute Configuration of the Phosphorus Center (2006) *Journal of Medicinal Chemistry* 49:452-455.
Eldrup et al., Structure-Activity Relationship of Purine Ribonucleosides for Inhibition of Hepatitis C Virus RNA-Dependent RNA Polymerase (2004) Journal of Medicinal Chemistry 47:2283-2295.
Gardelli et al., Phosphoramidate Prodrugs of 2'-C-Methylcytidine for Therapy of Hepatitis C Virus Infection (2009) *Journal of Medicinal Chemistry* 52:5394-5407.
Hollecker et al., Synthesis of β-enantiomers of N$^4$-hydroxy-3'-deoxypyrimidine nucleosides and their evaluation against bovine viral diarrhoea virus and hepatitis C virus in cell culture (2004) *Antiviral Chemistry & Chemotherapy* 14:43-55.
King et al., Inhibition of the replication of a hepatitis C virus-like RNA template by interferon and 3'-deoxycytidine (2002) *Antiviral Chemistry & Chemotherapy* 13:363-370.
Leisvuori et al., Synthesis of 3',5'-Cyclic Phosphate and Thiophosphate Esters of 2'-C-Methyl Ribonucleosides (2012) *Helvetica Chimica Acta* 95:1512-1520.
McGuigan et al., Phosphoramidate ProTides of 2'-C-Methylguanosine as Highly Potent Inhibitors of Hepatitis C Virus. Study of Their in Vitro and in Vivo Properties (2010) *Journal of Medicinal Chemistry* 53:4949-4957.
McGuigan et al., Phosphorodiamidates as a Promising New Phosphate Prodrug Motif for Antiviral Drug Discovery: Application to Anti-HCV Agents (2011) *Journal of Medicinal Chemistry* 54:8632-8645.
McGuigan et al., the application of phosphoramidate ProTide technology to the potent anti-HCV compound 4'-azidocytidine (R1479) (2009) *Bioorganic & Medicinal Chemistry Letters* 19:4250-4254.
Mehellou et al., Phosphoramidates of 2'-β-D-arabinouridine (AraU) as phosphate prodrugs; design, synthesis, in vitro activity and metabolism (2010) *Bioorganic & Medicinal Chemistry* 18:2439-2446.
Mehellou et al., The design, synthesis and antiviral evaluation of a series of 5-trimethylsilyl-1-β-D-(arabinofurano syl)uracil phosphoramidate ProTides (2010) *Antiviral Chemistry & Chemotherapy* 20:153-160.
Murakami et al., Mechanism of Activation of PSI-7851 and Its Diastereoisomer PSI-7977 (2010) *Journal of Biological Chemistry* 285:34337-34347.
Murakami et al., Mechanism of Activation of β-D-2'-Deoxy-2'-Fluoro-2'-C-Methylcytidine and Inhibition of Hepatitis C Virus NS5B RNA polymerase (2007) *Antimicrobial Agents and Chemotherapy* 51:503-509.

Olsen et al., A 7-Deaza-Adenosine Analog is a Potent and Selective Inhibitor of Hepatitis C Virus Replication with Excellent Pharmacokinetic Properties (2004) *Antimicrobial Agents and Chemotherapy* 28:3944-3953.
Perrone et al., Application of the Phosphoramidate ProTide Approach to 4'-Azidouridine Confers Sub-micromolar Potency versus Hepatitis C Virus on an Inactive Nucleoside (2007) *Journal of Medicinal Chemistry* 50:1840-1849.
Prakash et al., Synthesis and Evaluation of S-Acyl-2-thioethyl Esters of Modified Nucleoside 5'-Monophosphates as Inhibitors of Hepatitis C Virus RNA Replication (2005) *J. Med. Chem.* 48:1199-1210.
Saboulard et al., Characterization of the Activation Pathway of Phosphoramidate Triester Prodrugs of Stavudine and Zidovudine (2009) *Molecular Pharmacology* 56:693-704.
Shen et al., Design and synthesis of vidarabine prodrugs as antiviral agents (2009) *Bioorganic & Medicinal Chemistry Letters* 19:792-796.
Sofia et al., Discovery of a β-D-2'-Deoxy-2'-α-fluoro-2'-6-C-methyluridine Nucleotide Prodrug (PSI-7977) for the Treatment of Hepatitis C Virus (2010) *Journal of Medicinal Chemistry* 53:7202-7218.
Stein et al., Phosphorylation of Nucleoside Analog Antiretrovirals: A Review for Clinicians (2001) *Pharmacotherapy* 21:11-34.
Tomassini et al., Inhibitory Effect of 2'-Substituted Nucleosides on Hepatitis C Virus Replication Correlates with Metabolic Properties in Replicon Cells (2005) *Antimicrobial Agents and Chemotherapy* 49:2050-2058.
Pending claims filed Dec. 8, 2015 of U.S. Appl. No. 14/856,462, 16 pages.
Pending claims filed Dec. 8, 2015 of U.S. Appl. No. 14/920,830, 8 pages.
Aparna et al., 3D-QSAR studies on antitubercular thymidine monophosphate kinase inhibitors based on different alignment methods (2006) *Bioorganic & Medicinal Chemistry Letters* 16:1014-1020.
Benzaria et al., 2'-C-Methyl branched pyrimidine ribonucleoside analogues: potent inhibitors of RNA virus replication (2007) *Antiviral Chemistry & Chemotherapy* 18:225-242.
Bueno et al., Structural and chemical basis for enhanced affinity to a series of mycobacterial thymidine monophosphate kinase inhibitors: fragment-based QSAR and QM/MM docking studies (2013) *J Mol Model* 19:179-192.
Cahard et al., Aryloxy Phosphoramidate Triesters as Pro-Tides (2004) *Mini-Reviews in Medicinal Chemistry* 4:371-381.
Devogelaere et al., TMC647055, a Potent Nonnucleoside Hepatitis C Virus NS5B Polymerase Inhibitor with Cross-Genotypic Coverage (2012) *Antimicrobial Agents and Chemotherapy* 56:4676-4684.
Gopalakrishnan et al., A Virtual Screening Approach for Thymidine Monophosphate Kinase Inhibitors as Antitubercular Agents Based on Docking and Pharmacophore Models (2005) *J. Chem. Inf. Model.* 45:1101-1108.
Ivanov et al., Synthesis and biological properties of pyrimidine 4'-fluoronucleosides and 4'- fluorouridine 5'-O-triphosphate (2010) *Russian Journal of Bioorganic Chemistry* 36:488-496.
Kakefuda et al., Nucleosides and nucleotides. 120. Stereoselective Radical Deoxygenation of tert-Alcohols in the Sugar Moiety of Nucleosides: Synthesis of 2',3'-Dideoxy-2'-C-methyl- and -2'-C-ethynyl-β-d-threo-pentofuranosyl Pyrimidines and Adenine as Potential Antiviral and Antitumor Agents (1993) *Tetrahedron* 49:8513-8528.
Kawana et al., The deoxygenations of tosylated adenosine derivatives with Grignard reagents (1986) *Nucleic Acids Symp Ser.* 17:37-40.
Kawana et al., The Synthesis of C-Methyl Branched-Chain Deoxy Sugar Nucleosides by the Deoxygenative Methylation of O-Tosylated Adenosines with Grignard Reagents (1988) *Bull. Chem. Soc. Jpn.* 61:2437-2442.
Kusano-Kitazume et al., Identification of Novel N-(Morpholine-4-Carbonyloxy) Amidine Compounds as Potent Inhibitors against Hepatitis C Virus Replication (2011) *Antimicrobial Agents and Chemotherapy* 56:1315-1323.

(56) References Cited

OTHER PUBLICATIONS

Madela et al., Progress in the development of anti-hepatitis C virus nucleoside and nucleotide prodrugs (2012) *Future Med. Chem.* 4:625-650.

Müller et al., Novel Nucleotide Analogues as Potential Substrates for TMPK, a Key Enzyme in the Metabolism of AZT (2003) *Nucleosides, Nucleotides and Nucleic Acids* 22:821-823.

Pierra et al., Synthesis of 2'-C-Methylcytidine and 2'-C-Methyluridine Derivatives Modified in the 3'-Position as Potential Antiviral Agents (2006) *Collection of Czechoslovak Chemical Communications* 71:991-1010.

Sofia, M., Nucleotide prodrugs for HCV therapy (2011) Antiviral Chemistry Et Chemotherapy 22:23-49.

*The Merck Index*, An Encyclopedia of Chemicals, Drugs, and Biologicals (2013) Fifteenth Edition, p. 809 (GEMCITABINE).

Tong et al., Nucleosides of thioguanine and other 2-amino-6-substituted purines from 2-acetamido-5-chloropurine (1967) *J Org Chem.* 32:859-62.

Vernachio et al., INX-08189, a Phosphoramidate Prodrug of 6-O-Methyl-2'-C-Methyl Guanosine, is a Potent Inhibitor of Hepatitis C Virus Replication with Excellent Pharmacokinetic and Pharmacodynamic Properties (2011) *Antimicrobial Agents and Chemotherapy* 55:1843-1851.

Pending claims, as filed May 16, 2018, in U.S. Appl. No. 15/981,813, 13 pages.

\* cited by examiner

2'-CHLORO NUCLEOSIDE ANALOGS FOR HCV INFECTION

FIELD

Provided herein are compounds, methods and pharmaceutical compositions for use in treatment of viral infections, including hepatitis C virus infect ions in hosts in need thereof. In certain embodiments, 2'-chloro nucleoside analogs are provided which display remarkable efficacy and bioavailability for the treatment of, for example, HCV infection in a human.

BACKGROUND

The hepatitis C virus (HCV) is the leading cause of chronic liver disease worldwide. (Boyer, N. et al., *J. Hepatol.* 32:98-112, 2000). HCV causes a slow growing viral infection and is the major cause of cirrhosis and hepatocellular carcinoma (Di Besceglie, A. M. and Bacon, B. R., *Scientific American*, October: 80-85, 1999; Boyer, N. et al., *J. Hepatol.* 32:98-112, 2000). It is estimated there are about 150 million people with chronic hepatitis C virus infection, and it is estimated more than 350,000 people die from hepatitis C-related liver diseases each year (Hepatitis C Fact Sheet, *World Health Organization Fact Sheet No. 164*, July 2013). Cirrhosis caused by chronic hepatitis C infection accounts for 8,000-12,000 deaths per year in the United States, and HCV infection is the leading indication for liver transplantation.

HCV infection becomes chronic in about 75% of cases, with many patients initially being asymptomatic. The first symptoms of HCV infection are often those of chronic liver disease. About 20 to 30% of patients with chronic hepatitis due to HCV develop cirrhosis, although this may take decades. Development of cirrhosis due to HCV also increases the risk of hepatocellular cancer (The Merck Manual Online, *Chronic Hepatitis*, available at www.merckmanuals.com/professional/hepatic_and_biliary_disorders/hepatitis/chronic_hepatitis.html, last revision March 2013).

In light of the fact that HCV infection has reached epidemic levels worldwide, and has tragic effects on the infected patient, there remains a strong need to provide new effective pharmaceutical agents to treat hepatitis C that have low toxicity to the host. Further, given the rising threat of other flaviviridae infections, there remains a strong need to provide new effective pharmaceutical agents that have low toxicity to the host. Therefore, there is a continuing need for effective treatments of flavivirus infections and HCV infections.

SUMMARY

Provided herein are compounds useful, for example, for the treatment of flavivirus infections such as HCV infections. The compounds are 2'-chloro nucleoside analogs. In certain embodiments the 2'-chloro nucleoside analogs display remarkable efficacy or bioavailability, or both, for the treatment of, for example, HCV infection in a human.

In certain embodiments, the compounds provided herein are useful in the prevention and treatment of Flaviviridae infections and other related conditions such as anti-Flaviviridae antibody positive and Flaviviridae-positive conditions, chronic liver inflammation caused by HCV, cirrhosis, fibrosis, acute hepatitis, fulminant hepatitis, chronic persistent hepatitis and fatigue. These compounds or formulations can also be used prophylactically to prevent or retard the progression of clinical illness in individuals who are anti-Flaviviridae antibody or Flaviviridae-antigen positive or who have been exposed to a Flaviviridae. In particular embodiments, the Flaviviridae is hepatitis C. In certain embodiments, the compounds are used to treat any virus that replicates through an RNA-dependent RNA polymerase.

A method for the treatment of a Flaviviridae infection in a host, including a human, is also provided that includes administering an effective amount of a compound provided herein, administered either alone or in combination or alternation with another anti-Flaviviridae agent, optionally in a pharmaceutically acceptable carrier.

In certain embodiments, provided herein are compounds according to Formula 2001:

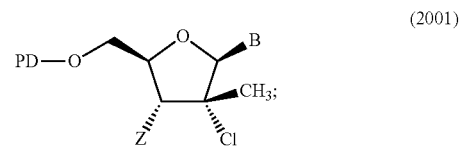

(2001)

or a pharmaceutically acceptable salt, solvate, stereoisomeric form, tautomeric form or polymorphic form thereof, wherein: PD is hydrogen, monophosphate, diphosphate, triphosphate, or

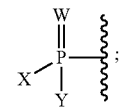

B is a nucleobase; W is S or O; one of X and Y is hydrogen, —OR$^1$, —SR$^1$, —NR$^1$R$^2$, an N-linked amino alcohol or an N-linked amino acid, an O-linked amino acid, or a derivative thereof, and the other of X and Y is —OR$^1$; Z is —OH; or, in the alternative, Z and Y join to form a six-membered heterocyclic ring wherein Z and Y together represent a single divalent —O—, and X is —OR$^1$, —SR$^1$, —NR$^1$R$^2$, an N-linked amino alcohol or an N-linked amino acid, an O-linked amino acid, or a derivative thereof; each R$^1$ is independently hydrogen, alkyl, cycloalkyl, aryl, heteroaryl, arylalkyl, heteroarylalkyl, alkylcarbonylthioalkyl, alkoxycarbonylalkyl, arylalkoxycarbonylalkyl, alkylcarbonylalkoxy(arylalkyl), cycloalkylcarbonylalkoxyl, alkoxycarbonylaminoalkylcarbonylthioalkyl, hydroxylalkylcarbonylthioalkyl, alkylcarbonylalkoxyl or aminoalkylcarbonylalkoxycarbonylthioalkyl; and each R$^2$ is independently hydrogen or alkyl.

In certain embodiments, provided herein are compounds according to Formula (1001):

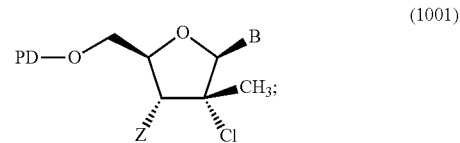

(1001)

or a pharmaceutically acceptable salt, solvate, stereoisomeric form, tautomeric form or polymorphic form thereof, wherein: PD is hydrogen, triphosphate, or

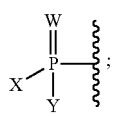

B is a nucleobase; W is S or O; one of X and Y is hydrogen, —OR¹, —SR¹, —NR¹R², an O-linked amino acid residue, an N-linked amino alcohol or an N-linked amino acid residue, or an ester thereof, and the other of X and Y is —OR¹; Z is —OH; or, in the alternative, Z and Y join to form a six-membered heterocyclic ring wherein Z and Y together represent a single divalent —O—, and X is —OR¹, —SR¹, —NR¹R², an O-linked amino acid residue, an N-linked amino alcohol or an N-linked amino acid residue, or an ester thereof; each R¹ is independently alkyl, cycloalkyl, aryl, heteroaryl, arylalkyl, heteroarylalkyl, alkylcarbonylthioalkyl, alkoxycarbonylalkyl, arylalkoxycarbonylalkyl, alkylcarbonylalkoxy(arylalkyl), cycloalkylcarbonylalkoxyl, alkoxycarbonylaminoalkylcarbonylthioalkyl, hydroxylalkylcarbonylthioalkyl, or aminoalkylcarbonylalkoxycarbonylthioalkyl; and each R² is independently hydrogen or alkyl.

In certain embodiments, provided herein are compounds according to Formula (I):

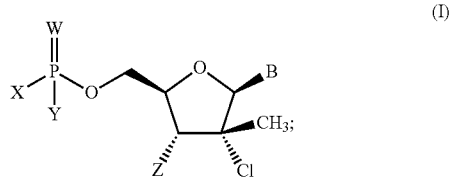

or a pharmaceutically acceptable salt, solvate, stereoisomeric form, tautomeric form or polymorphic form thereof, wherein: B is a nucleobase; W is S or O; one of X and Y is hydrogen, —OR¹, —SR¹, —NR¹R², an O-linked amino acid residue, an N-linked amino alcohol or an N-linked amino acid residue, or an ester thereof, and the other of X and Y is —OR¹; Z is —OH; or, in the alternative, Z and Y join to form a six-membered heterocyclic ring wherein Z and Y together represent a single divalent —O—, and X is —OR¹, —SR¹, —NR¹R², an O-linked amino acid residue, an N-linked amino alcohol or an N-linked amino acid residue, or an ester thereof; each R¹ is independently alkyl, cycloalkyl, aryl, heteroaryl, arylalkyl, or heteroarylalkyl; and each R² is independently hydrogen or alkyl.

In one aspect, the compounds provided herein are provided or administered in combination with a second therapeutic agent, such as one useful for the treatment or prevention of HCV infections. Exemplary second therapeutic agents are provided in detail elsewhere herein.

In another aspect, provided herein are pharmaceutical compositions, single unit dosage forms, and kits suitable for use in treating or preventing disorders such as HCV infections which comprise a therapeutically or prophylactically effective amount of a compound provided herein, e.g., of Formula 1001, 2001-2003, I-XXVII, 1-104iib, 201-213iib, 301-315, 401-415, or i-ivH and a therapeutically or prophylactically effective amount of a second therapeutic agent such as one useful for the treatment or prevention of HCV infections.

In certain embodiments, a method of treatment of a liver disorder is provided comprising administering to an individual in need thereof a treatment effective amount of a 2'-chloro nucleoside analog compound.

Flaviviridae which can be treated are, e.g., discussed generally in *Fields Virology*, Fifth Ed., Editors: Knipe, D. M., and Howley, P. M., Lippincott Williams & Wilkins Publishers, Philadelphia, Pa., Chapters 33-35, 2006. In a particular embodiment of the invention, the Flaviviridae is HCV. In an alternate embodiment, the Flaviviridae is a flavivirus or pestivirus. In certain embodiments, the Flaviviridae can be from any class of Flaviviridae. In certain embodiments, the Flaviviridae is a mammalian tick-borne virus. In certain embodiments, the Flaviviridae is a seabird tick-borne virus. In certain embodiments, the Flaviviridae is a mosquito-borne virus. In certain embodiments, the Flaviviridae is an Aroa virus. In certain embodiments, the Flaviviridae is a Dengue virus. In certain embodiments, the Flaviviridae is a Japanese encephalitis virus. In certain embodiments, the Flaviviridae is a Kokobera virus. In certain embodiments, the Flaviviridae is a Ntaya virus. In certain embodiments, the Flaviviridae is a Spondweni virus. In certain embodiments, the Flaviviridae is a Yellow fever virus. In certain embodiments, the Flaviviridae is a Entebbe virus. In certain embodiments, the Flaviviridae is a Modoc virus. In certain embodiments, the Flaviviridae is a Rio Bravo virus.

Specific flaviviruses include, without limitation: Absettarov, Aedes, Alfuy, Alkhurma, Apoi, Aroa, Bagaza, Banzi, Bukalasa bat, Bouboui, Bussuquara, Cacipacore, Calbertado, Carey Island, Cell fusing agent, Cowbone Ridge, Culex, Dakar bat, Dengue 1, Dengue 2, Dengue 3, Dengue 4, Edge Hill, Entebbe bat, Gadgets Gully, Hanzalova, Hypr, Ilheus, Israel turkey meningoencephalitis, Japanese encephalitis, Jugra, Jutiapa, Kadam, Kamiti River, Karshi, Kedougou, Kokobera, Koutango, Kumlinge, Kunjin, Kyasanur Forest disease, Langat, Louping ill, Meaban, Modoc, Montana myotis leukoencephalitis, Murray valley encephalitis, Nakiwogo, Naranjal, Negishi, Ntaya, Omsk hemorrhagic fever, Phnom-Penh bat, Powassan, Quang Binh, Rio Bravo, Rocio, Royal Farm, Russian spring-summer encephalitis, Saboya, St. Louis encephalitis, Sal Vieja, San Perlita, Saumarez Reef, Sepik, Sokuluk, Spondweni, Stratford, Tembusu, Tick-borne encephalitis, Turkish sheep encephalitis, Tyuleniy, Uganda S, Usutu, Wesselsbron, West Nile, Yaounde, Yellow fever, Yokose, and Zika.

Pestiviruses which can be treated are discussed generally in *Fields Virology*, Fifth Ed., Editors: Knipe, D. M., and Howley, P. M., Lippincott Williams & Wilkins Publishers, Philadelphia, Pa., Chapters 33-35, 2006. Specific pestiviruses include, without limitation: bovine viral diarrhea virus ("BVDV"), classical swine fever virus ("CSFV," also called hog cholera virus), and border disease virus ("BDV").

DESCRIPTION OF EXEMPLARY EMBODIMENTS

Provided herein are compounds, compositions and methods useful for treating liver disorders such as HCV infection in a subject. Further provided are dosage forms useful for such methods.

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

The term "alkyl," as used herein, unless otherwise specified, refers to a saturated straight or branched hydrocarbon. In certain embodiments, the alkyl group is a primary, secondary, or tertiary hydrocarbon. In certain embodiments, the alkyl group includes one to ten carbon atoms, i.e., $C_1$ to $C_{10}$ alkyl. In certain embodiments, the alkyl group is selected from the group consisting of methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, and 2,3-dimethylbutyl. The term includes both substituted and unsubstituted alkyl groups, including halogenated alkyl groups. In certain embodiments, the alkyl group is a fluorinated alkyl group. Non-limiting examples of moieties with which the alkyl group can be substituted are selected from the group consisting of halogen (fluoro, chloro, bromo or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference.

The term "lower alkyl," as used herein, and unless otherwise specified, refers to a saturated straight or branched hydrocarbon having one to six carbon atoms, i.e., $C_1$ to $C_6$ alkyl. In certain embodiments, the lower alkyl group is a primary, secondary, or tertiary hydrocarbon. The term includes both substituted and unsubstituted moieties.

The term "upper alkyl," as used herein, and unless otherwise specified, refers to a saturated straight or branched hydrocarbon having seven to thirty carbon atoms, i.e., $C_7$ to $C_{30}$ alkyl. In certain embodiments, the upper alkyl group is a primary, secondary, or tertiary hydrocarbon. The term includes both substituted and unsubstituted moieties.

The term "cycloalkyl," as used herein, unless otherwise specified, refers to a saturated cyclic hydrocarbon. In certain embodiments, the cycloalkyl group may be a saturated, and/or bridged, and/or non-bridged, and/or a fused bicyclic group. In certain embodiments, the cycloalkyl group includes three to ten carbon atoms, i.e., $C_3$ to $C_{10}$ cycloalkyl. In some embodiments, the cycloalkyl has from 3 to 15 ($C_{3-15}$), from 3 to 10 ($C_{3-10}$), or from 3 to 7 ($C_{3-7}$) carbon atoms. In certain embodiments, the cycloalkyl group is cyclopropyl, cyclobutyl, cyclopentyl, cyclohexyl, cyclohexylmethyl, cycloheptyl, bicyclo[2.1.1]hexyl, bicyclo[2.2.1]heptyl, decalinyl or adamantyl. The term includes both substituted and unsubstituted cycloalkyl groups, including halogenated cycloalkyl groups. In certain embodiments, the cycloalkyl group is a fluorinated cycloalkyl group. Non-limiting examples of moieties with which the cycloalkyl group can be substituted are selected from the group consisting of halogen (fluoro, chloro, bromo or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

"Alkylene" refers to divalent saturated aliphatic hydrocarbon groups particularly having from one to eleven carbon atoms which can be straight-chained or branched. In certain embodiments, the alkylene group contains 1 to 10 carbon atoms. The term includes both substituted and unsubstituted moieties. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like. The term includes halogenated alkylene groups. In certain embodiments, the alkylene group is a fluorinated alkylene group. Non-limiting examples of moieties with which the alkylene group can be substituted are selected from the group consisting of halogen (fluoro, chloro, bromo or iodo), hydroxyl, carbonyl, sulfanyl, amino, alkylamino, alkylaryl, arylamino, alkoxy, aryloxy, nitro, cyano, sulfonic acid, sulfate, phosphonic acid, phosphate, and phosphonate, either unprotected, or protected as necessary.

"Alkenyl" refers to monovalent olefinically unsaturated hydrocarbon groups, in certain embodiments, having up to about 11 carbon atoms, from 2 to 8 carbon atoms, or from 2 to 6 carbon atoms, which can be straight-chained or branched and having at least 1 or from 1 to 2 sites of olefinic unsaturation. The term includes both substituted and unsubstituted moieties. Exemplary alkenyl groups include ethenyl (i.e., vinyl, or —CH=$CH_2$), n-propenyl (—$CH_2$CH=$CH_2$), isopropenyl (—$C(CH_3)$=$CH_2$), and the like. The term includes halogenated alkenyl groups. In certain embodiments, the alkenyl group is a fluorinated alkenyl group. Non-limiting examples of moieties with which the alkenyl group can be substituted are selected from the group consisting of halogen (fluoro, chloro, bromo or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

The term "cycloalkenyl," as used herein, unless otherwise specified, refers to an unsaturated cyclic hydrocarbon. In certain embodiments, cycloalkenyl refers to mono- or multicyclic ring systems that include at least one double bond. In certain embodiments, the cycloalkenyl group may be a bridged, non-bridged, and/or a fused bicyclic group. In certain embodiments, the cycloalkyl group includes three to ten carbon atoms, i.e., $C_3$ to $C_{10}$ cycloalkyl. In some embodiments, the cycloalkenyl has from 3 to 7 ($C_{3-10}$), or from 4 to 7 ($C_{3-7}$) carbon atoms. The term includes both substituted and unsubstituted cycloalkenyl groups, including halogenated cycloalkenyl groups. In certain embodiments, the cycloalkenyl group is a fluorinated cycloalkenyl group. Non-limiting examples of moieties with which the cycloalkenyl group can be substituted are selected from the group consisting of halogen (fluoro, chloro, bromo or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

"Alkenylene" refers to divalent olefinically unsaturated hydrocarbon groups, in certain embodiments, having up to about 11 carbon atoms or from 2 to 6 carbon atoms which can be straight-chained or branched and having at least 1 or from 1 to 2 sites of olefinic unsaturation. This term is exemplified by groups such as ethenylene (—CH=CH—), the propenylene isomers (e.g., —CH=$CHCH_2$— and —$C(CH_3)$=CH— and —CH=$C(CH_3)$—) and the like. The term includes both substituted and unsubstituted alkenylene groups, including halogenated alkenylene groups. In certain embodiments, the alkenylene group is a fluorinated alkenylene group. Non-limiting examples of moieties with which the alkenylene group can be substituted are selected from the group consisting of halogen (fluoro, chloro, bromo or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

"Alkynyl" refers to acetylenically unsaturated hydrocarbon groups, in certain embodiments, having up to about 11 carbon atoms or from 2 to 6 carbon atoms which can be straight-chained or branched and having at least 1 or from 1 to 2 sites of alkynyl unsaturation. Non-limiting examples of alkynyl groups include acetylenic, ethynyl (—C≡CH), propargyl (—CH$_2$C≡CH), and the like. The term includes both substituted and unsubstituted alkynyl groups, including halogenated alkynyl groups. In certain embodiments, the alkynyl group is a fluorinated alkynyl group. Non-limiting examples of moieties with which the alkynyl group can be substituted are selected from the group consisting of halogen (fluoro, chloro, bromo or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

The term "aryl," as used herein, and unless otherwise specified, refers to a substituent derived from an aromatic ring. In an embodiment, an aryl group is a C$_6$-C$_{12}$ aryl group. In an embodiment, an aryl group is phenyl, biphenyl or naphthyl. The term includes both substituted and unsubstituted moieties. An aryl group can be substituted with any described moiety, including, but not limited to, one or more moieties selected from the group consisting of halogen (fluoro, chloro, bromo or iodo), alkyl, haloalkyl, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The terms "alkoxy" and "alkoxyl" are synonymous and refer to the group —OR' where R' is alkyl or cycloalkyl, where alkyl and cycloalkyl are as described herein. Alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" refers to a radical —C(O)-alkoxy where alkoxy is as defined herein.

The term "alkylcarbonylthioalkyl" refers to a radical -alkyl-S—C(O)-alkyl, where alkyl is as defined herein.

The term "alkylcarbonylalkoxyl" refers to a radical -alkoxyl-C(O)-alkyl, wherein alkyl and alkoxyl are as defined herein.

The term "alkoxycarbonylalkyl" refers to a radical -alkyl-C(O)-alkoxy, where alkyl and alkoxy are as defined herein.

The term "arylalkoxycarbonylalkyl" refers to a radical -alkyl-C(O)-alkoxy-aryl, where alkyl, alkoxy and aryl are as defined herein.

The term "alkylcarbonylalkoxy(arylalkyl)" refers to a radical -alkoxy(-alkyl-aryl)-C(O)-alkyl, where alkyl, alkoxy and aryl are as defined herein.

The term "cycloalkylcarbonylalkoxyl" refers to a radical -alkoxyl-C(O)-cycloalkyl, where alkoxyl and cycloalkyl are as defined herein.

The term "alkoxycarbonylaminoalkylcarbonylthioalkyl" refers to a radical -alkyl-S—C(O)—NH-alkyl-C(O)-alkoxy or -alkyl-S—C(O)-alkyl-NH—C(O)-alkoxy, where alkyl and alkoxy are as defined herein.

The term "hydroxylalkylcarbonylthioalkyl" refers to a radical -alkyl-S—C(O)-alkyl-OH, where alkyl is as defined herein.

The term "aminoalkylcarbonylalkoxycarbonylthioalkyl" refers to a radical -alkyl-S—C(O)-alkoxy-C(O)—NH-alkyl or -alkyl-S—C(O)-alkoxy-C(O)-alkyl-NH$_2$, where alkyl and alkoxy are as defined herein.

The term "alkoxycarbonylaminoalkyl" refers to a radical -alkyl-NH—C(O)-alkoxy or —NH-alkyl-C(O)-alkoxy, where alkyl and alkoxy are as defined herein.

The term "hydroxylalkyl" refers to a radical -alkyl-OH, where alkyl is as defined herein.

The term "aminoalkylcarbonylalkoxyl" refers to a radical -alkoxy-C(O)-alkyl-NH$_2$ or -alkoxy-C(O)—NH-alkyl, where alkyl and alkoxy are as defined herein.

"Amino" refers to the radical —NH$_2$ or —NH—R, where each R is independently alkyl, aryl, or cycloalkyl.

"Amino alcohol" refers to the radical —NHLOH, wherein L is alkylene.

"Carboxyl" or "carboxy" refers to the radical —C(O)OH.

The term "alkylamino" or "arylamino" refers to an amino group that has one or two alkyl or aryl substituents, respectively. In certain embodiments, the alkyl substituent is upper alkyl. In certain embodiments, the alkyl substituent is lower alkyl. In another embodiment, the alkyl, upper alkyl, or lower alkyl is unsubstituted.

"Halogen" or "halo" refers to chloro, bromo, fluoro or iodo.

"Monoalkylamino" refers to the group alkyl-NR'—, wherein R' is selected from hydrogen and alkyl or cycloalkyl.

"Thioalkoxy" refers to the group —SR' where R' is alkyl or cycloalkyl.

The term "heterocyclyl" or "heterocyclic" refers to a monovalent monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of the molecule through the non-aromatic ring. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein.

The term "heteroaryl" refers to refers to a monovalent monocyclic aromatic group and/or multicyclic aromatic group that contain at least one aromatic ring, wherein at least one aromatic ring contains one or more heteroatoms independently selected from O, S and N in the ring. Heteroaryl groups are bonded to the rest of the molecule through the aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl and xanthenyl. In certain embodiments, heteroaryl may also be optionally substituted as described herein.

The term "alkylaryl" refers to an aryl group with an alkyl substituent. The term "aralkyl" or "arylalkyl" refers to an alkyl group with an aryl substituent.

The term "alkylheterocyclyl" refers to a heterocyclyl group with an alkyl substituent. The term heterocyclylalkyl refers to an alkyl group with a heterocyclyl substituent.

The term "alkylheteroaryl" refers to a heteroaryl group with an alkyl substituent. The term heteroarylalkyl refers to an alkyl group with a heteroaryl substituent.

The term "protecting group" as used herein and unless otherwise defined refers to a group that is added to an oxygen, nitrogen or phosphorus atom to prevent its further reaction or for other purposes. A wide variety of oxygen and nitrogen protecting groups are known to those skilled in the art of organic synthesis.

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) base addition salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts further include, by way of example only and without limitation, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

As used herein, the term "nucleobase" refers to the base portion of a nucleoside or nucleotide. In certain embodiments, a nucleobase is a purine or pyrimidine base, as defined herein.

The terms "purine" or "pyrimidine" base refer to, but are not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-alkylaminopurine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-iodopyrimidine, $C^6$-iodo-pyrimidine, $C^5$—Br-vinyl pyrimidine, $C^6$—Br-vinyl pyrimidine, $C^5$-nitropyrimidine, $C^5$-amino-pyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 7-deazaguanine, 7-deazaadenine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "acyl" or "O-linked ester" refers to a group of the formula C(O)R', wherein R' is alkyl or cycloalkyl (including lower alkyl), carboxylate reside of amino acid, aryl including phenyl, alkaryl, arylalkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or arylalkyl sulphonyl including methanesulfonyl, the mono, di or triphosphate ester, trityl or monomethoxy-trityl, substituted benzyl, alkaryl, arylalkyl including benzyl, alkoxyalkyl including methoxymethyl, aryloxyalkyl such as phenoxymethyl. Aryl groups in the esters optimally comprise a phenyl group. In particular, acyl groups include acetyl, trifluoroacetyl, methylacetyl, cyclopropylacetyl, propionyl, butyryl, hexanoyl, heptanoyl, octanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoro-heptanoyl, 7H-dodecafluoro-heptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxy-benzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl.

The term "amino acid" refers to naturally occurring and synthetic α, β γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration. In certain embodiments, the amino acid is in the D-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl.

The term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is -G-C(O)-Q, wherein Q is sulfanyl, amino or alkoxyl and G is $C_1$-$C_2$ alkyl. In an embodiment, an amino acid derivative is provided as a substituent of a compound described herein, wherein the substituent is —NH-G($S_C$)—C(O)-$Q^1$, wherein $Q^1$ is —SR, —NRR or alkoxyl, R is hydrogen or alkyl, $S_C$ is a side chain of a naturally occurring or non-naturally occurring amino acid and G is $C_1$-$C_2$ alkyl. In an embodiment, an amino acid derivative is provided as a substituent of a compound described herein, wherein the substituent is —O—C(O)-G($S_C$)—NH-$Q^2$, wherein $Q^2$ is hydrogen or alkoxyl, $S_C$ is a side chain of a naturally occurring or non-naturally occurring amino acid and G is $C_1$-$C_2$ alkyl. In certain embodiments, G is $C_1$ alkyl and $S_C$ is selected from the group consisting of hydrogen, alkyl, heteroalkyl, arylalkyl and heteroarylalkyl. In an embodiment, an amino acid derivative is provided as a substituent of a compound described herein, wherein the amino acid derivative is in the D-configuration. In an embodiment, an amino acid derivative is provided as a substituent of a compound described herein, wherein the amino acid derivative is in the L-configuration.

The term "substantially free of" or "substantially in the absence of" with respect to a nucleoside composition refers to a nucleoside composition that includes at least 85 or 90% by weight, in certain embodiments 95%, 98%, 99% or 100% by weight, of the designated enantiomer of that nucleoside. In certain embodiments, in the methods and compounds provided herein, the compounds are substantially free of enantiomers.

Similarly, the term "isolated" with respect to a nucleoside composition refers to a nucleoside composition that includes at least 85, 90%, 95%, 98%, 99% to 100% by weight, of the nucleoside, the remainder comprising other chemical species or enantiomers.

"Solvate" refers to a compound provided herein or a salt thereof, that further includes a stoichiometric or non-stoichiometric amount of solvent bound by non-covalent intermolecular forces. Where the solvent is water, the solvate is a hydrate.

"Isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

"Isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "cycloalkyl," "alkenyl," "cycloalkenyl," "alkynyl," "aryl," "alkoxy," "alkoxycarbonyl," "amino," "carboxyl," "alkylamino," "arylamino," "thioalkyoxy," "heterocyclyl," "heteroaryl," "alkylheterocyclyl," "alkylheteroaryl," "acyl," "aralkyl," "alkaryl," "purine," "pyrimidine," "carboxyl" and "amino acid" groups optionally comprise deuterium at one or more positions where hydrogen atoms are present, and wherein the deuterium composition of the atom or atoms is other than the natural isotopic composition.

Also as used herein, "alkyl," "cycloalkyl," "alkenyl," "cycloalkenyl," "alkynyl," "aryl," "alkoxy," "alkoxycarbonyl," "carboxyl," "alkylamino," "arylamino," "thioalkyoxy," "heterocyclyl," "heteroaryl," "alkylheterocyclyl," "alkylheteroaryl," "acyl," "aralkyl," "alkaryl," "purine," "pyrimidine," "carboxyl" and "amino acid" groups optionally comprise carbon-13 at an amount other than the natural isotopic composition.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, the $IC_{50}$ refers to an amount, concentration or dosage of a particular test compound that achieves a 50% inhibition of a maximal response in an assay that measures such response.

The term "host," as used herein, refers to any unicellular or multicellular organism in which the virus can replicate, including cell lines and animals, and in certain embodiments, a human. Alternatively, the host can be carrying a part of the Flaviviridae viral genome, whose replication or function can be altered by the compounds of the present invention. The term host specifically includes infected cells, cells transfected with all or part of the Flaviviridae genome and animals, in particular, primates (including chimpanzees) and humans. In most animal applications of the present invention, the host is a human patient. Veterinary applications, in certain indications, however, are clearly anticipated by the present invention (such as chimpanzees).

As used herein, the terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and for example, a human. In certain embodiments, the subject is refractory or non-responsive to current treatments for hepatitis C infection. In another embodiment, the subject is a farm animal (e.g., a horse, a cow, a pig, etc.) or a pet (e.g., a dog or a cat). In certain embodiments, the subject is a human.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In certain embodiments, a therapeutic agent is an agent which is known to be useful for, or has been or is currently being used for the treatment or prevention of a disorder or one or more symptoms thereof.

"Therapeutically effective amount" refers to an amount of a compound or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" includes a compound provided herein. In certain other embodiments, the term "prophylactic agent" does not refer a compound provided herein. For example, a prophylactic agent is an agent which is known to be useful for, or has been or is currently being used to prevent or impede the onset, development, progression and/or severity of a disorder.

As used herein, the phrase "prophylactically effective amount" refers to the amount of a therapy (e.g., prophylactic agent) which is sufficient to result in the prevention or reduction of the development, recurrence or onset of one or more symptoms associated with a disorder, or to enhance or improve the prophylactic effect(s) of another therapy (e.g., another prophylactic agent).

Compounds

Provided herein are 2'-chloro nucleoside analog compounds useful for the treatment of Flaviviridae infections such as HCV infection. The 2'-chloro nucleoside analog compounds can be formed as described herein and used for the treatment of Flaviviridae infections such as HCV infection.

In certain embodiments, provided herein are compounds according to Formula 2001:

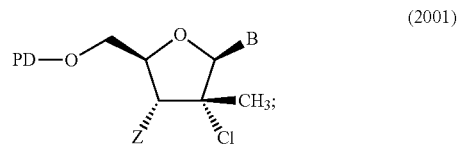

(2001)

or a pharmaceutically acceptable salt, solvate, stereoisomeric form, tautomeric form or polymorphic form thereof, wherein: PD is hydrogen, monophosphate, diphosphate, triphosphate, or

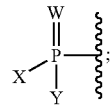

B is a nucleobase; W is S or O; one of X and Y is hydrogen, —$OR^1$, —$SR^1$, —$NR^1R^2$, an N-linked amino alcohol or an N-linked amino acid, an O-linked amino acid, or a derivative thereof, and the other of X and Y is —$OR^1$; Z is —OH; or, in the alternative, Z and Y join to form a six-membered heterocyclic ring wherein Z and Y together represent a single divalent —O—, and X is —$OR^1$, —$SR^1$, —$NR^1R^2$, an N-linked amino alcohol or an N-linked amino acid, an O-linked amino acid, or a derivative thereof; each $R^1$ is independently hydrogen, alkyl, cycloalkyl, aryl, heteroaryl, arylalkyl, heteroarylalkyl, alkylcarbonylthioalkyl, alkoxycarbonylalkyl, arylalkoxycarbonylalkyl, alkylcarbonylalkoxy(arylalkyl), cycloalkylcarbonylalkoxyl, alkoxycarbonylaminoalkylcarbonylthioalkyl, hydroxylalkylcarbonylthioalkyl, alkylcarbonylalkoxy or aminoalkylcarbonylalkoxycarbonylthioalkyl; and each $R^2$ is independently hydrogen or alkyl.

In certain embodiments, provided herein are compounds according to Formula (1001):

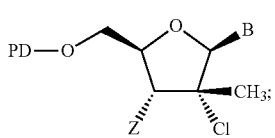

(1001)

or a pharmaceutically acceptable salt, solvate, stereoisomeric form, tautomeric form or polymorphic form thereof, wherein: PD is hydrogen, triphosphate, or

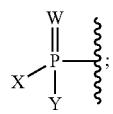

B is a nucleobase; W is S or O; one of X and Y is hydrogen, $-OR^1$, $-SR^1$, $-NR^1R^2$, an O-linked amino acid residue, an N-linked amino alcohol or an N-linked amino acid residue, or an ester thereof, and the other of X and Y is $-OR^1$; Z is $-OH$; or, in the alternative, Z and Y join to form a six-membered heterocyclic ring wherein Z and Y together represent a single divalent $-O-$, and X is $-OR^1$, $-SR^1$, $-NR^1R^2$, an O-linked amino acid residue, an N-linked amino alcohol or an N-linked amino acid residue, or an ester thereof; each $R^1$ is independently alkyl, cycloalkyl, aryl, heteroaryl, arylalkyl, heteroarylalkyl, alkylcarbonylthioalkyl, alkoxycarbonylalkyl, arylalkoxycarbonylalkyl, alkylcarbonylalkoxy(arylalkyl), cycloalkylcarbonylalkoxyl, alkoxycarbonylaminoalkylcarbonylthioalkyl, hydroxylalkylcarbonylthioalkyl, or aminoalkylcarbonylalkoxycarbonylthioalkyl; and each $R^2$ is independently hydrogen or alkyl.

In certain embodiments, provided herein are compounds according to Formula (I):

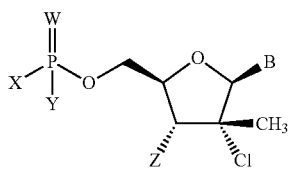

(I)

or a pharmaceutically acceptable salt, solvate, stereoisomeric form, tautomeric form or polymorphic form thereof, wherein: B is a nucleobase; W is S or O; one of X and Y is hydrogen, $-OR^1$, $-SR^1$, $-NR^1R^2$, an O-linked amino acid residue, an N-linked amino alcohol or an N-linked amino acid residue, or an ester thereof, and the other of X and Y is $-OR^1$; Z is $-OH$; or, in the alternative, Z and Y join to form a six-membered heterocyclic ring wherein Z and Y together represent a single divalent $-O-$, and X is $-OR^1$, $-SR^1$, $-NR^1R^2$, an O-linked amino acid residue, an N-linked amino alcohol or an N-linked amino acid residue, or an ester thereof; each $R^1$ is independently alkyl, cycloalkyl, aryl, heteroaryl, arylalkyl, or heteroarylalkyl; and each $R^2$ is independently hydrogen or alkyl.

In certain embodiments, provided herein are compounds according to Formula II:

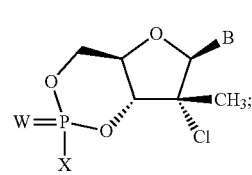

(II)

wherein each X is independently $-OR^1$, $-SR^1$, $-NR^1R^2$, an O-linked amino acid residue, an N-linked amino alcohol or an N-linked amino acid residue, or an ester thereof; and B, W, $R^1$, and $R^2$ are as defined in the context of Formula I, Formula 1001 or Formula 2001. In certain embodiments, a compound according to Formula II is provided wherein each X is independently $-OR^1$, $-SR^1$, $-NR^1R^2$, an N-linked amino alcohol or an N-linked amino acid, an O-linked amino acid, or a derivative thereof; and B, W, $R^1$, and $R^2$ are as defined in the context of Formula I, Formula 1001 or Formula 2001.

In certain embodiments, provided herein are compounds according to Formulas IIa or IIb:

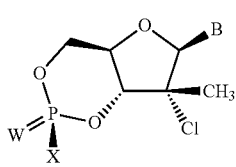

(IIa)

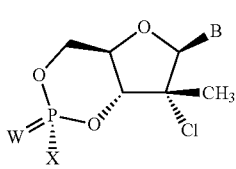

(IIb)

or pharmaceutically acceptable salts, solvates, stereoisomeric forms, tautomeric forms or polymorphic forms thereof, wherein each X is independently $-OR^1$, $-SR^1$, $-NR^1R^2$, an O-linked amino acid residue, an N-linked amino alcohol or an N-linked amino acid residue, or an ester thereof; and B, W, $R^1$, and $R^2$ are as defined in the context of Formula I, Formula 1001 or Formula 2001. In certain embodiments, a compound according to Formula IIa or IIb is provided wherein each X is independently $-OR^1$, $-SR^1$, $-NR^1R^2$, an N-linked amino alcohol or an N-linked amino acid, an O-linked amino acid, or a derivative thereof; and B, W, $R^1$, and $R^2$ are as defined in the context of Formula I, Formula 1001 or Formula 2001.

In certain embodiments, provided herein are compounds according to Formula III:

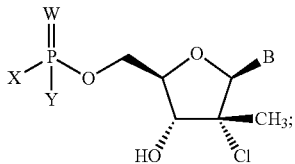

(III)

or pharmaceutically acceptable salts, solvates, stereoisomeric forms, tautomeric forms or polymorphic forms thereof, wherein one of X and Y is hydrogen, —OR$^1$, —SR$^1$, —NR$^1$R$^2$, an O-linked amino acid residue, an N-linked amino alcohol or an N-linked amino acid residue, or an ester thereof, and the other of X and Y is —OR$^1$; and B, W, R$^1$, and R$^2$ are as defined in the context of Formula I, Formula 1001 or Formula 2001. In certain embodiments, a compound of Formula III is provided wherein one of X and Y is —OR$^1$, —NR$^1$R$^2$, an O-linked amino acid residue, an N-linked amino alcohol or an N-linked amino acid residue, or an ester thereof, and the other of X and Y is —OR$^1$. In certain embodiments, a compound according to Formula III is provided wherein one of X and Y is hydrogen, —OR$^1$, —SR$^1$, —NR$^1$R$^2$, an N-linked amino alcohol or an N-linked amino acid, an O-linked amino acid, or a derivative thereof, and the other of X and Y is —OR$^1$; and B, W, R$^1$, and R$^2$ are as defined in the context of Formula I, Formula 1001 or Formula 2001.

In an embodiment, a compound according to any of Formulas 1001, 2001 or I-III is provided wherein: PD is monophosphate, diphosphate, triphosphate, or

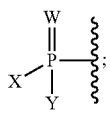

and W, X, and Y are as described in the context of Formula 1001, 2001 or I.

In certain embodiments a compound of any of Formulas I-III is provided wherein W is O. In certain embodiments a compound of any of Formulas I-III is provided wherein W is S. In certain embodiments a compound of any of Formulas 1001 or I-III is provided wherein W is O. In certain embodiments a compound of any of Formulas 1001 or I-III is provided wherein W is S. In certain embodiments a compound of any of Formulas 1001, 2001 or I-III is provided wherein W is O. In certain embodiments a compound of any of Formulas 1001, 2001 or I-III is provided wherein W is S.

In certain embodiments a compound of any of Formulas I-III is provided wherein each X is independently an O-linked amino acid residue, or an ester thereof. In certain embodiments a compound of any of Formulas I-III is provided wherein each X is independently an O-linked serine or tyrosine amino acid residue, or an ester thereof. In certain embodiments a compound of any of Formulas I-III is provided wherein each X is independently an O-linked serine amino acid residue, or an ester thereof. In certain embodiments a compound of any of Formulas I-III is provided wherein each X is independently an O-linked tyrosine amino acid residue, or an ester thereof.

In certain embodiments a compound of any of Formulas 1001 or I-III is provided wherein each X is independently an O-linked amino acid residue, or an ester thereof. In certain embodiments a compound of any of Formulas 1001 or I-III is provided wherein each X is independently an O-linked serine or tyrosine amino acid residue, or an ester thereof. In certain embodiments a compound of any of Formulas 1001 or I-III is provided wherein each X is independently an O-linked serine amino acid residue, or an ester thereof. In certain embodiments a compound of any of Formulas 1001 or I-III is provided wherein each X is independently an O-linked tyrosine amino acid residue, or an ester thereof.

In certain embodiments a compound of any of Formulas 1001, 2001 or I-III is provided wherein each X is independently an O-linked amino acid, or a derivative thereof. In certain embodiments a compound of any of Formulas 1001, 2001 or I-III is provided wherein each X is independently an O-linked serine or tyrosine amino acid, or a derivative thereof. In certain embodiments a compound of any of Formulas 1001, 2001 or I-III is provided wherein each X is independently an O-linked serine amino acid, or a derivative thereof. In certain embodiments a compound of any of Formulas 1001, 2001 or I-III is provided wherein each X is independently an O-linked tyrosine amino acid, or a derivative thereof. In certain embodiments, a compound according to any of Formulas 1001, 2001 or I-III is provided wherein each X is independently an N-linked L-amino acid, or a derivative thereof. In certain embodiments, a compound according to any of Formulas 1001, 2001 or I-III is provided wherein each X is independently an N-linked D-amino acid, or a derivative thereof. In certain embodiments, a compound according to any of Formulas 1001, 2001 or I-III is provided wherein each X is independently an N-linked alanine, or a derivative thereof. In certain embodiments, a compound according to any of Formulas 1001, 2001 or I-III is provided wherein each X is independently an N-linked D-alanine, or a derivative thereof. In certain embodiments, a compound according to any of Formulas 1001, 2001 or I-III is provided wherein each X is independently an N-linked L-alanine, or a derivative thereof. In certain embodiments, a compound according to any of Formulas 1001, 2001 or I-III is provided wherein each X is independently an N-linked phenylalanine, or a derivative thereof.

In certain embodiments, a compound of any of Formulas 1001, 2001, I, II, IIa, IIb, or III is provided wherein: W is O; each X is independently —OR$^1$ or —NR$^1$R$^2$; R$^2$ is hydrogen; each R$^1$ is independently -(L)$_p$CR$_3$, -(L)$_p$Ar, -LC(O)O(L)$_p$CR$_3$, -LSC(O)(L)$_p$CR$_3$, -LOC(O)(L)$_p$CR$_3$, -LOC(O)(L)$_p$Cy, -LSC(O)LNHC(O)OCR$_3$, -LSC(O)LOC(O)LNH$_2$, -LC(O)LOAr, -LC(O)OLAr, or -LSC(O)LOH; each L is independently alkylene; each R is independently hydrogen, alkyl, aryl, or heteroaryl; each Ar is independently aryl, or heteroaryl; each Cy is independently cycloalkyl; and each p is independently 0 or 1. In certain embodiments, each R$^1$ is independently -(L)$_p$CR$_3$. In certain embodiments, each R$^1$ is independently -(L)$_p$Ar. In certain embodiments, each R$^1$ is independently -LC(O)O(L)$_p$CR$_3$. In certain embodiments, each R$^1$ is independently -LSC(O)(L)$_p$CR$_3$. In certain embodiments, each R$^1$ is independently -LOC(O)(L)$_p$CR$_3$. In certain embodiments, each R$^1$ is independently -LSC(O)LNHC(O)OCR$_3$. In certain embodiments, each R$^1$ is independently -LSC(O)LOC(O)LNH$_2$. In certain embodiments, each R$^1$ is independently -LSC(O)LOH.

In certain embodiments, a compound of any of Formulas 1001, I, II, IIa, IIb, or III is provided wherein: W is O; each X is independently —OR$^1$ or —NR$^1$R$^2$; R$^2$ is hydrogen; each R$^1$ is independently -(L)$_p$CR$_3$, -(L)$_p$Ar, -LC(O)O(L)$_p$CR$_3$, -LSC(O)(L)$_p$CR$_3$, -LOC(O)(L)$_p$CR$_3$, -LOC(O)(L)$_p$Cy, -LSC(O)LNHC(O)OCR$_3$, -LSC(O)LOC (O)LNH$_2$, -LC(O)LOAr, -LC(O)OLAr, or -LSC(O)LOH; each L is independently alkylene; each R is independently hydrogen, alkyl, aryl, or heteroaryl; each Ar is independently aryl, or heteroaryl; each Cy is independently cycloalkyl; and each p is independently 0 or 1. In certain embodiments, each R$^1$ is independently -(L)$_p$CR$_3$. In certain embodiments, each R$^1$ is independently -(L)$_p$Ar. In certain embodiments, each R$^1$ is independently -LC(O)O(L)$_p$CR$_3$. In certain embodiments, each R$^1$ is independently -LSC(O)(L)$_p$CR$_3$. In certain embodiments, each R$^1$ is independently -LOC(O)(L)$_p$CR$_3$. In certain embodiments, each R$^1$ is independently -LSC(O)LNHC(O)OCR$_3$. In certain embodiments, each R$^1$ is independently -LSC(O)LOC(O)LNH$_2$. In certain embodiments, each R$^1$ is independently -LSC(O)LOH.

In certain embodiments, a compound of any of Formulas I, II, IIa, IIb, or III is provided wherein: W is O; each X is independently —OR$^1$ or —NR$^1$R$^2$; R$^2$ is hydrogen; each R$^1$ is independently -(L)$_p$CR$_3$, -(L)$_p$Ar, -LC(O)O(L)$_p$CR$_3$, -LSC(O)(L)$_p$CR$_3$, -LOC(O)(L)$_p$CR$_3$, -LOC(O)(L)$_p$Cy, -LSC(O)LNHC(O)OCR$_3$, -LSC(O)LOC(O)LNH$_2$, or -LSC(O)LOH; each L is independently alkylene; each R is independently hydrogen, alkyl, aryl, or heteroaryl; each Ar is independently aryl, or heteroaryl; each Cy is independently cycloalkyl; and each p is independently 0 or 1. In certain embodiments, each R$^1$ is independently -(L)$_p$CR$_3$. In certain embodiments, each R$^1$ is independently -(L)$_p$Ar. In certain embodiments, each R$^1$ is independently -LC(O)O(L)$_p$CR$_3$. In certain embodiments, each R$^1$ is independently -LSC(O)(L)$_p$CR$_3$. In certain embodiments, each R$^1$ is independently -LOC(O)(L)$_p$CR$_3$. In certain embodiments, each R$^1$ is independently -LSC(O)LNHC(O)OCR$_3$. In certain embodiments, each R$^1$ is independently -LSC(O)LOC(O)LNH$_2$. In certain embodiments, each R$^1$ is independently -LSC(O)LOH.

In certain embodiments, a compound of any of Formulas 1001, 2001, I or III is provided wherein: W is O; each Y is hydrogen, each Z is —OH, and each X is —OR$^1$. In certain embodiments, a compound of any of Formulas 1001, 2001, I or III is provided wherein: W is O; each Y is —OR$^1$, each Z is —OH, and each X is independently —OR$^1$, —NR$^1$R$^2$, an O-linked amino acid residue, an N-linked amino alcohol or an N-linked amino acid residue, or an ester thereof. In certain embodiments, a compound of any of Formulas 1001, 2001, I or III is provided wherein: W is O; each Y is —OR$^1$, each Z is —OH, and each X is independently hydrogen, —OR$^1$, —NR$^1$R$^2$, an O-linked amino acid residue, an N-linked amino alcohol or an N-linked amino acid residue, or an ester thereof. In certain embodiments, a compound of any of Formulas 1001, 2001, I or III is provided wherein: W is O; each Y is —NR$^1$R$^2$, each Z is —OH, and each X is —OR$^1$, an O-linked amino acid residue, an N-linked amino alcohol or an N-linked amino acid residue, or an ester thereof. In certain embodiments, a compound of any of Formulas 1001, 2001, I or III is provided wherein: W is O; each Y is an N-linked amino acid residue, or an ester thereof, each Z is —OH, and each X is —OR$^1$. In certain embodiments, each Y is an N-linked amino alcohol, each Z is —OH, and each X is —OR$^1$. In certain embodiments, a compound of any of Formulas 1001, 2001, I or III is provided wherein: W is O; Y is an O-linked amino acid residue, or an ester thereof, each Z is —OH, and each X is —OR$^1$.

In certain embodiments, a compound of any of Formulas 1001, 2001 or I is provided wherein: W is O; Z and Y join to form a six-membered heterocyclic ring wherein Z and Y together represent a single divalent —O—, and each X is independently —OR$^1$, —NR$^1$R$^2$, an O-linked amino acid residue, an N-linked amino alcohol or an N-linked amino acid residue, or an ester thereof. In certain embodiments, a compound of any of Formulas 1001, 2001 or I is provided wherein: W is O; Z and Y join to form a six-membered heterocyclic ring wherein Z and Y together represent a single divalent —O—, and each X is —OR$^1$. In certain embodiments, a compound of any of Formulas 1001, 2001 or I is provided wherein: W is O; Z and Y join to form a six-membered heterocyclic ring wherein Z and Y together represent a single divalent —O—, and each X is —NR$^1$R$^2$. In certain embodiments, a compound of any of Formulas 1001, 2001 or I is provided wherein: W is O; Z and Y join to form a six-membered heterocyclic ring wherein Z and Y together represent a single divalent —O—, and each X is an O-linked amino acid residue. In certain embodiments, a compound of any of Formulas 1001, 2001 or I is provided wherein: W is O; Z and Y join to form a six-membered heterocyclic ring wherein Z and Y together represent a single divalent —O—, and each X is an N-linked amino alcohol. In certain embodiments, a compound of any of Formulas 1001, 2001 or I is provided wherein: W is O; Z and Y join to form a six-membered heterocyclic ring wherein Z and Y together represent a single divalent —O—, and each X is an N-linked amino acid residue, or an ester thereof.

In certain embodiments, a compound of any of Formulas 1001, 2001, I, II, IIa, IIb, or III is provided wherein: W is S; each X is independently —OR$^1$ or —NR$^1$R$^2$; R$^2$ is hydrogen; each R$^1$ is independently -(L)$_p$CR$_3$, -(L)$_p$Ar, -LC(O)O(L)$_p$CR$_3$, -LSC(O)(L)$_p$CR$_3$, -LOC(O)(L)$_p$CR$_3$, -LOC(O)(L)$_p$Cy, -LSC(O)LNHC(O)OCR$_3$, -LSC(O)LOC(O)LNH$_2$, or -LSC(O)LOH; each L is independently alkylene; each R is independently hydrogen, alkyl, aryl, or heteroaryl; each Ar is independently aryl, or heteroaryl; each Cy is independently cycloalkyl; and each p is independently 0 or 1. In certain embodiments, each R$^1$ is independently -(L)$_p$CR$_3$. In certain embodiments, a compound of any of Formulas 1001, 2001, I, II, IIa, IIb, or III is provided wherein each R$^1$ is independently -(L)$_p$Ar. In certain embodiments, a compound of any of Formulas 1001, 2001, I, II, IIa, IIb, or III is provided wherein each R$^1$ is independently -LC(O)O(L)$_p$CR$_3$. In certain embodiments, a compound of any of Formulas 1001, 2001, I, II, IIa, IIb, or III is provided wherein each R$^1$ is independently -LSC(O)(L)$_p$CR$_3$. In certain embodiments, a compound of any of Formulas 1001, 2001, I, II, IIa, IIb, or III is provided wherein each R$^1$ is independently -LOC(O)(L)$_p$CR$_3$. In certain embodiments, a compound of any of Formulas 1001, 2001, I, II, IIa, IIb, or III is provided wherein each R$^1$ is independently -LSC(O)LNHC(O)OCR$_3$. In certain embodiments, a compound of any of Formulas 1001, 2001, I, II, IIa, IIb, or III is provided wherein each R$^1$ is independently -LSC(O)LOC(O)LNH$_2$. In certain embodiments, a compound of any of Formulas 1001, 2001, I, II, IIa, IIb, or III is provided wherein each R$^1$ is independently -LSC(O)LOH.

In certain embodiments, a compound of any of Formulas 1001, 2001, I or III is provided wherein: W is S; each Y is hydrogen, each Z is —OH, and each X is —OR$^1$. In certain embodiments, a compound of any of Formulas 1001, 2001, I or III is provided wherein: W is S; each Y is —OR$^1$, each Z is —OH, and each X is independently —OR$^1$, —NR$^1$R$^2$, an O-linked amino acid residue, an N-linked amino alcohol or an N-linked amino acid residue, or an ester thereof. In certain embodiments, a compound of any of Formulas 1001, 2001, I or III is provided wherein: W is S; each Y is —OR$^1$, each Z is —OH, and each X is independently hydrogen, —OR$^1$, —NR$^1$R$^2$, an O-linked amino acid residue, an N-linked amino alcohol or an N-linked amino acid residue, or an ester thereof. In certain embodiments, a compound of any of Formulas 1001, 2001, I or III is provided wherein: W is S; each Y is —$NR^1R^2$, each Z is —OH, and each X is —$OR^1$, an O-linked amino acid residue, an N-linked amino alcohol or an N-linked amino acid residue, or an ester thereof. In certain embodiments, a compound of any of Formulas 1001, 2001, I or III is provided wherein: W is S; each Y is an N-linked amino acid residue, or an ester thereof, each Z is —OH, and each X is —$OR^1$. In certain embodiments, each Y is an N-linked amino alcohol, each Z is —OH, and each X is —$OR^1$. In certain embodiments, a compound of any of Formulas 1001, 2001, I or III is provided wherein: W is S; Y is an O-linked amino acid residue, or an ester thereof, each Z is —OH, and each X is —$OR^1$.

In certain embodiments, a compound of any of Formulas 1001, 2001 or I is provided wherein: W is S; Z and Y join to form a six-membered heterocyclic ring wherein Z and Y together represent a single divalent —O—, and each X is independently —$OR^1$, —$NR^1R^2$, an O-linked amino acid residue, an N-linked amino alcohol or an N-linked amino acid residue, or an ester thereof. In certain embodiments, a compound of any of Formulas 1001, 2001 or I is provided wherein: W is S; Z and Y join to form a six-membered heterocyclic ring wherein Z and Y together represent a single divalent —O—, and each X is —$OR^1$. In certain embodiments, a compound of any of Formulas 1001, 2001 or I is provided wherein: W is S; Z and Y join to form a six-membered heterocyclic ring wherein Z and Y together represent a single divalent —O—, and each X is —$NR^1R^2$. In certain embodiments, a compound of any of Formulas 1001, 2001 or I is provided wherein: W is S; Z and Y join to form a six-membered heterocyclic ring wherein Z and Y together represent a single divalent —O—, and each X is an O-linked amino acid residue. In certain embodiments, a compound of any of Formulas 1001, 2001 or I is provided wherein: W is S; Z and Y join to form a six-membered heterocyclic ring wherein Z and Y together represent a single divalent —O—, and each X is an N-linked amino alcohol. In certain embodiments, a compound of any of Formulas 1001, 2001 or I is provided wherein: W is S; Z and Y join to form a six-membered heterocyclic ring wherein Z and Y together represent a single divalent —O—, and each X is an N-linked amino acid residue, or an ester thereof.

In certain embodiments, a compound of Formula IV is provided:

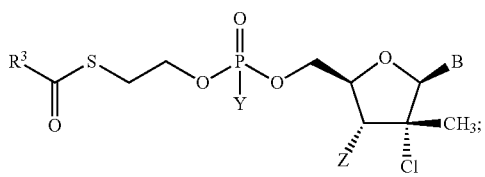

(IV)

wherein: $R^3$ is alkyl, alkoxycarbonylaminoalkyl, hydroxylalkyl, or aminoalkylcarbonylalkoxyl; and Y, Z, and B are as defined in the context of Formulas 1001, 2001 or I. In certain embodiments, a compound of Formula IV is provided wherein: each $R^3$ is independently -$(L)_pCR_3$, -LNHC(O)OCR$_3$, -LOC(O)LNH$_2$, or -LOH, wherein: each L is independently alkylene; each R is independently hydrogen, alkyl, aryl, or heteroaryl; and each p is independently 0 or 1. In certain embodiments, a compound of Formula IV is provided wherein: each $R^3$ is independently -$(L)_pCR_3$. In certain embodiments, a compound of Formula IV is provided wherein: each $R^3$ is independently -LNHC(O)OCR$_3$. In certain embodiments, a compound of Formula IV is provided wherein: each $R^3$ is independently -LOC(O)LNH$_2$. In certain embodiments, a compound of Formula IV is provided wherein: each $R^3$ is independently -LOH. In certain embodiments, a compound of Formula IV is provided wherein: each L is independently $C_1$-$C_{10}$ alkylene; and each R is independently hydrogen, $C_1$-$C_{10}$ alkyl, $C_3$-$C_{10}$ aryl, or $C_3$-$C_{10}$ heteroaryl.

In certain embodiments, a compound of Formula IV is provided:

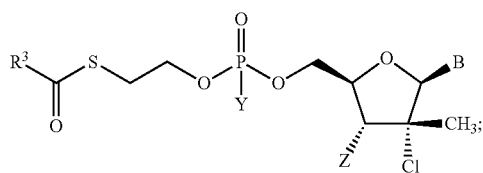

(IV)

wherein: $R^3$ is alkyl; and Y, Z, and B are as defined in the context of Formula (I). In certain embodiments, each $R^3$ is independently -$(L)_pCR_3$, -LNHC(O)OCR$_3$, -LOC(O)LNH$_2$, or -LOH, wherein: each L is independently alkylene; each R is independently hydrogen, alkyl, aryl, or heteroaryl; and each p is independently 0 or 1. In certain embodiments, each $R^3$ is independently -$(L)_pCR_3$. In certain embodiments, each $R^3$ is independently -LNHC(O)OCR$_3$. In certain embodiments, each $R^3$ is independently -LOC(O)LNH$_2$. In certain embodiments, each $R^3$ is independently -LOH.

In certain embodiments a compound of Formula IV is provided wherein: Y is hydrogen, Z is —OH, and each $R^3$ is independently -$(L)_pCR_3$, -LNHC(O)OCR$_3$, -LOC(O)LNH$_2$, or -LOH. In certain embodiments, a compound of Formula IV is provided wherein: Y is —$OR^1$, Z is —OH, and each $R^3$ is independently -$(L)_pCR_3$, -LNHC(O)OCR$_3$, -LOC(O)LNH$_2$, or -LOH. In certain embodiments, a compound of Formula IV is provided wherein: Y is —$NR^1R^2$, Z is —OH, and each $R^3$ is independently -$(L)_pCR_3$, -LNHC(O)OCR$_3$, -LOC(O)LNH$_2$, or -LOH. In certain embodiments, a compound of Formula IV is provided wherein: Y is an N-linked amino acid residue, or an ester thereof, Z is —OH, and each $R^3$ is independently -$(L)_pCR_3$, -LNHC(O)OCR$_3$, -LOC(O)LNH$_2$, or -LOH. In certain embodiments, a compound of Formula IV is provided wherein: Z and Y join to form a six-membered heterocyclic ring wherein Z and Y together represent a single divalent —O— and each $R^3$ is independently -$(L)_pCR_3$, -LNHC(O)OCR$_3$, -LOC(O)LNH$_2$, or -LOH.

In certain embodiments, a compound of any of Formulas 1001, 2001, I, II, IIa, IIb, III, or IV is provided wherein: each L is independently $C_1$-$C_{10}$ alkylene; and each R is independently $C_1$-$C_{10}$ alkyl, $C_3$-$C_{10}$ aryl, or $C_3$-$C_{10}$ heteroaryl.

In certain embodiments, a compound of any of Formulas 1001, 2001, I, II, IIa, IIb, III, or IV is provided wherein: each B is independently

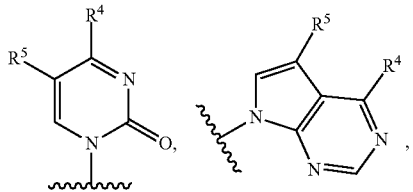

-continued

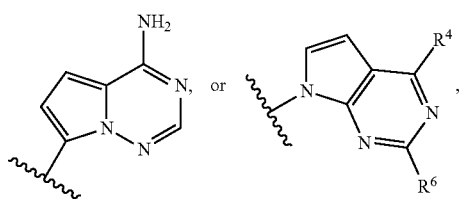

or a tautomer thereof; each $R^4$ is independently hydrogen, hydroxyl, hydroxylamine, alkylamino, halogen, sulfanyl, amino or alkoxy; each $R^5$ is independently hydrogen, halogen or methyl; and each $R^6$ is independently hydrogen, amino, or halogen.

In certain embodiments, a compound of any of Formulas 1001, 2001, I, II, IIa, IIb, III or IV is provided wherein: each B is independently:

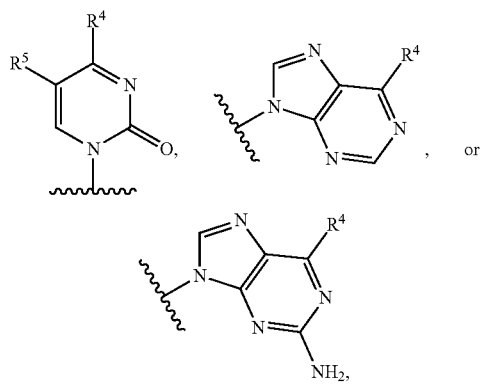

or a tautomer thereof; wherein each $R^4$ is independently hydrogen, hydroxyl, hydroxylamine, halogen, sulfanyl, amino or alkoxy; and each $R^5$ is independently hydrogen, halogen or methyl. In an embodiment, a compound of any of Formulas 1001, 2001, I, II, IIa, IIb, III or IV is provided wherein: each B is independently:

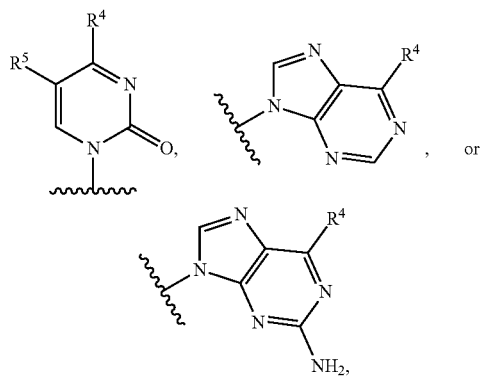

or a tautomer thereof; wherein each $R^4$ is alkylamino; and each $R^5$ is independently hydrogen, halogen or methyl. In an embodiment, a compound of any of Formulas 1001, 2001, I, II, IIa, IIb, III or IV is provided wherein: each B is independently:

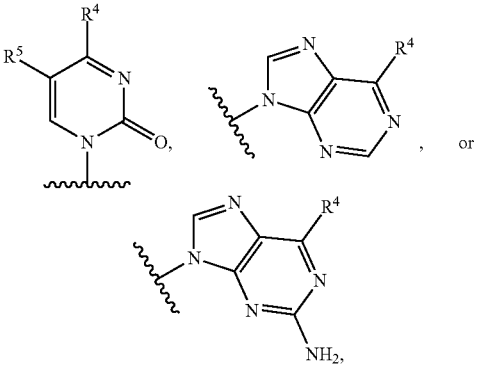

or a tautomer thereof; wherein each $R^4$ is alkylamino having from seven to thirty carbon atoms; and each $R^5$ is independently hydrogen, halogen or methyl. In an embodiment, a compound of any of Formulas 1001, 2001, I, II, IIa, IIb, III or IV is provided wherein: each B is independently:

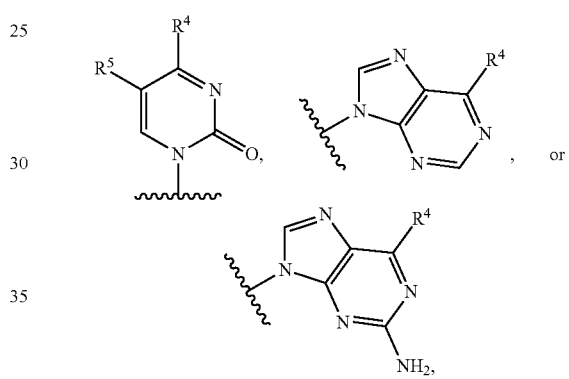

or a tautomer thereof; wherein each $R^4$ is alkylamino having from fifteen to thirty carbon atoms; and each $R^5$ is independently hydrogen, halogen or methyl. In an embodiment, a compound of any of Formulas 1001, 2001, I, II, IIa, IIb, III or IV is provided wherein: each B is independently:

or a tautomer thereof; wherein each $R^4$ is alkylamino having from twenty to thirty carbon atoms; and each $R^5$ is independently hydrogen, halogen or methyl. In an embodiment, a compound of any of Formulas 1001, 2001, I, II, IIa, IIb, III or IV is provided wherein: each B is independently:

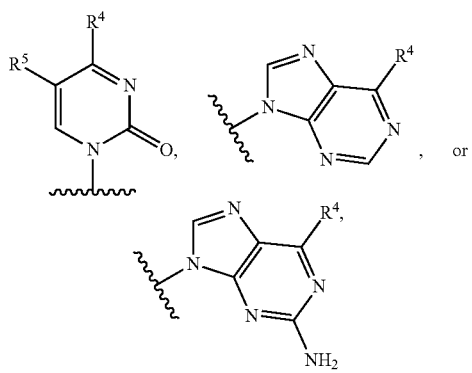

or a tautomer thereof; wherein each $R^4$ is alkylamino having from seven to fifteen carbon atoms; and each $R^5$ is independently hydrogen, halogen or methyl. In an embodiment, a compound of any of Formulas 1001, 2001, I, II, IIa, IIb, III or IV is provided wherein: each B is independently:

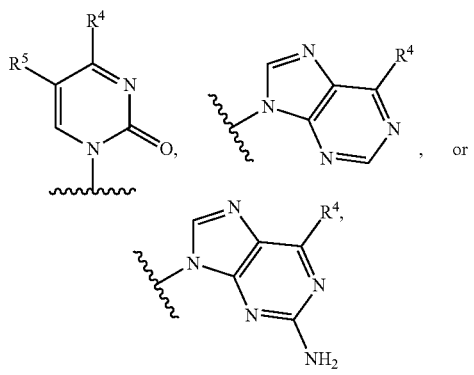

or a tautomer thereof; wherein each $R^4$ is alkylamino having from seven to twenty carbon atoms; and each $R^5$ is independently hydrogen, halogen or methyl. In an embodiment, a compound of any of Formulas 1001, 2001, I, II, IIa, IIb, III or IV is provided wherein: each B is independently:

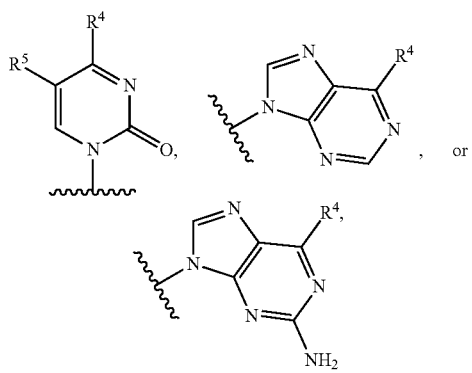

or a tautomer thereof; wherein each $R^4$ is alkylamino having from ten to twenty carbon atoms; and each $R^5$ is independently hydrogen, halogen or methyl.

In certain embodiments, provided herein are compounds according to Formula (2002):

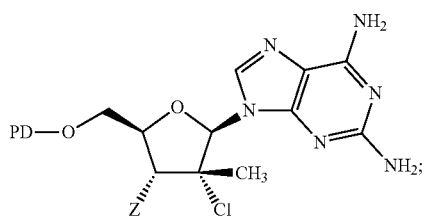

(2002)

or a pharmaceutically acceptable salt, solvate, stereoisomeric form, tautomeric form or polymorphic form thereof, wherein: PD and Z are as described in the context of Formula 1001, 2001 or Formula I.

In certain embodiments, provided herein are compounds according to Formula (2003):

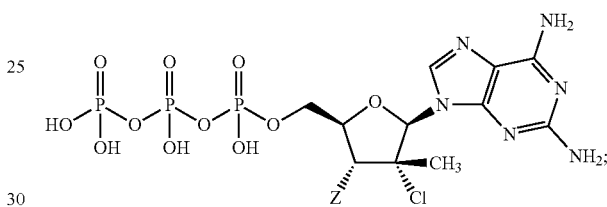

(2003)

or a pharmaceutically acceptable salt, solvate, stereoisomeric form, tautomeric form or polymorphic form thereof, wherein: Z is as described in the context of Formula 1001, 2001 or I.

In certain embodiments, a compound of any of Formulas (V)-(XVI) is provided:

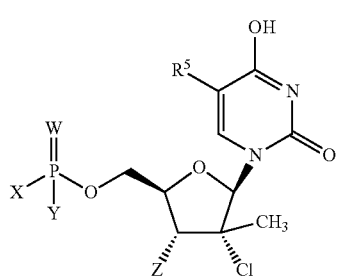

(V)

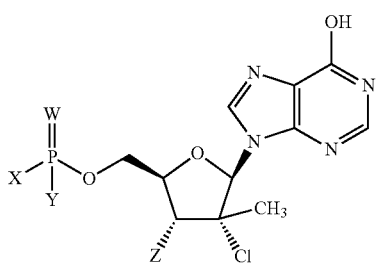

(VI)

27
-continued

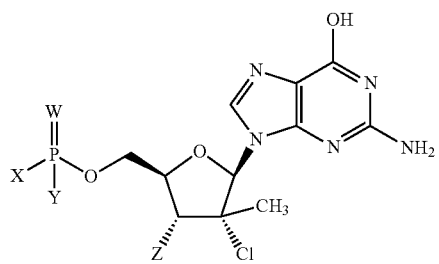
(VII)

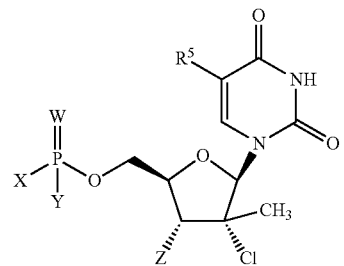
(VIII)

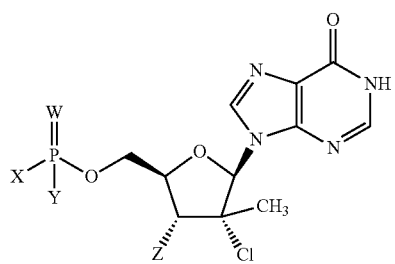
(IX)

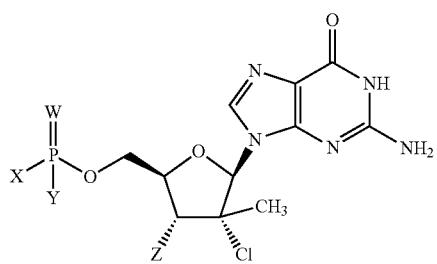
(X)

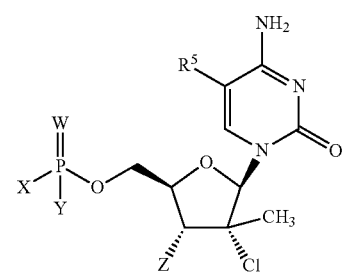
(XI)

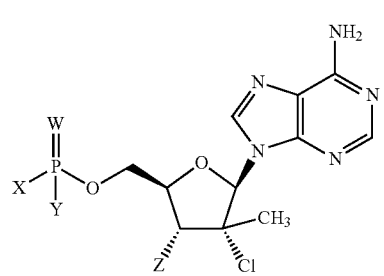
(XII)

28
-continued

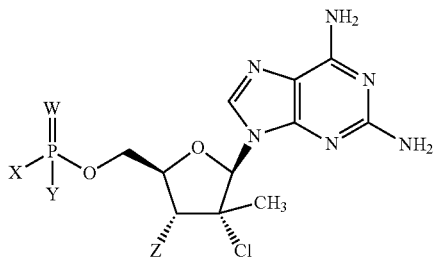
(XIII)

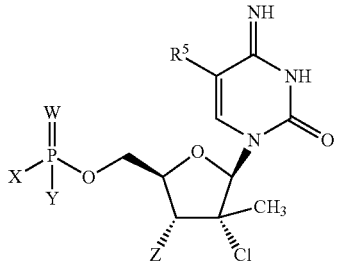
(XIV)

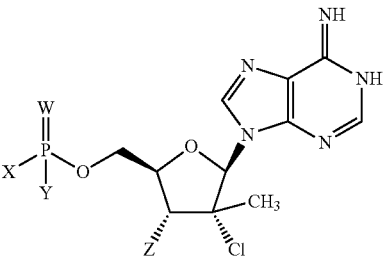
(XV)

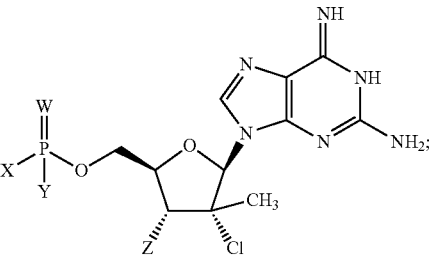
(XVI)

or a pharmaceutically acceptable salt, solvate, stereoisomeric form, tautomeric form or polymorphic form thereof, wherein: W, X, Y, and Z are as defined in the context of Formula 1001, 2001 or I; and each $R^5$ is independently hydrogen, halogen or methyl.

In certain embodiments, provided herein is a compound of any of Formulas VIII-XIII, XXV or XXVI:

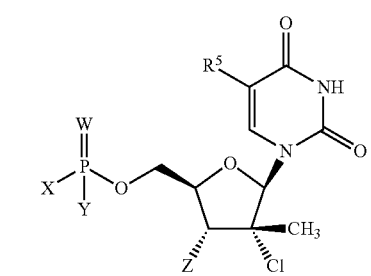
(VIII)

(IX)
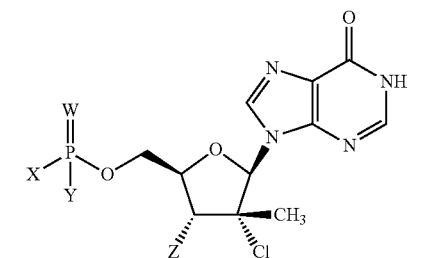

(X)
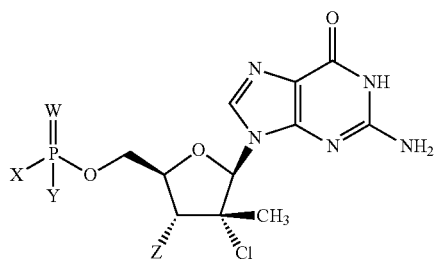

(XI)
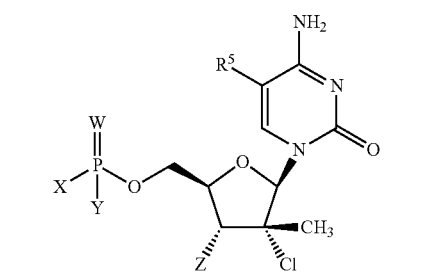

(XII)
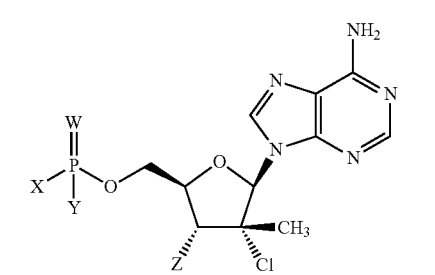

(XIII)
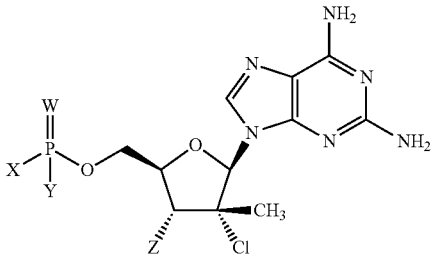

(XXV)
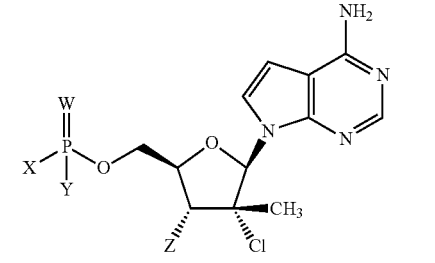

(XXVI)
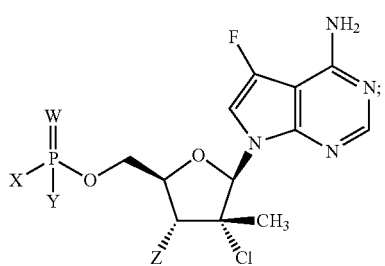

or a pharmaceutically acceptable salt, solvate, stereoisomeric form, tautomeric form or polymorphic form thereof, wherein: W, X, Y, and Z are as defined in the context of Formula 1001, 2001 or I; and each $R^5$ is independently hydrogen, halogen or methyl.

In certain embodiments, provided herein are compounds according to any of Formulas XVII-XX or XXVII:

(XVII)
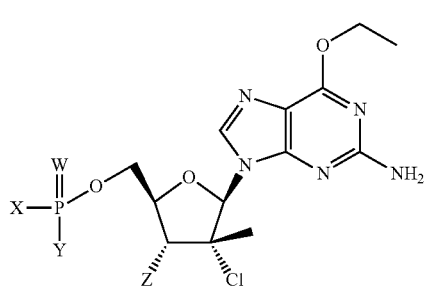

(XVIII)
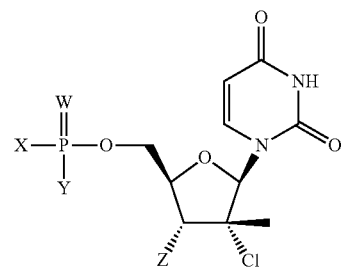

(XIX)
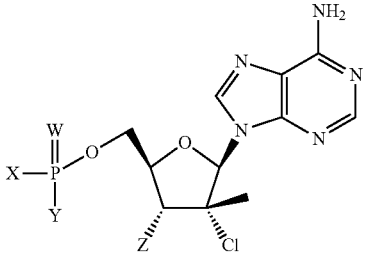

(XX)
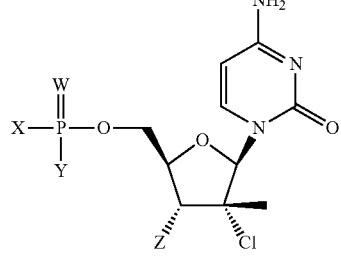

-continued (XXVII)

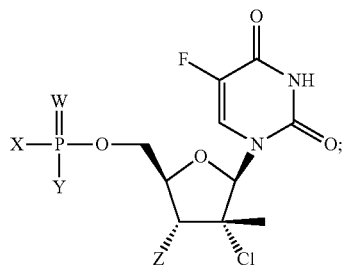

or a pharmaceutically acceptable salt, solvate, stereoisomeric form, tautomeric form or polymorphic form thereof, wherein X, Y, and Z are as defined in the context of Formula 1001, 2001 or I. In certain embodiments, a compound of Formula XVII is provided. In certain embodiments, a compound of Formula XVIII is provided. In certain embodiments, a compound of Formula XIX is provided. In certain embodiments, a compound of Formula XX is provided. In certain embodiments, a compound of Formula XXV is provided. In certain embodiments, a compound of Formula XXVI is provided.

In an embodiment, a compound of any of Formulas 1001, 2001, I-III, V-XX, XXV or XXVI is provided, wherein each X is independently an N-linked amino acid residue, or an ester thereof. In an embodiment, a compound of any of Formulas 1001, 2001, I-III, V-XX, XXV or XXVI is provided, wherein each X is independently an N-linked L-amino acid residue, or an ester thereof. In an embodiment, a compound of any of Formulas 1001, 2001, I-III, V-XX, XXV or XXVI is provided, wherein each X is independently an N-linked D-amino acid residue, or an ester thereof. In an embodiment, a compound of any of Formulas 1001, 2001, I-III, V-XX, XXV or XXVI is provided, wherein each X is independently an N-linked alanine amino acid residue, or an ester thereof. In an embodiment, a compound of any of Formulas 1001, 2001, I-III, V-XX, XXV or XXVI is provided, wherein each X is independently an N-linked phenylalanine amino acid residue, or an ester thereof.

In certain embodiments, provided herein are compounds according to any of Formulas XXI-XXIV:

-continued (XXII)

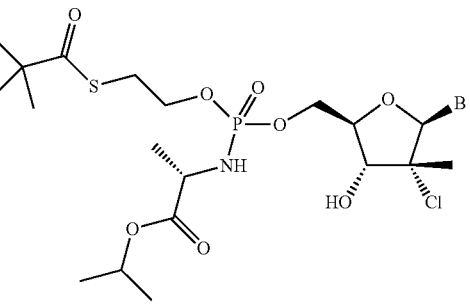

(XXIII)

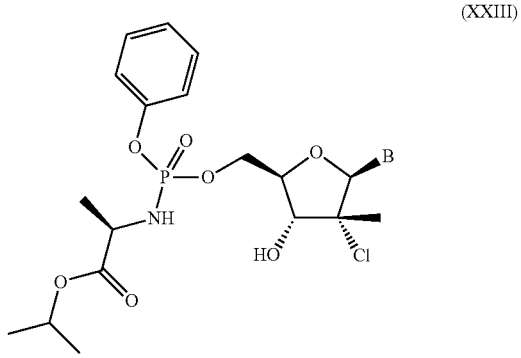

(XXIV)

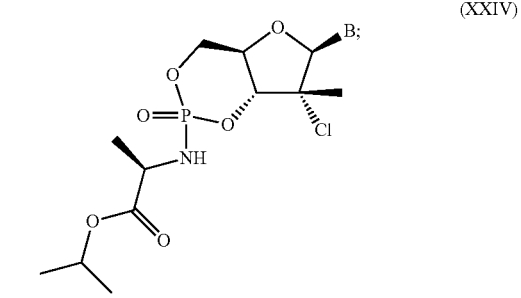

or a pharmaceutically acceptable salt, solvate, stereoisomeric form, tautomeric form or polymorphic form thereof, wherein B is as defined in the context of Formula 1001, 2001 or I. In certain embodiments, a compound of Formula XXI is provided. In certain embodiments, a compound of Formula XXII is provided. In certain embodiments, a compound of Formula XXIII is provided. In certain embodiments, a compound of Formula XXIV is provided.

In certain embodiments, provided herein are compounds according to any of Formulas 1-35bii:

(XXI)

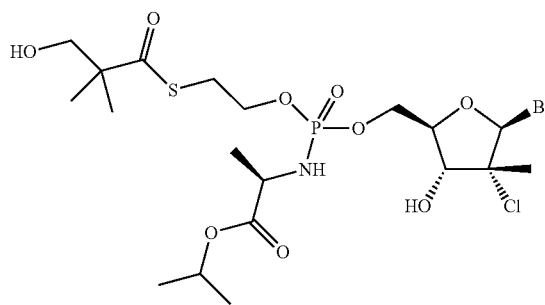

(1)

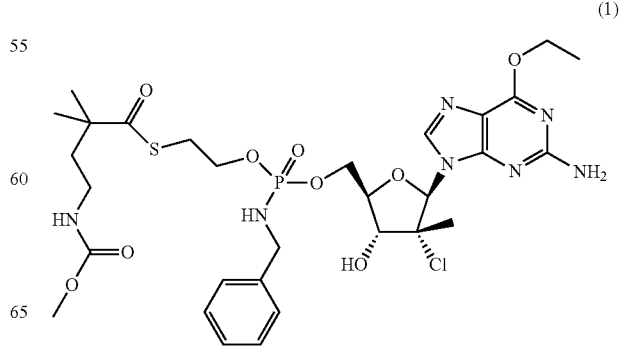

(1a)
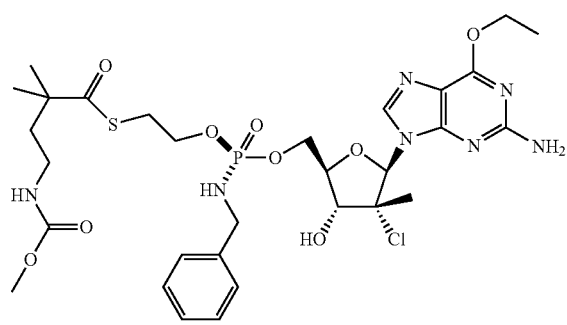
(1b)
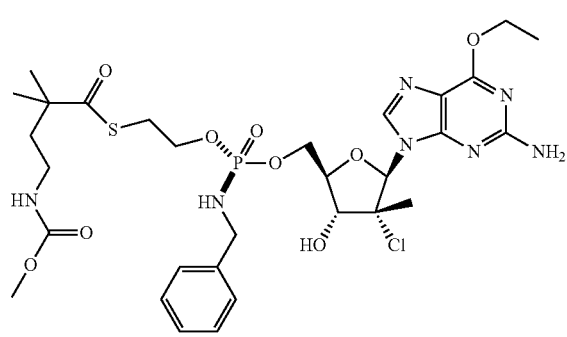
(2)
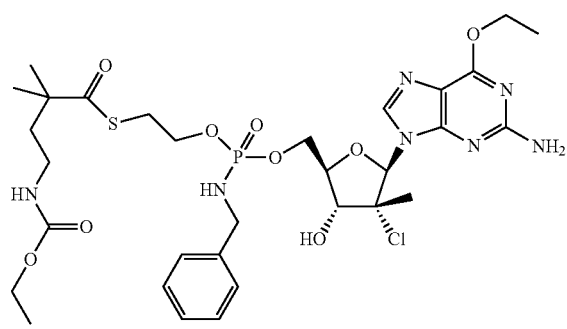
(2a)
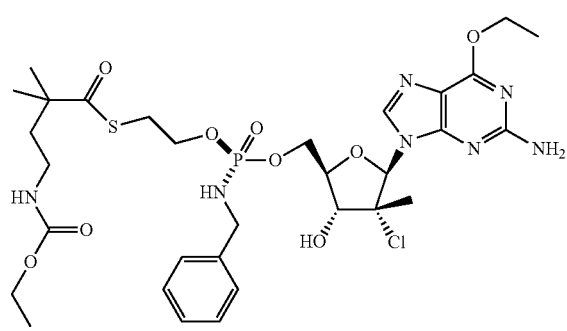
(2b)
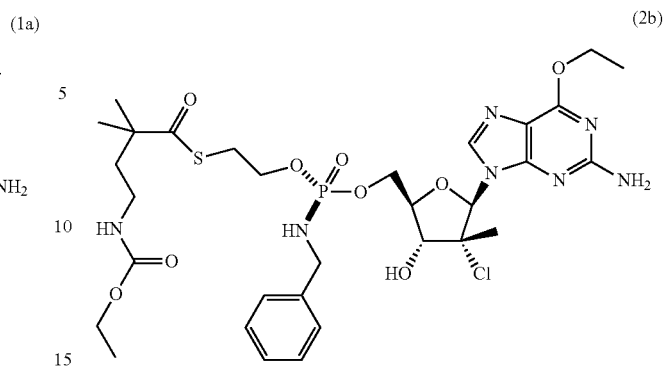
(3)
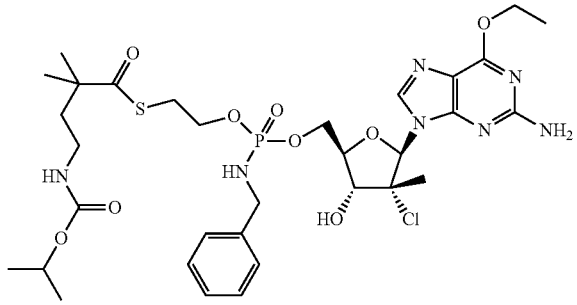
(3a)
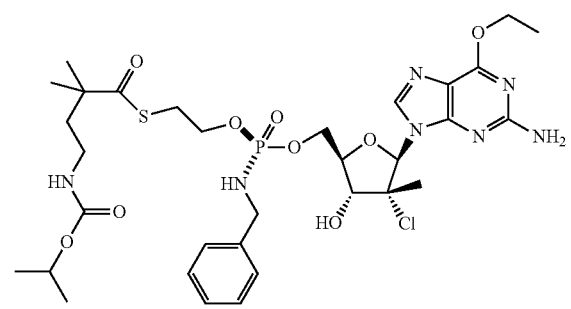
(3b)
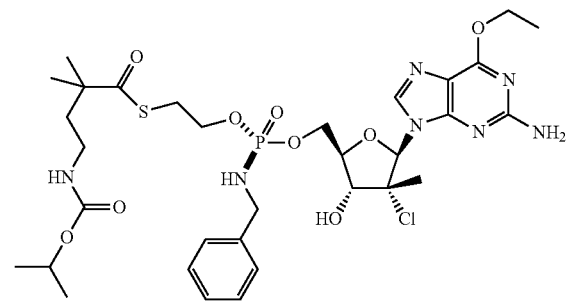
(4)
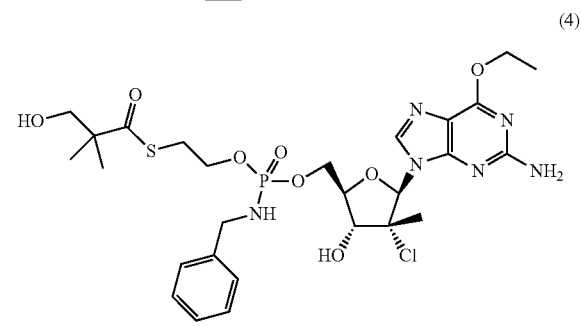

(4a)
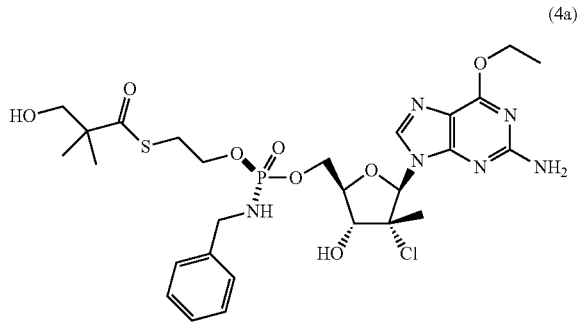
(4b)
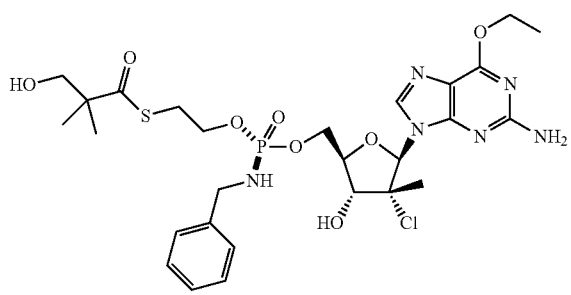
(5)
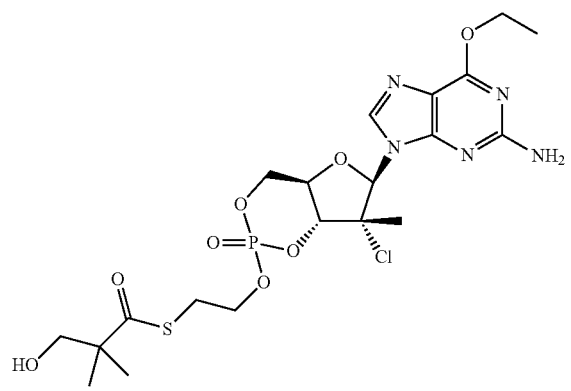
(5a)
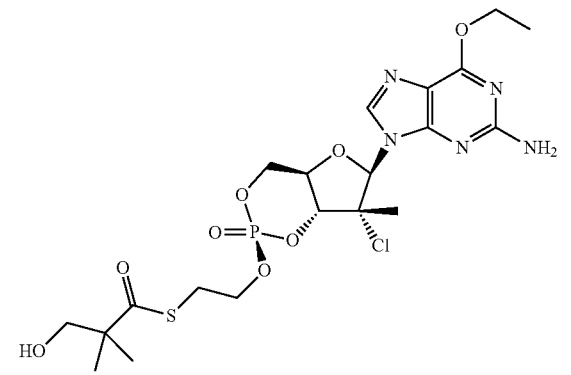
(5b)
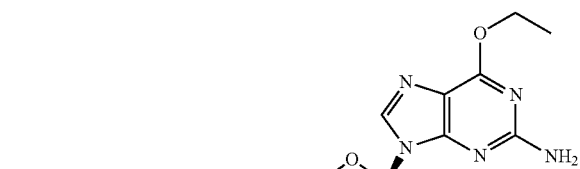
(6)
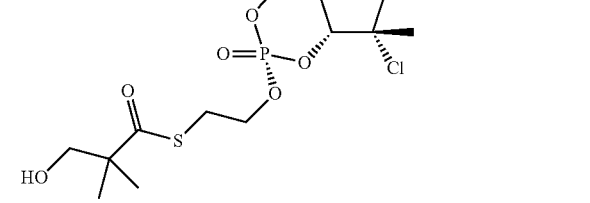
(6a)
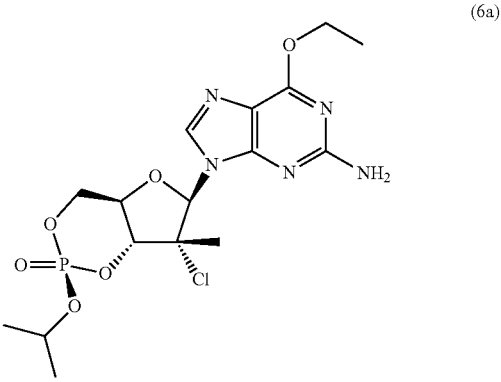
(6b)
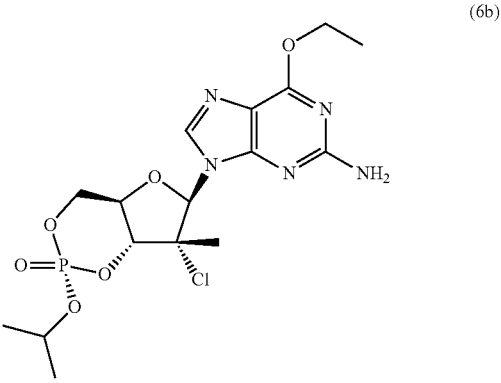

(7)
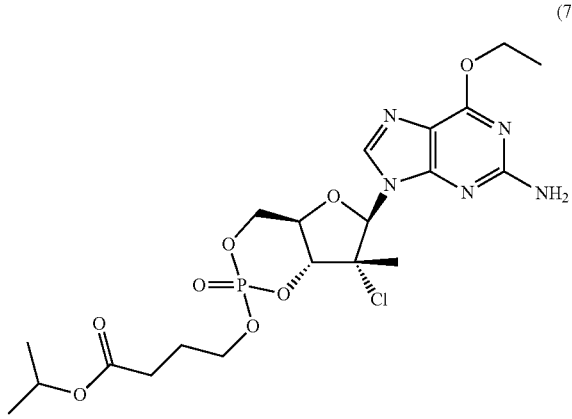
(7a)
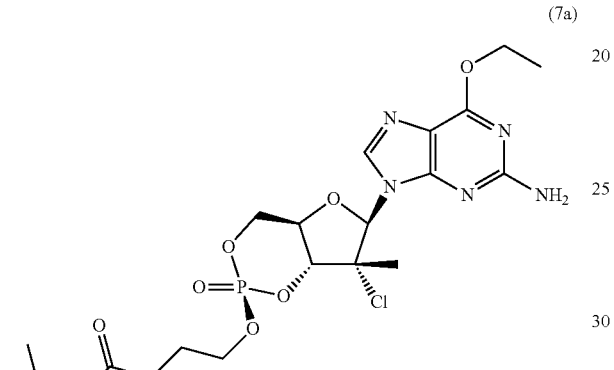
(7b)
(8)
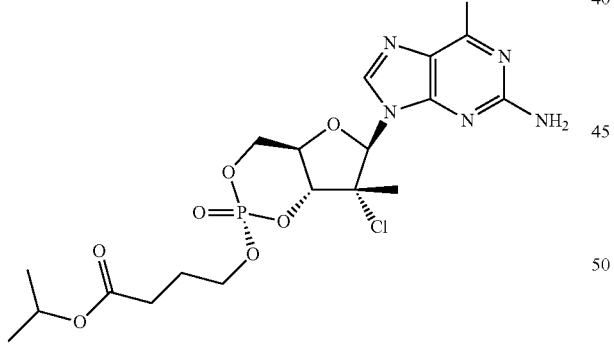
(8i)
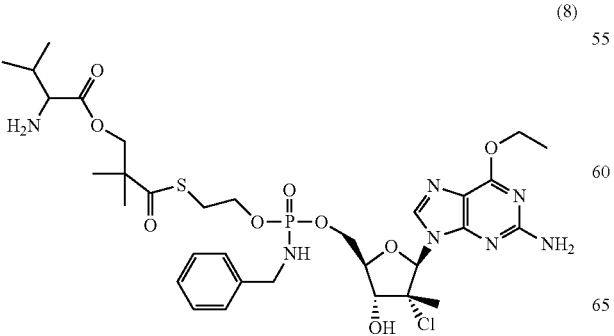
(8ii)
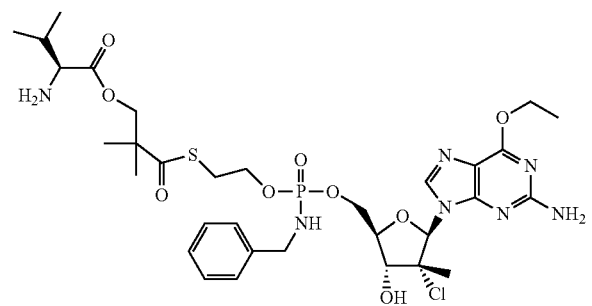
(8ia)
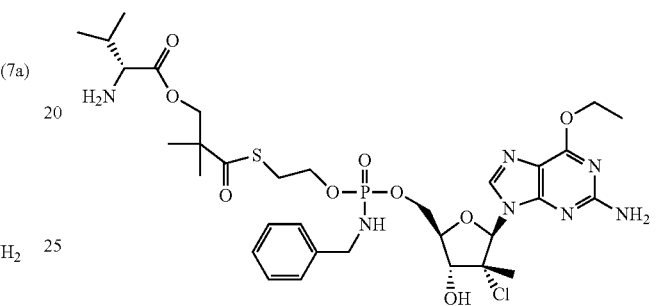
(8ib)
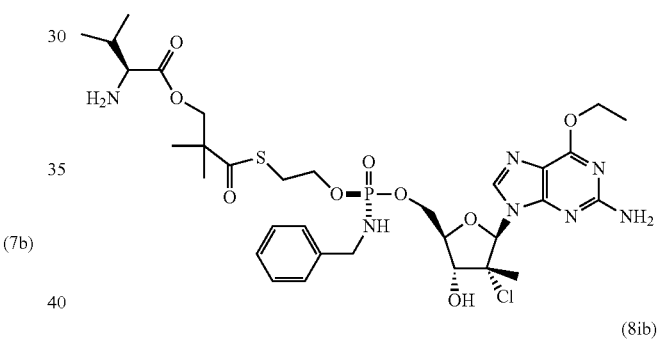
(8iia)
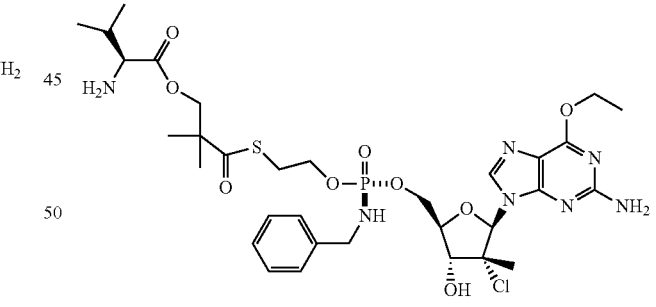

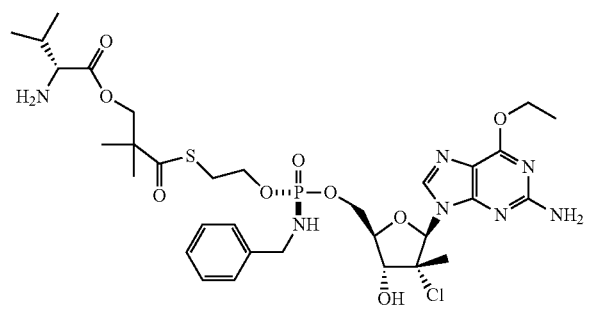
(8iib)
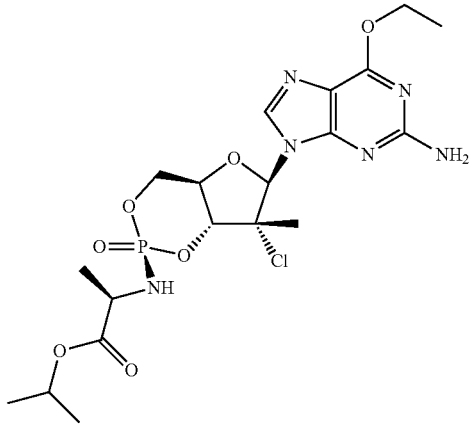
(9)
(9i)
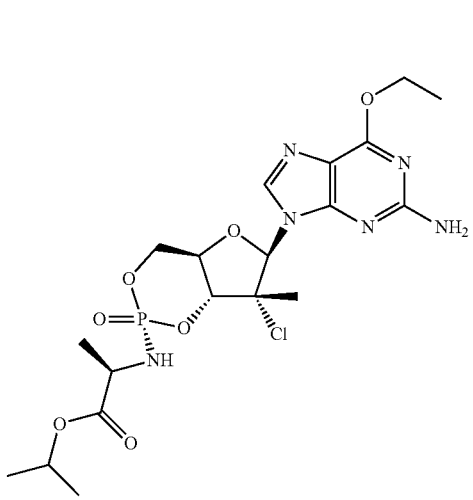
(9ia)
(9ib)
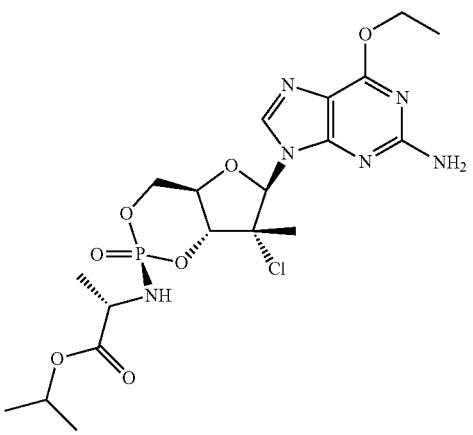
(9ii)
(9iia)

(9iib)
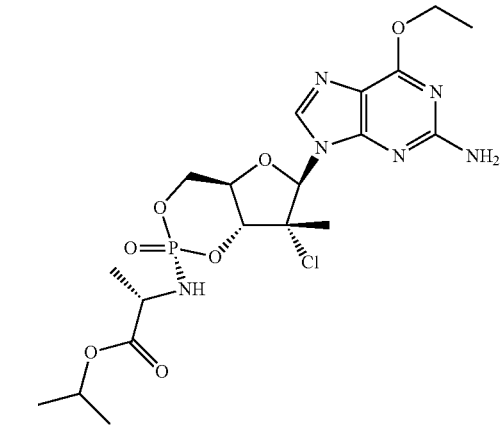
(11)
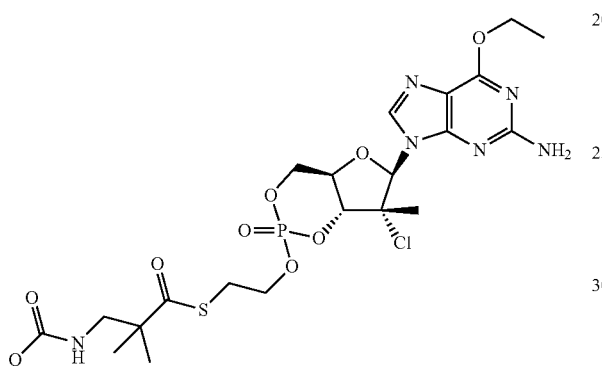
(11a)
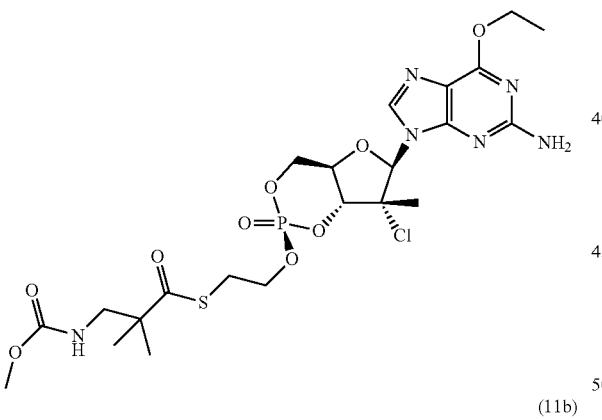
(11b)
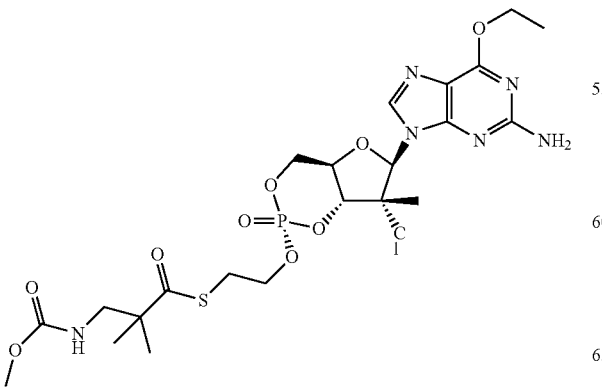
(12)
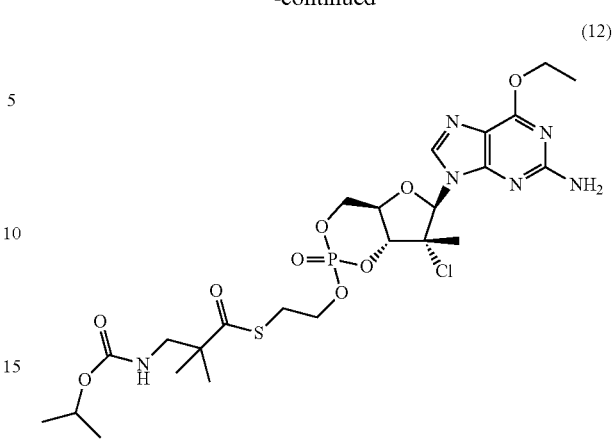
(12a)
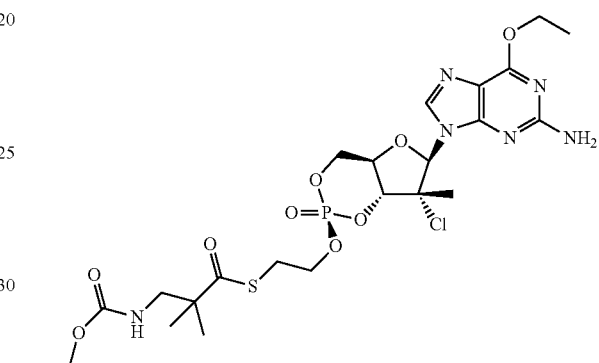
(12b)
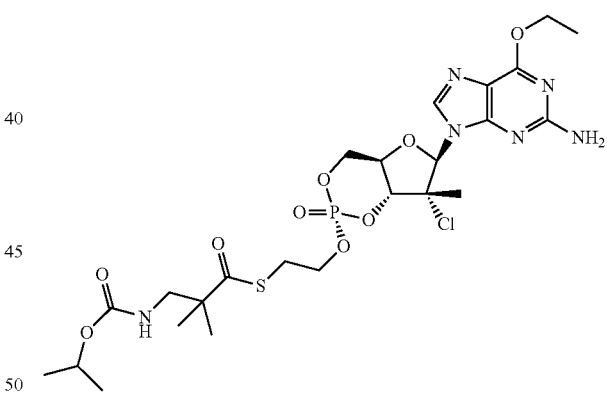
(13)
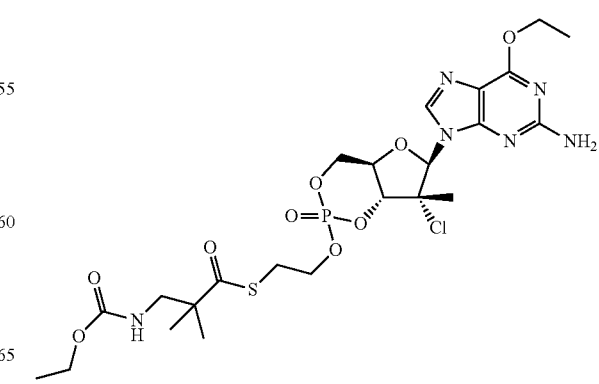

(13a)
(13b)
(14)
(14a)
(14b)
(15)
(15a)
(15b)

-continued
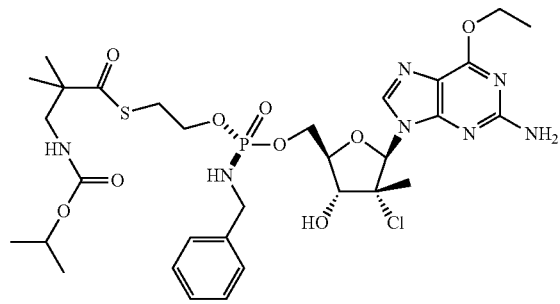
(16)
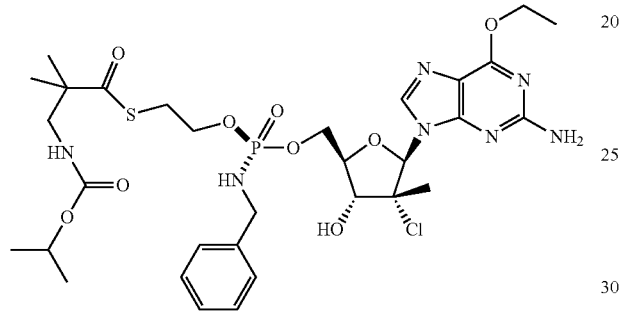
(16a)
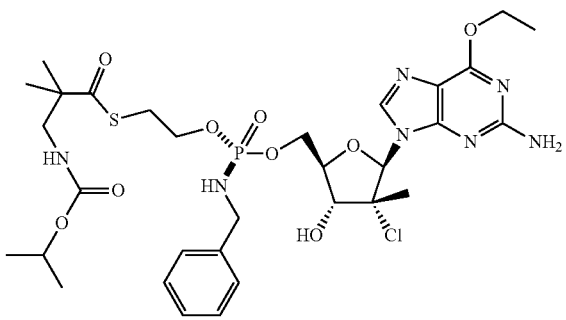
(16b)
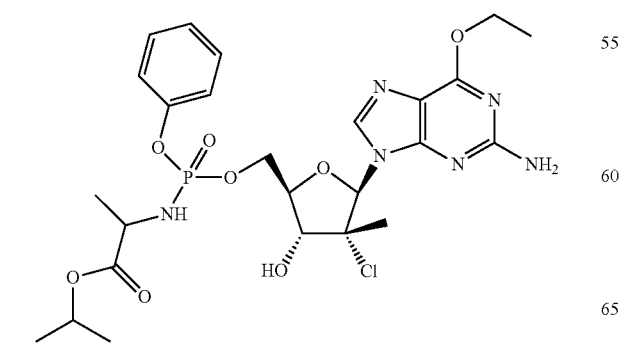
(17)
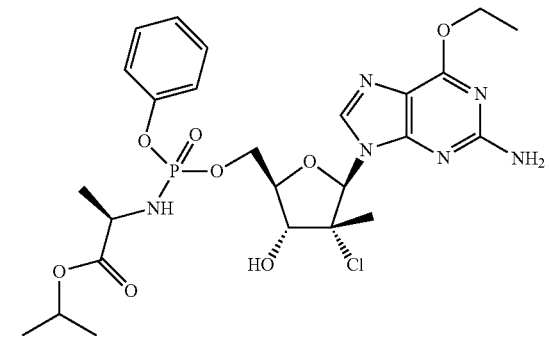
(17i)
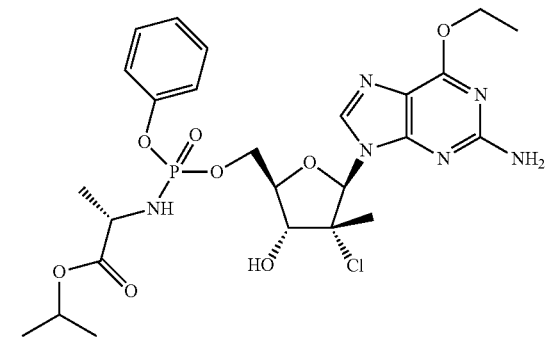
(17ii)
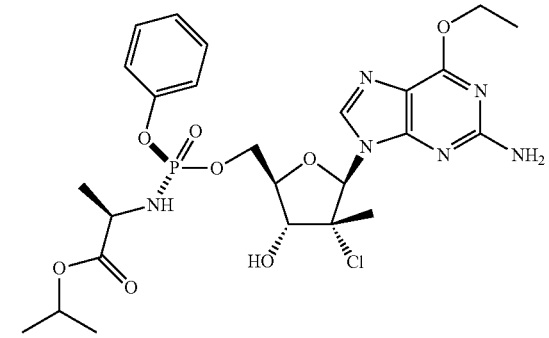
(17ia)
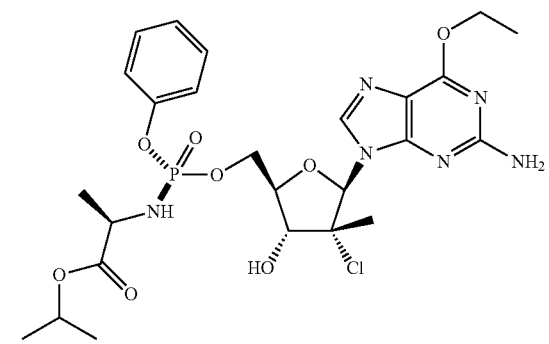
(17ib)

(17iia)
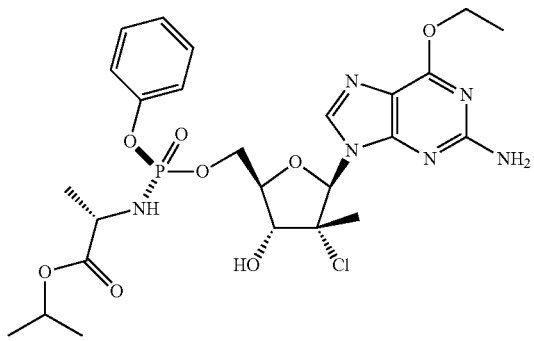
(17iib)
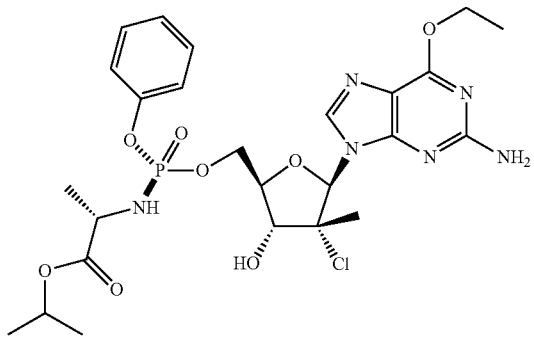
(19)
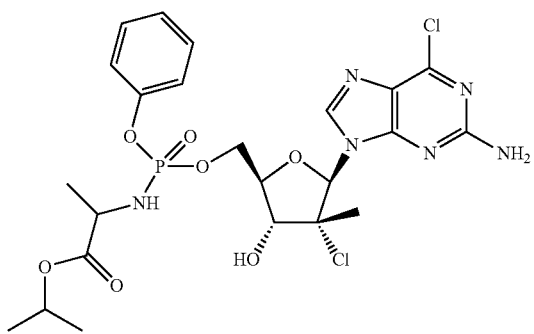
(19i)
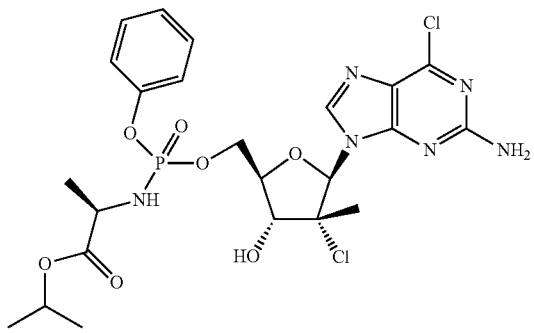
(19ii)
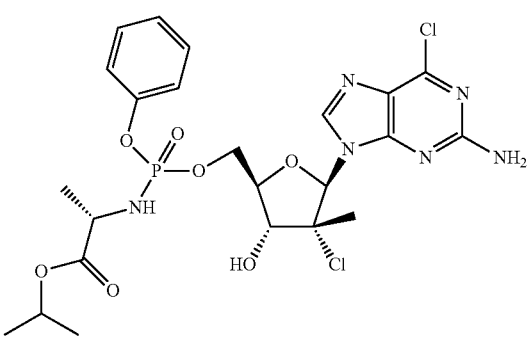
(19ia)
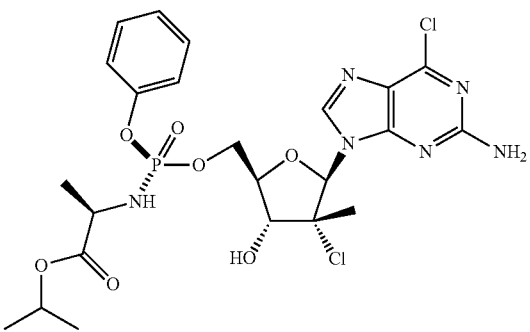
(19ib)
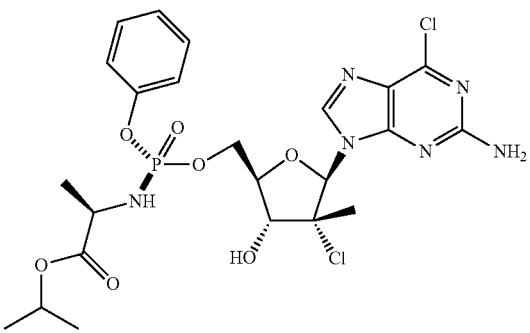
(19iia)
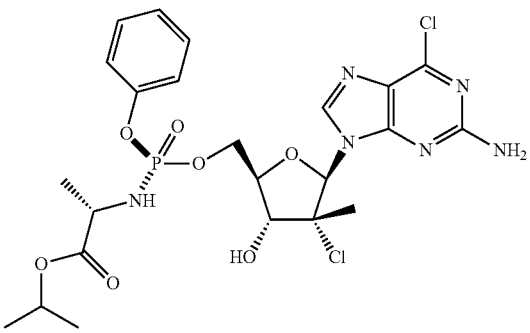

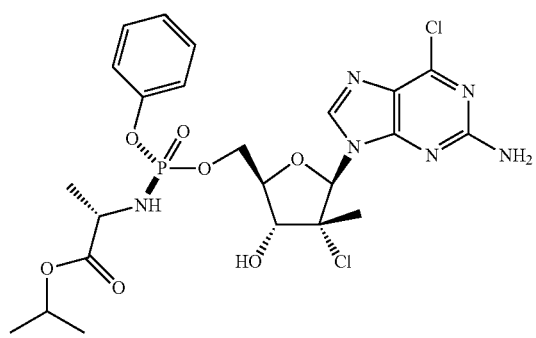
(19iib)
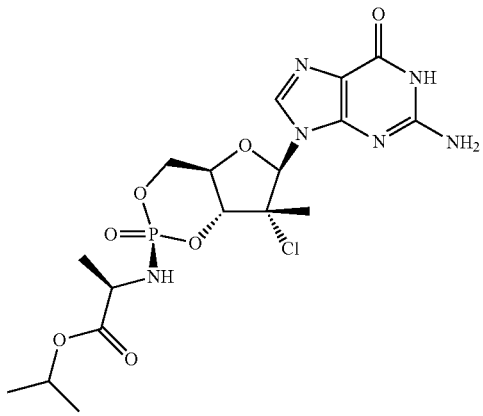
(20ai)
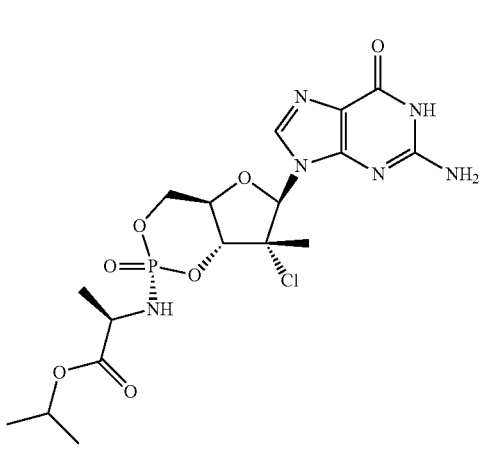
(20)
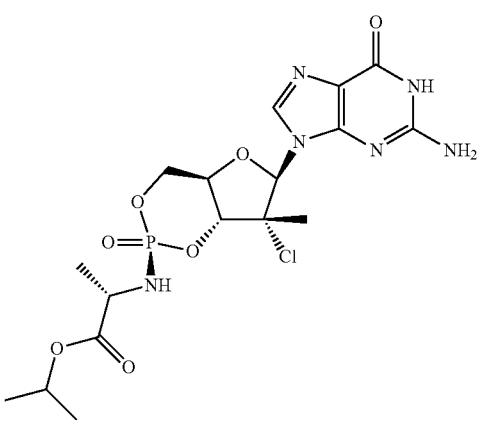
(20i)
(20ii)
(20bi)
(20aii)

(20bii)
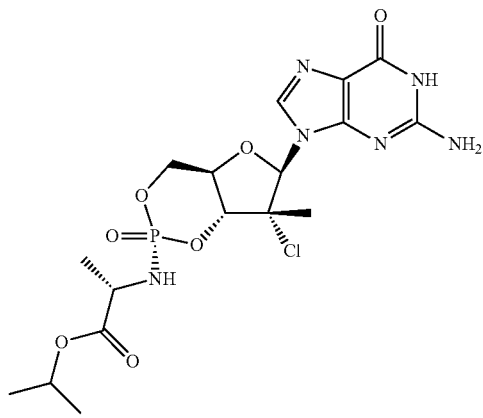
(21)
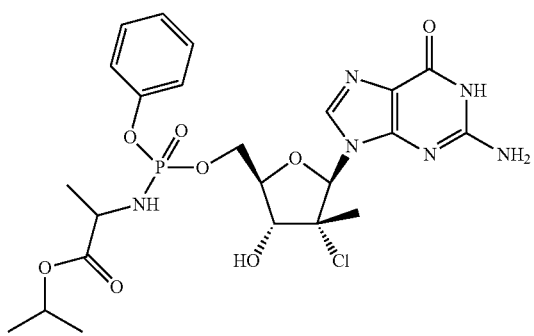
(21i)
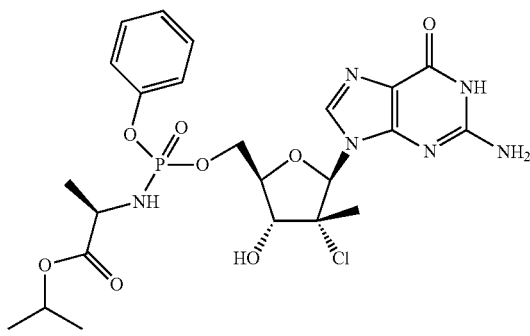
(21ii)
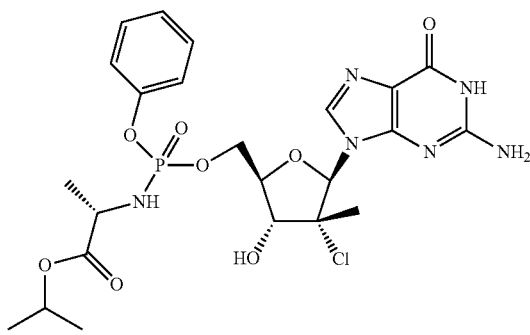
(21ai)
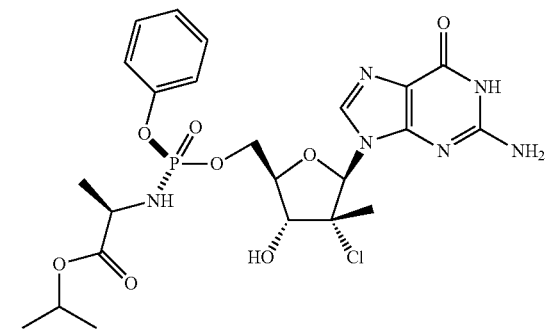
(21bi)
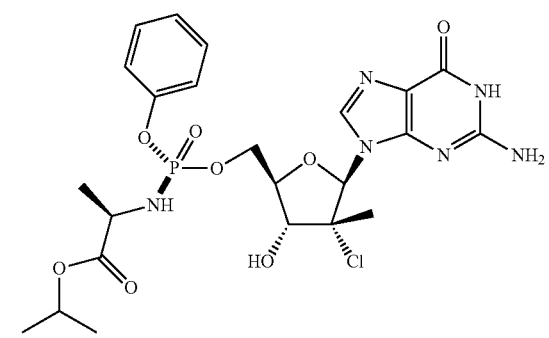
(21aii)
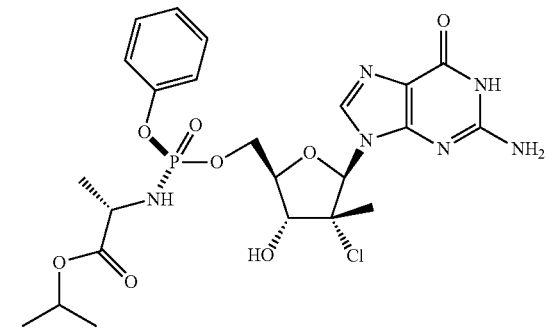
(21bii)
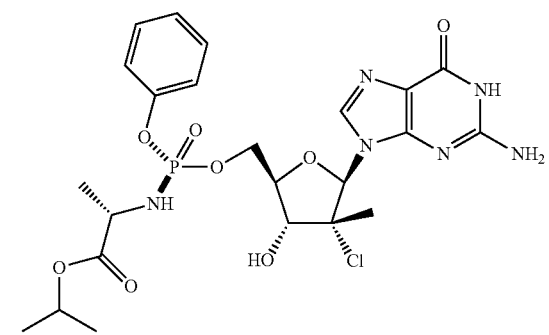

(22)
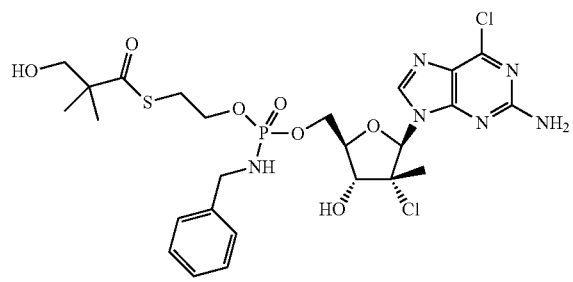
(22a)
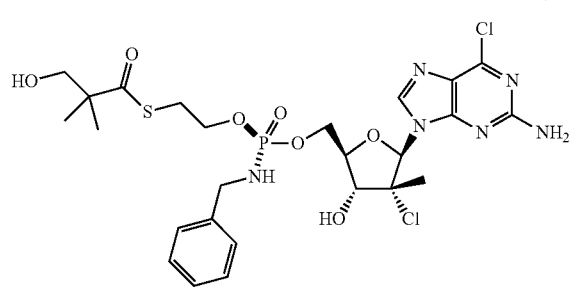
(22b)
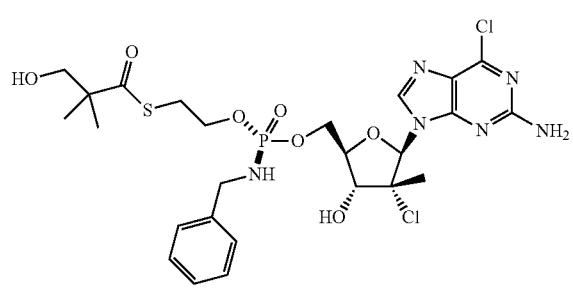
(23)
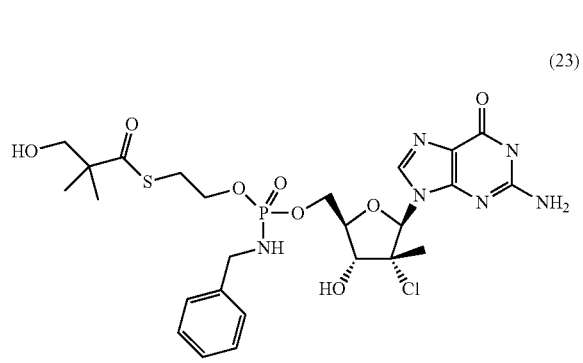
(23a)
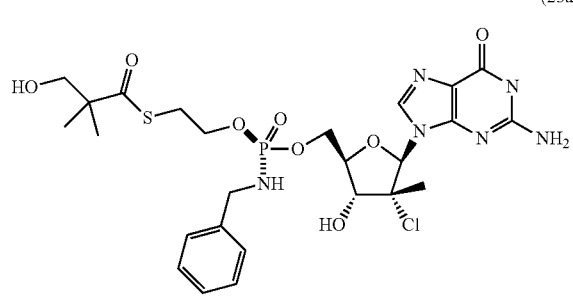
(23b)
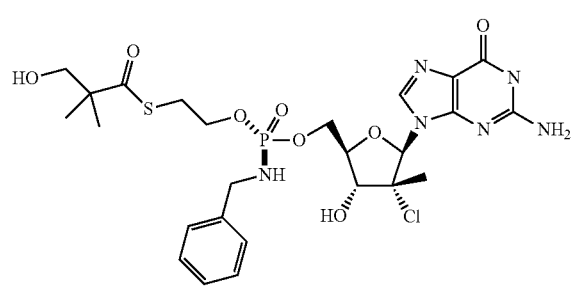
(24)
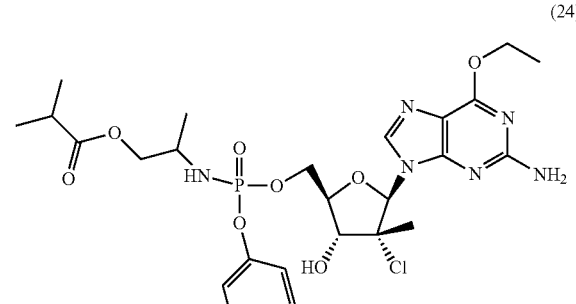
(24i)
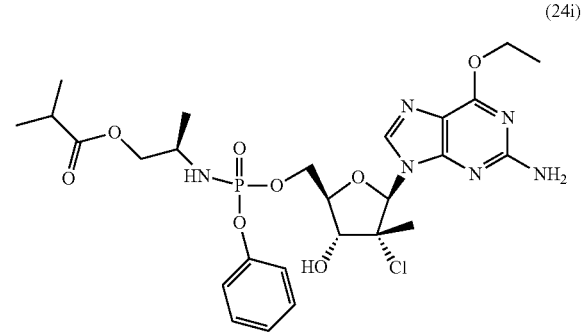
(24ii)
(24ai)
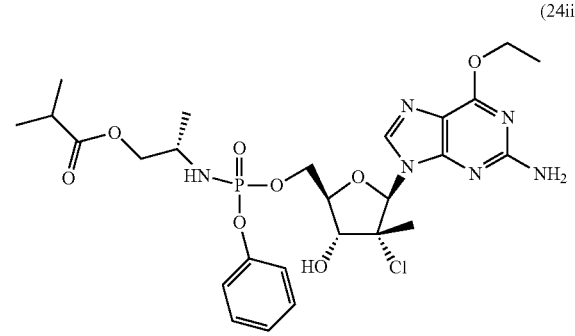

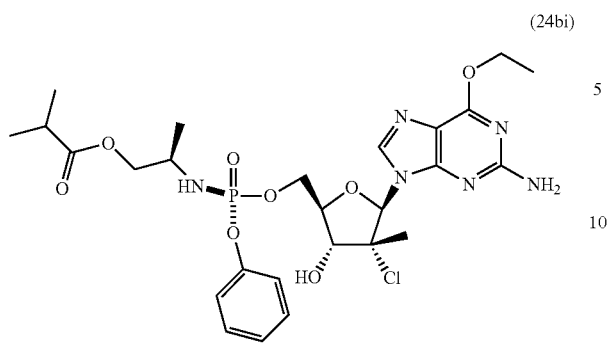
(24bi)
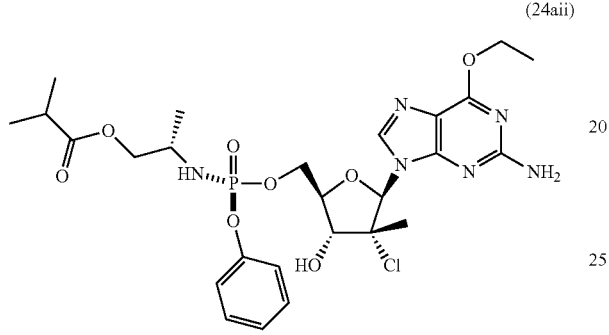
(24aii)
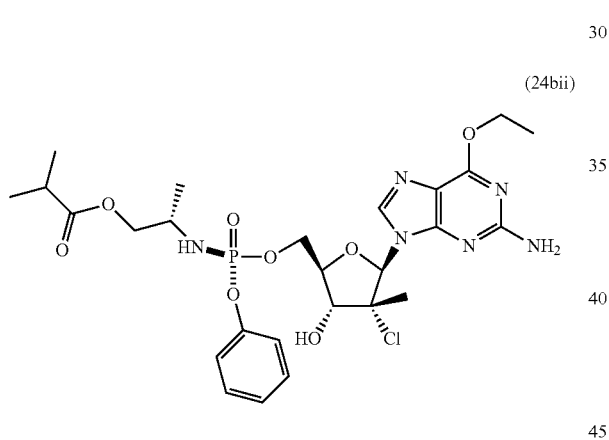
(24bii)
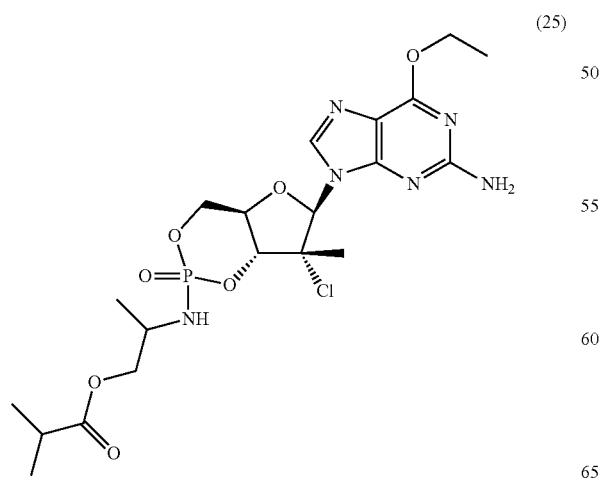
(25)
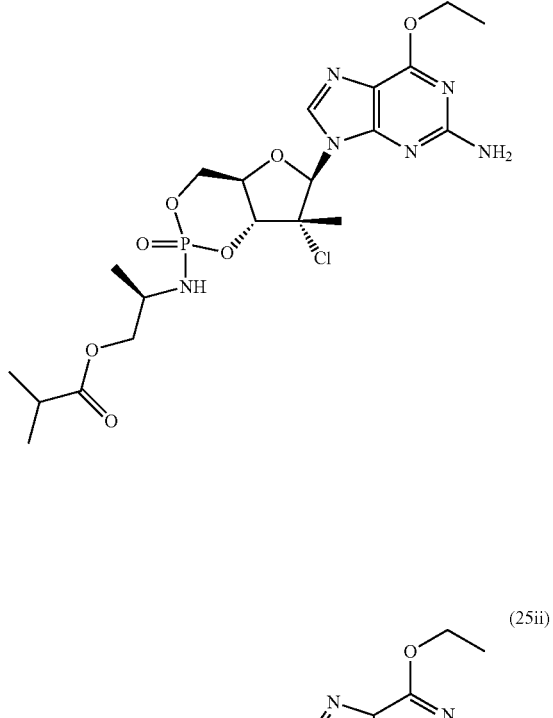
(25i)
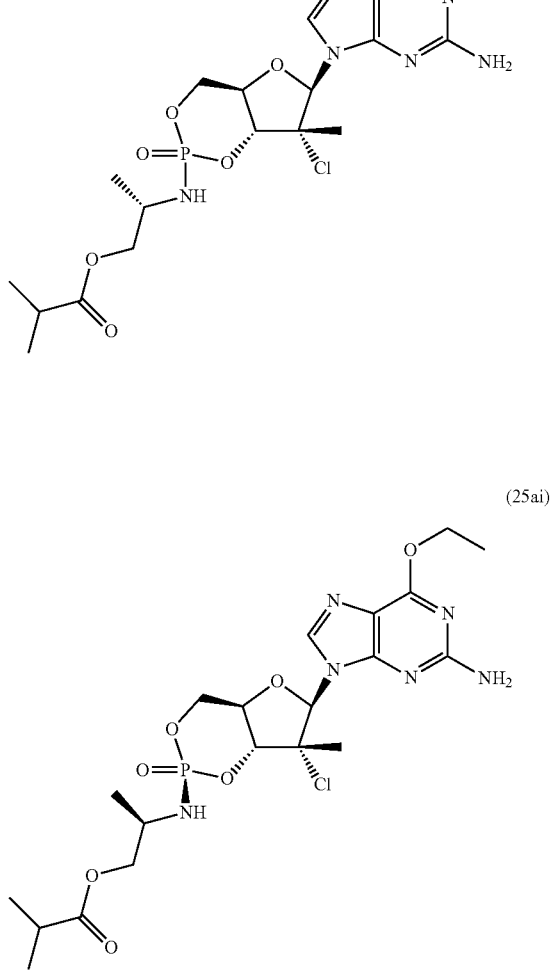
(25ii)
(25ai)

57
-continued
(25bi)
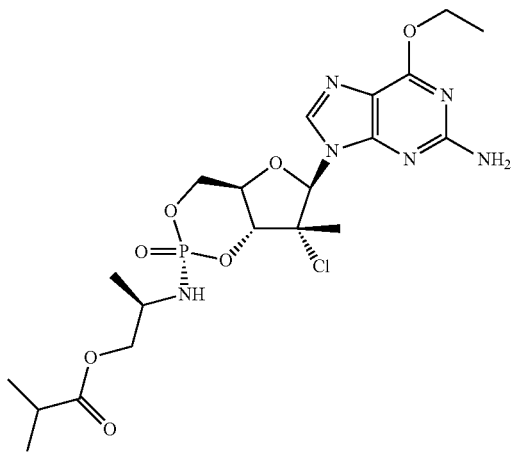
(25aii)
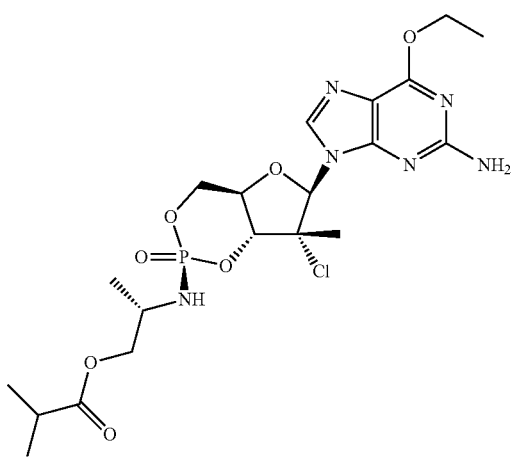
(25bii)
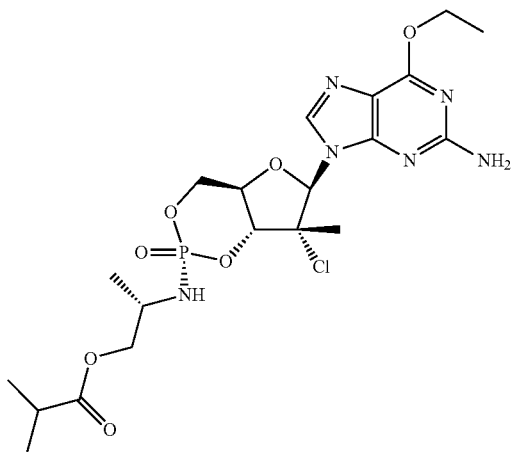
58
-continued
(26)
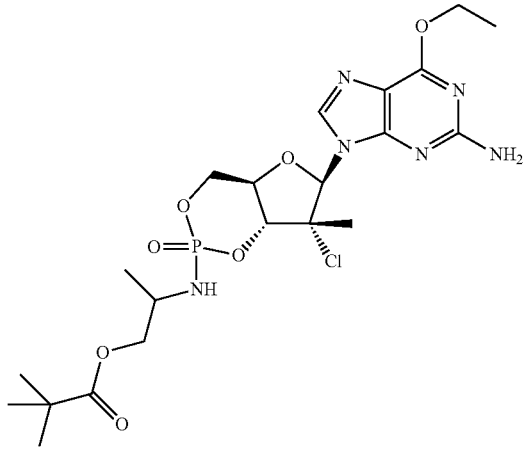
(26i)
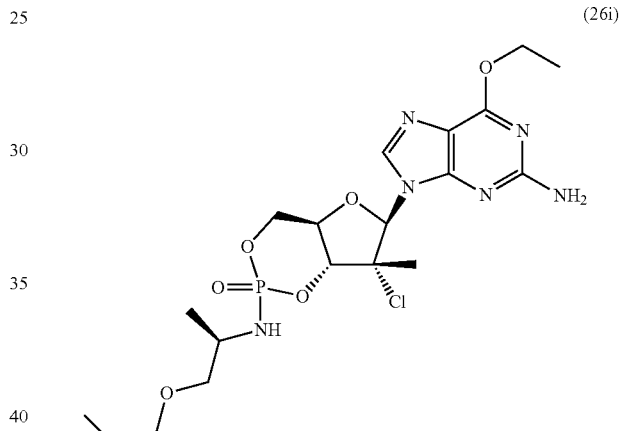
(26ii)
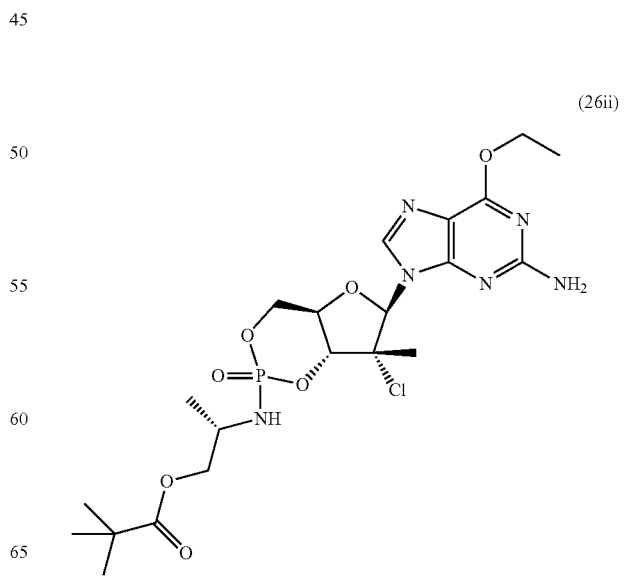

59
-continued
(26ai)
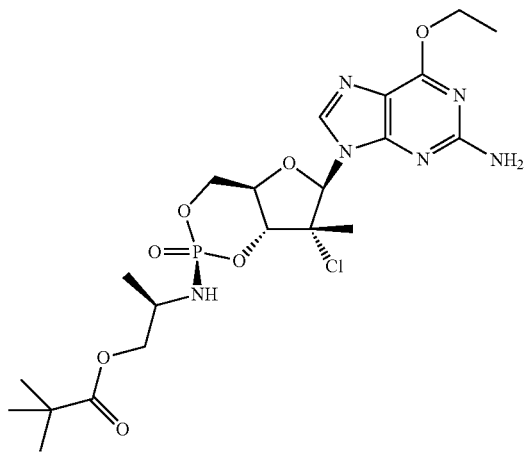
60
-continued
(26bii)
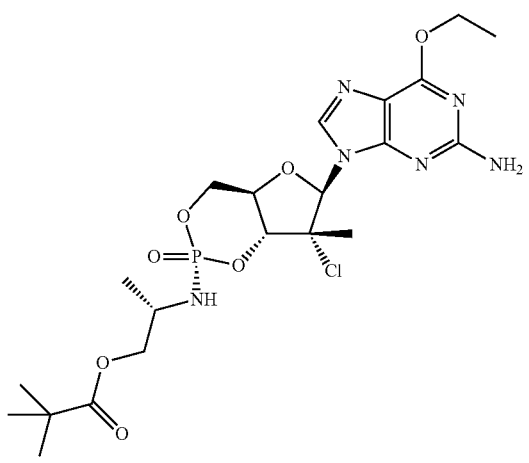
(26bi)
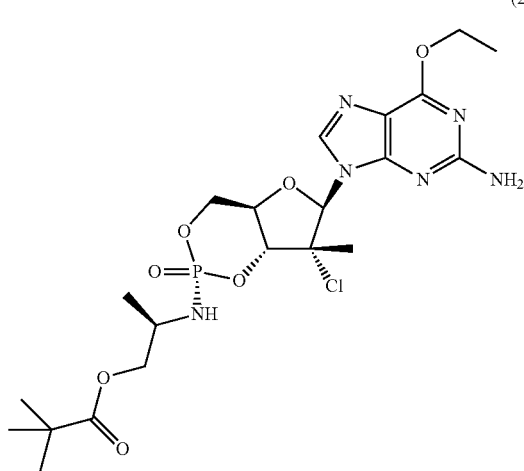
(28)
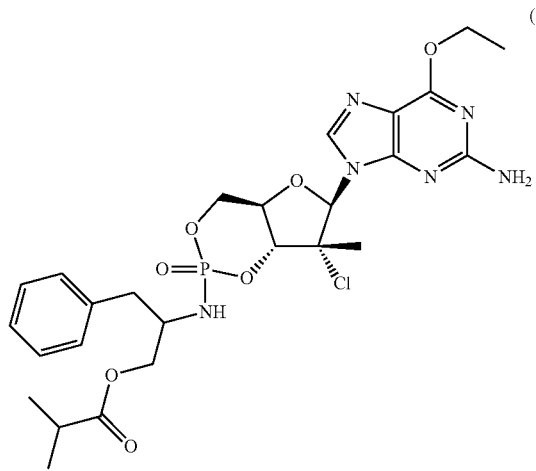
(26aii)
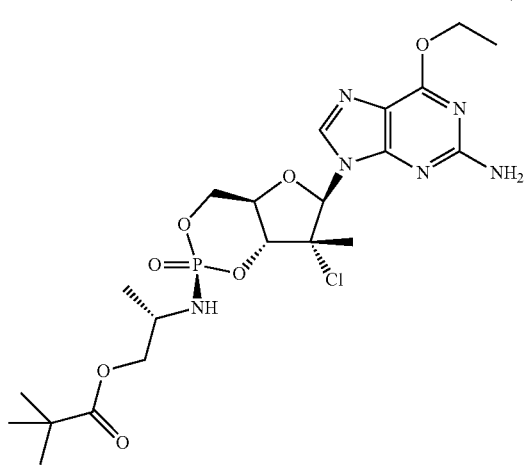
(28i)
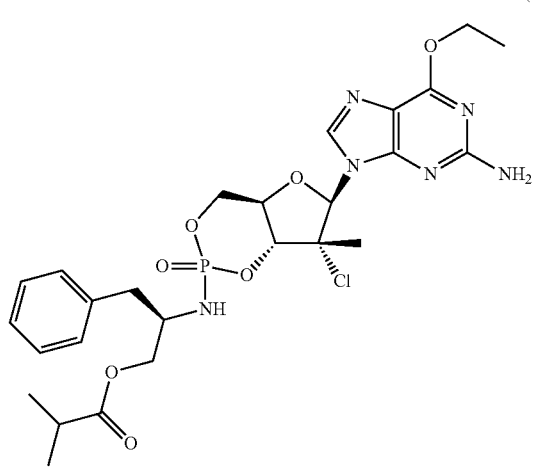

-continued
(28ii)
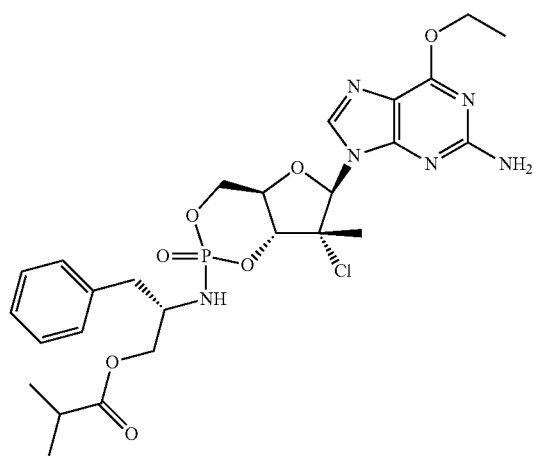
(28aii)
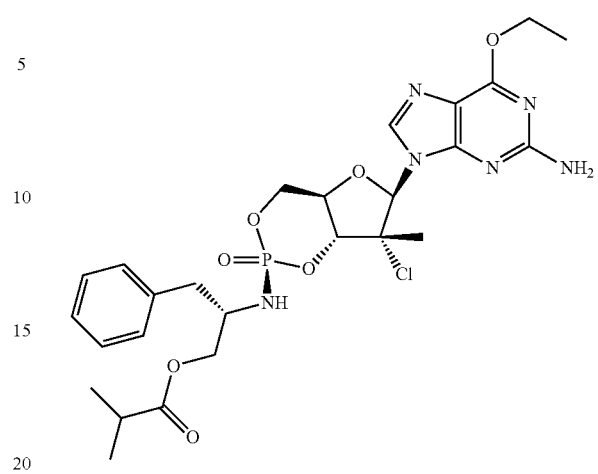
(28ai)
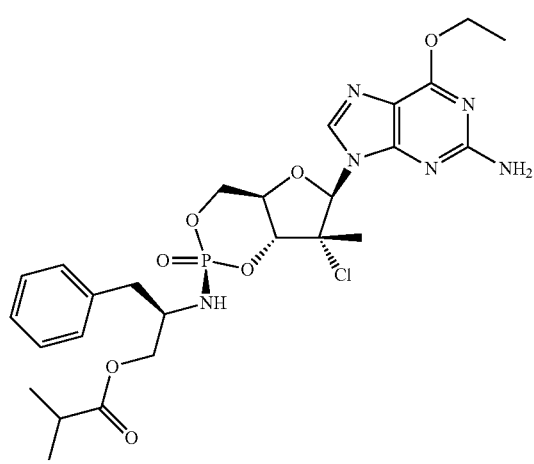
(28bii)
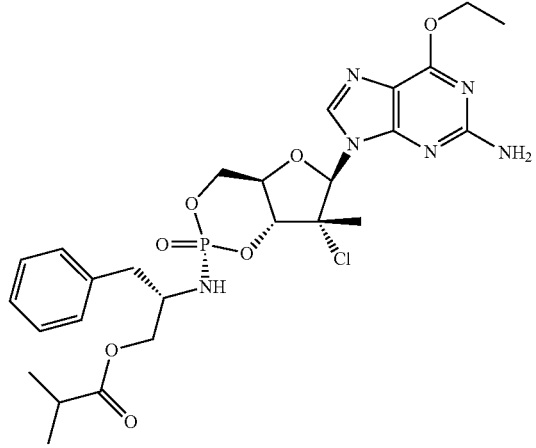
(28bi)
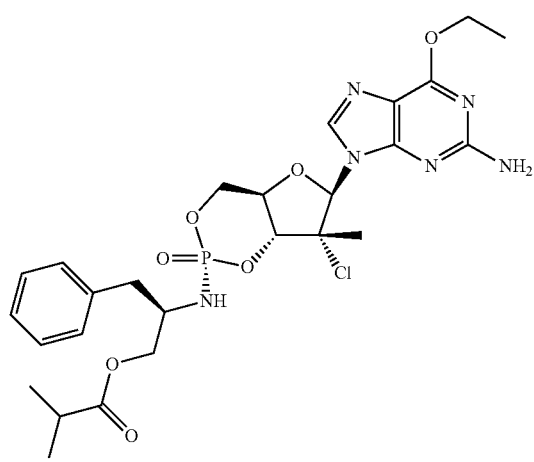
(29)
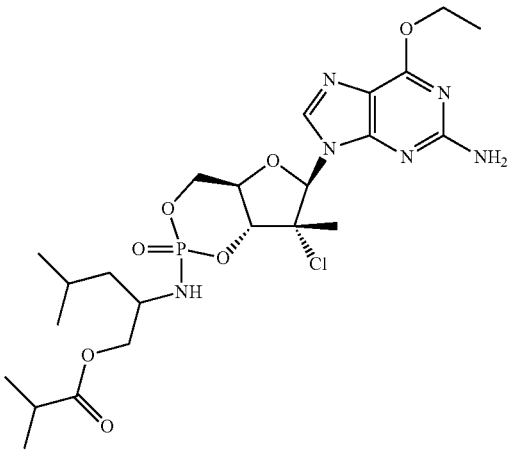

(29i)
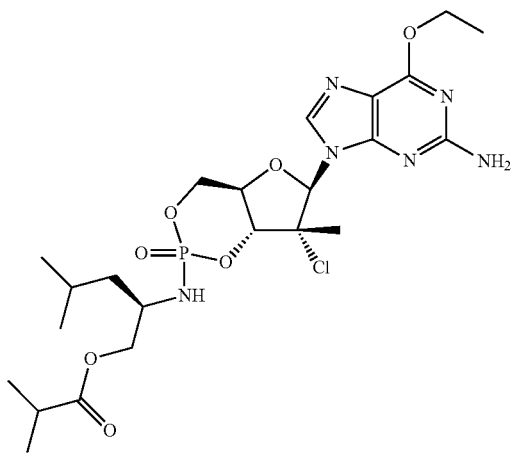
(29bi)
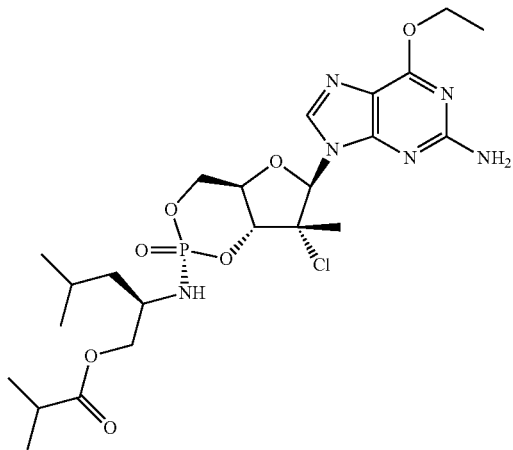
(29ii)
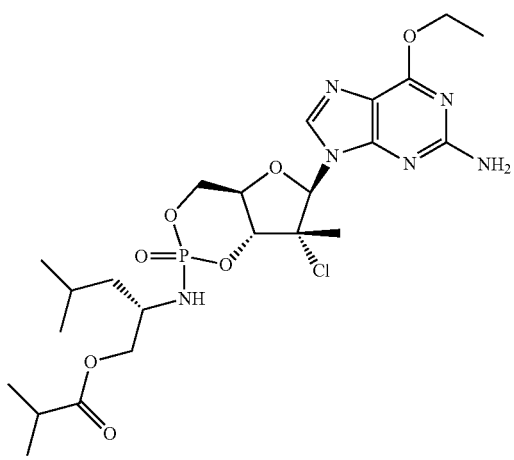
(29aii)
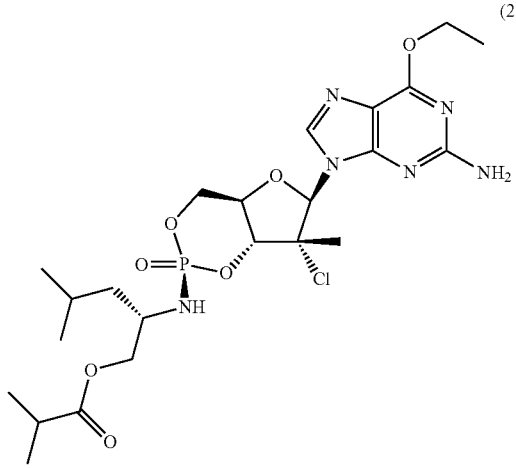
(29ai)
(29bii)
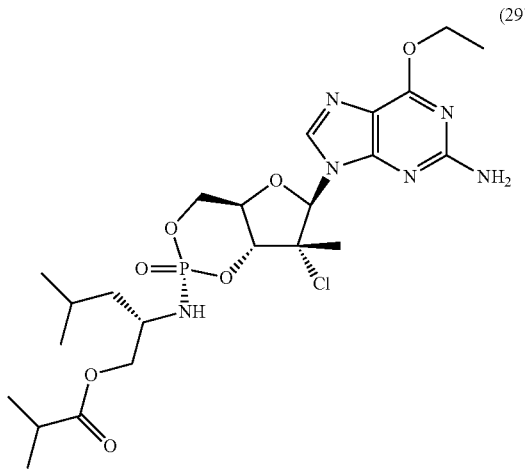

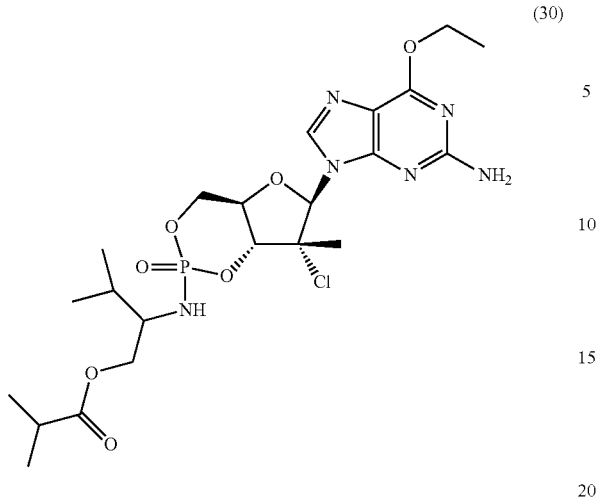
(30)
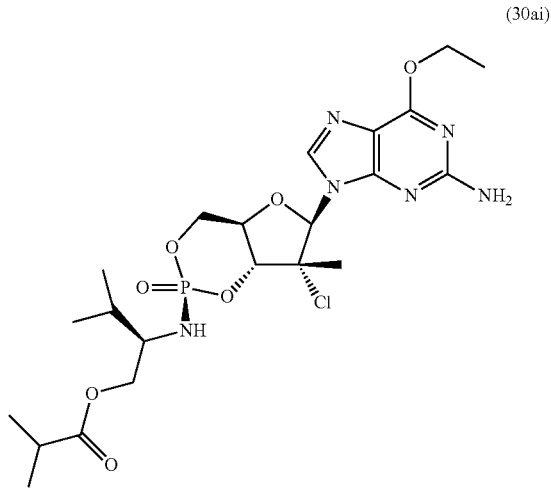
(30ai)
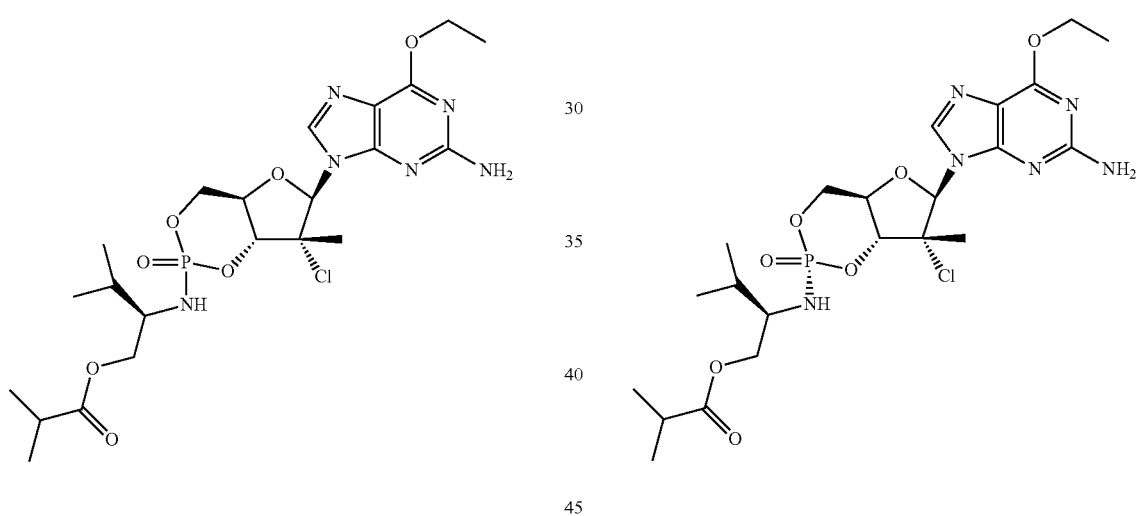
(30i)
(30bi)
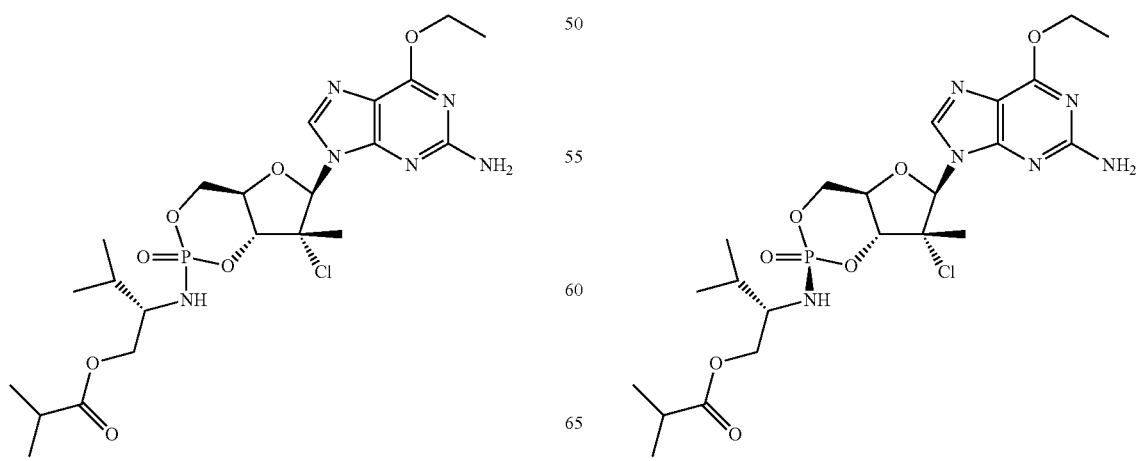
(30ii)
(30aii)

(30bii)
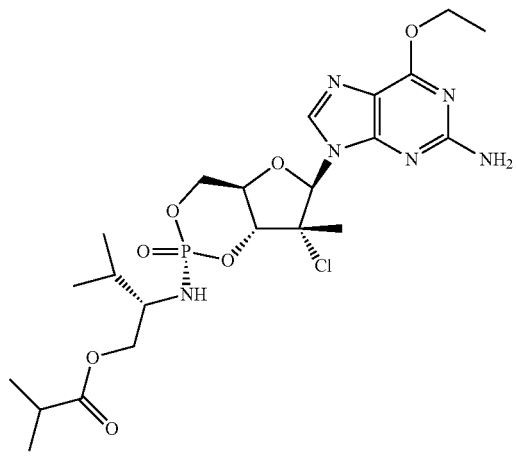
(31ii)
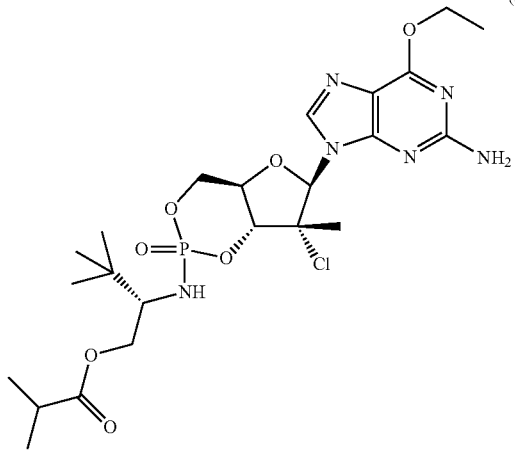
(31)
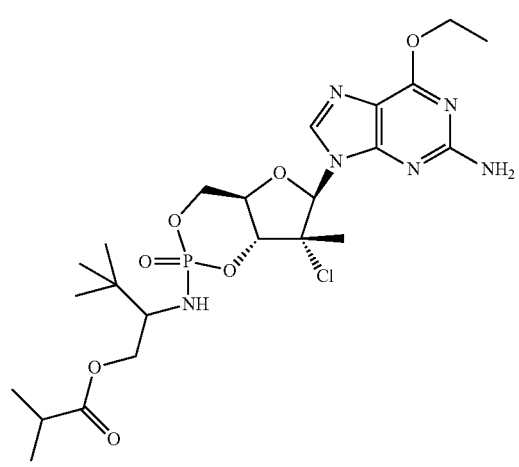
(31ai)
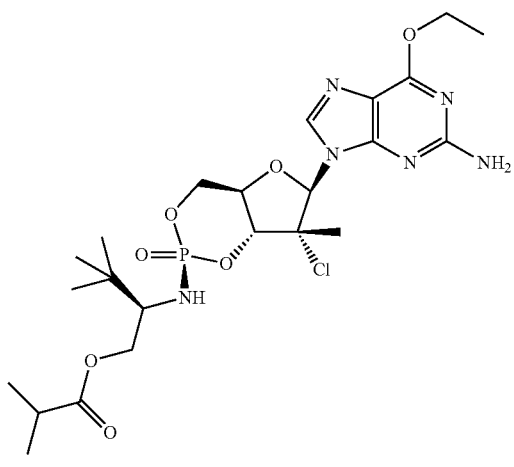
(31i)
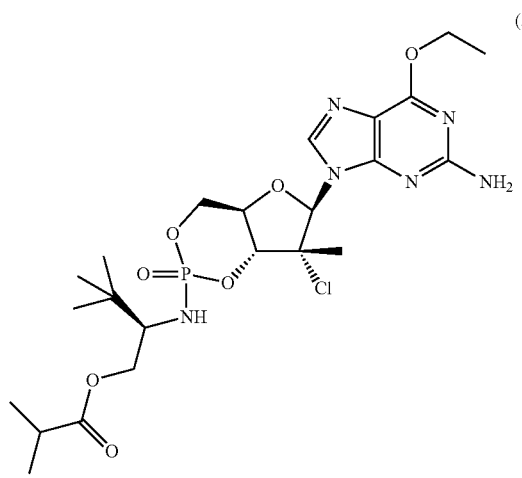
(31bi)
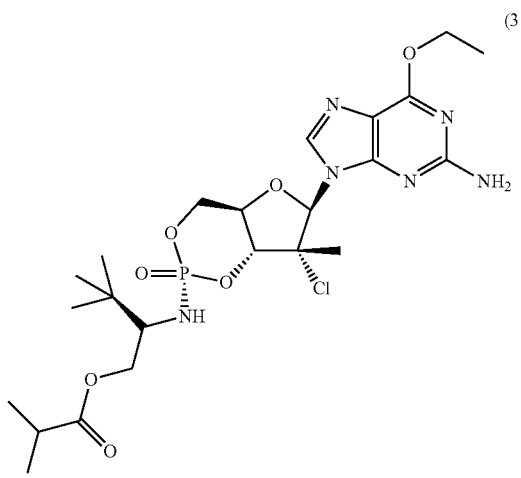

69
-continued
(31aii)
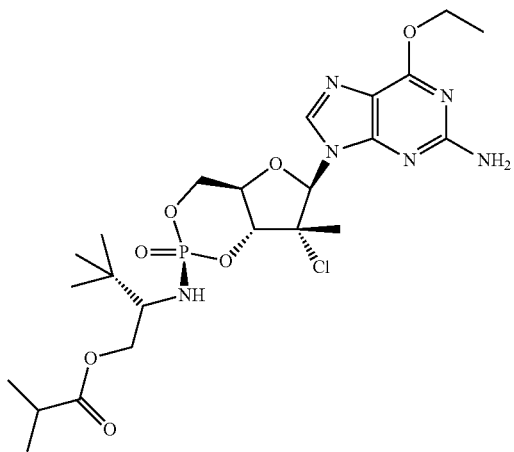
(31bii)
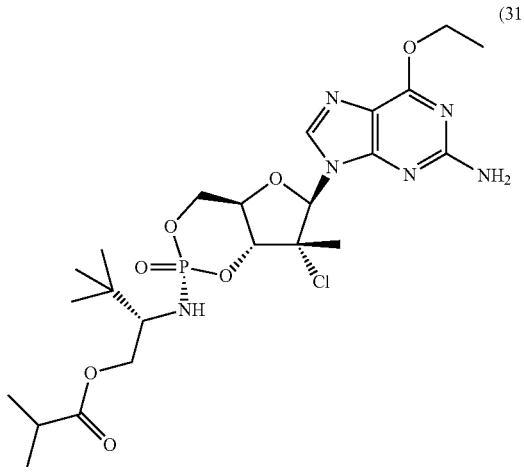
(32)
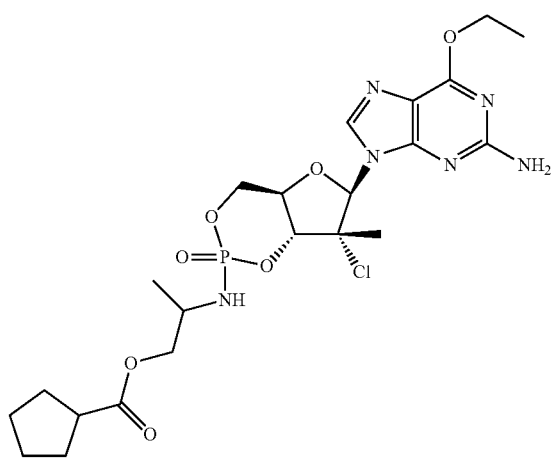
70
-continued
(32i)
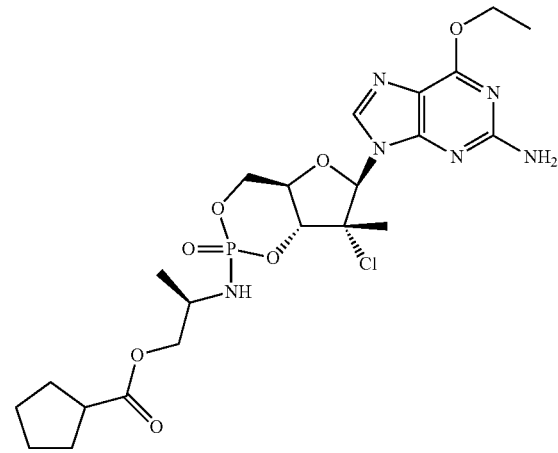
(32ii)
(32ai)
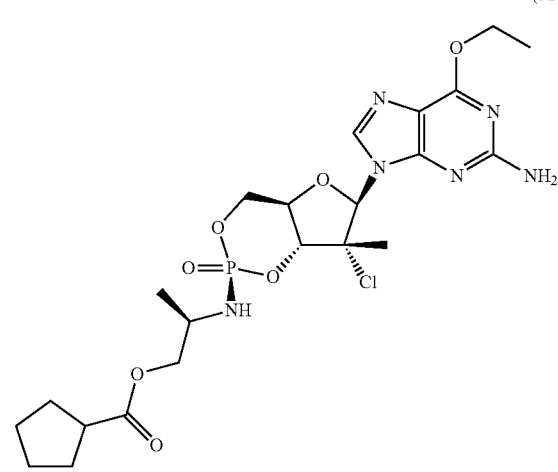

-continued
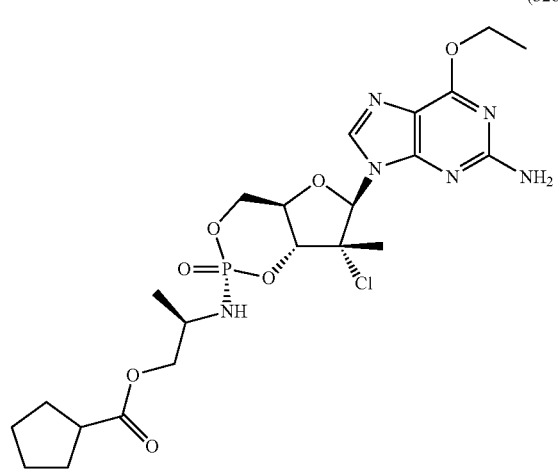
(32bi)
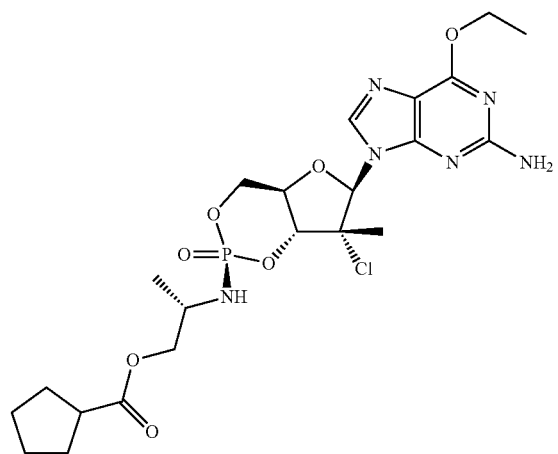
(32aii)
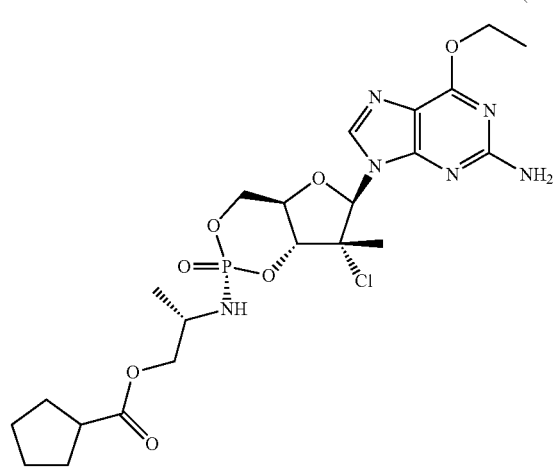
(32bii)
-continued
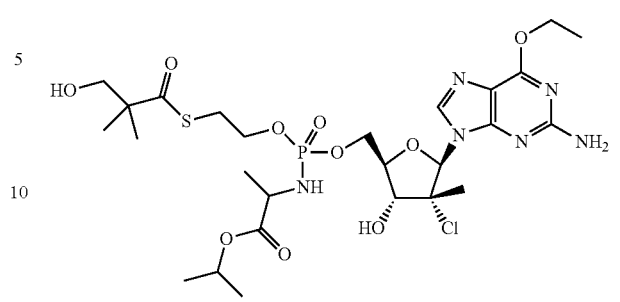
(33)
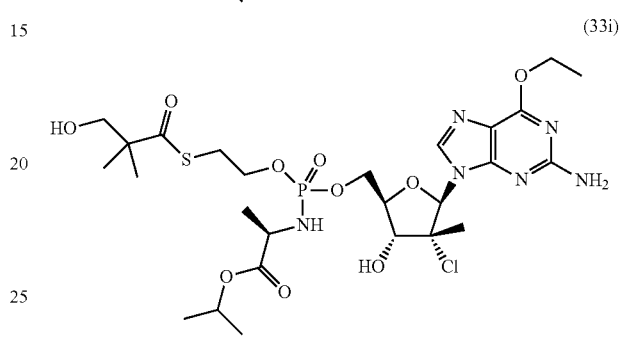
(33i)
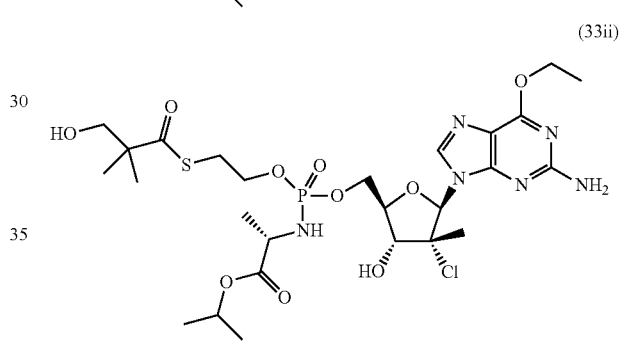
(33ii)
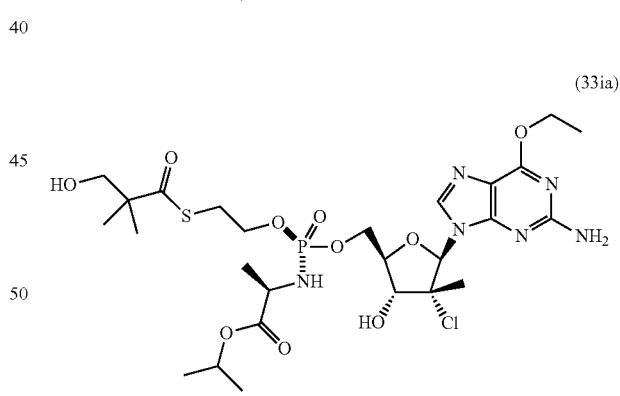
(33ia)
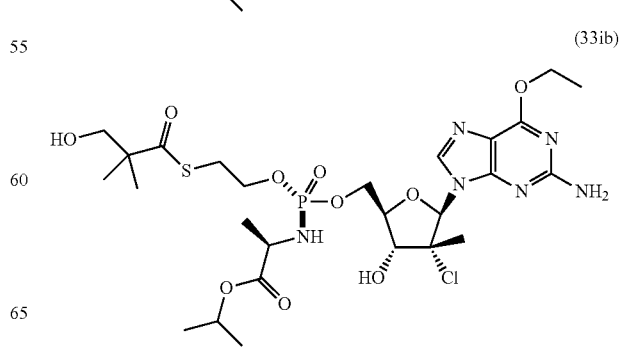
(33ib)

(33aii)
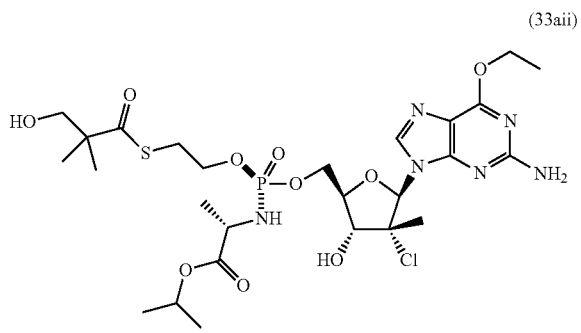
(33bii)
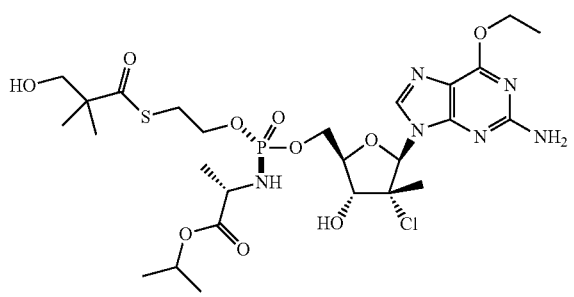
(35)
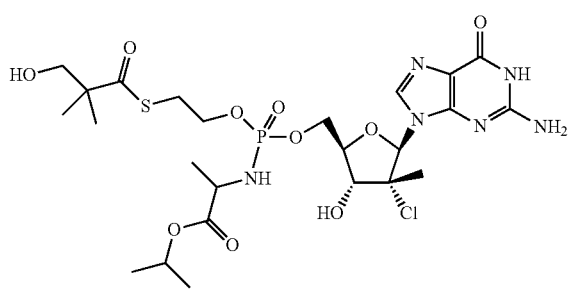
(35i)
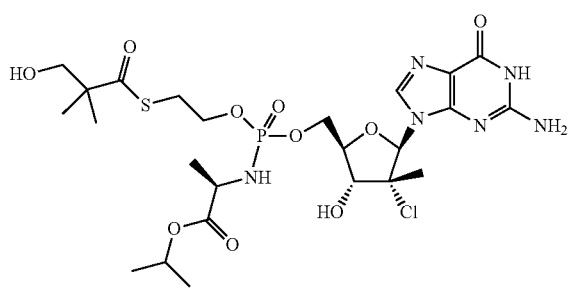
(35ii)
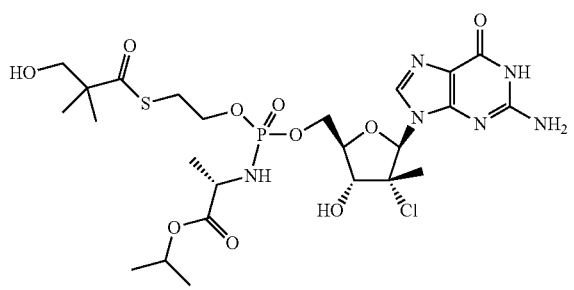
(35ai)
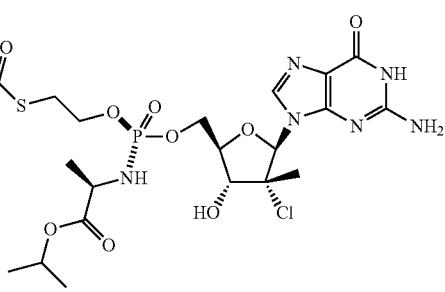
(35bi)
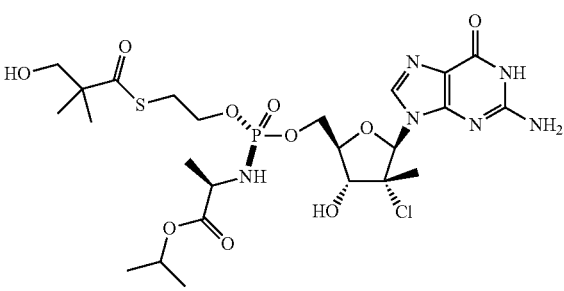
(35aii)
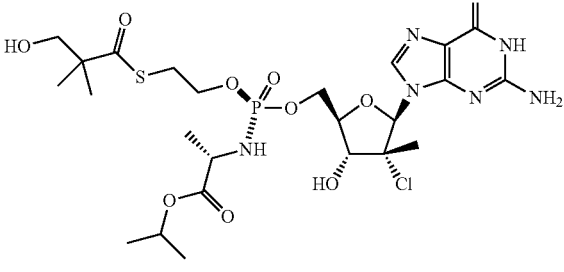
(35bii)
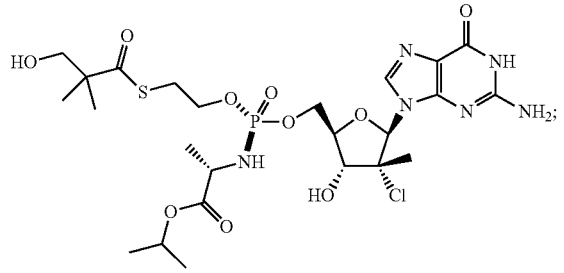
or a pharmaceutically acceptable salt, solvate, stereoisomeric form, tautomeric form or polymorphic form thereof.
In certain embodiments, provided herein are compounds according to any of Formulas (37)-(72b):

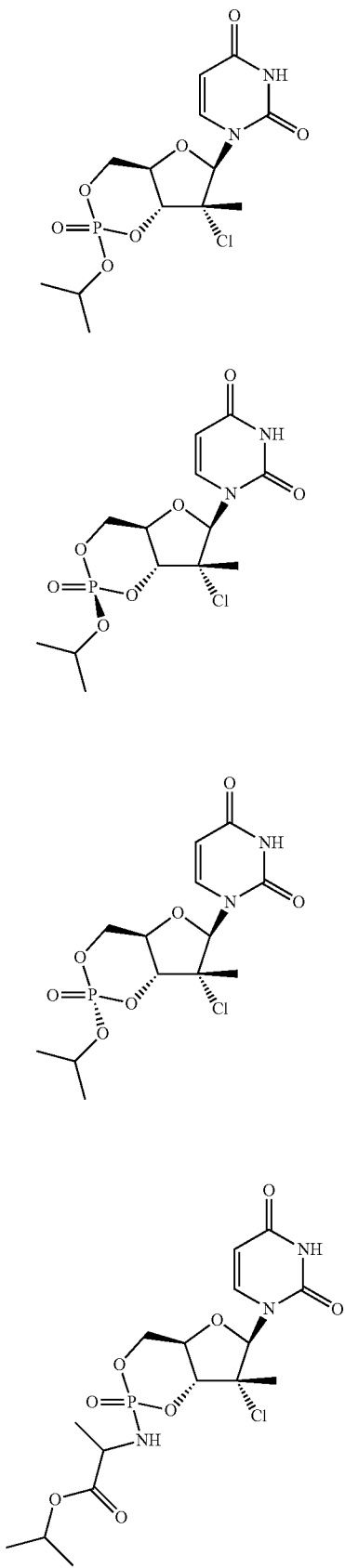
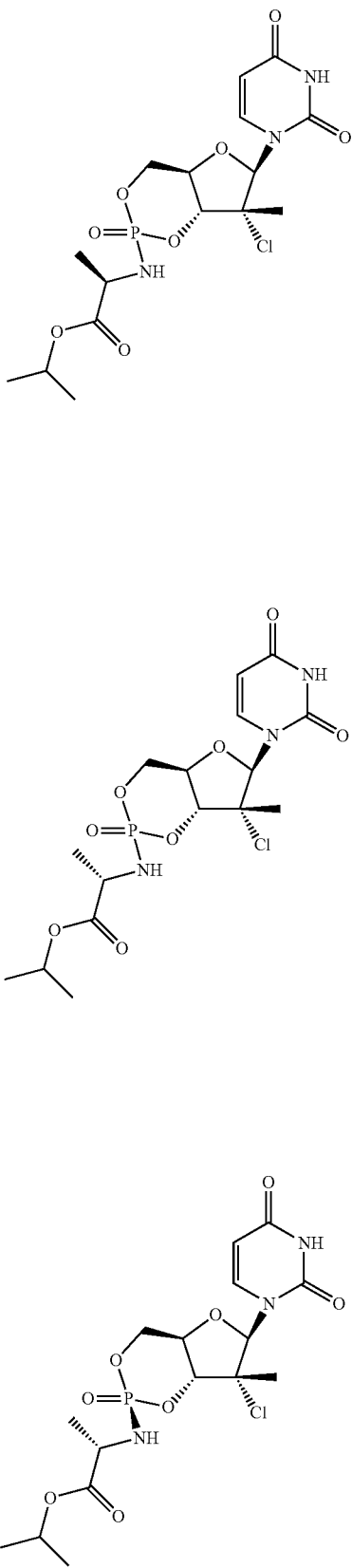

(38iib) 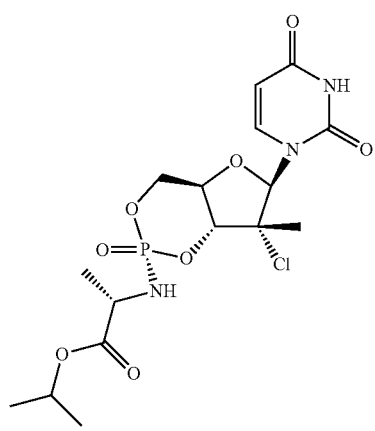
(38ia) 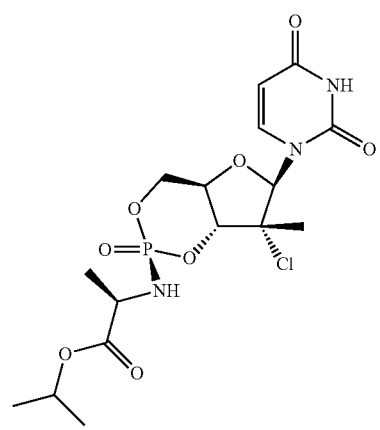
(38ib) 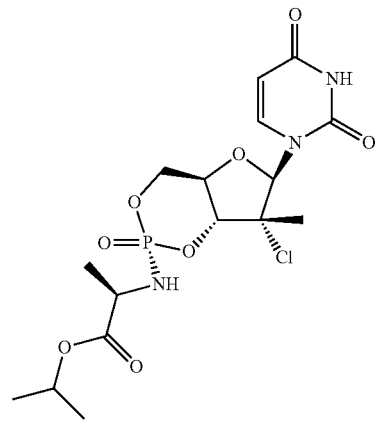
(40) 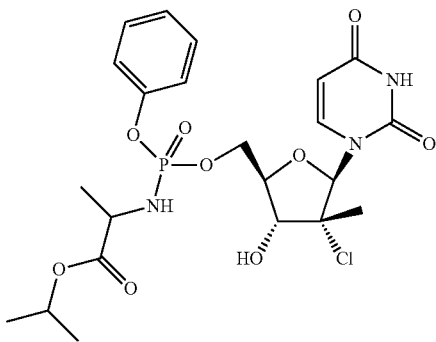
(40i) 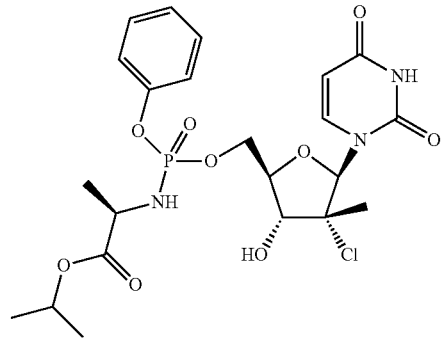
(40ii) 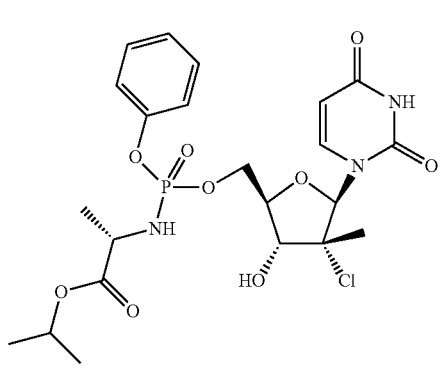
(40ia) 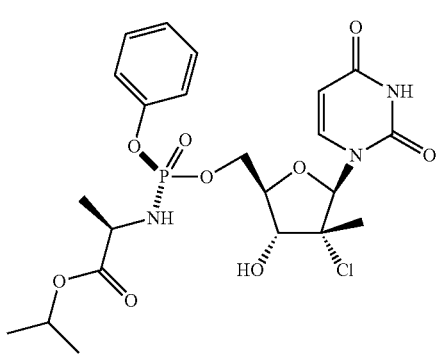
(40ib) 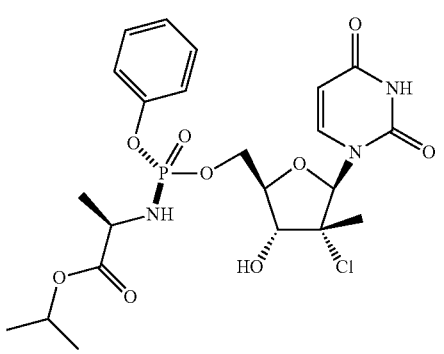

(40iia)
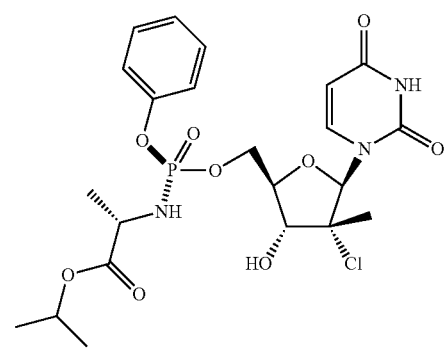
(40iib)
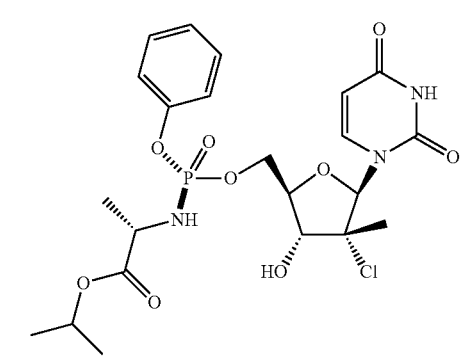
(41)
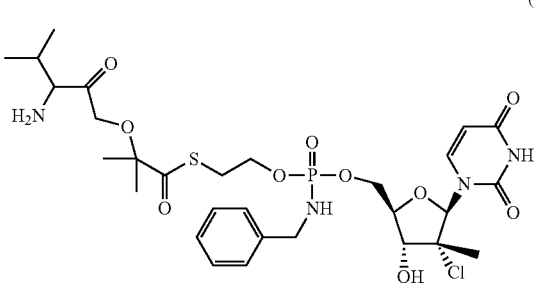
(41i)
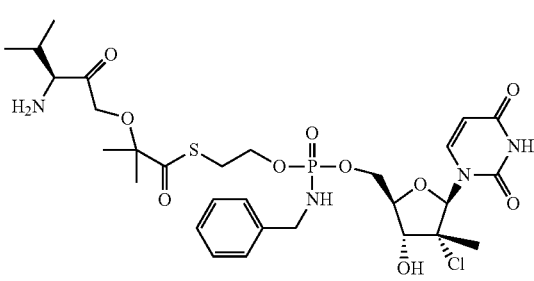
(41ii)
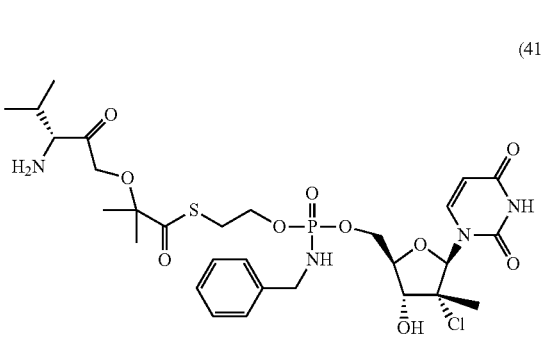
(41ia)
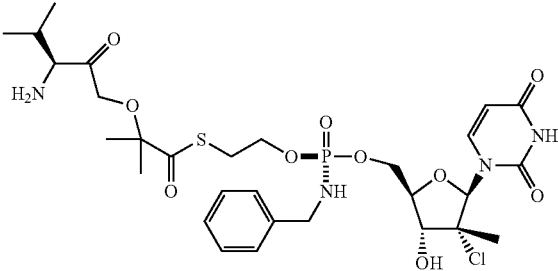
(41ib)
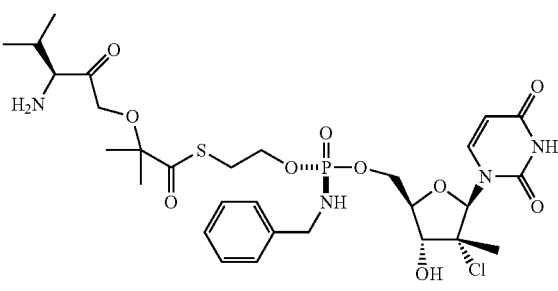
(41iia)
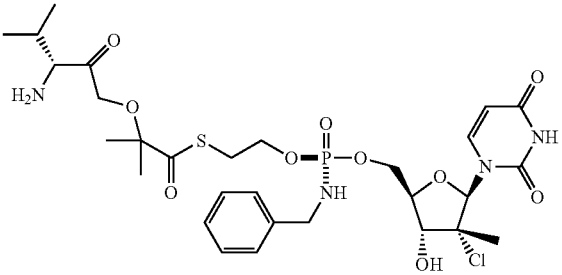
(41iib)
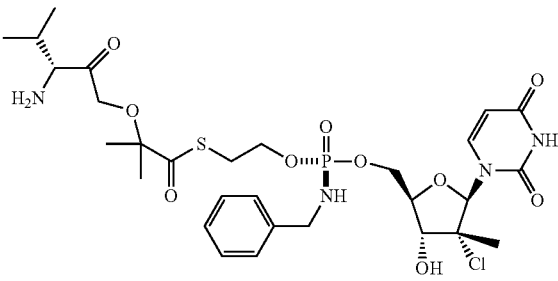
(42)
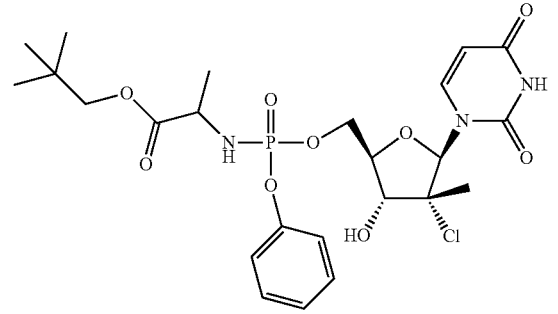

(42i)
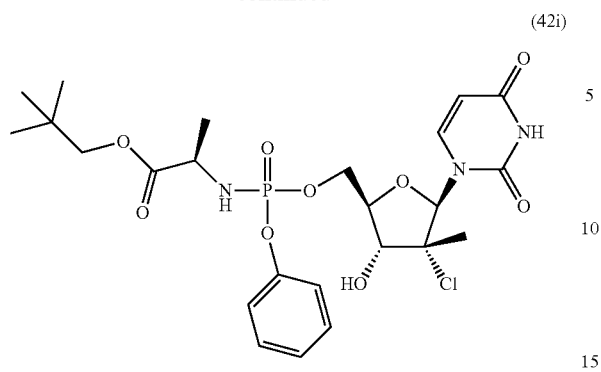
(42iia)
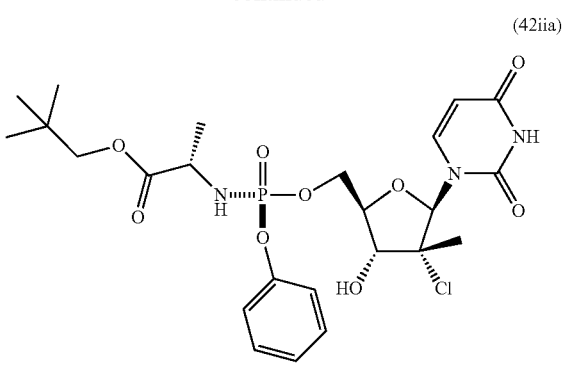
(42ii)
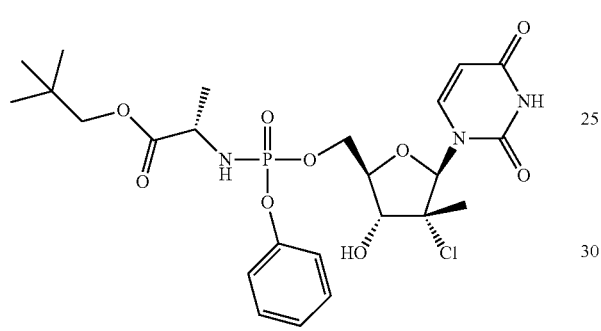
(42iib)
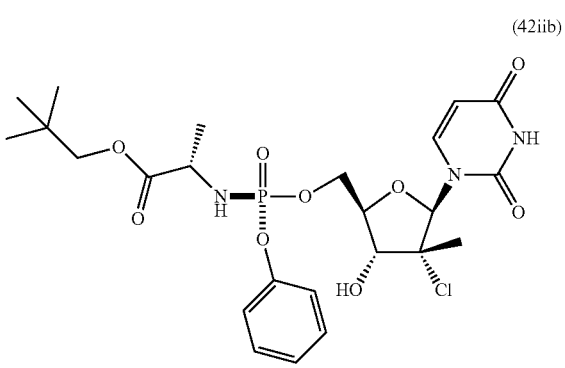
(42ia)
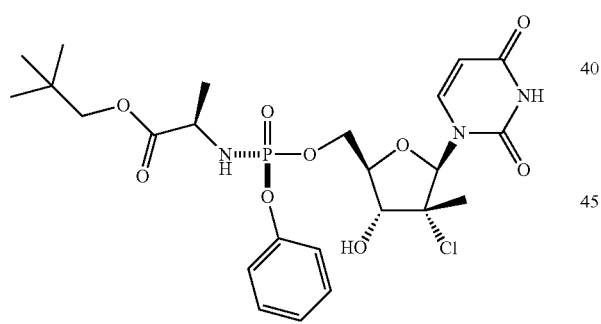
(43)
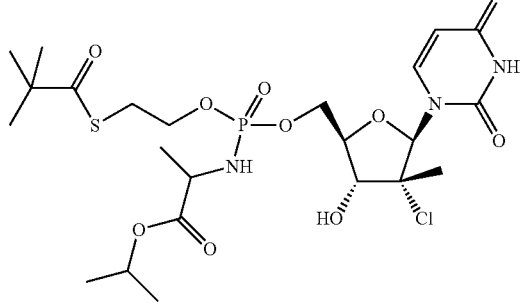
(42ib)
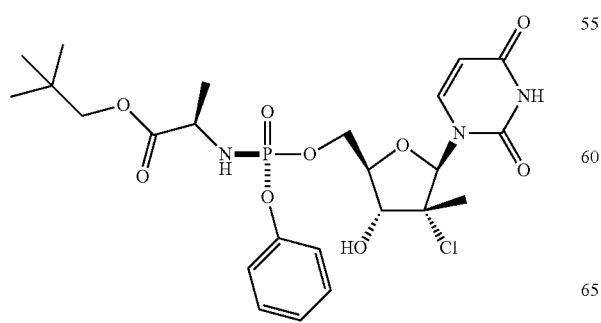
(43i)
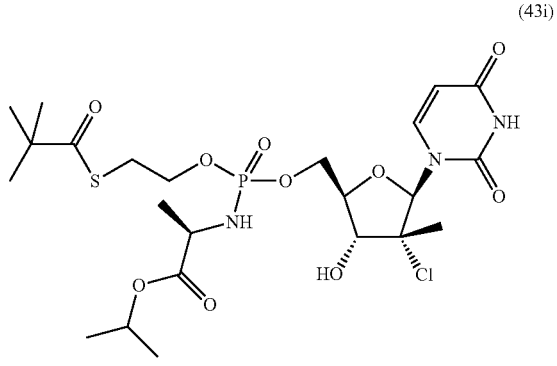

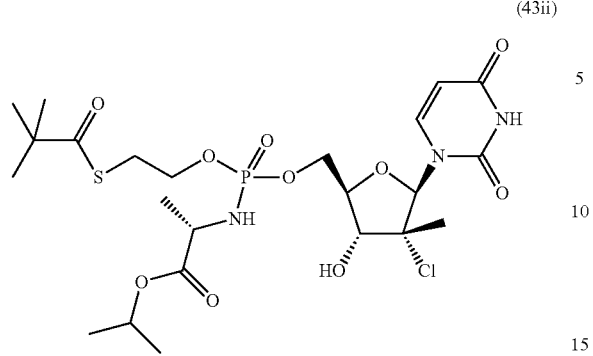
(43ii)
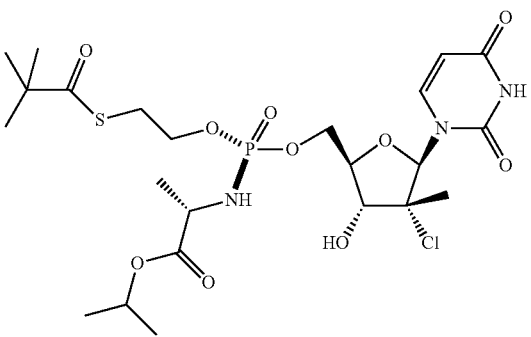
(43iib)
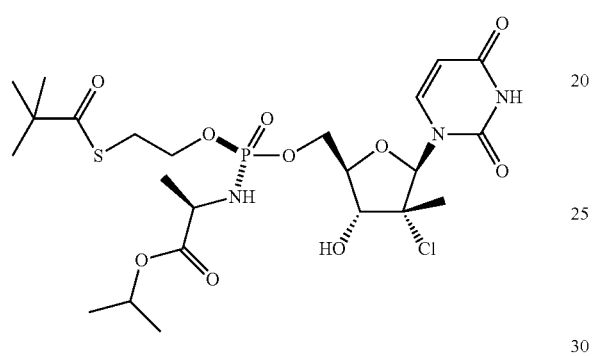
(43ia)
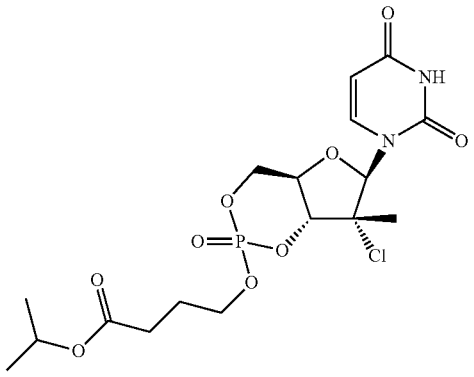
(45)

(43ib)

(45a)
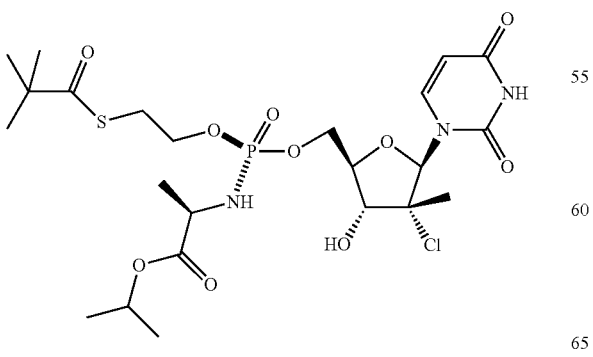
(43iia)
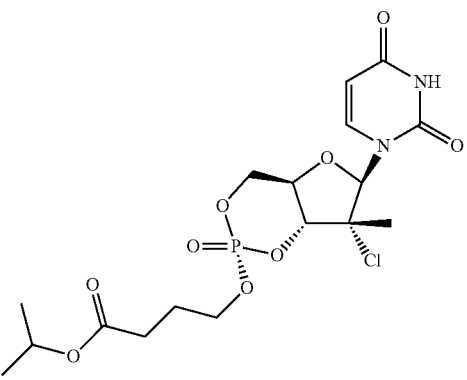
(45b)

(46)
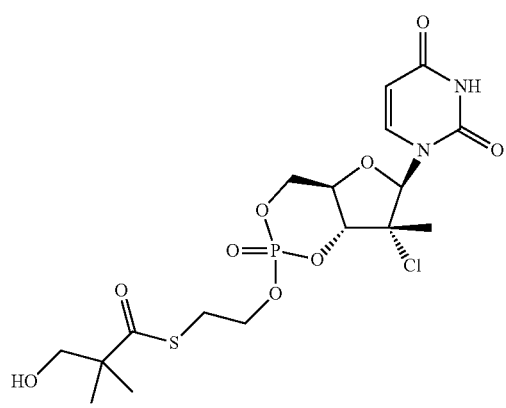
(46a)
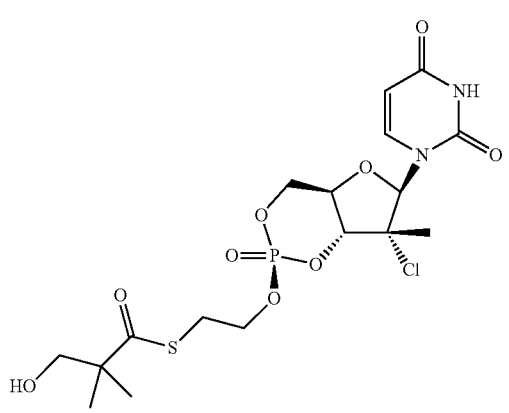
(46b)
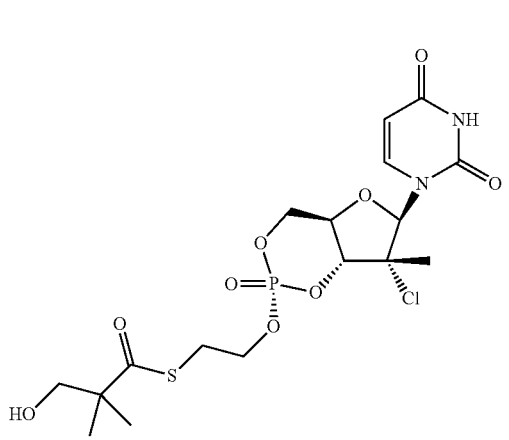
(47)
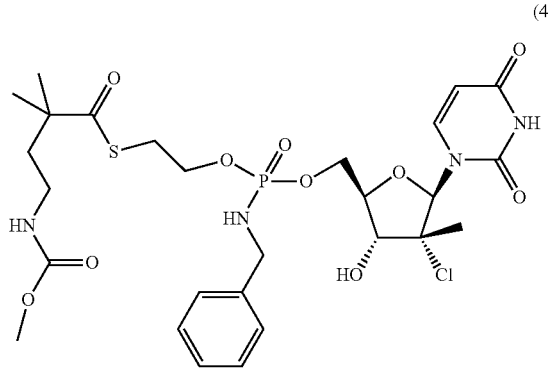
(47a)
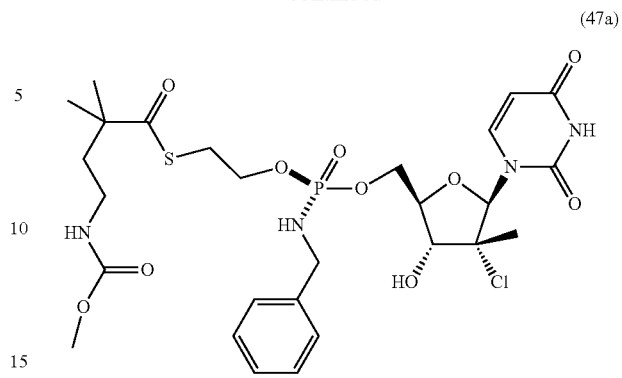
(47b)
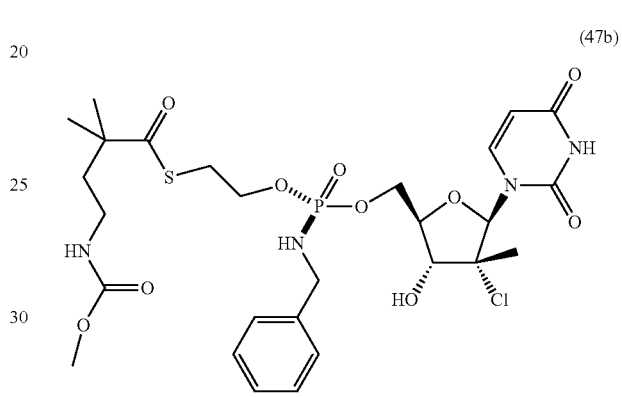
(48)
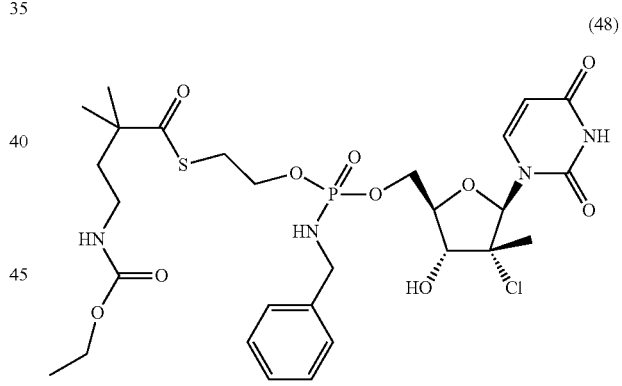
(48a)
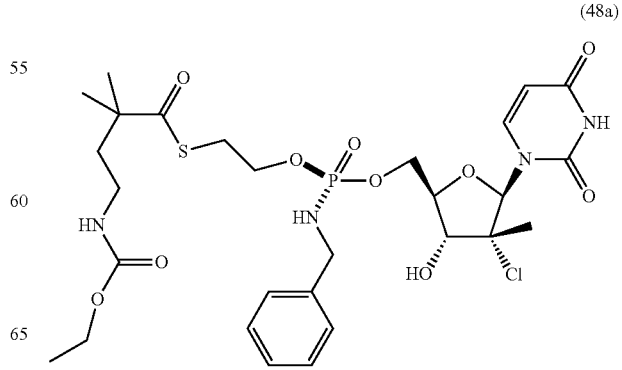

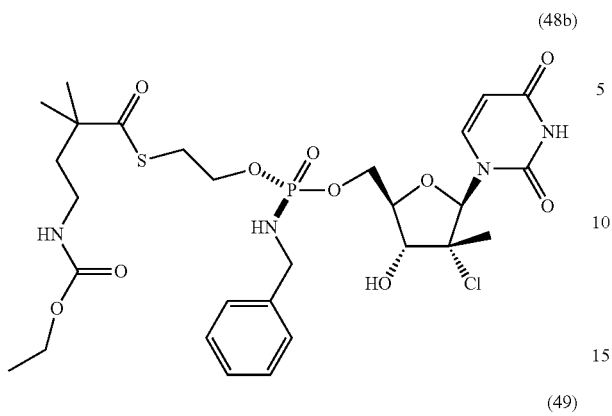
(48b)
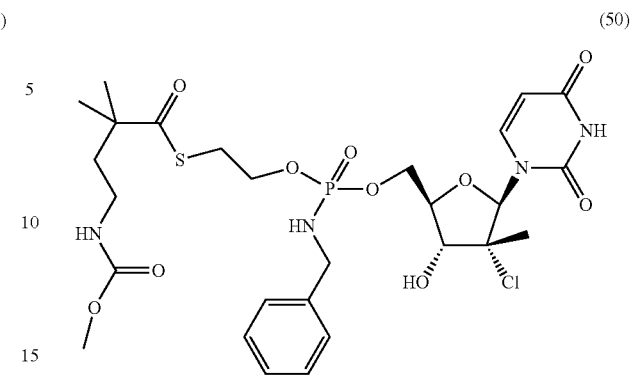
(50)
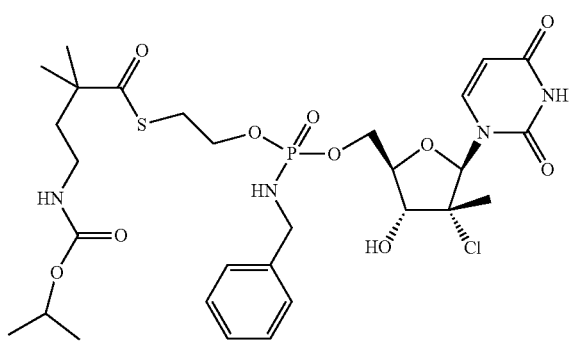
(49)
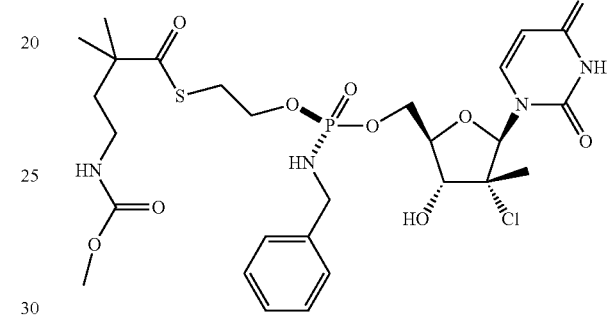
(50a)
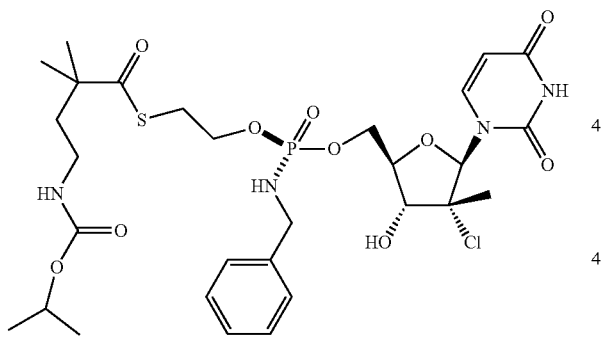
(49a)
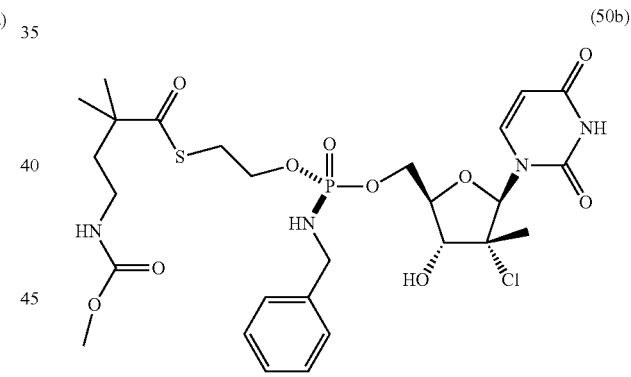
(50b)
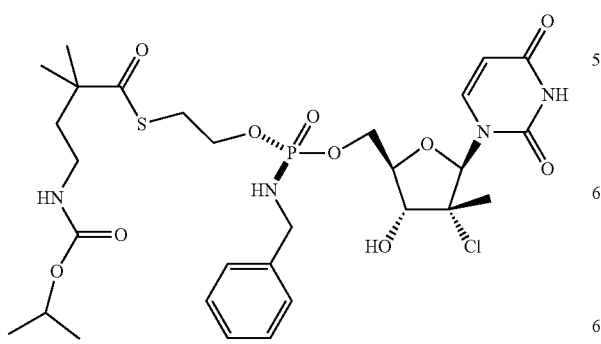
(49b)
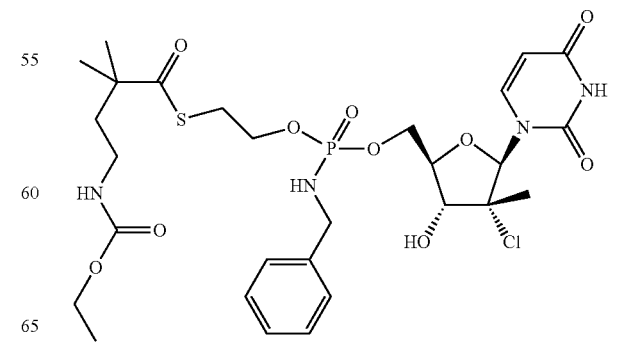
(51)

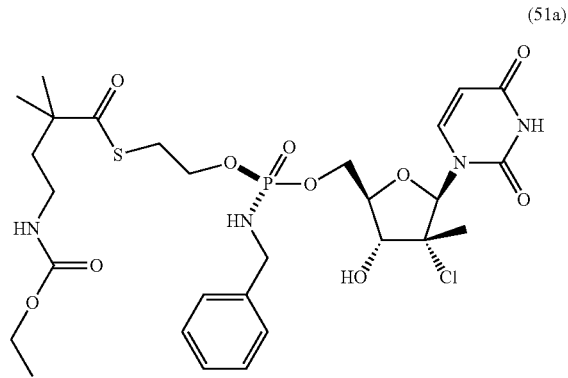
(51a)
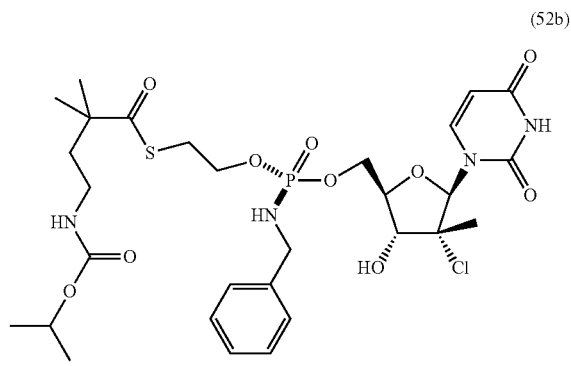
(52b)
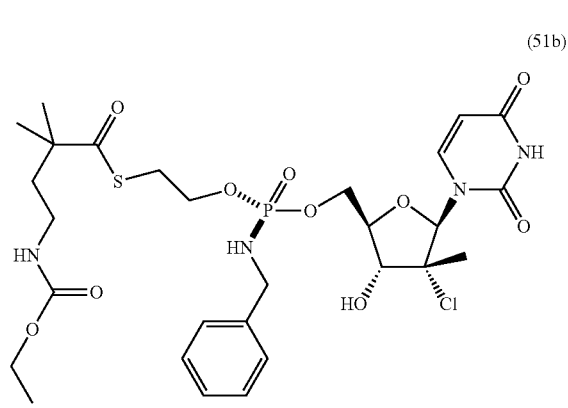
(51b)
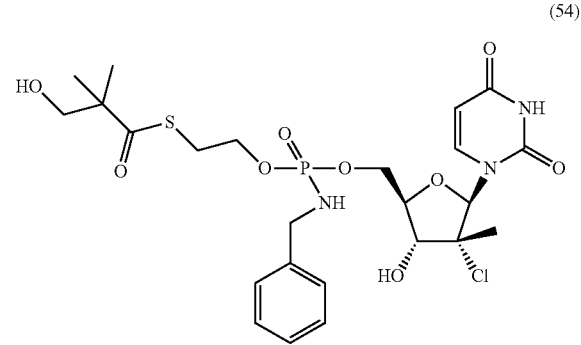
(54)
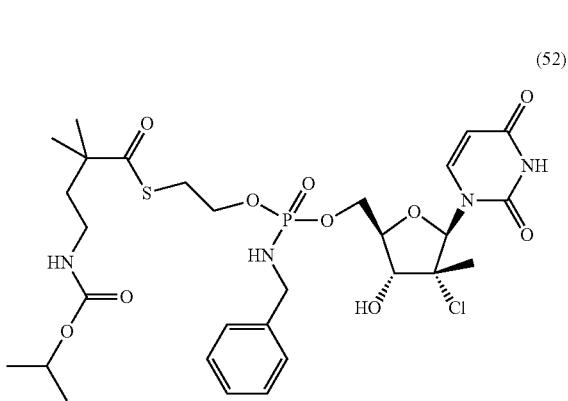
(52)
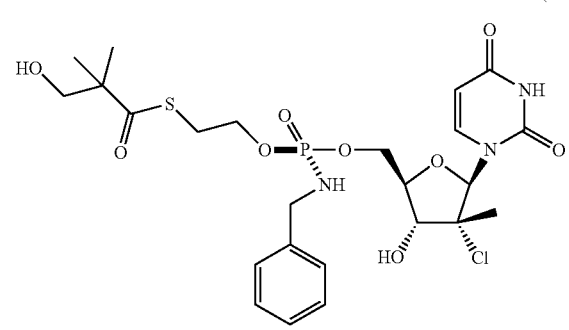
(54a)
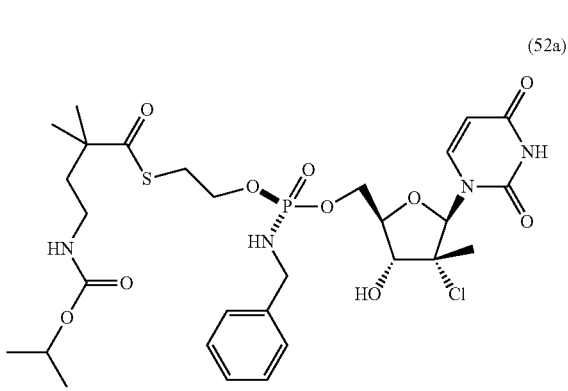
(52a)
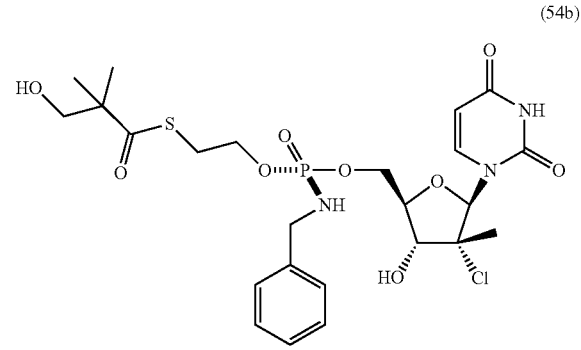
(54b)

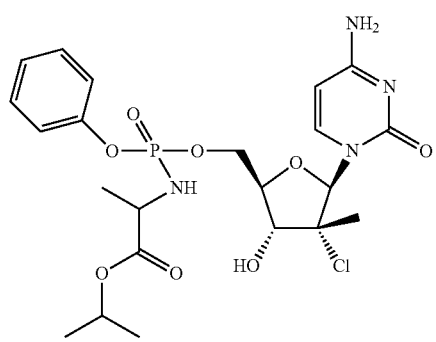
(56)
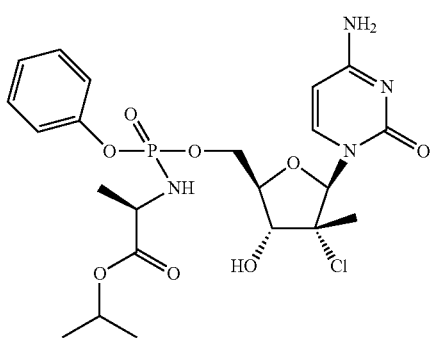
(56i)
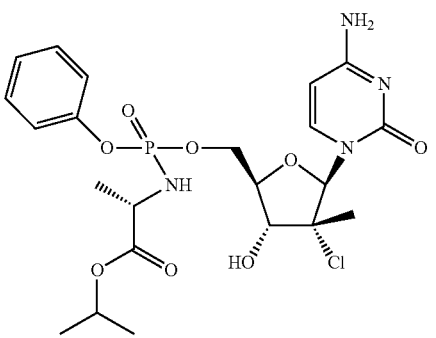
(56ii)
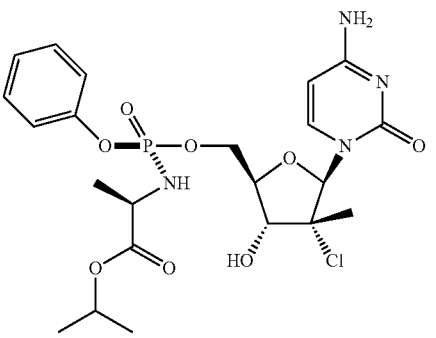
(56ia)
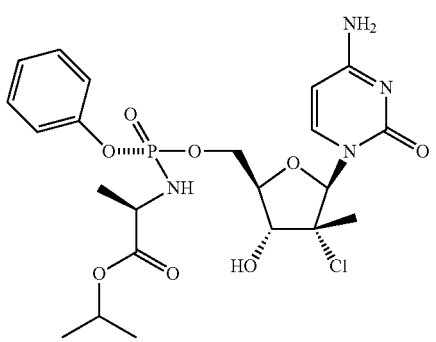
(56ib)
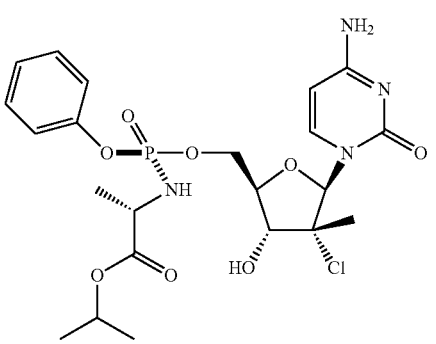
(56iia)
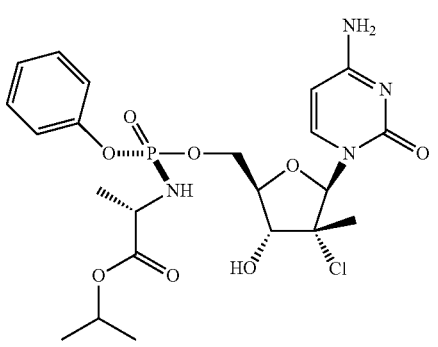
(56iib)
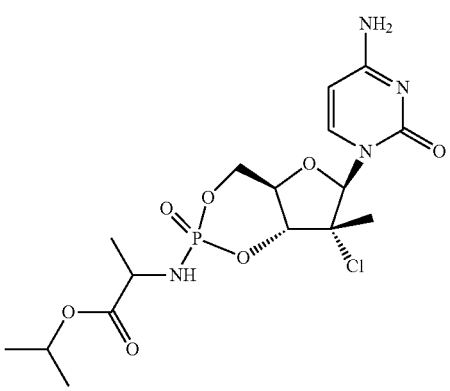
(58)

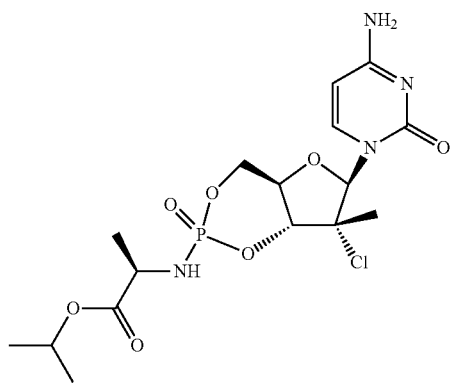
(58i)
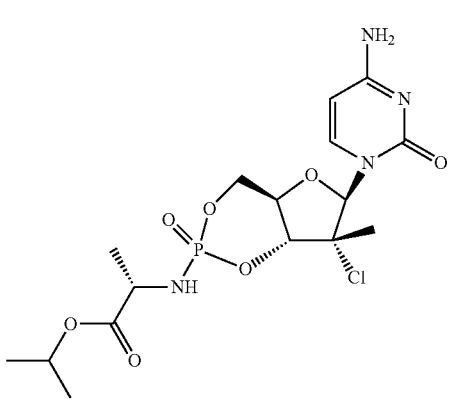
(58ii)
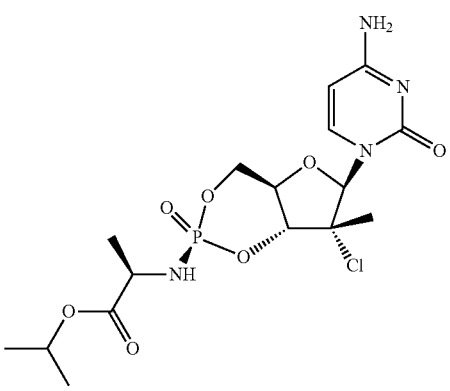
(58ia)
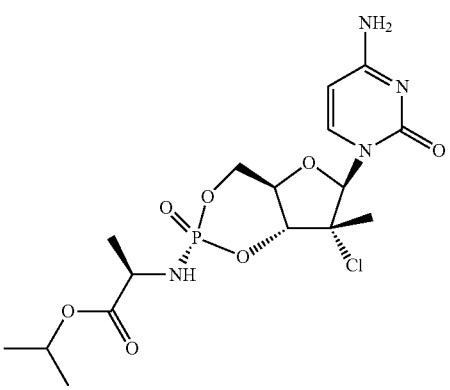
(58ib)
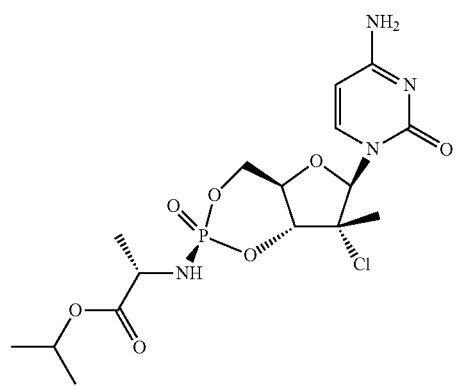
(58iia)
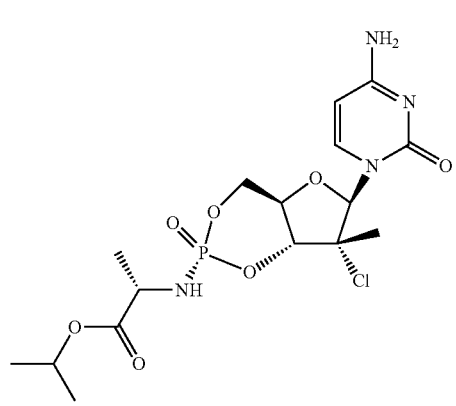
(58iib)
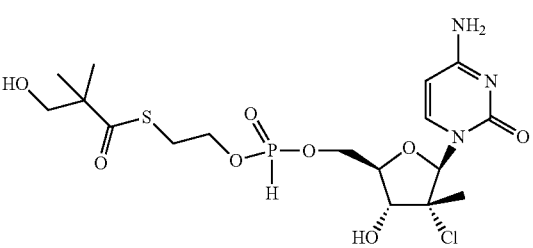
(59)
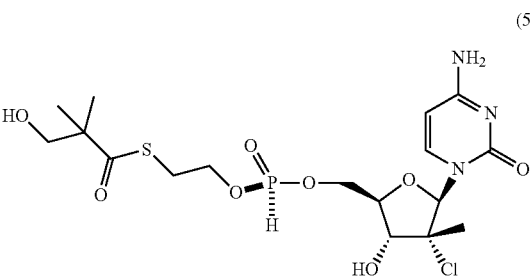
(59a)
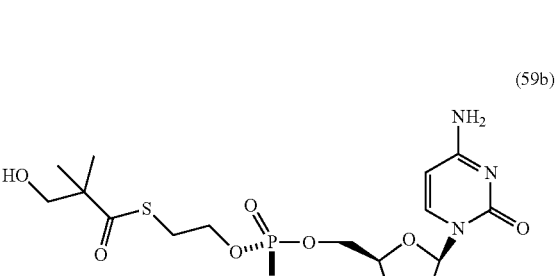
(59b)

-continued
(60)
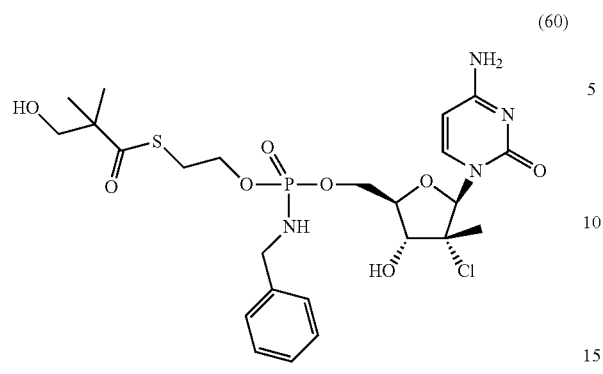
(60a)
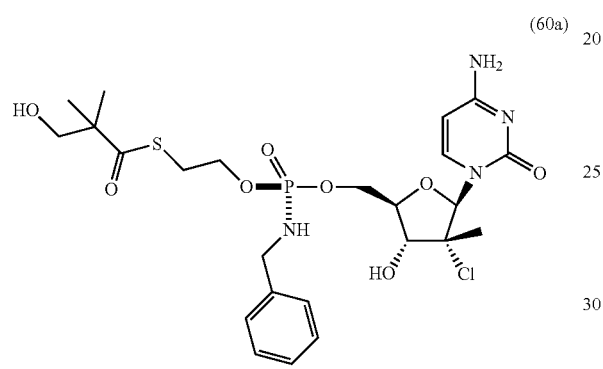
(60b)
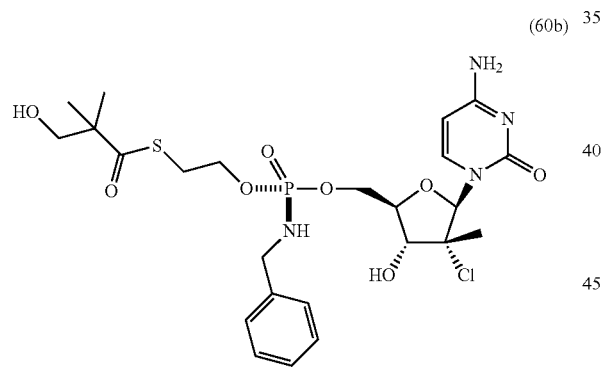
(61)
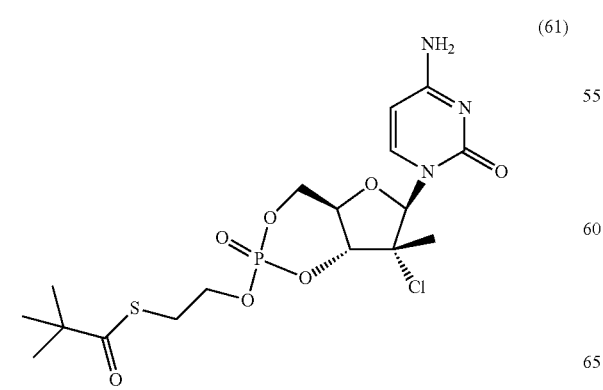
-continued
(61a)
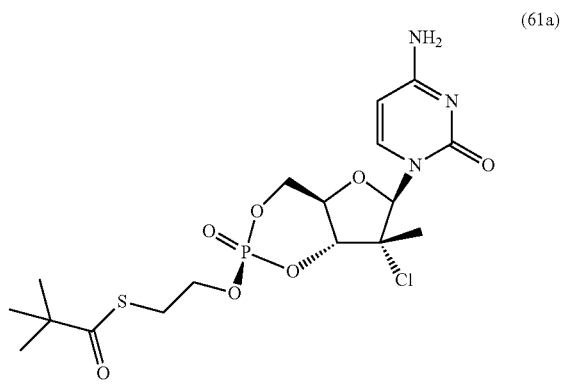
(61b)
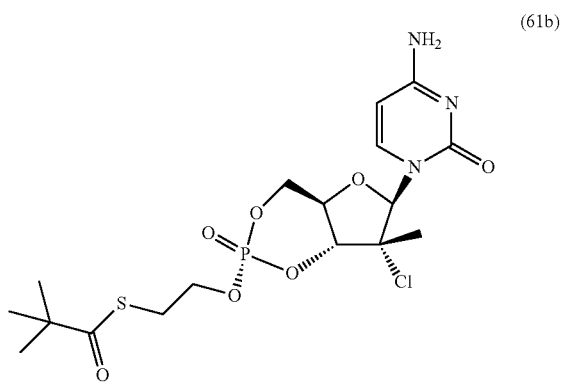
(62)
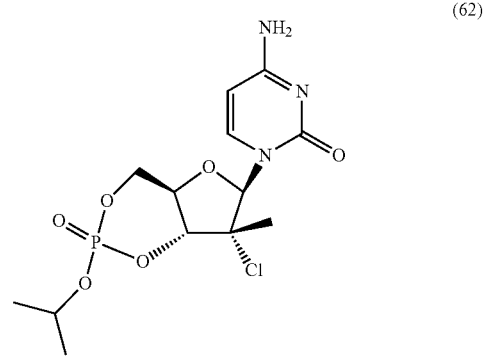
(62a)
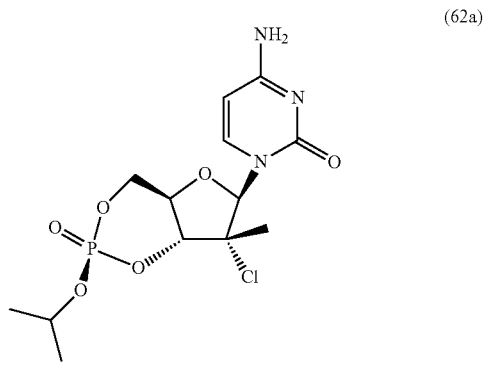

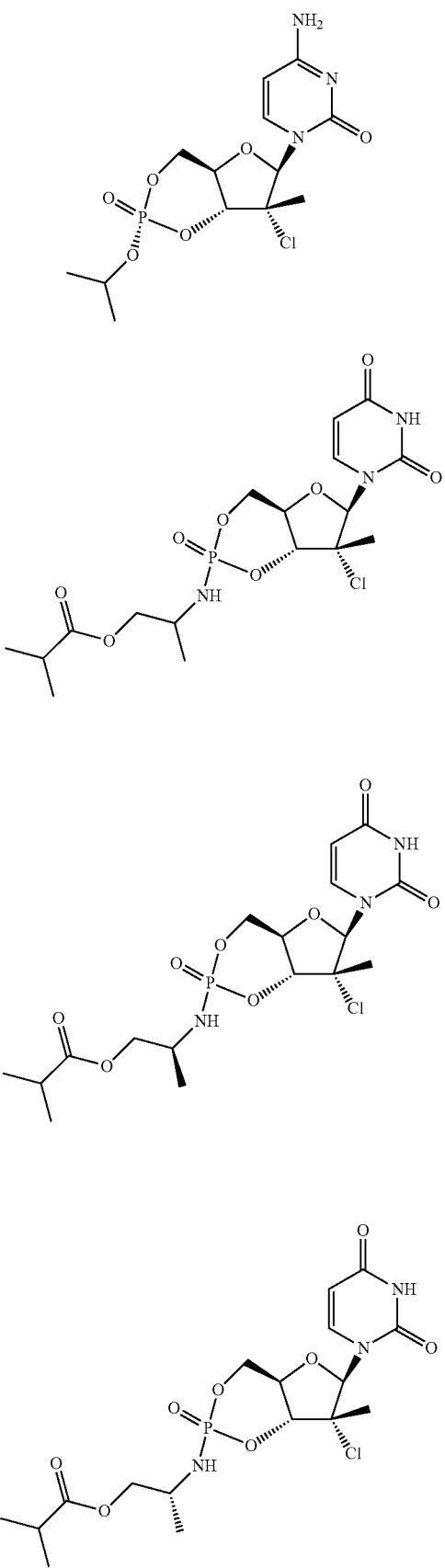
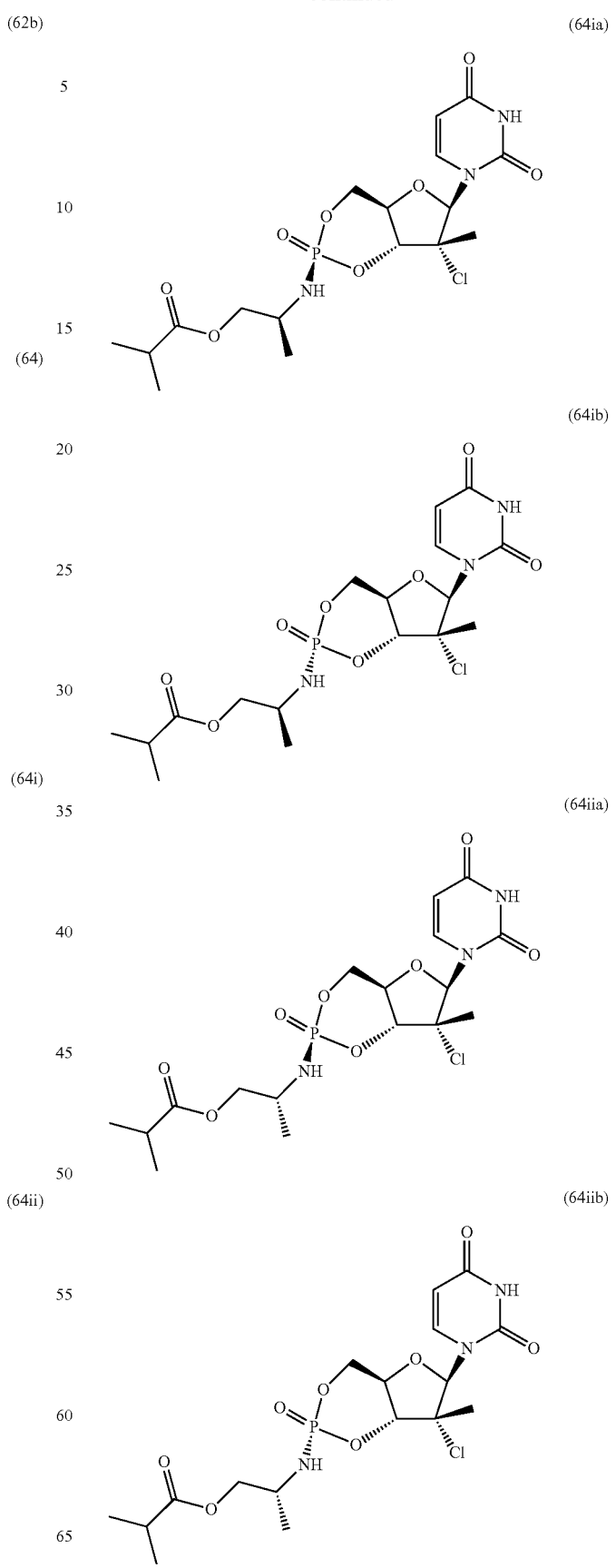

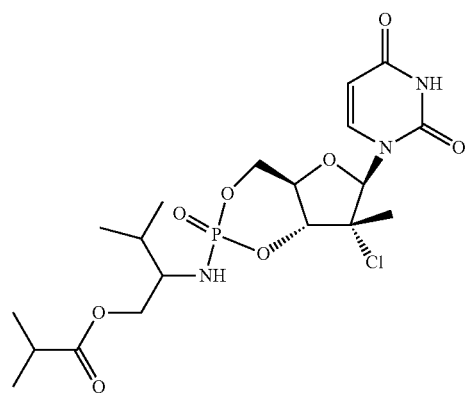
(65)
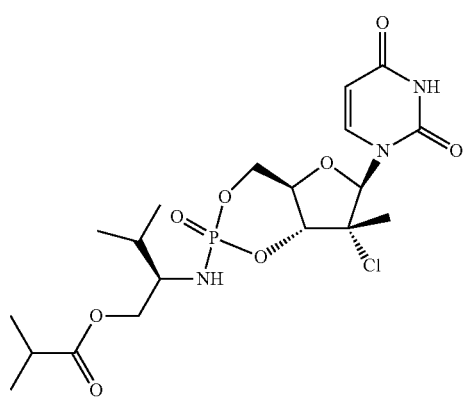
(65i)
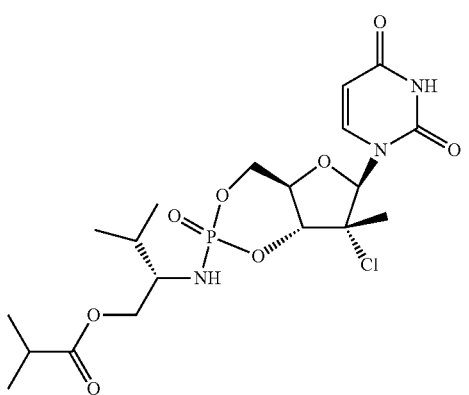
(65ii)
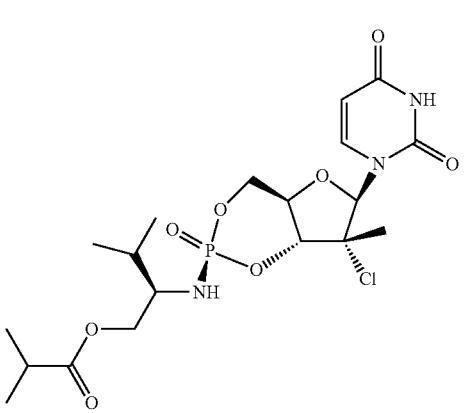
(65ia)
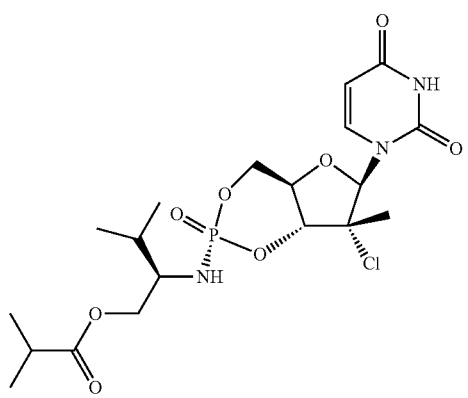
(65ib)
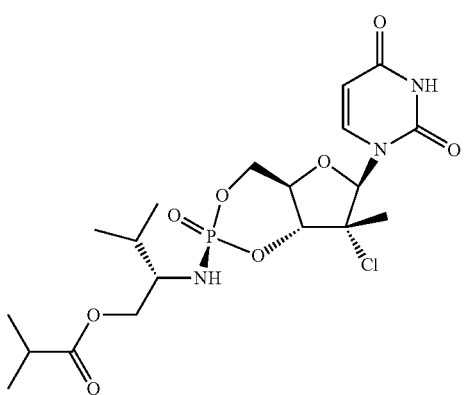
(65iia)
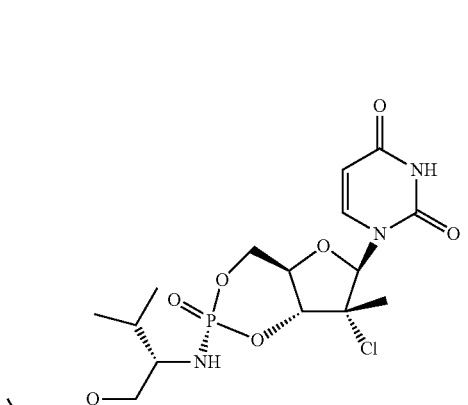
(65iib)
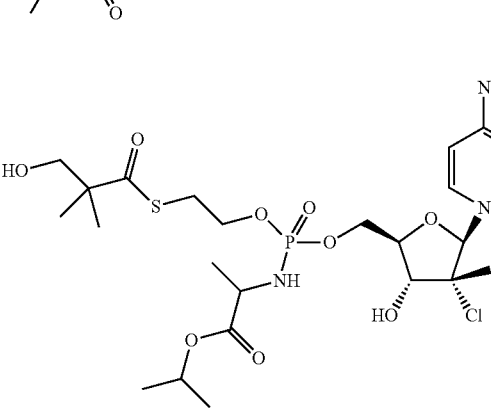
(66)

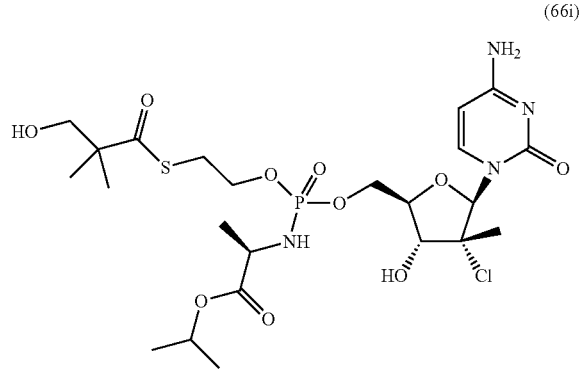
(66i)
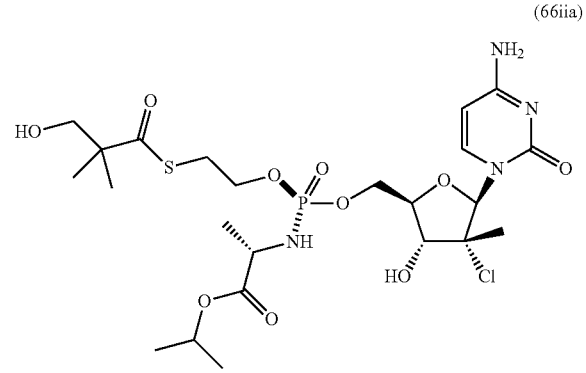
(66iia)
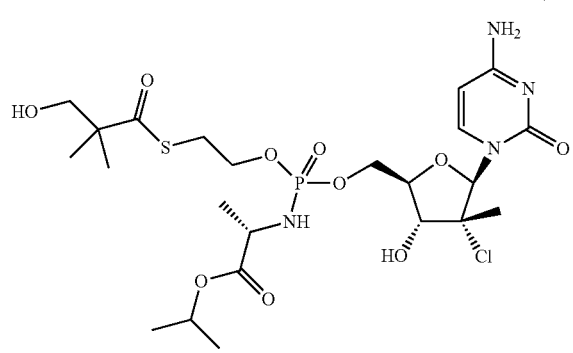
(66ii)
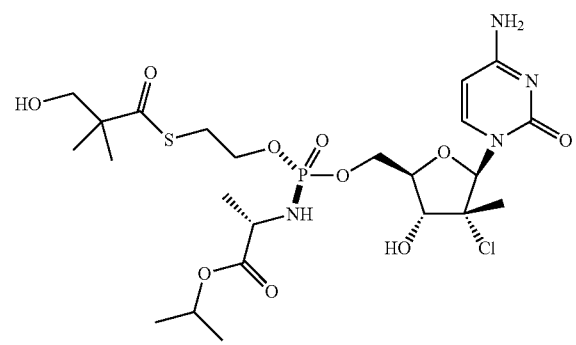
(66iib)
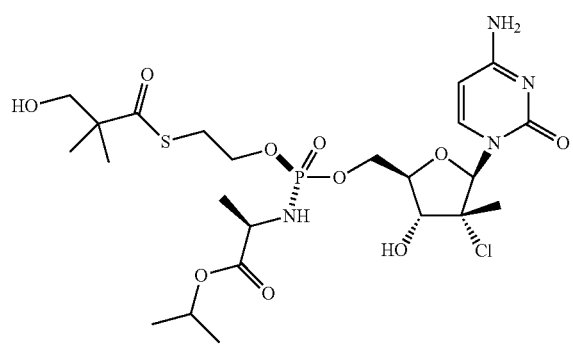
(66ia)
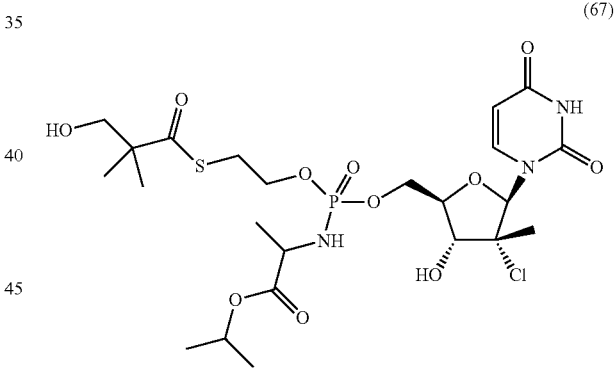
(67)
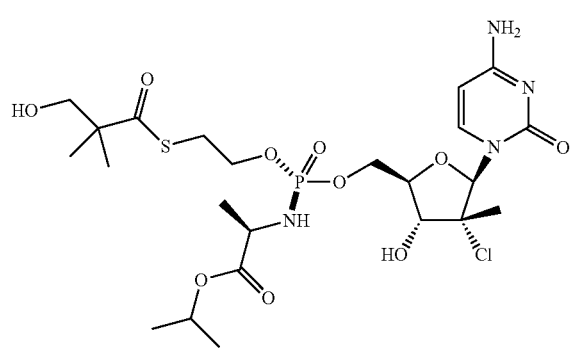
(66ib)
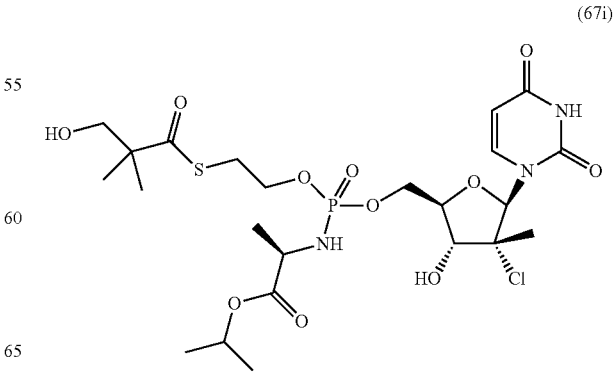
(67i)

(67ii)
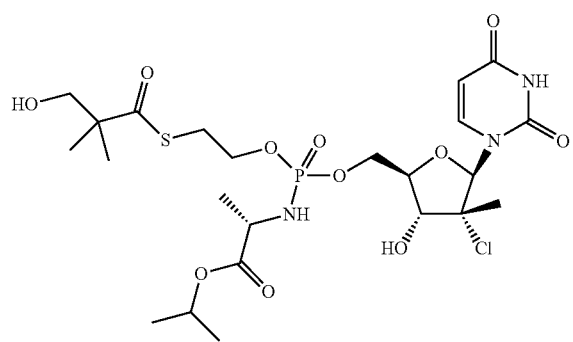
(67ia)
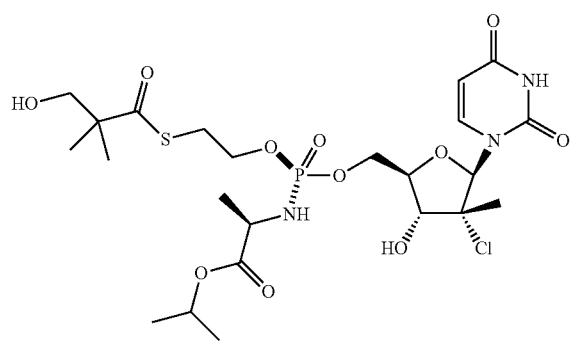
(67ib)
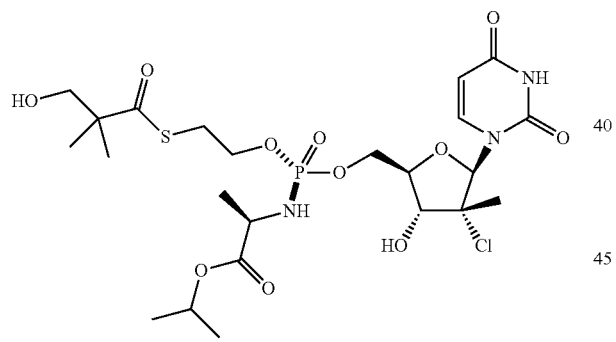
(67iia)
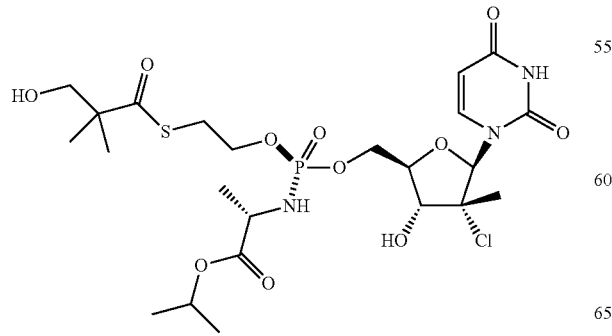
(67iib)
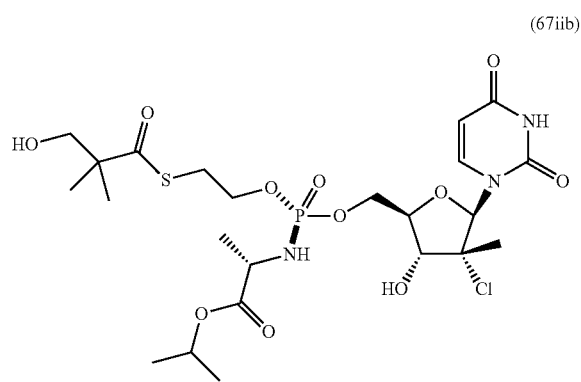
(70)
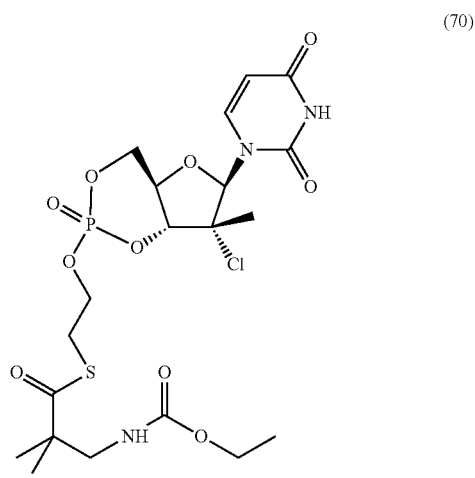
(70a)
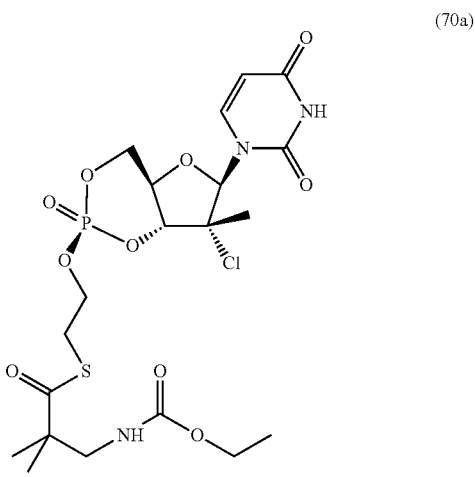

(70b)
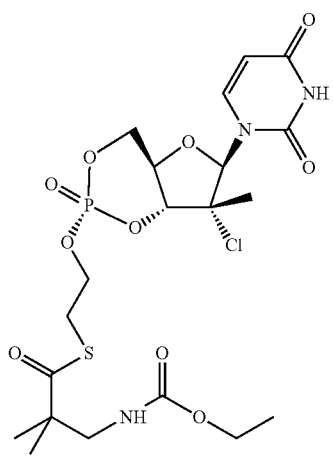
(71)
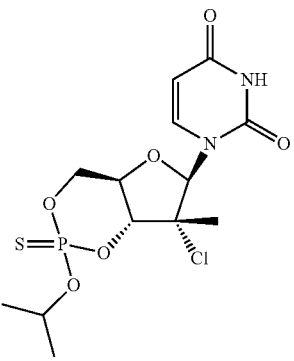
(71a)
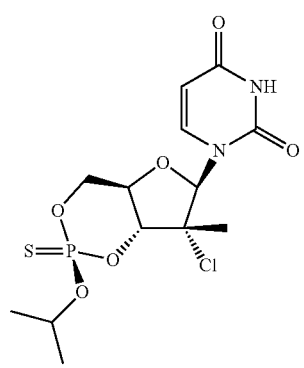
(71b)
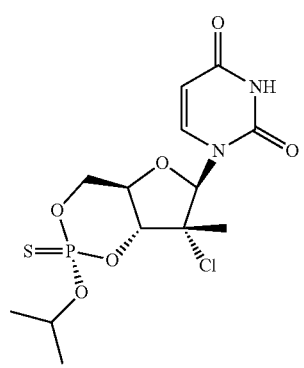
(72)
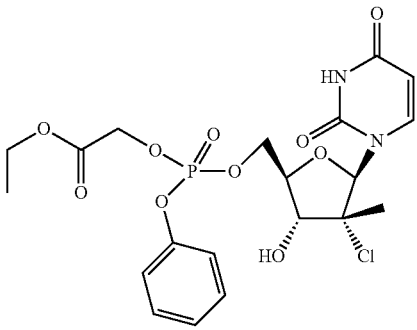
(72a)
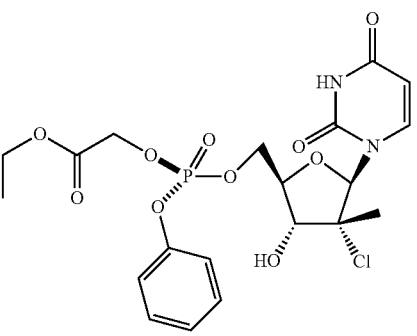
(72b)
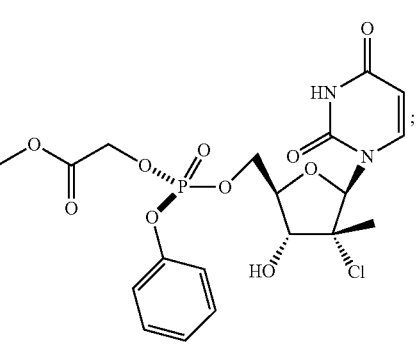
or a pharmaceutically acceptable salt, solvate, stereoisomeric form, tautomeric form or polymorphic form thereof.
In certain embodiments, provided herein are compounds according to any of Formulas (76)-(104iib):
(76)
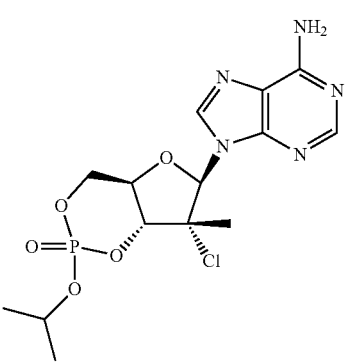

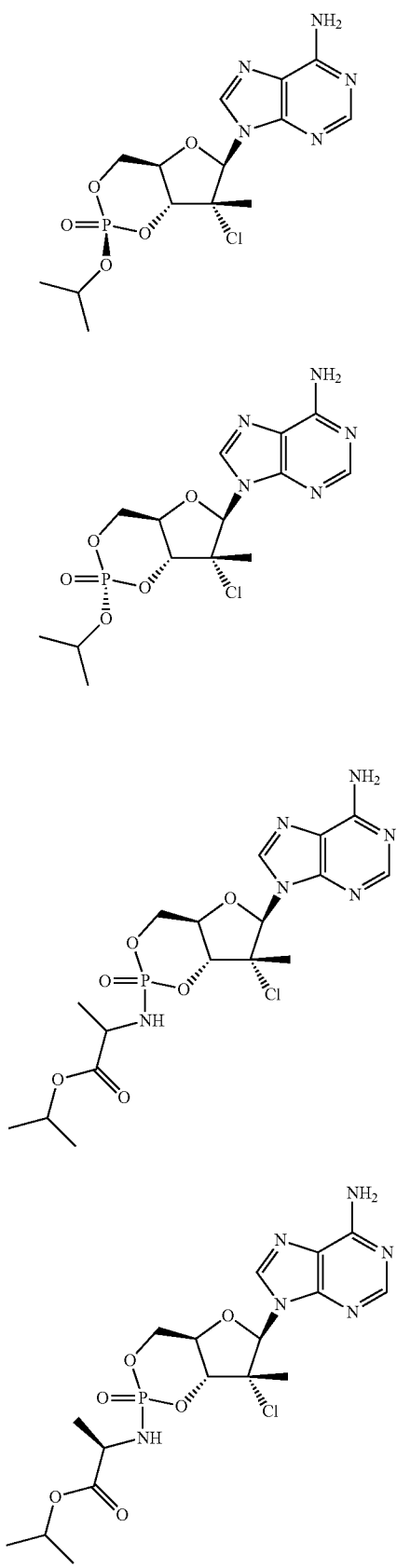
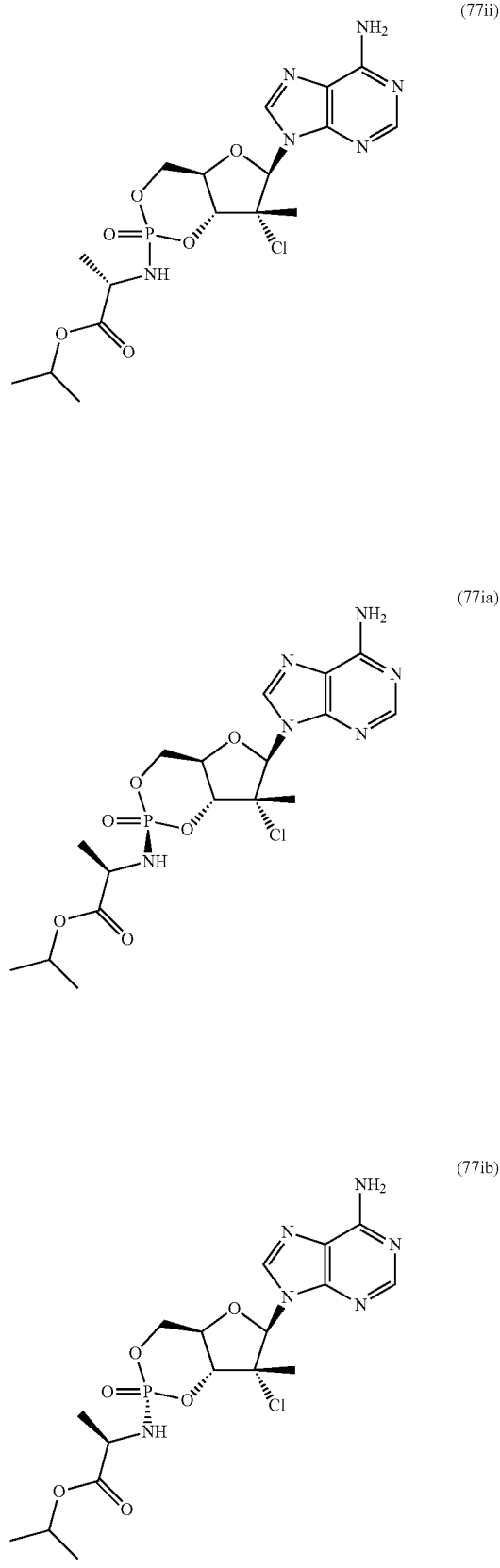

109
-continued
(77iia)
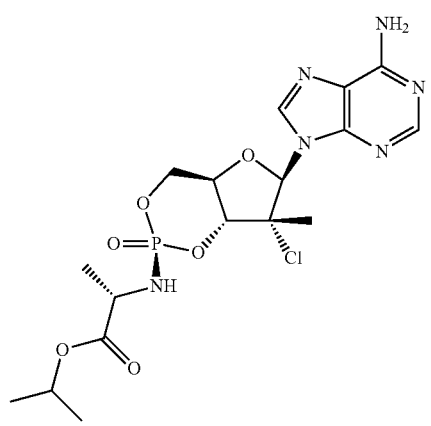
(77iib)
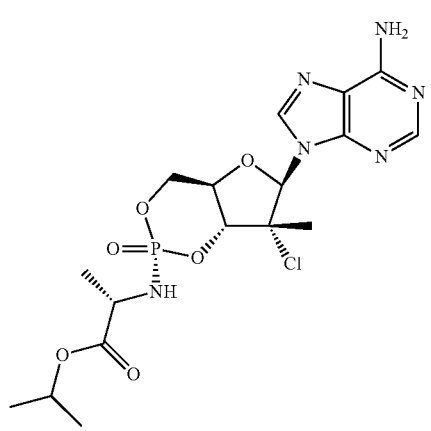
(79)
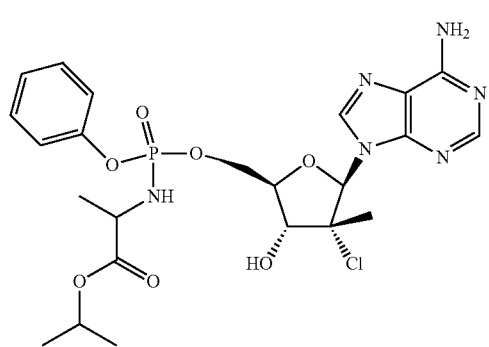
(79i)
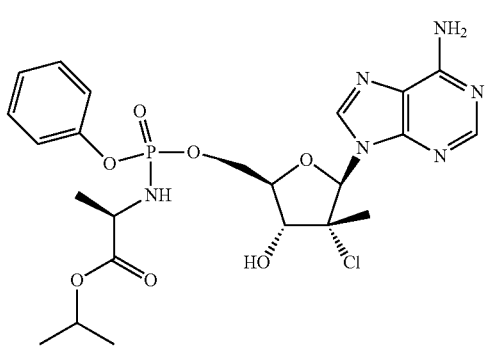
110
-continued
(79ii)
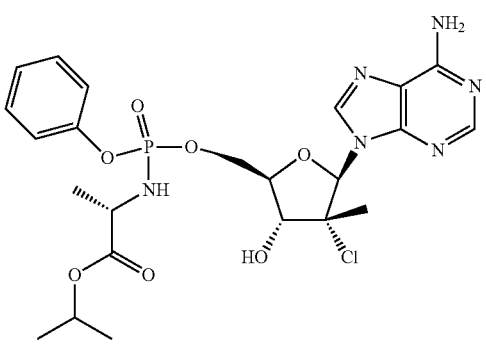
(79ia)
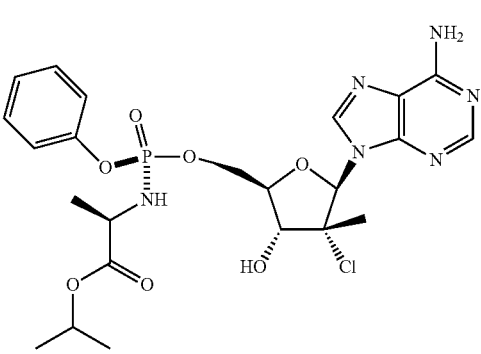
(79ib)
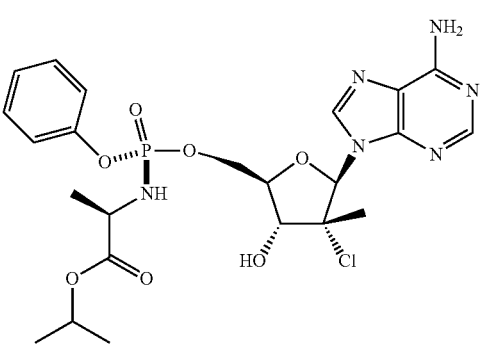
(79iia)
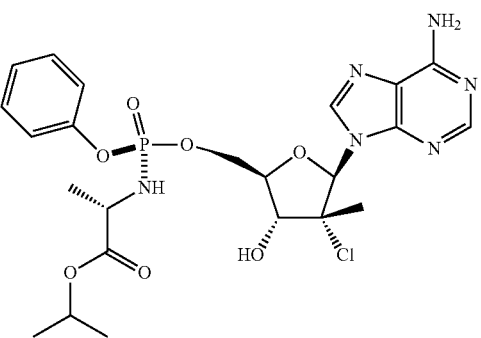

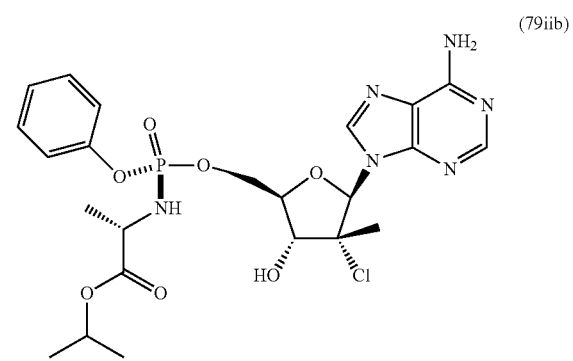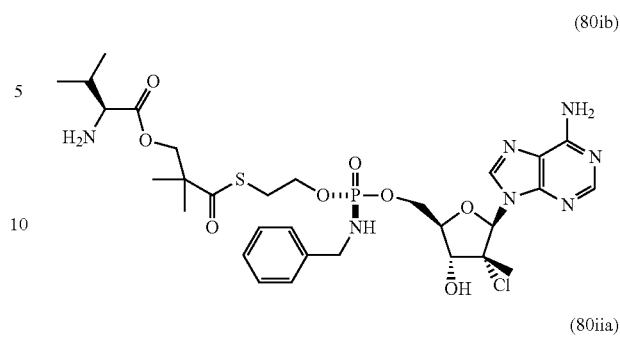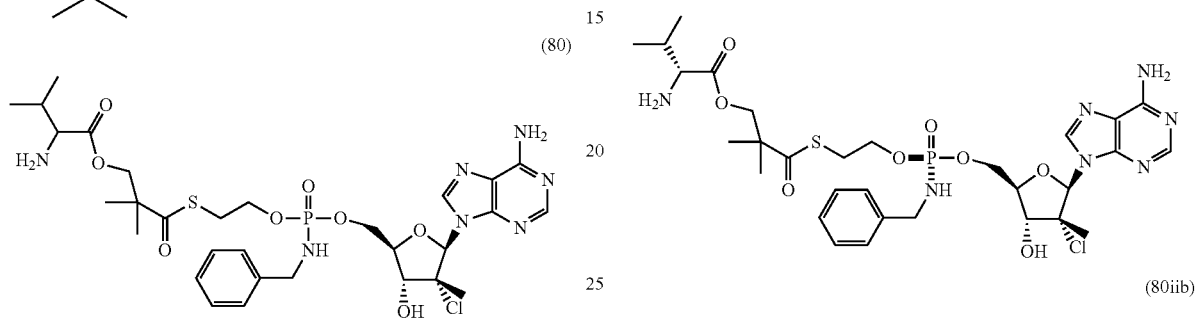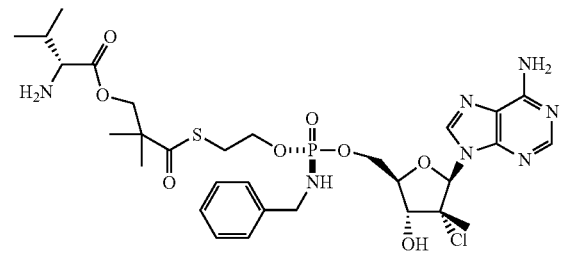

113                                                                                    114
-continued                                                                         -continued
(81ii) 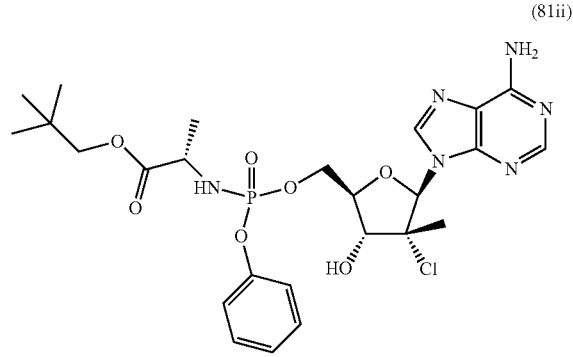
(81iib) 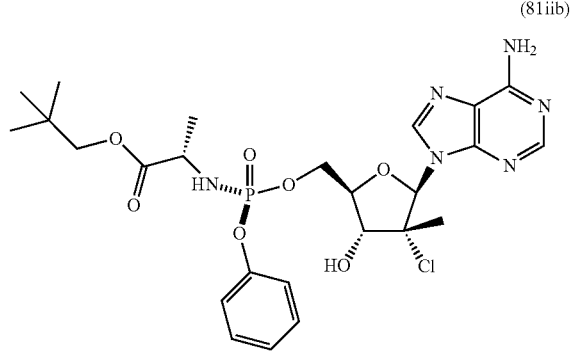
(81ia) 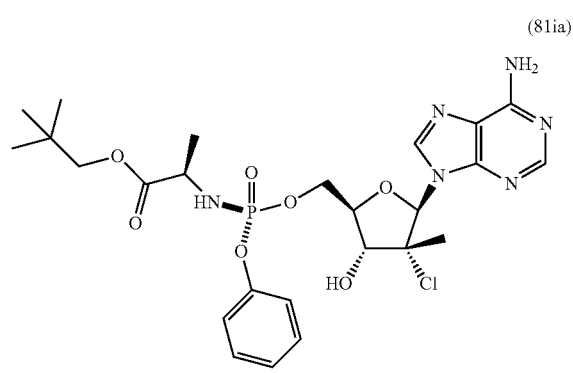
(82) 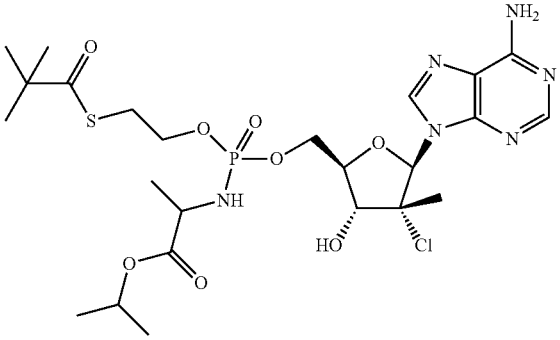
(81ib) 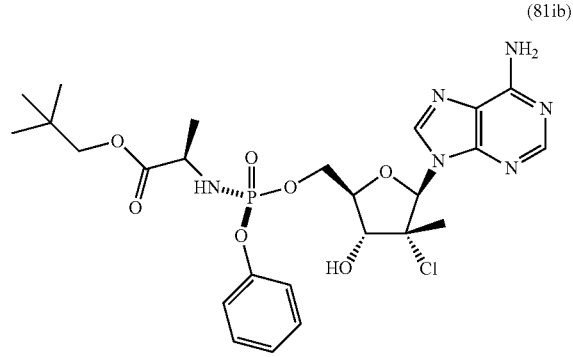
(82i) 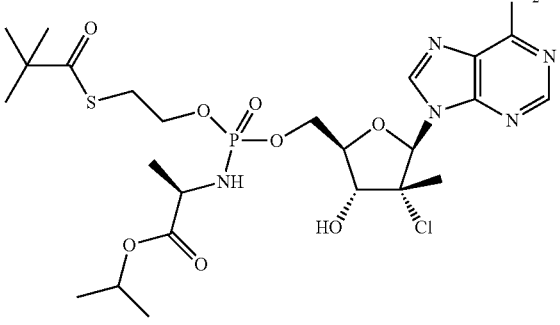
(81iia) 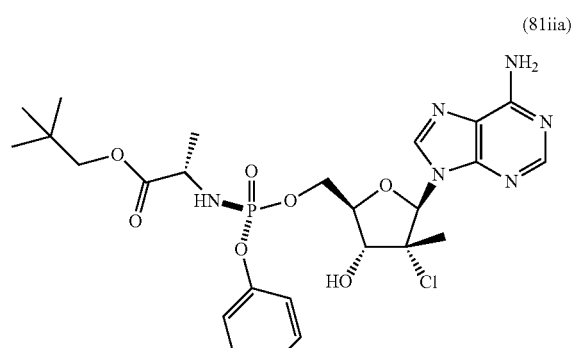
(82ii)

115
-continued
(82ia)
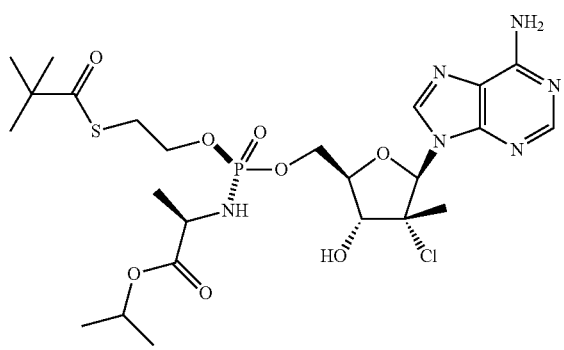
(82ib)
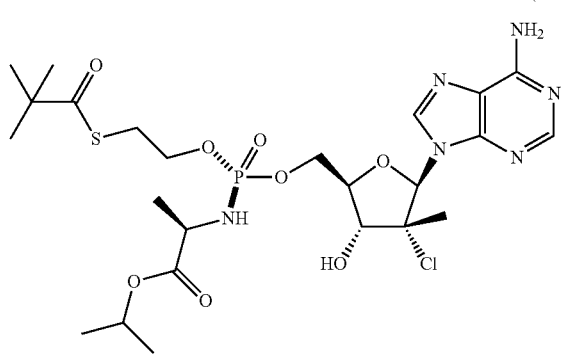
(82iia)
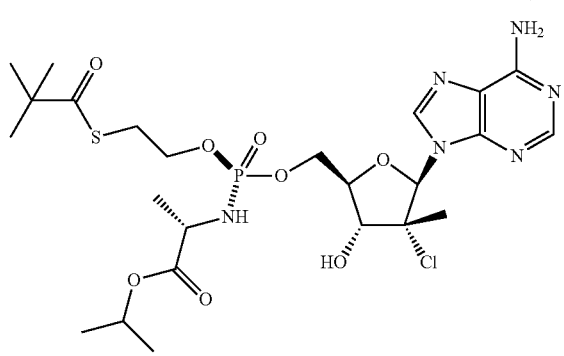
(82iib)
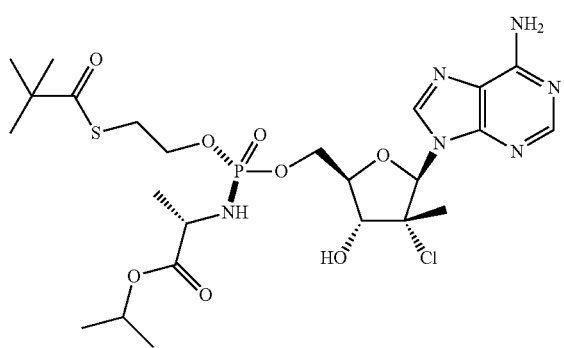
116
-continued
(84)
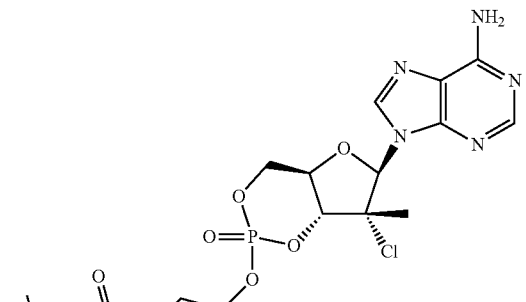
(84a)
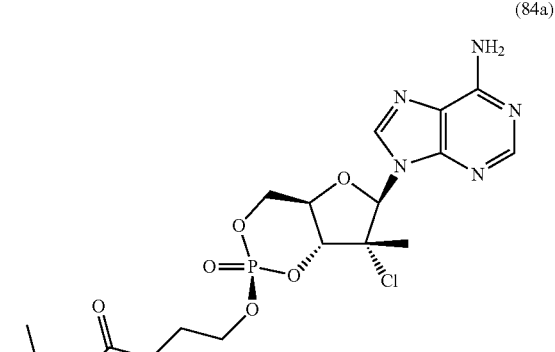
(84b)
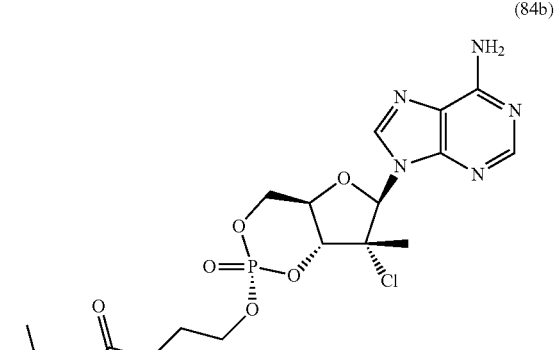
(85)
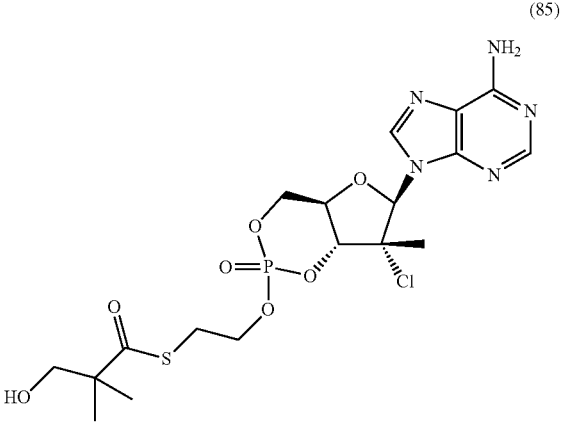

(85a)
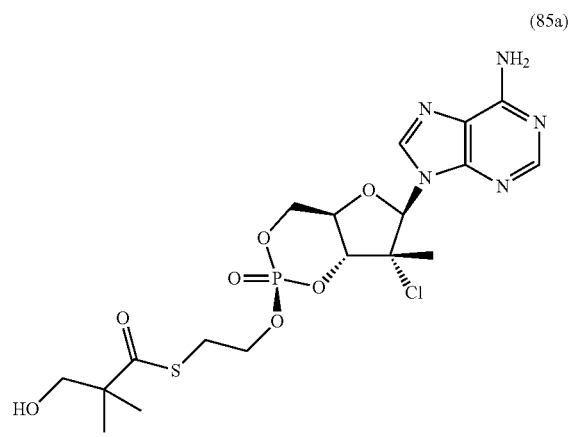
(85b)
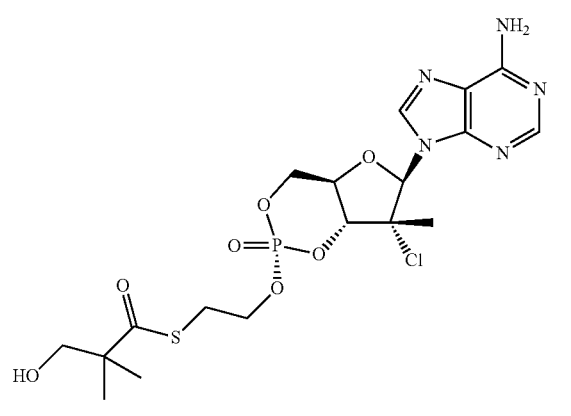
(86)
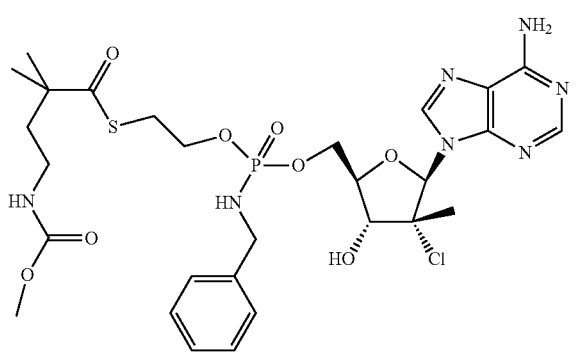
(86a)
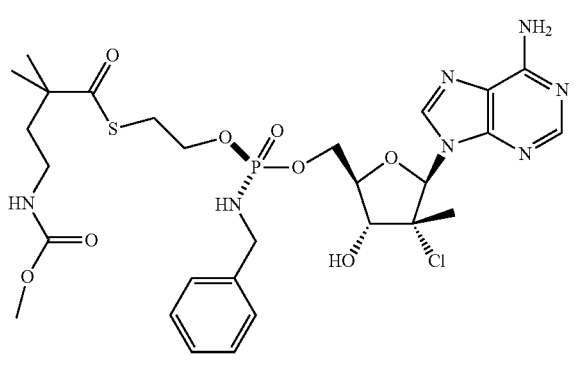
(86b)
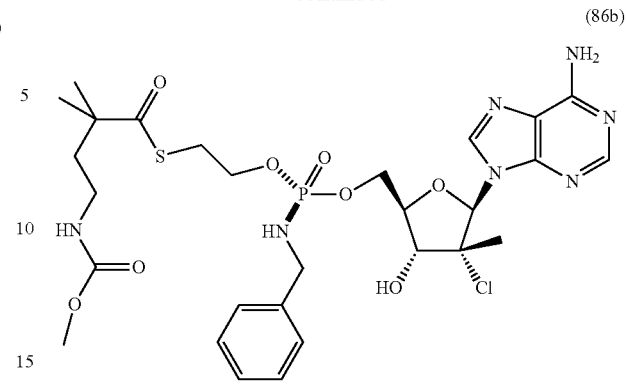
(87)
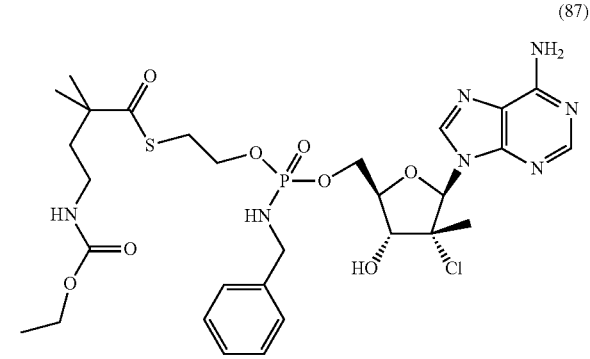
(87a)
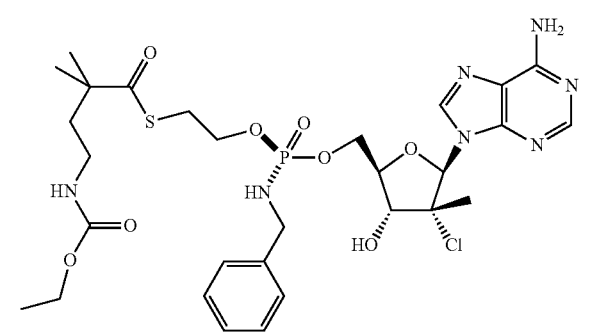
(87b)
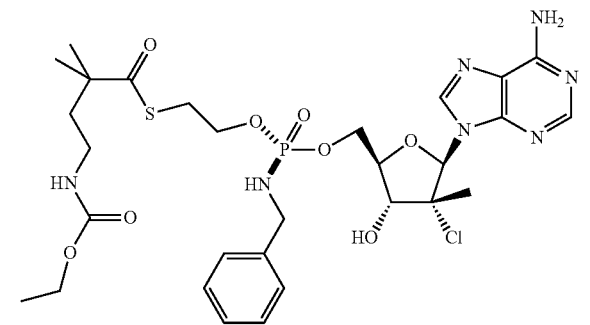

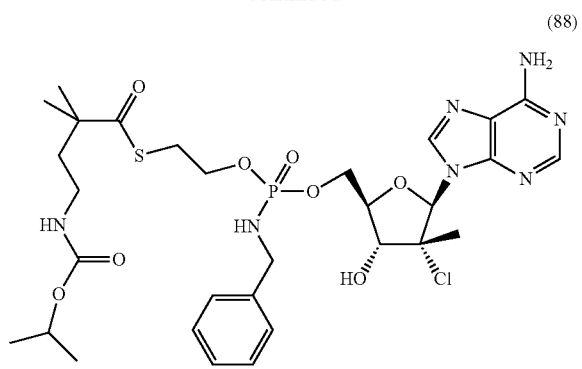
(88)
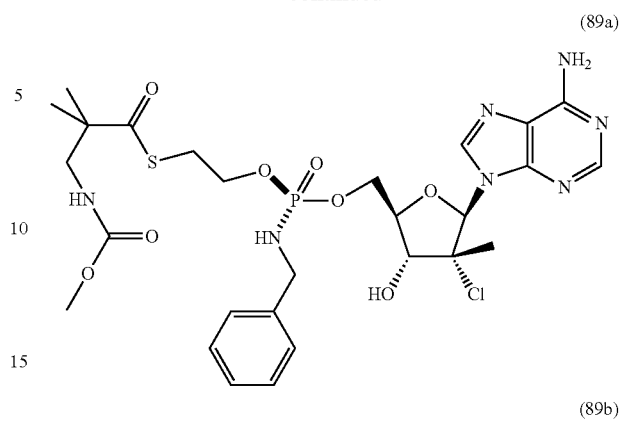
(89a)
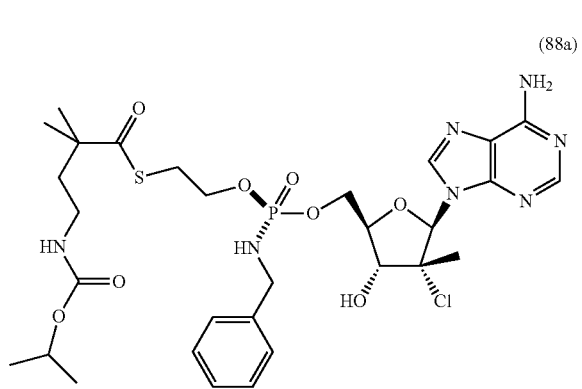
(88a)
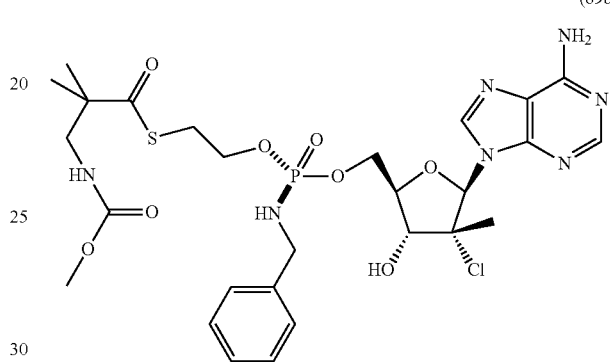
(89b)
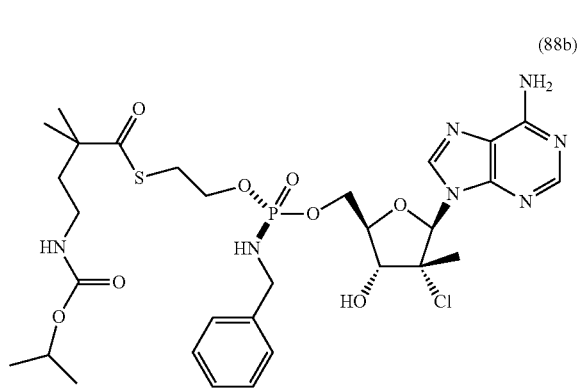
(88b)
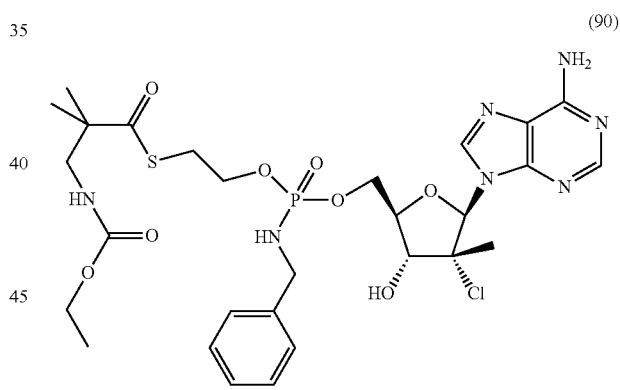
(90)
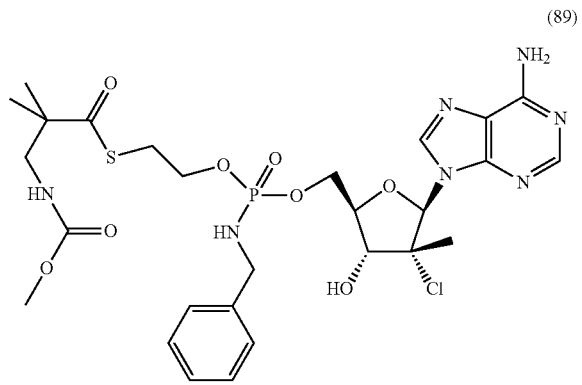
(89)
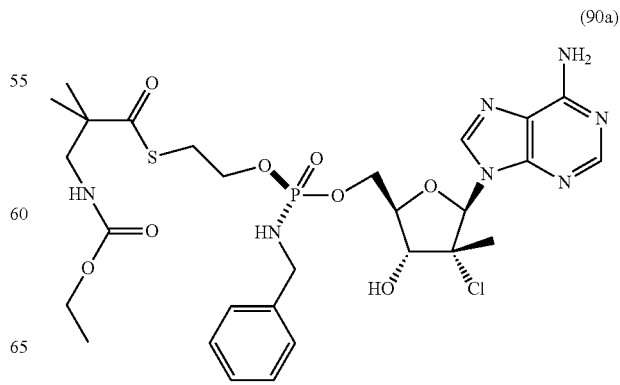
(90a)

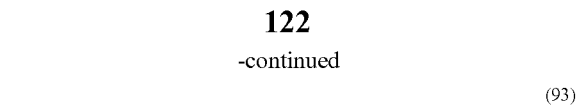
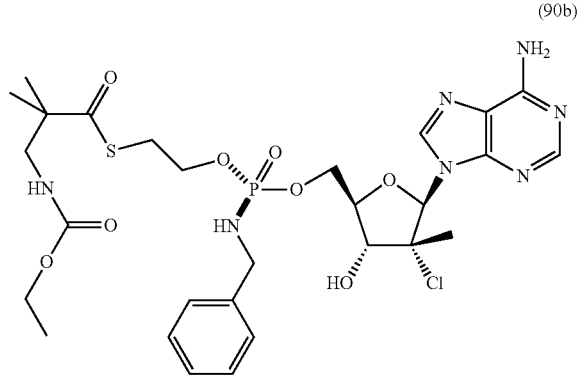
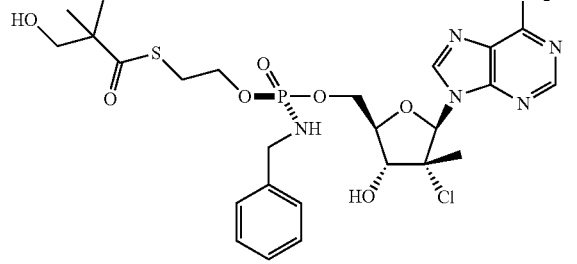
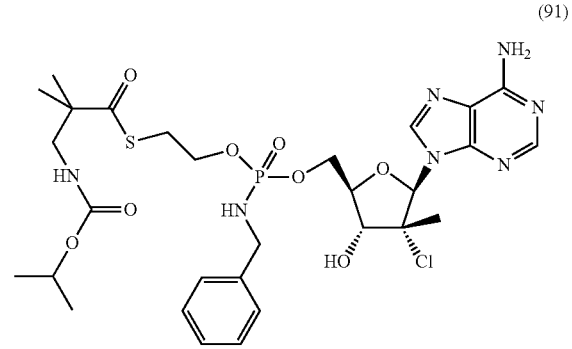
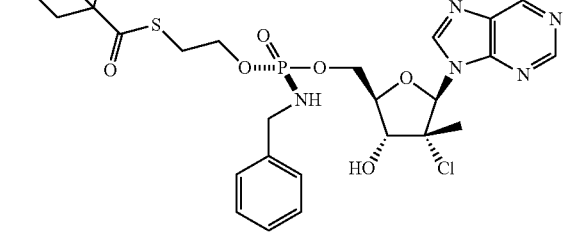
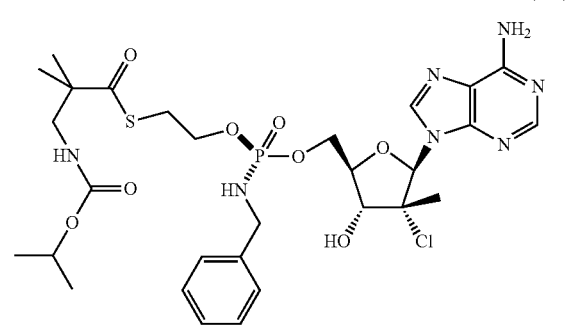
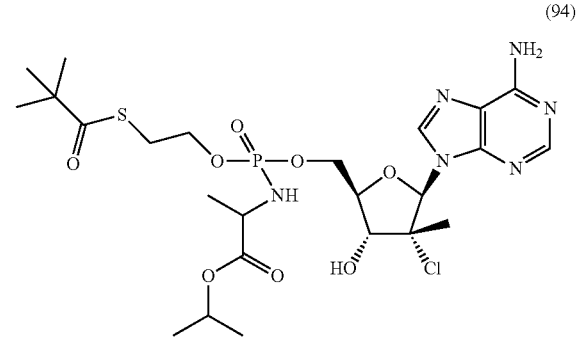
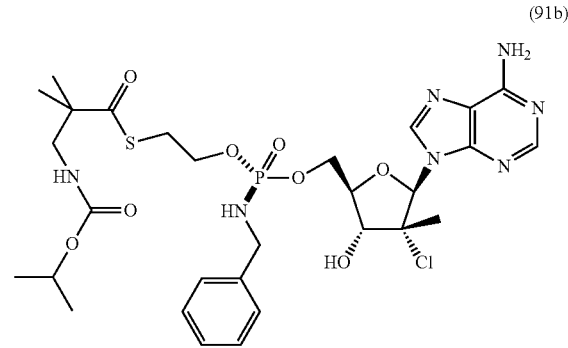
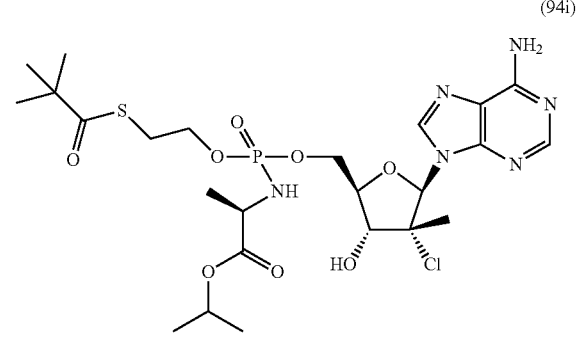

(94ii)
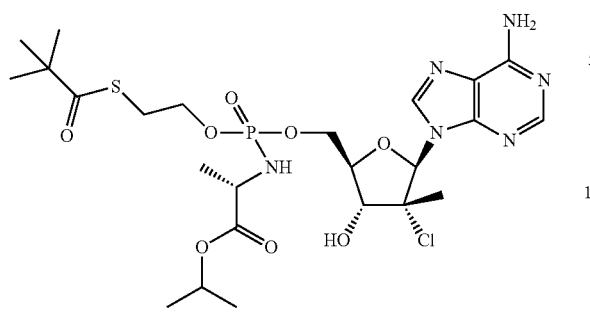
(94ia)
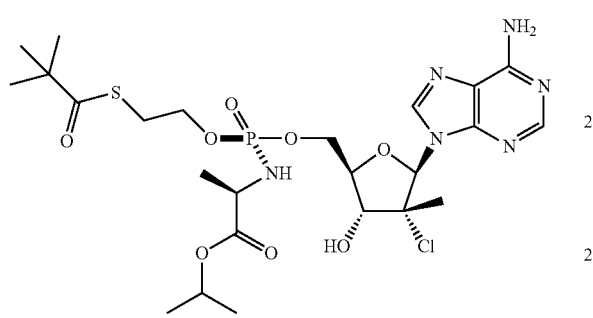
(94ib)
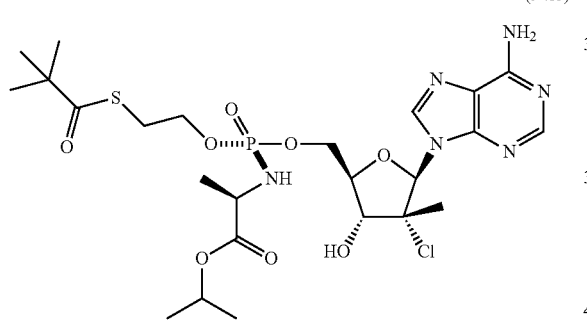
(94iia)
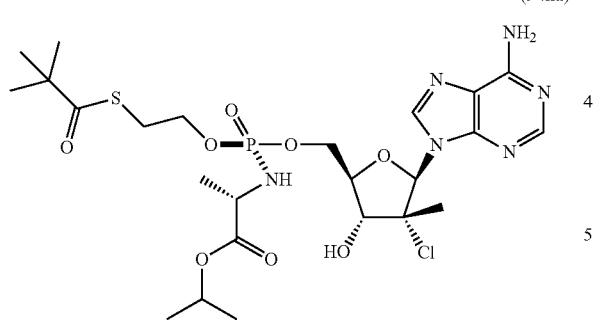
(94iib)
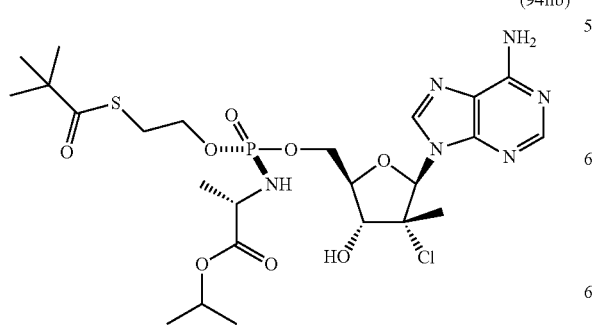
(95)
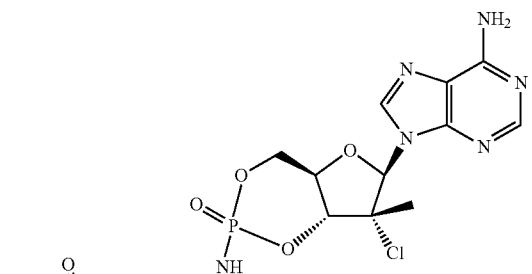
(95i)
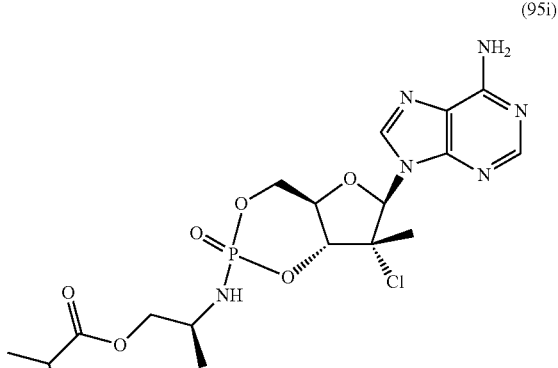
(95ii)
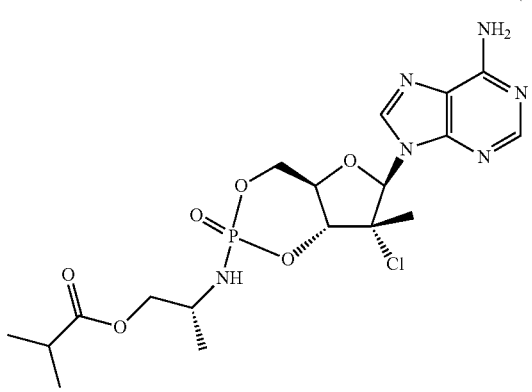
(95ia)
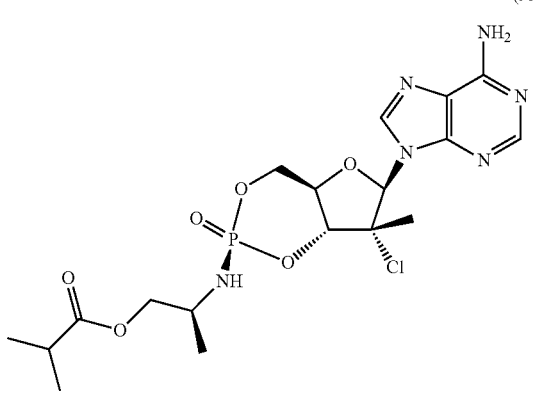

125
-continued
(95ib)
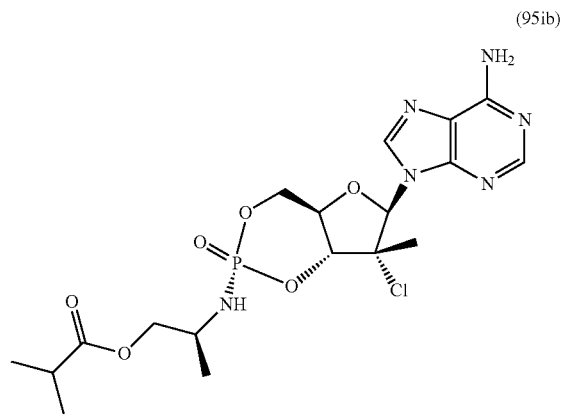
(95iia)
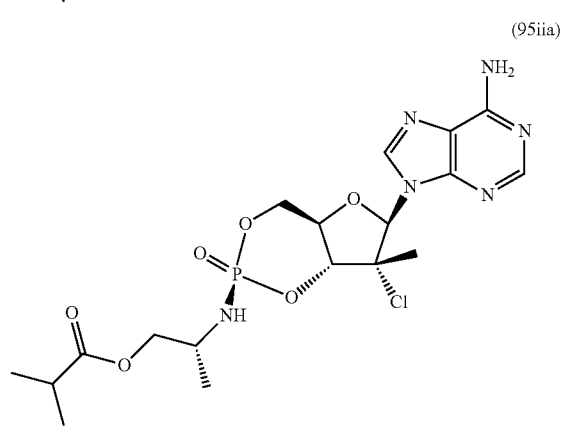
(95iib)
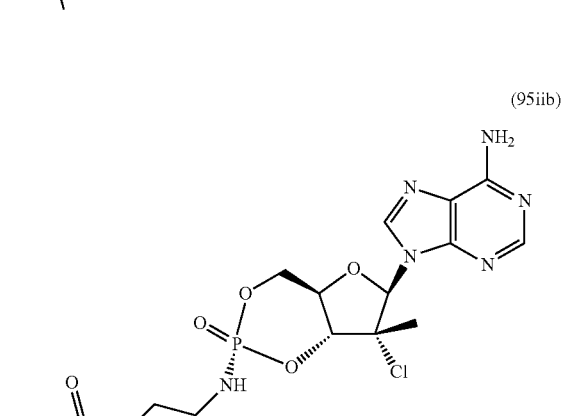
(96)
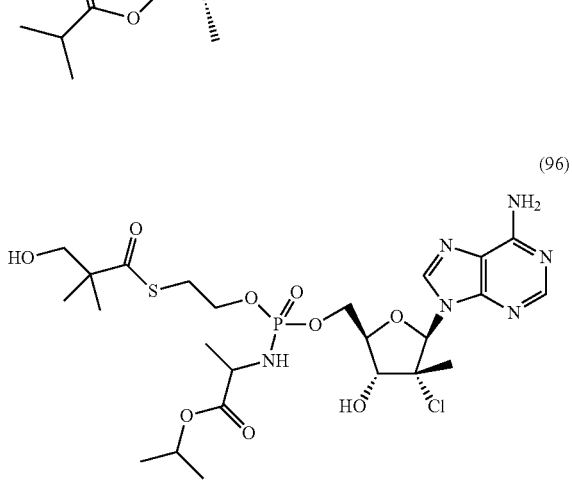
126
-continued
(96i)
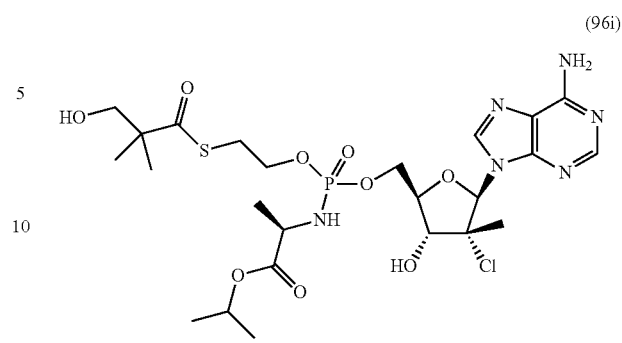
(96ii)
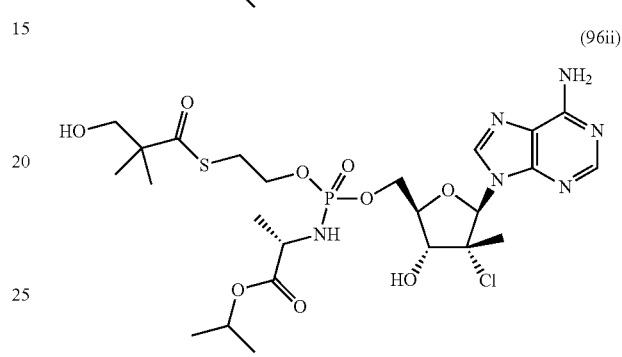
(96ia)
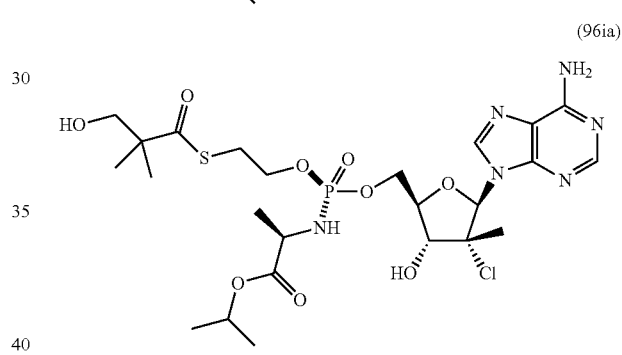
(96ib)
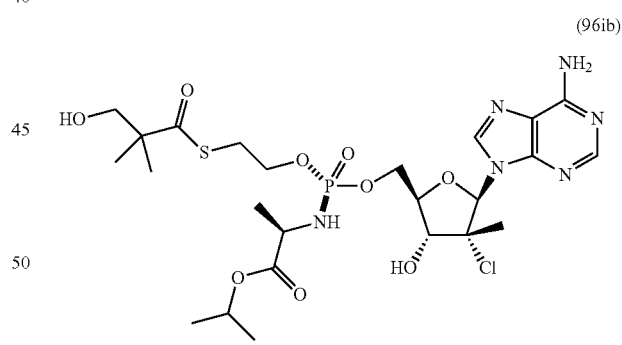
(96iia)
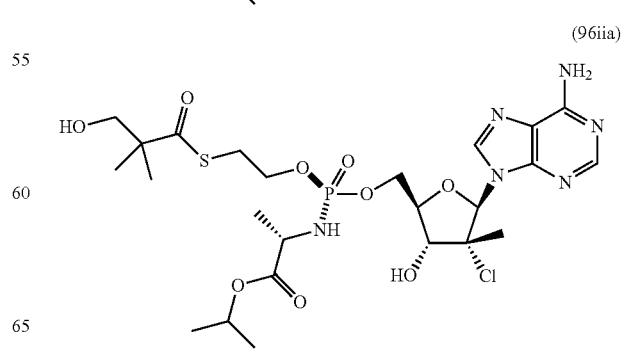

(96iib)
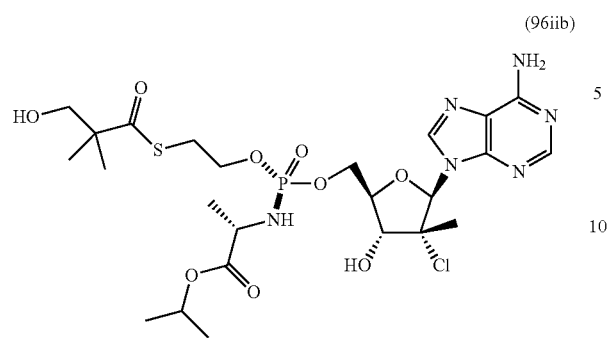
(98)
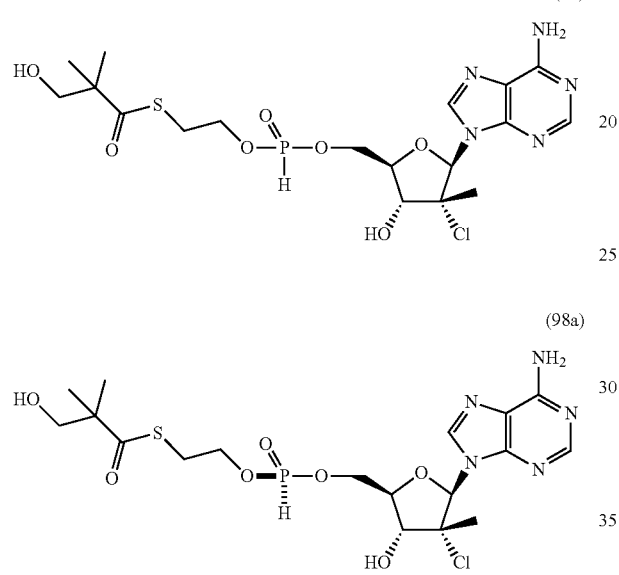
(98a)
(98b)
(100)
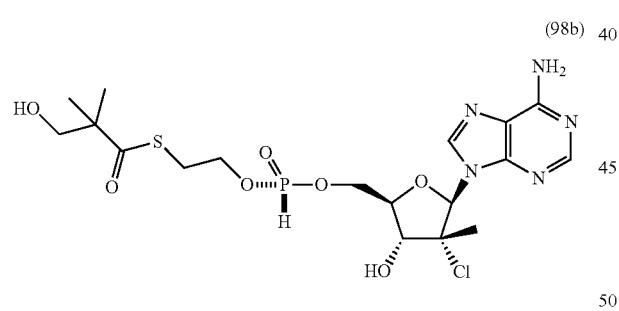
(100a)
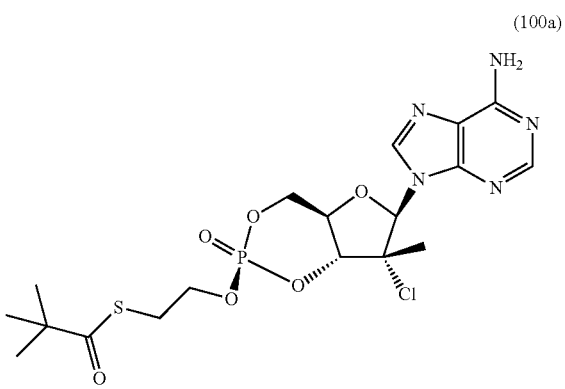
(100b)
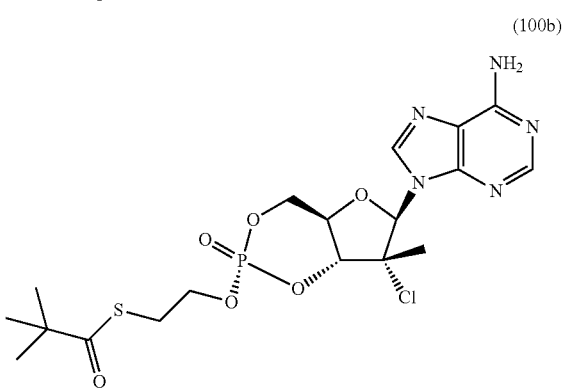
(104)
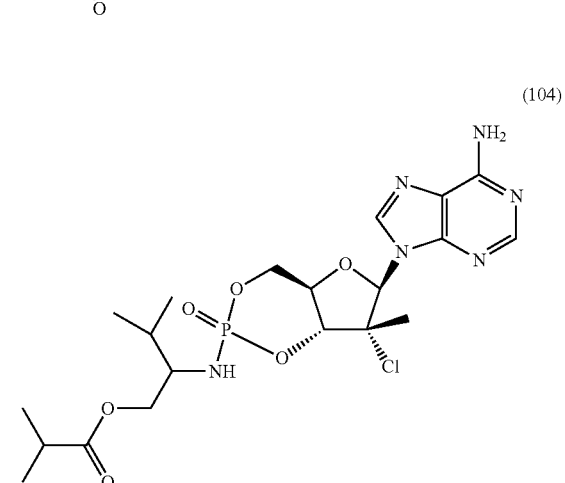
(104i)
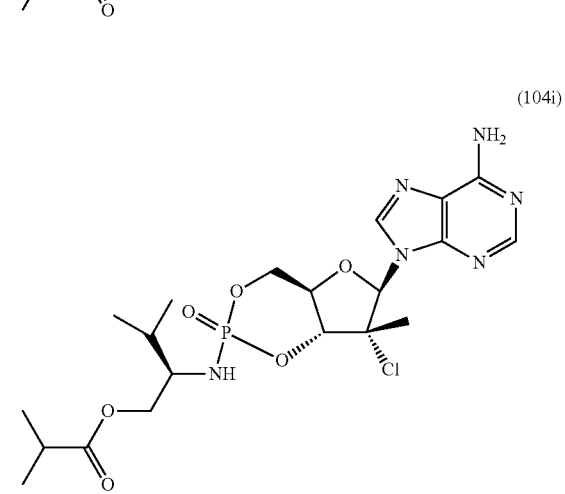

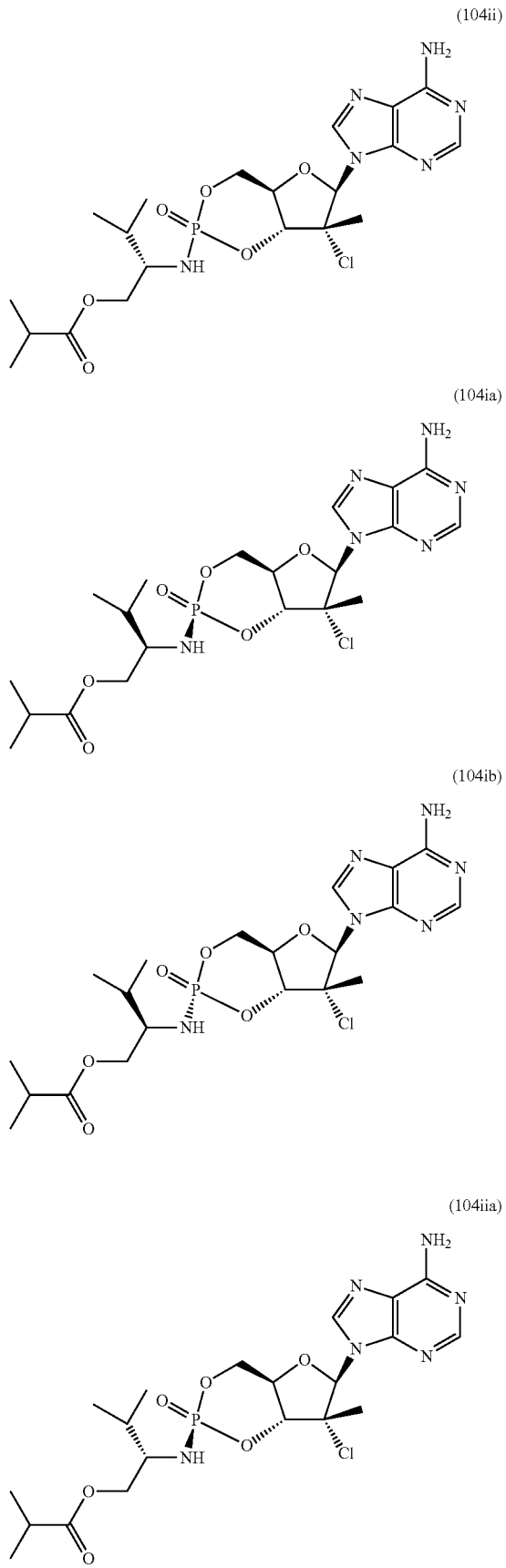
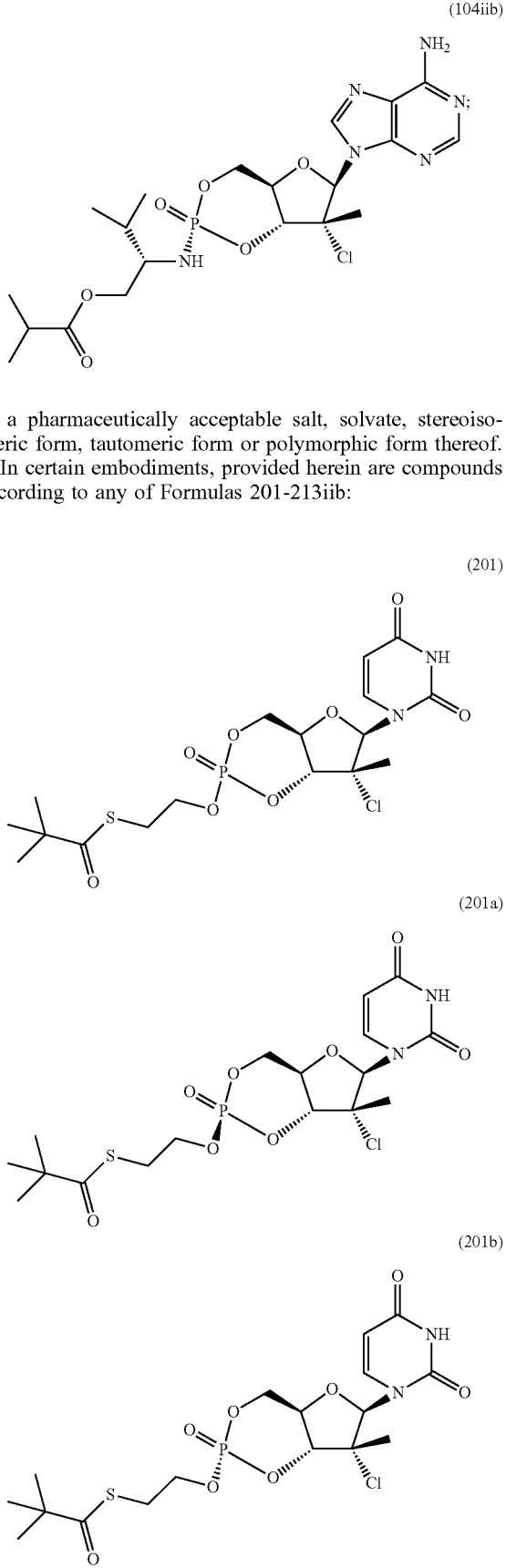
or a pharmaceutically acceptable salt, solvate, stereoisomeric form, tautomeric form or polymorphic form thereof.
In certain embodiments, provided herein are compounds according to any of Formulas 201-213iib:

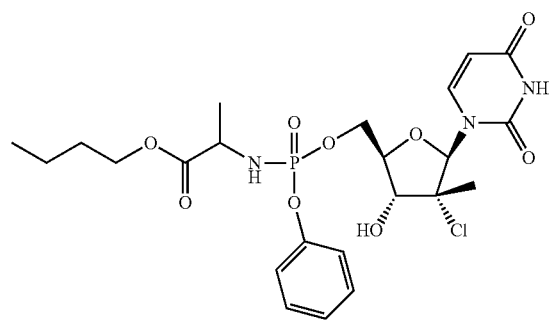
(202)
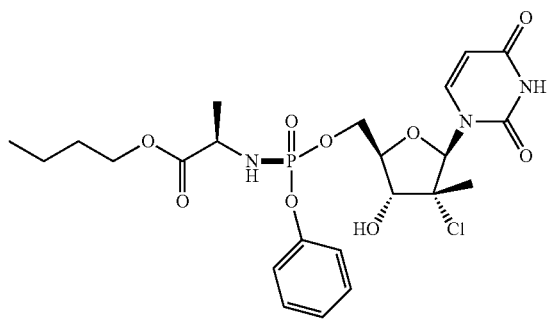
(202ib)
(202i)
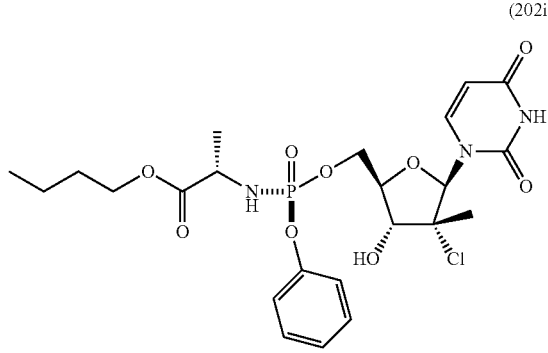
(202iia)
(202ii)
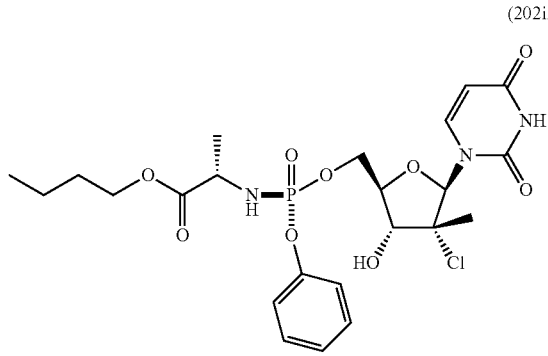
(202iib)
(202ia)
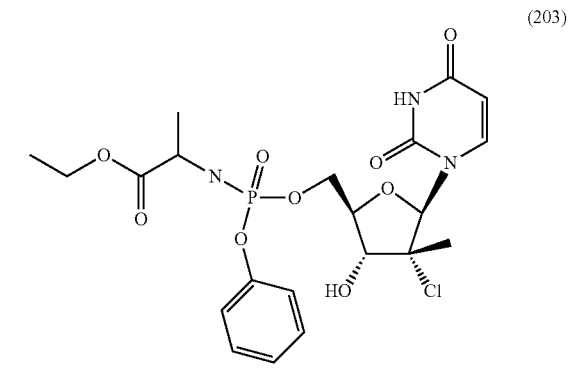
(203)

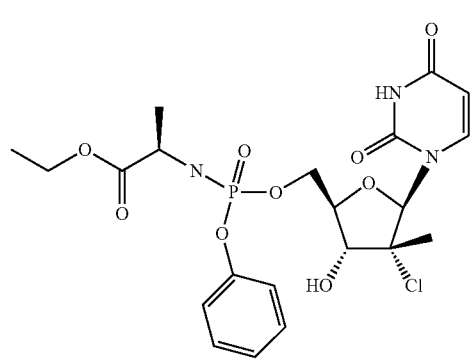
(203i)
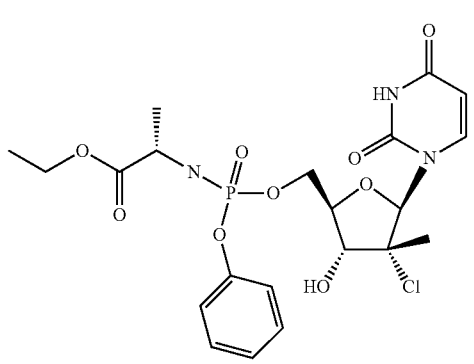
(203ii)
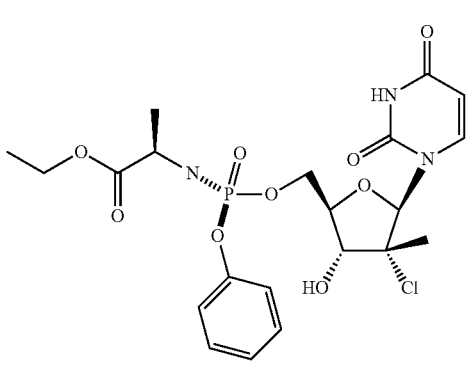
(203ia)
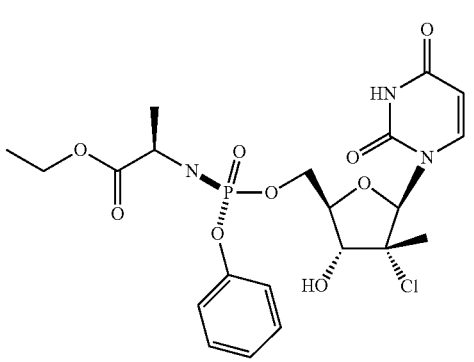
(203ib)
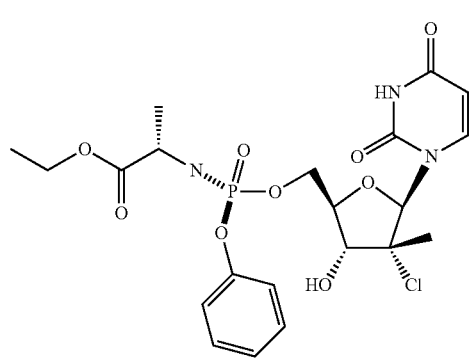
(203iia)
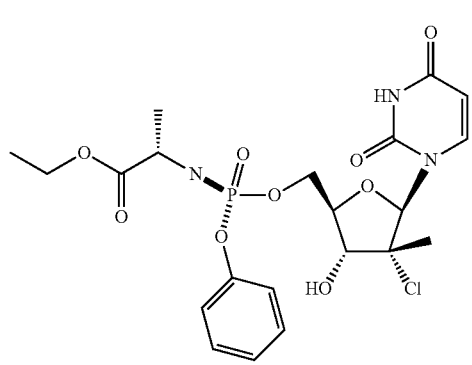
(203iib)
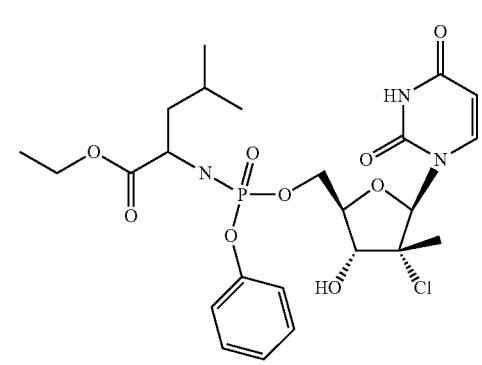
(204)
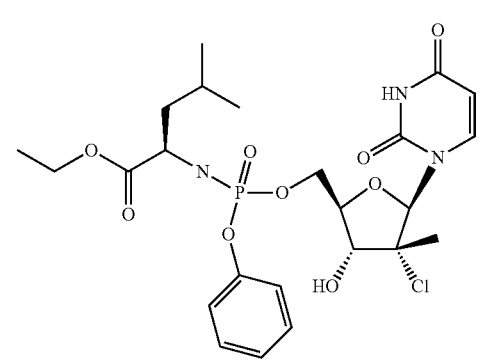
(204i)

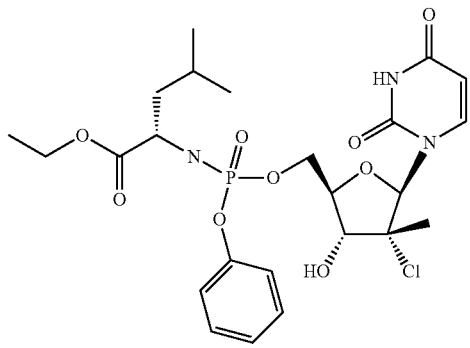
(204ii)
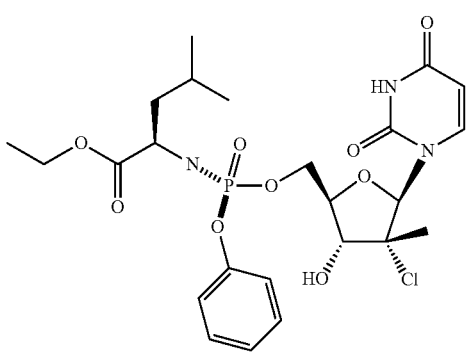
(204ia)
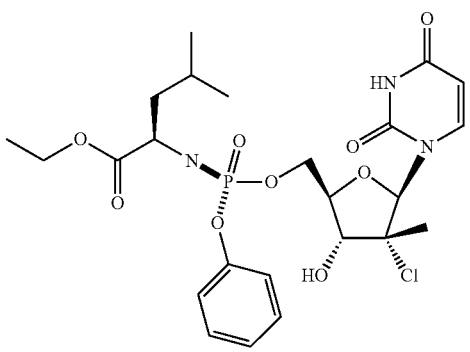
(204ib)
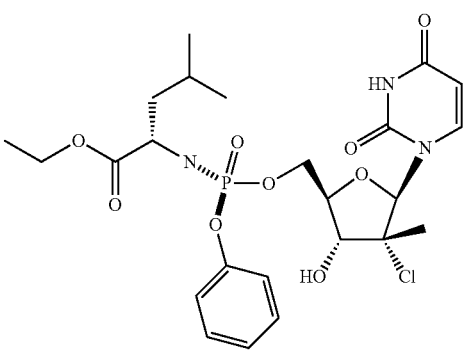
(204iia)
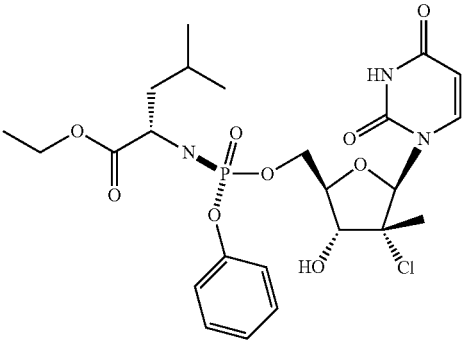
(204iib)
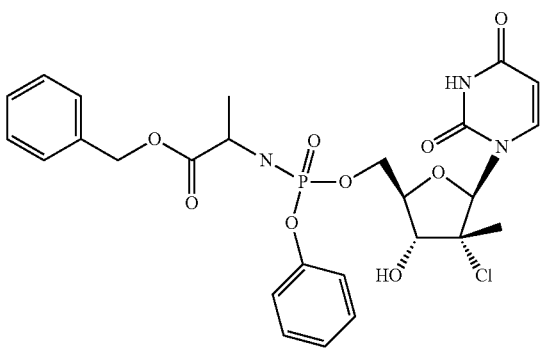
(205)
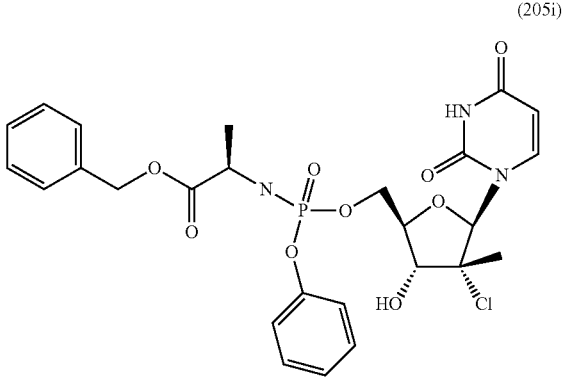
(205i)
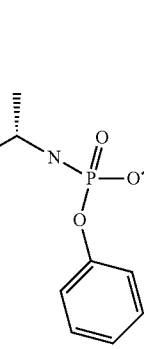
(205ii)

(205ia)
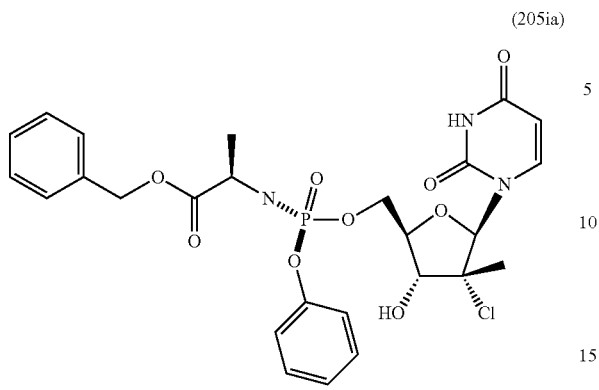
(205ib)
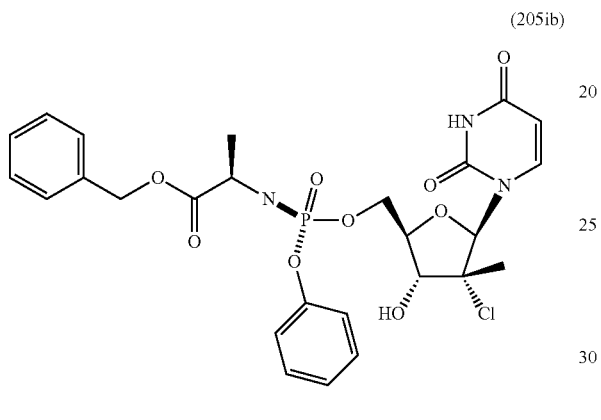
(205iia)
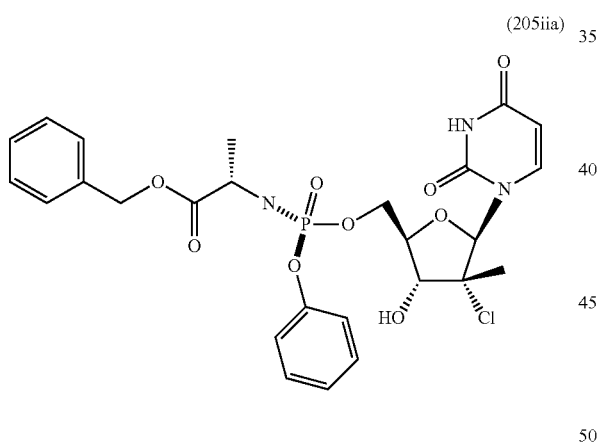
(205iib)
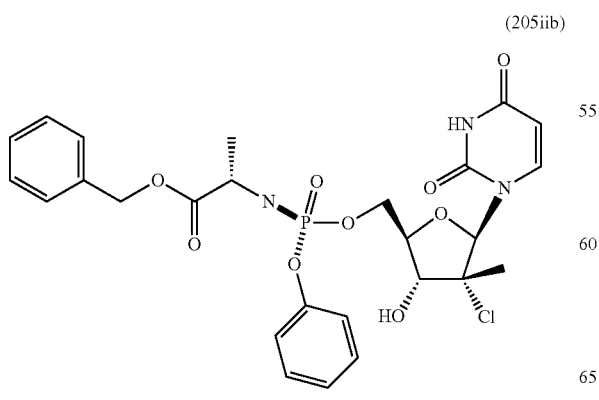
(206)
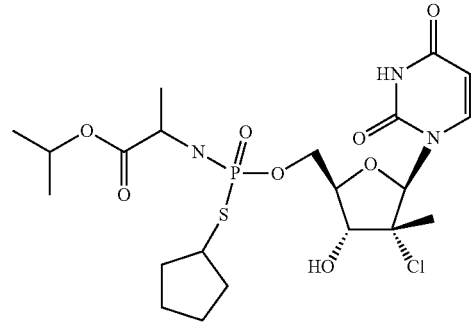
(206i)
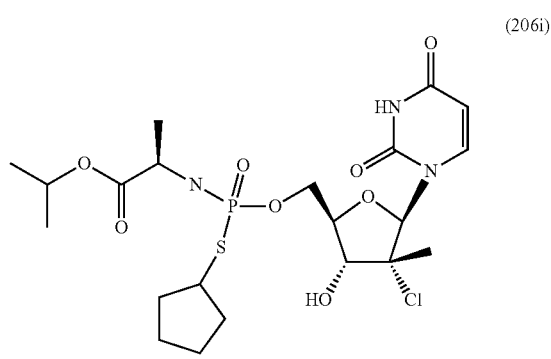
(206ii)
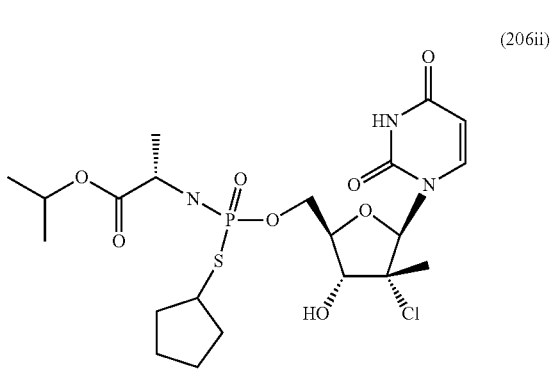
(206ia)
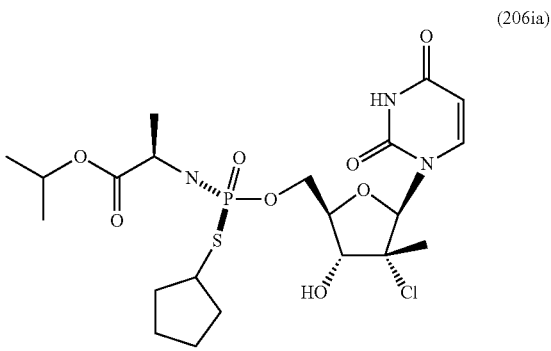

(206ib)
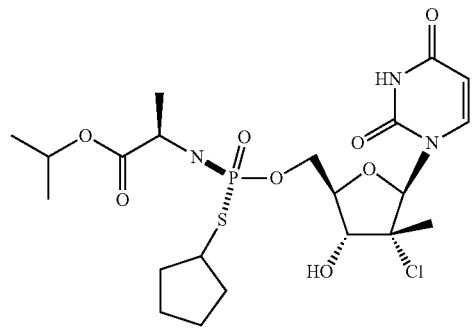
(206iia)
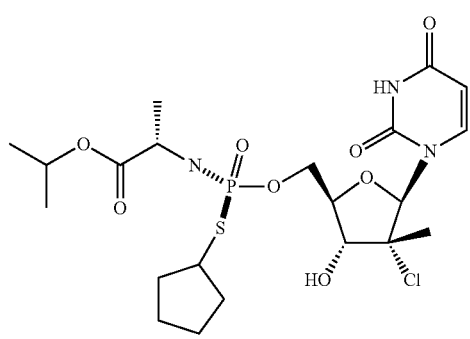
(206iib)
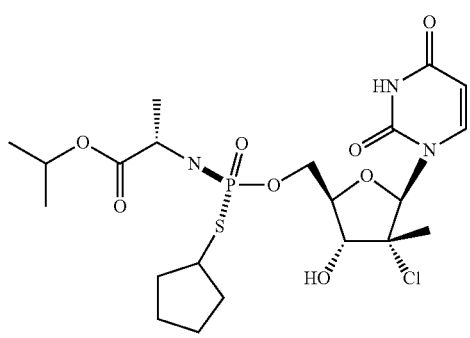
(207)
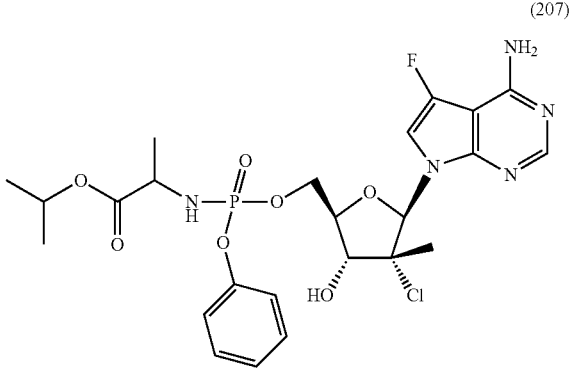
(207i)
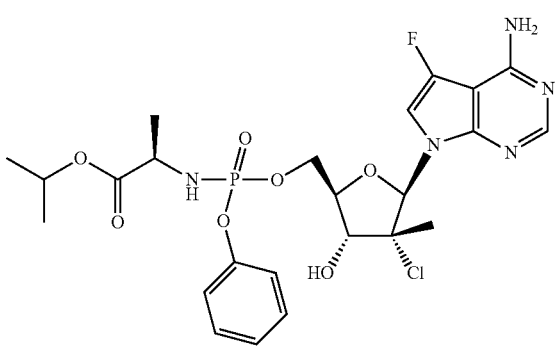
(207ii)
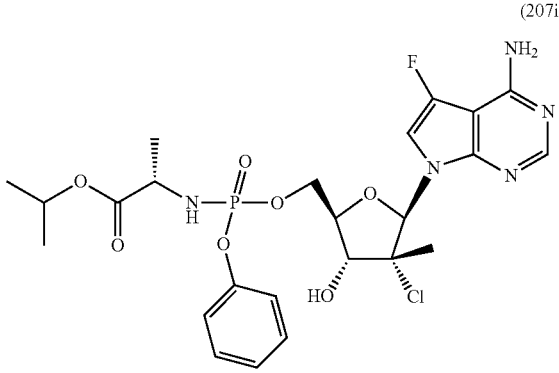
(207ia)
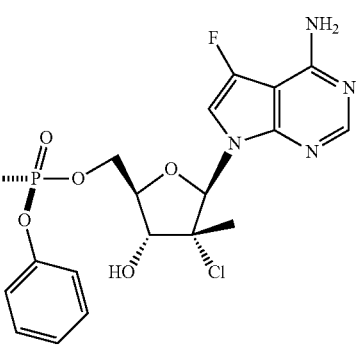
(207ib)
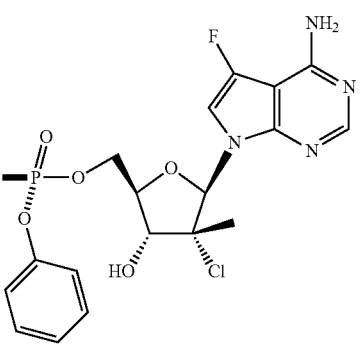

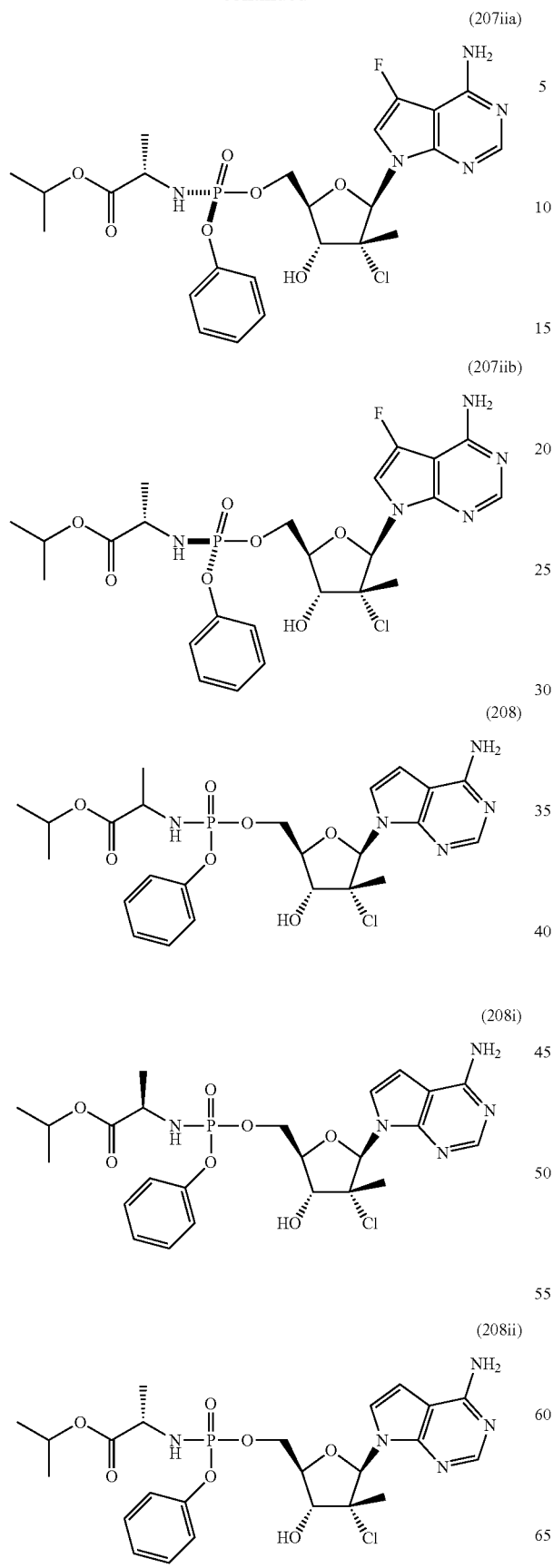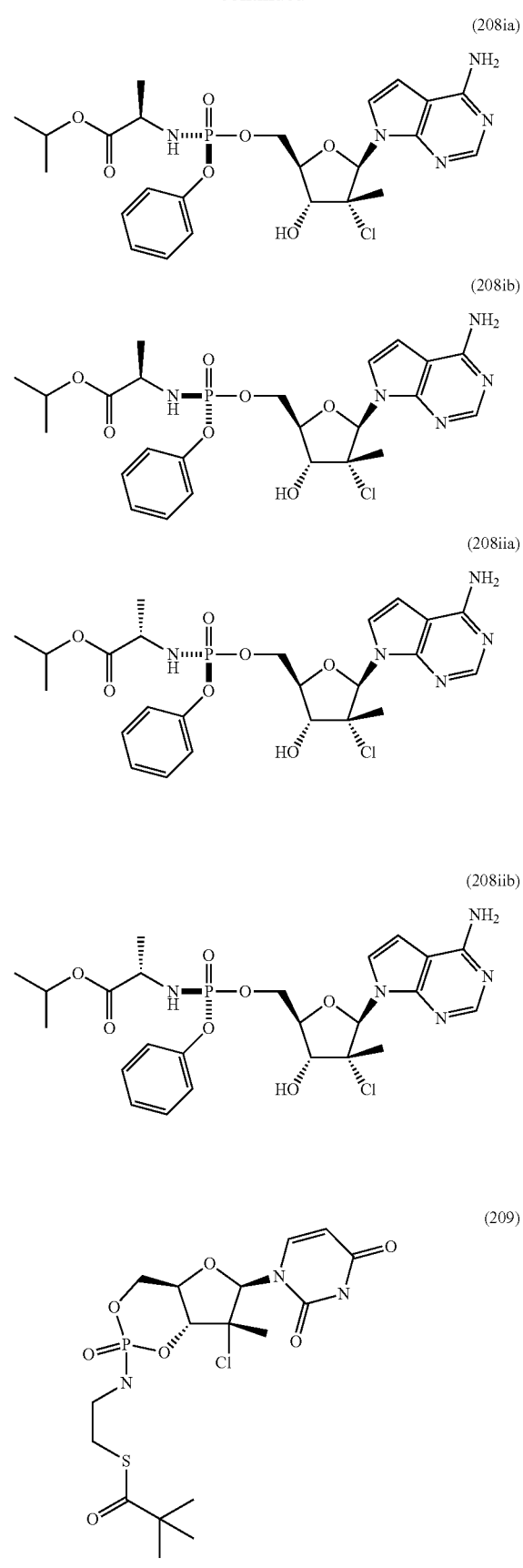

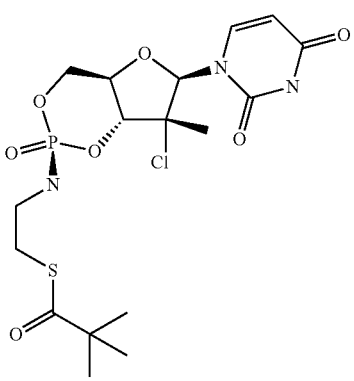
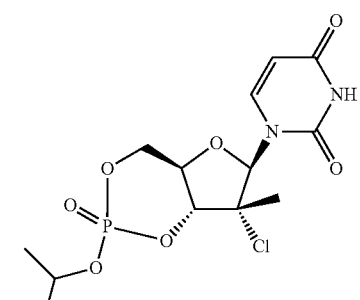
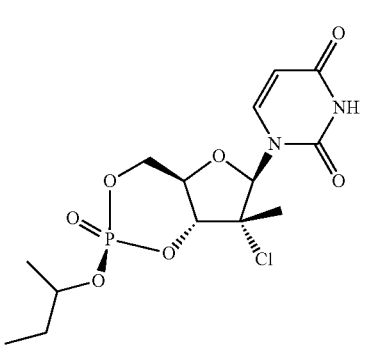
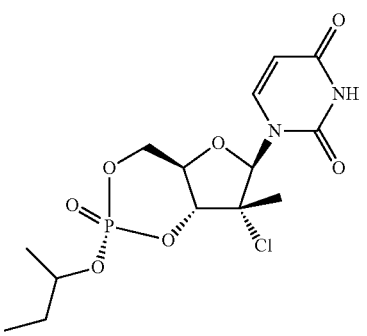
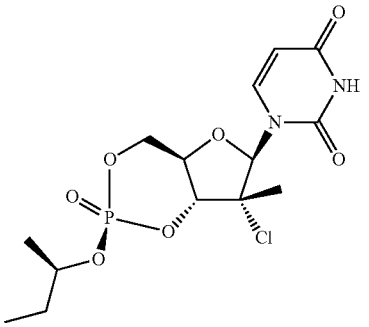

(211ib)
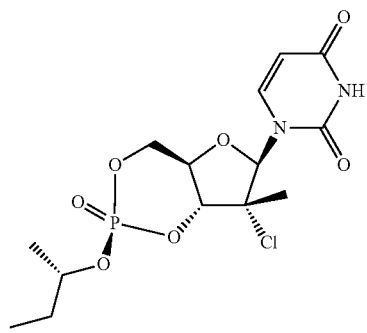
(211iia)
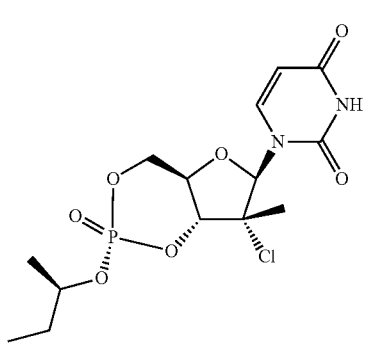
(211iib)
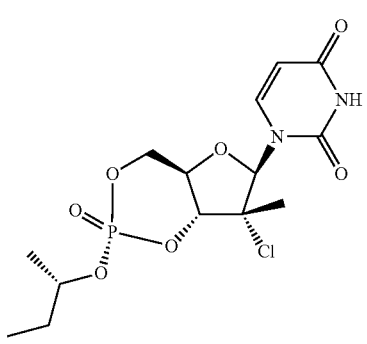
(212)
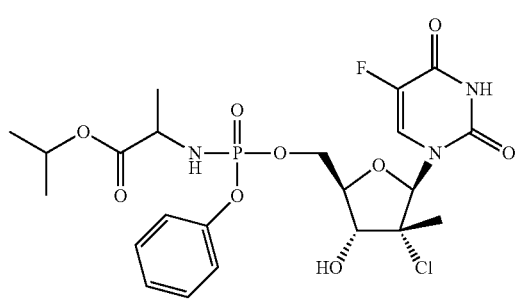
(212i)
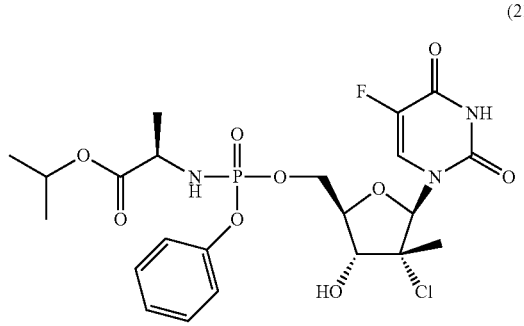
(212ii)
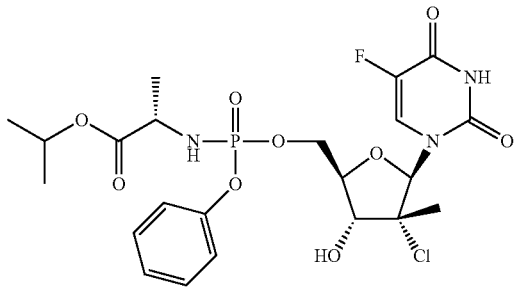
(212ia)
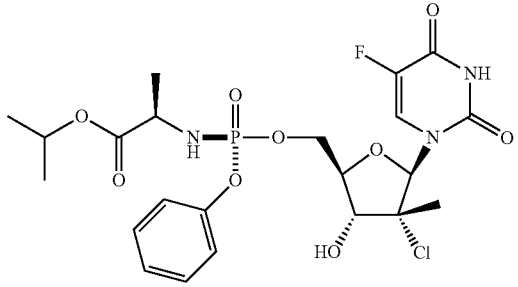
(212bi)
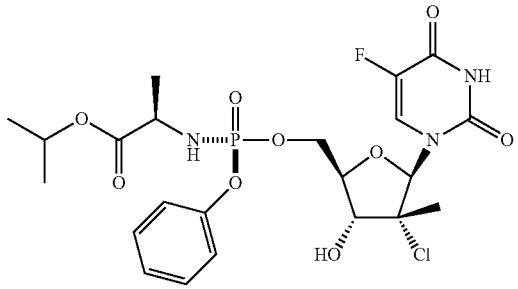
(212iia)
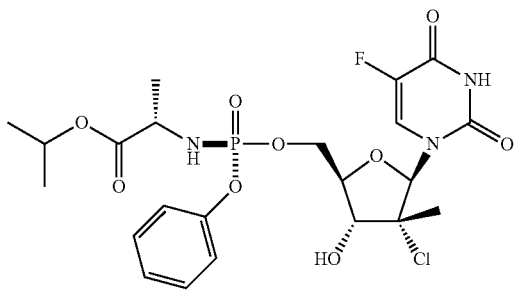
(212iib)
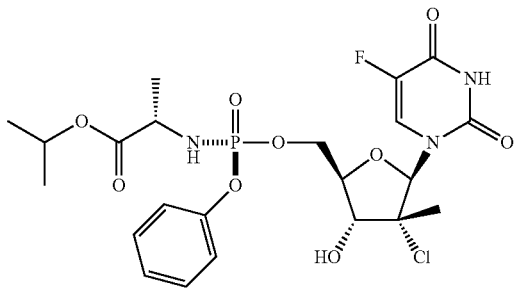

(213)
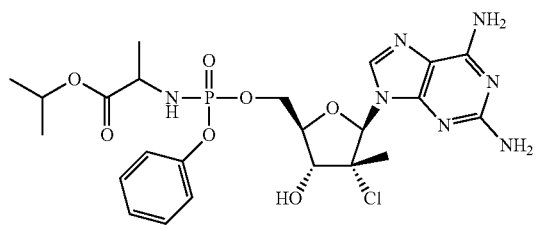
(213i)
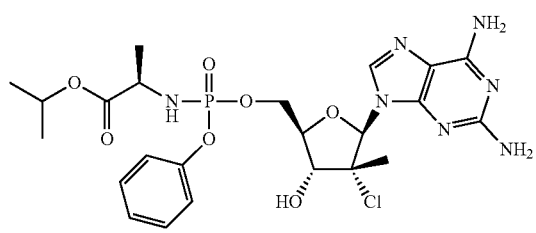
(213ii)
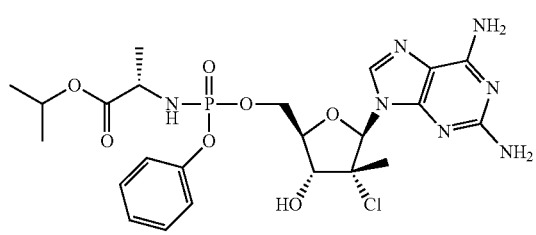
(213ia)
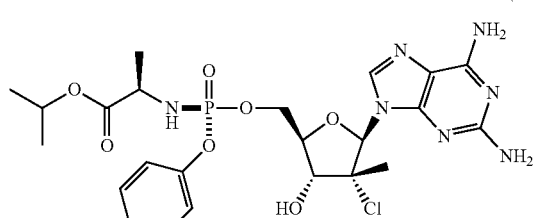
(213ib)
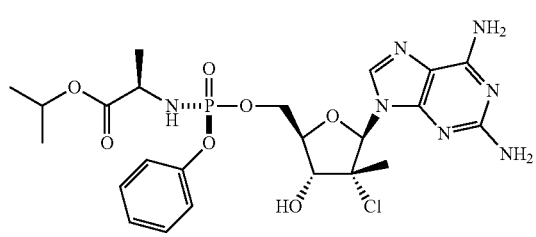
(213iia)
(213iib)
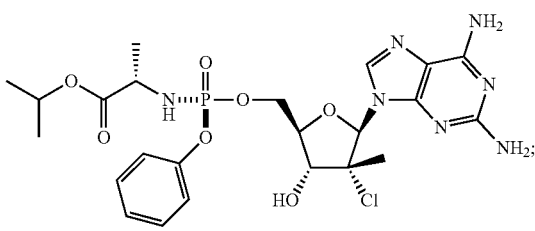
or a pharmaceutically acceptable salt, solvate, stereoisomeric form, tautomeric form or polymorphic form thereof.
In certain embodiments, provided herein are compounds according to any of Formulas 301-315:
(301)
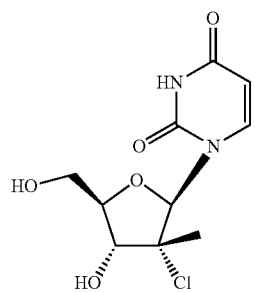
(302)
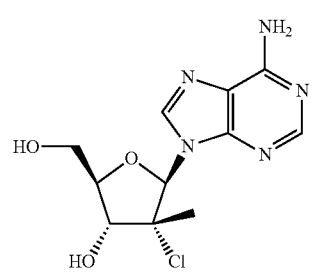
(303)
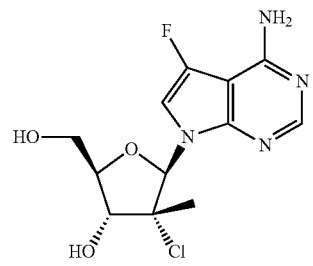
(304)
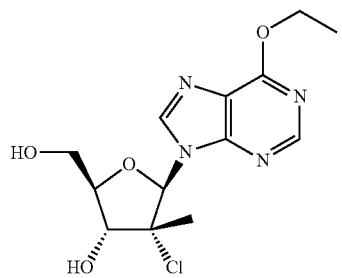

(305)
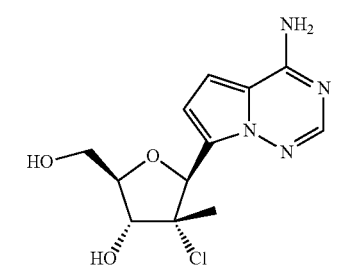
(306)
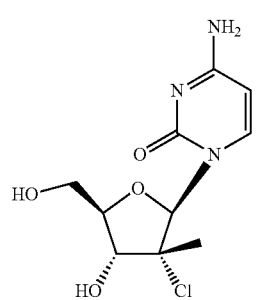
(307)
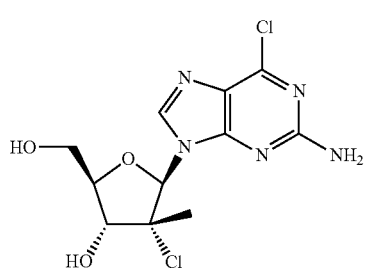
(308)
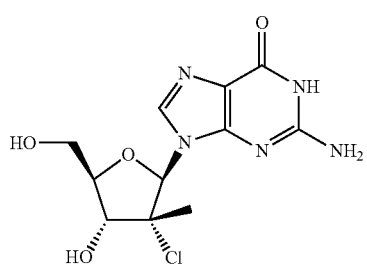
(309)
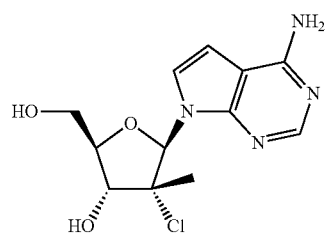
(310)
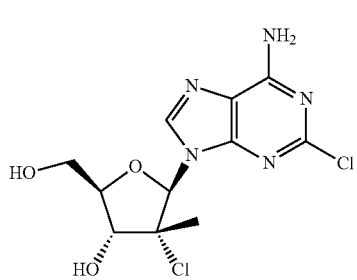
(311)
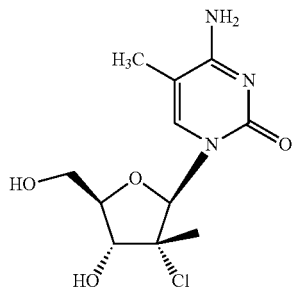
(312)
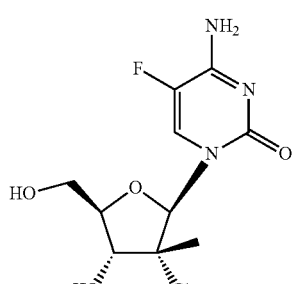
(313)
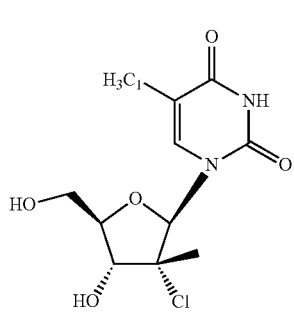
(314)
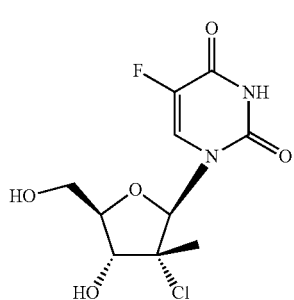
(315)
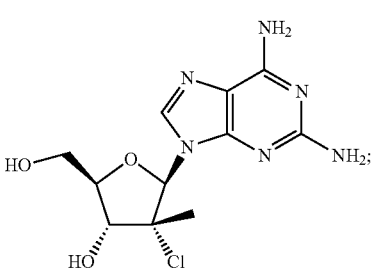
or a pharmaceutically acceptable salt, solvate, stereoisomeric form, tautomeric form or polymorphic form thereof.
In certain embodiments, provided herein are compounds according to any of Formulas 401-415:

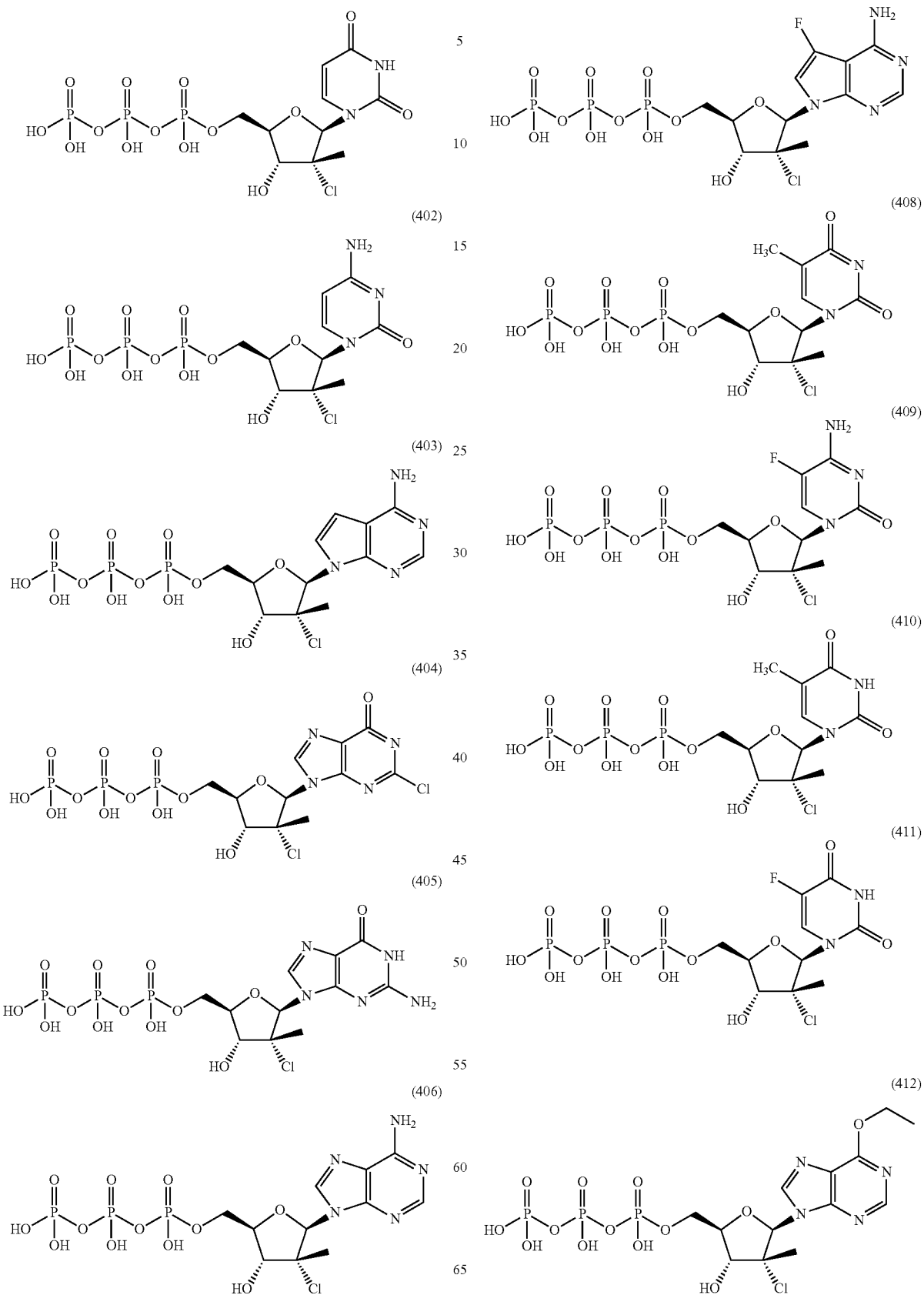

-continued (413)

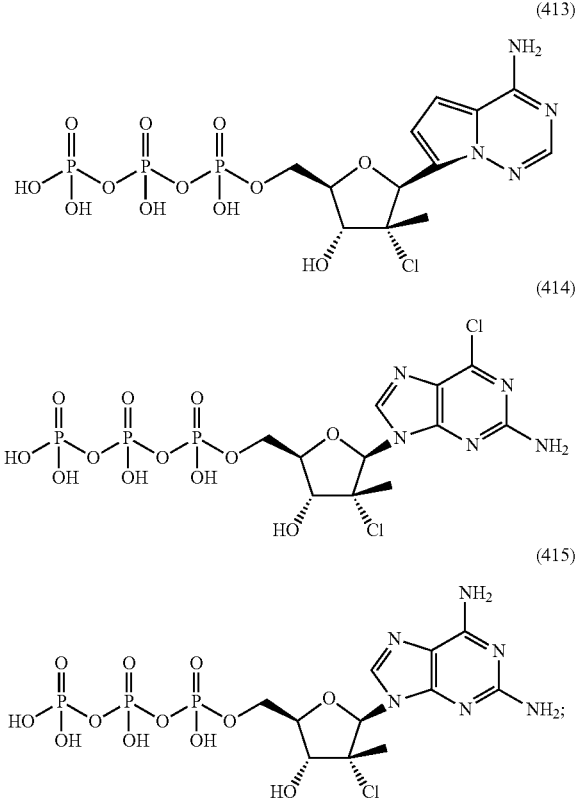

(414)

(415)

or a pharmaceutically acceptable salt, solvate, stereoisomeric form, tautomeric form or polymorphic form thereof.

In certain embodiments, provided herein are compounds according to Formula (i):

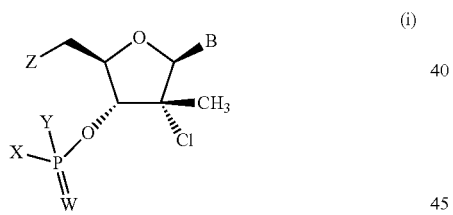

(i)

or a pharmaceutically acceptable salt, solvate, stereoisomeric form, tautomeric form or polymorphic form thereof, wherein: B is a nucleobase; W is O or S; one of X and Y is hydrogen, —$OR^1$, —$SR^1$, —$NR^1R^2$, an O-linked amino acid residue, an N-linked amino alcohol or an N-linked amino acid residue, or an ester thereof, and the other of X and Y is —$OR^1$; Z is —OH; or, in the alternative, Z and Y join to form a six-membered heterocyclic ring wherein Z and Y together represent a single divalent —O—, and X is —$OR^1$, —$SR^1$, —$NR^1R^2$, an O-linked amino acid residue, an N-linked amino alcohol or an N-linked amino acid residue, or an ester thereof; each $R^1$ is independently alkyl, cycloalkyl, aryl, heteroaryl, arylalkyl, or heteroarylalkyl; and each $R^2$ is independently hydrogen or alkyl. In certain embodiments, a compound of Formula (i) is provided wherein W is O. In certain embodiments, a compound of Formula (i) is provided wherein W is S.

In certain embodiments, provided herein are compounds of any of Formulas (I)-(XX) or (i) wherein each X is independently an O-linked amino acid residue, or an ester thereof. In certain embodiments, provided herein are compounds of any of Formulas (I)-(XX) or (i) wherein each X is independently an O-linked serine or tyrosine amino acid residue, or an ester thereof. In certain embodiments, provided herein are compounds of any of Formulas (I)-(XX) or (i) wherein each X is independently an N-linked amino acid residue, or an ester thereof. In certain embodiments, provided herein are compounds of any of Formulas (I)-(XX) or (i) wherein each X is independently an N-linked L-amino acid residue, or an ester thereof. In certain embodiments, provided herein are compounds of any of Formulas (I)-(XX) or (i) wherein each X is independently an N-linked D-amino acid residue, or an ester thereof.

In certain embodiments, provided herein is a compound according to Formula (iia):

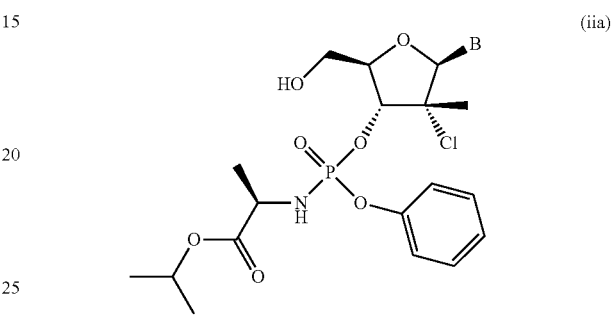

(iia)

or a pharmaceutically acceptable salt, solvate, stereoisomeric form, tautomeric form or polymorphic form thereof; wherein B is as described in the context of Formula (i). In an embodiment, a compound of any of Formulas (iiaA)-(iiaH) is provided:

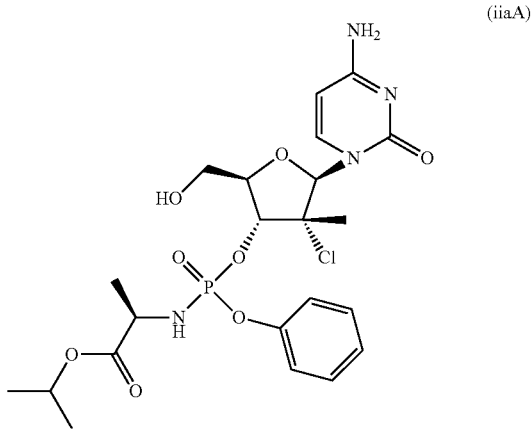

(iiaA)

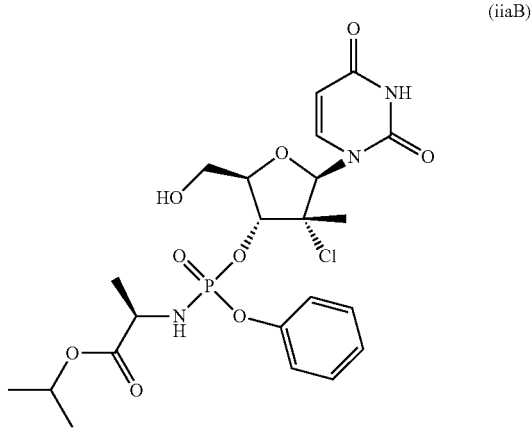

(iiaB)

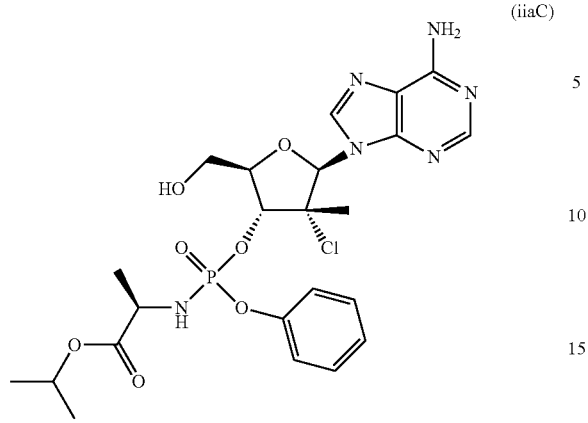
(iiaC)
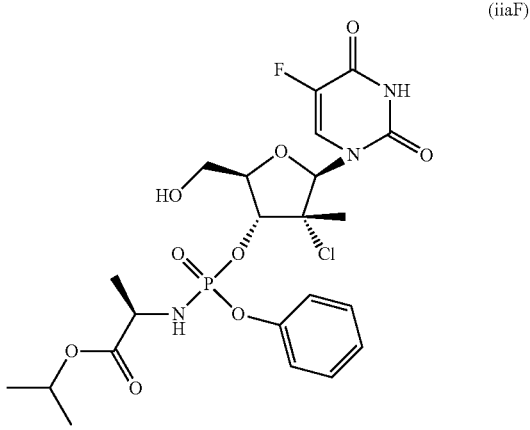
(iiaF)
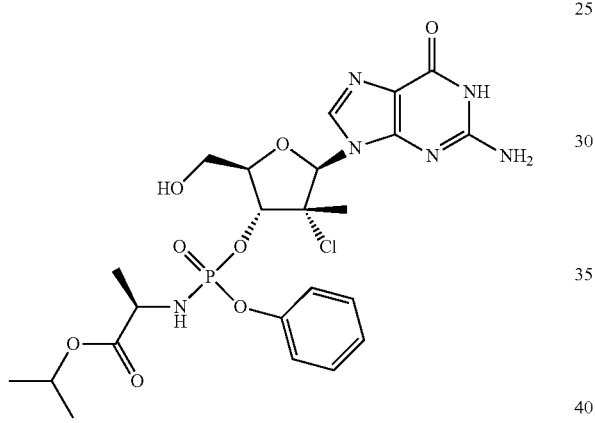
(iiaD)
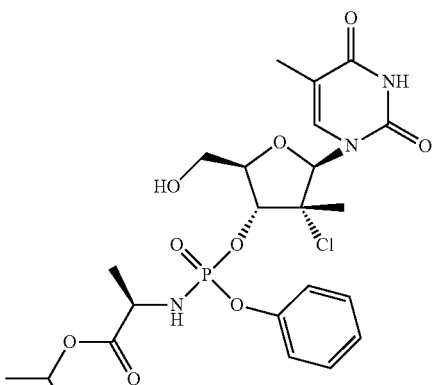
(iiaG)
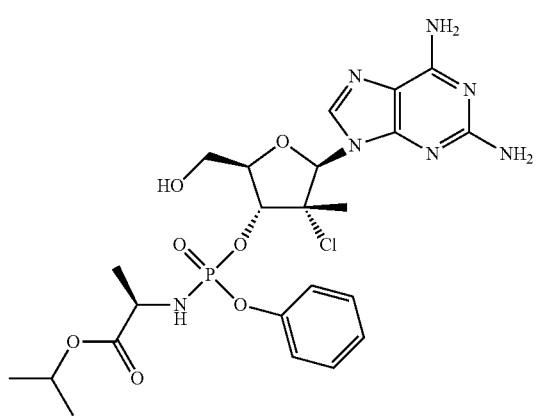
(iiaE)
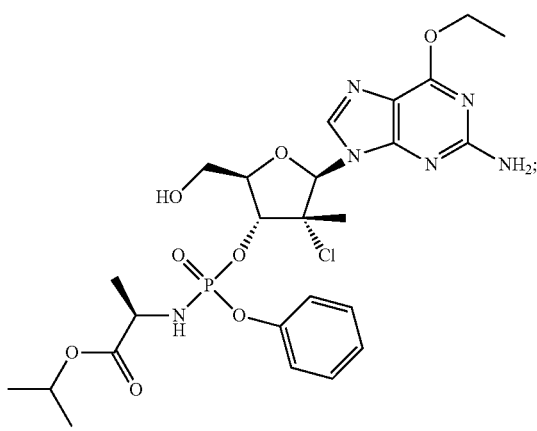
(iiaH)
or a pharmaceutically acceptable salt, solvate, stereoisomeric form, tautomeric form or polymorphic form thereof. In an embodiment, a compound of Formula (iiB) is provided.
In certain embodiments, provided herein is a compound according to Formula (iib):

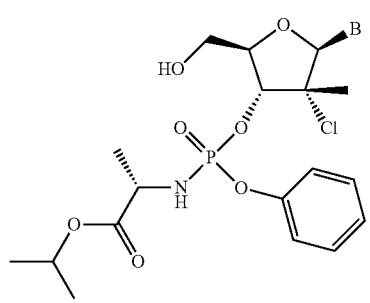
(iib)
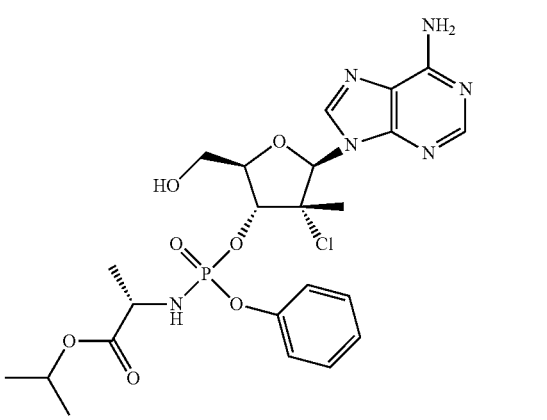
(iibC)
or a pharmaceutically acceptable salt, solvate, stereoisomeric form, tautomeric form or polymorphic form thereof wherein B is as described in the context of Formula (i). In an embodiment, a compound of any of Formulas (iibA)-(iibH) is provided:
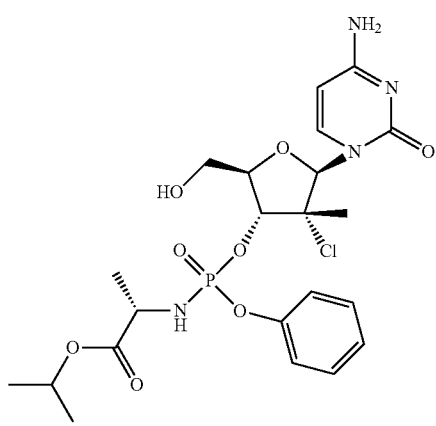
(iibA)
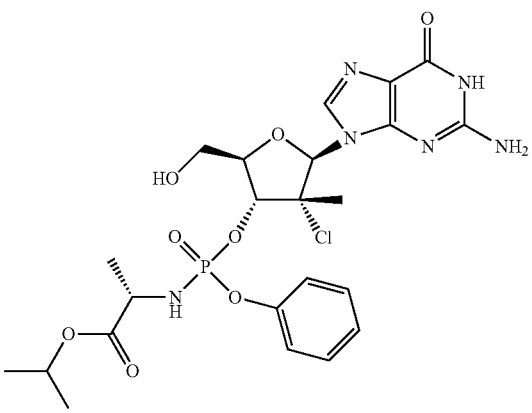
(iibD)
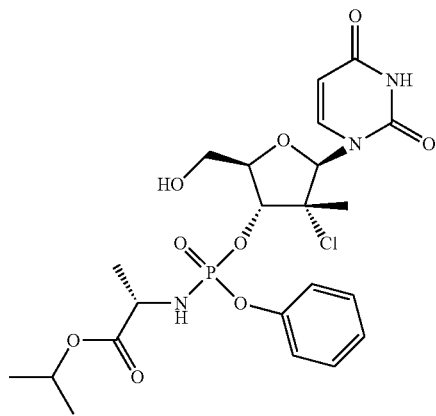
(iibB)
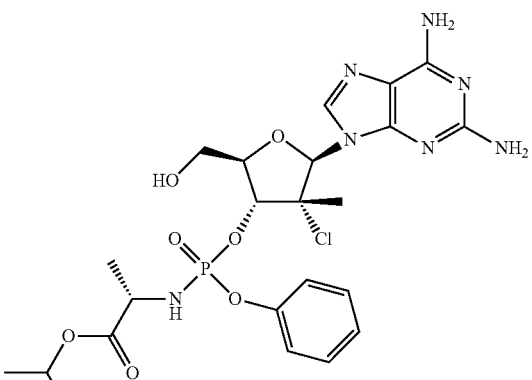
(iibE)

(iibF)

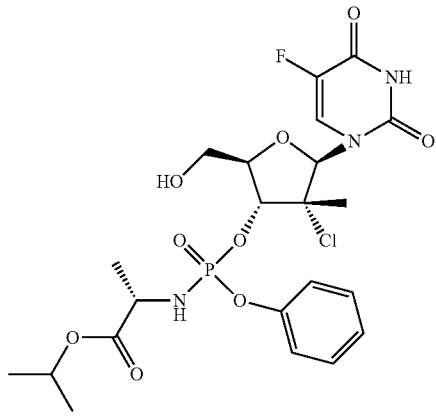

(iibG)

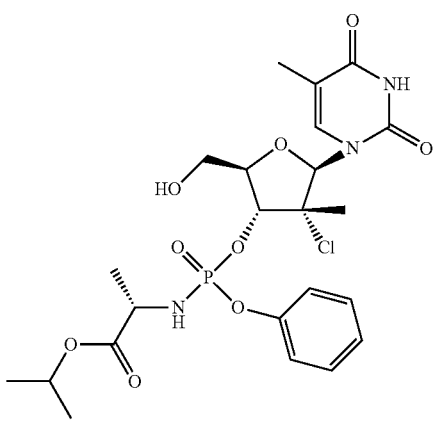

(iibH)

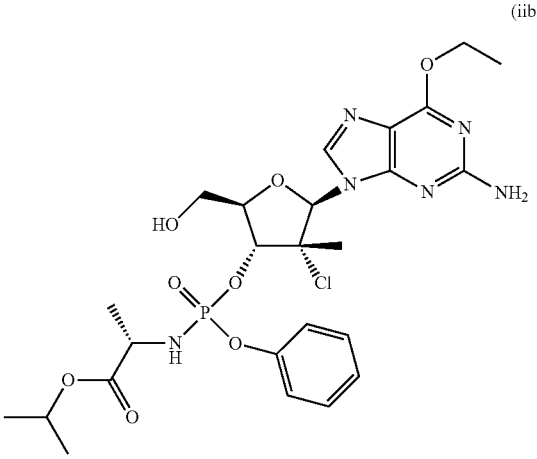

or a pharmaceutically acceptable salt, solvate, stereoisomeric form, tautomeric form or polymorphic form thereof. In an embodiment, a compound of Formula (iiB) is provided.

In certain embodiments, provided herein are compounds according to Formula (iii) for the treatment of Flaviviridae infections, such as HCV infection:

(iii)

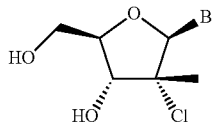

or a pharmaceutically acceptable salt, solvate, stereoisomeric form, tautomeric form or polymorphic form thereof; wherein B is as described in the context of Formula (i). In an embodiment, a compound of any of Formulas (iiiA)-(iiiH) is provided:

(iiiA)

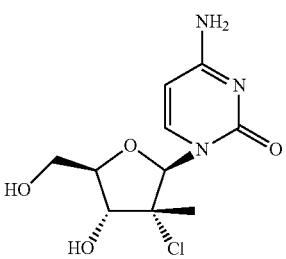

(iiiB)

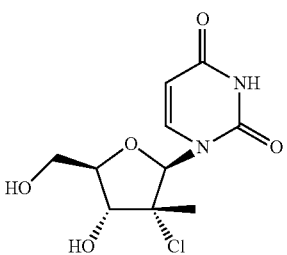

(iiiC)

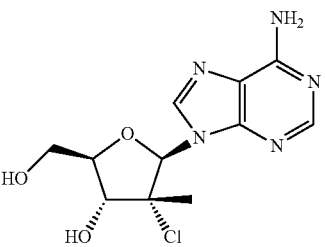

(iiiD)

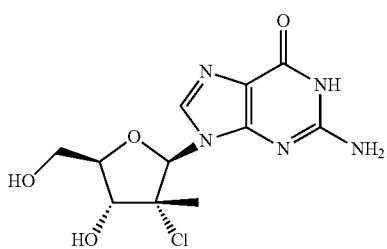

(iiiE)

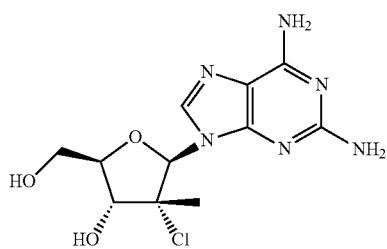

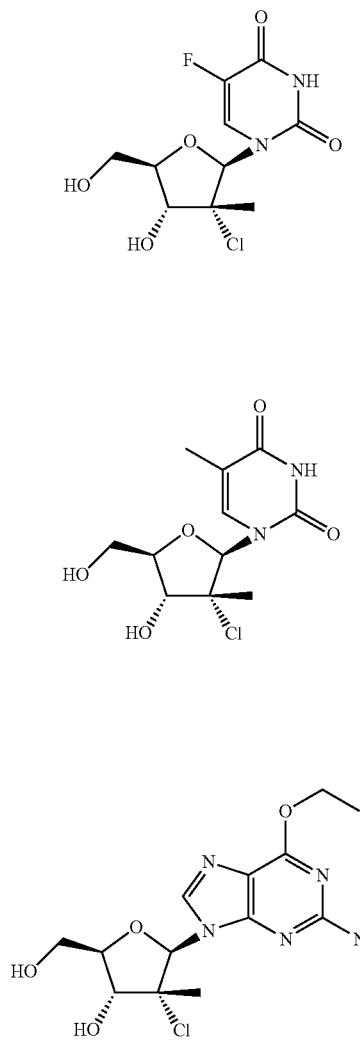

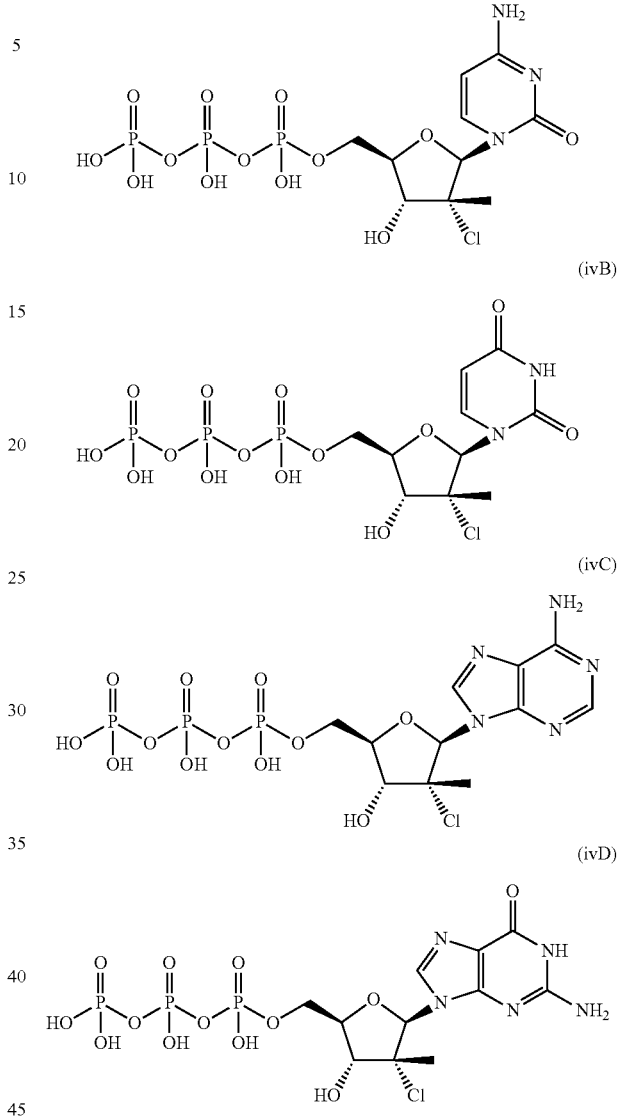

or a pharmaceutically acceptable salt, solvate, stereoisomeric form, tautomeric form or polymorphic form thereof. In an embodiment, a compound of Formula (iiiB) is provided.

In certain embodiments, provided herein is a compound according to Formula (iv) for the treatment of Flaviviridae infections, such as HCV infection:

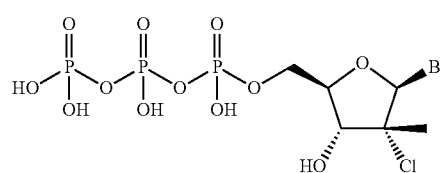

(iv)

or a pharmaceutically acceptable salt, solvate, stereoisomeric form, tautomeric form or polymorphic form thereof wherein B is as described in the context of Formula (i). In an embodiment, a compound of any of Formulas (ivA)-(ivH) is provided:

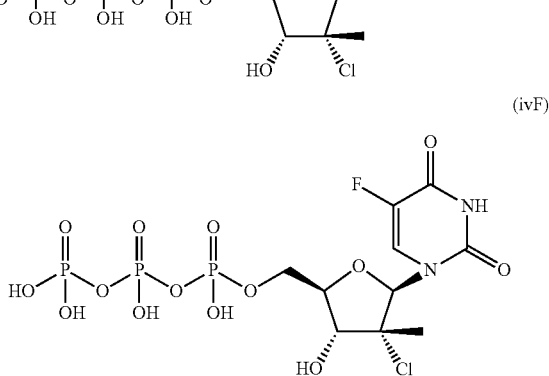

-continued (ivG)

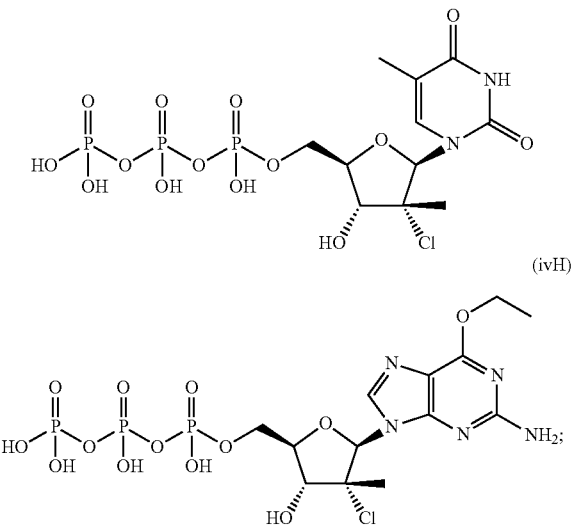

(ivH)

or a pharmaceutically acceptable salt, solvate, stereoisomeric form, tautomeric form, monophosphate, diphosphate, triphosphate, or polymorphic form thereof. In an embodiment, a compound of Formula (ivB) is provided.

In some embodiments, provided herein are:
(a) compounds as described herein, e.g., of Formula 1001, 2001-2003, I-XXVII, 1-104iib, 201-213iib, 301-315, 401-415, or i-ivH, and pharmaceutically acceptable salts and compositions thereof;
(b) compounds as described herein, e.g., of Formula 1001, 2001-2003, I-XXVII, 1-104iib, 201-213iib, 301-315, 401-415, or i-ivH, and pharmaceutically acceptable salts and compositions thereof for use in the treatment and/or prophylaxis of a liver disorder including Flaviviridae infection, especially in individuals diagnosed as having a Flaviviridae infection or being at risk of becoming infected by hepatitis C;
(c) processes for the preparation of compounds as described herein, e.g., of Formula 1001, 2001-2003, I-XXVII, 1-104iib, 201-213iib, 301-315, 401-415, or i-ivH, as described in more detail elsewhere herein;
(d) pharmaceutical formulations comprising a compound as described herein, e.g., of Formula 1001, 2001-2003, I-XXVII, 1-104iib, 201-213iib, 301-315, 401-415, or i-ivH, or a pharmaceutically acceptable salt thereof together with a pharmaceutically acceptable carrier or diluent;
(e) pharmaceutical formulations comprising a compound as described herein, e.g., of Formula 1001, 2001-2003, I-XXVII, 1-104iib, 201-213iib, 301-315, 401-415, or i-ivH, or a pharmaceutically acceptable salt thereof together with one or more other effective anti-HCV agents, optionally in a pharmaceutically acceptable carrier or diluent;
(f) a method for the treatment and/or prophylaxis of a host infected with Flaviviridae that includes the administration of an effective amount of a compound as described herein, e.g., of Formula 1001, 2001-2003, I-XXVII, 1-104iib, 201-213iib, 301-315, 401-415, or i-ivH, its pharmaceutically acceptable salt or composition; or
(g) a method for the treatment and/or prophylaxis of a host infected with Flaviviridae that includes the administration of an effective amount of a compounds as described herein, e.g., of Formula 1001, 2001-2003, I-XXVII, 1-104iib, 201-213iib, 301-315, 401-415, or i-ivH, its pharmaceutically acceptable salt or composition in combination and/or alternation with one or more effective anti-HCV agent.

Optically Active Compounds

It is appreciated that compounds provided herein have several chiral centers and may exist in and be isolated in optically active and racemic forms. Some compounds may exhibit polymorphism. It is to be understood that any racemic, optically-active, diastereomeric, polymorphic, or stereoisomeric form, or mixtures thereof, of a compound provided herein, which possess the useful properties described herein is within the scope of the invention. It being well known in the art how to prepare optically active forms (for example, by resolution of the racemic form by recrystallization techniques, by synthesis from optically-active starting materials, by chiral synthesis, or by chromatographic separation using a chiral stationary phase).

In particular, since the 1' and 4' carbons of a nucleoside are chiral, their non-hydrogen substituents (the base and the CHOR groups, respectively) can be either cis (on the same side) or trans (on opposite sides) with respect to the sugar ring system. The four optical isomers therefore are represented by the following configurations (when orienting the sugar moiety in a horizontal plane such that the oxygen atom is in the back): cis (with both groups "up", which corresponds to the configuration of naturally occurring β-D nucleosides), cis (with both groups "down", which is a non-naturally occurring β-L configuration), trans (with the CT substituent "up" and the C4' substituent "down"), and trans (with the CT substituent "down" and the C4' substituent "up"). The "D-nucleosides" are cis nucleosides in a natural configuration and the "L-nucleosides" are cis nucleosides in the non-naturally occurring configuration.

Likewise, most amino acids are chiral (designated as L or D, wherein the L enantiomer is the naturally occurring configuration) and can exist as separate enantiomers.

Examples of methods to obtain optically active materials are known in the art, and include at least the following.
i) physical separation of crystals—a technique whereby macroscopic crystals of the individual enantiomers are manually separated. This technique can be used if crystals of the separate enantiomers exist, i.e., the material is a conglomerate, and the crystals are visually distinct;
ii) simultaneous crystallization—a technique whereby the individual enantiomers are separately crystallized from a solution of the racemate, possible only if the latter is a conglomerate in the solid state;
iii) enzymatic resolutions—a technique whereby partial or complete separation of a racemate by virtue of differing rates of reaction for the enantiomers with an enzyme;
iv) enzymatic asymmetric synthesis—a synthetic technique whereby at least one step of the synthesis uses an enzymatic reaction to obtain an enantiomerically pure or enriched synthetic precursor of the desired enantiomer;
v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;
vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

In some embodiments, compositions of 2'-chloro nucleoside analog compounds that are substantially free of a designated enantiomer of that compound. In certain embodiments, in the methods and compounds of this invention, the compounds are substantially free of enantiomers. In some embodiments, the composition includes that includes a compound that is at least 85, 90%, 95%, 98%, 99% to 100% by weight, of the compound, the remainder comprising other chemical species or enantiomers.

Isotopically Enriched Compounds

Also provided herein are isotopically enriched compounds, including but not limited to isotopically enriched 2'-chloro nucleoside analog compounds.

Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrees the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g., Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein will produce a detectable KIE that will affect the pharmacokinetic, pharmacologic, and/or toxicological profiles of a compound provided herein in comparison with a similar compound having a natural isotopic composition.

Preparation of Compounds

The compounds provided herein can be prepared, isolated or obtained by any method apparent to those of skill in the art. Compounds provided herein can be prepared according to the Exemplary Preparation Scheme provided below. Reaction conditions, steps and reactants not provided in the Exemplary Preparation Scheme would be apparent to, and known by, those skilled in the art.

Exemplary Preparation Scheme

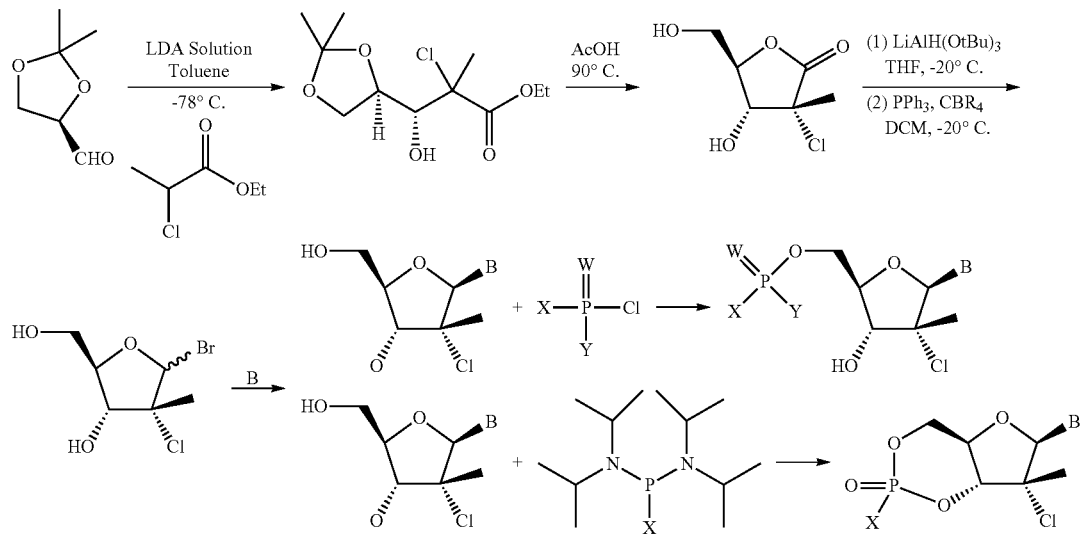

In the exemplary preparation scheme, W, X, Y, and B are defined as described in the context of Formula (I). Exemplary methods of preparation are described in detail in the examples below.

Pharmaceutical Compositions and Methods of Administration

2'-chloro nucleoside analog compounds can be formulated into pharmaceutical compositions using methods available in the art and those disclosed herein. Any of the compounds disclosed herein can be provided in the appropriate pharmaceutical composition and be administered by a suitable route of administration.

The methods provided herein encompass administering pharmaceutical compositions containing at least one compound as described herein, including a compound of general Formula 1001, 2001-2003, I-XXVII, 1-104iib, 201-213iib, 301-315, 401-415, or i-ivH, if appropriate in the salt form, either used alone or in the form of a combination with one or more compatible and pharmaceutically acceptable carriers, such as diluents or adjuvants, or with another anti-HCV agent.

In certain embodiments, the second agent can be formulated or packaged with the compound provided herein. Of course, the second agent will only be formulated with the compound provided herein when, according to the judgment of those of skill in the art, such co-formulation should not interfere with the activity of either agent or the method of administration. In certain embodiments, the compound provided herein and the second agent are formulated separately. They can be packaged together, or packaged separately, for the convenience of the practitioner of skill in the art.

In clinical practice the active agents provided herein may be administered by any conventional route, in particular orally, parenterally, rectally or by inhalation (e.g. in the form of aerosols). In certain embodiments, the compound provided herein is administered orally.

Use may be made, as solid compositions for oral administration, of tablets, hard gelatin capsules, powders or granules. In these compositions, the active product is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E.W. Martin.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, for example, in the U.S. Pharmocopia (USP)SP(XXI)/NF (XVI). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, New York, 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, for example, an animal subject, such as a mammalian subject, for example, a human subject.

A pharmaceutical composition is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intratumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. For example, a dosage form used in the initial treatment of viral infection may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington's Pharmaceutical Sciences, 20th ed., Mack Publishing, Easton Pa. (2000).

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound.

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 20th ed., Mack Publishing, Easton Pa. (2000).

In certain embodiments, the oral dosage forms are solid and prepared under anhydrous conditions with anhydrous ingredients, as described in detail herein. However, the scope of the compositions provided herein extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB 0 SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; each of which is incorporated herein by reference in its entirety. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompassed herein are single unit dosage forms suitable for oral administration such as, but not limited to, tablets, capsules, gelcaps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug may be administered using intravenous infusion, an implantable osmotic pump, a transdermal patch, liposomes, or other modes of administration. In certain embodiments, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (Science 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, $16^{th}$, 18th and $20^{th}$ eds., Mack Publishing, Easton Pa. (1980, 1990 & 2000); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are nontoxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, $16^{th}$, 18th and $20^{th}$ eds., Mack Publishing, Easton Pa. (1980, 1990 & 2000).

Depending on the specific tissue to be treated, additional components may be used prior to, in conjunction with, or subsequent to treatment with active ingredients provided. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Dosage and Unit Dosage Forms

In human therapeutics, the doctor will determine the posology which he considers most appropriate according to a preventive or curative treatment and according to the age, weight, stage of the infection and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

In further aspects, provided are methods of treating or preventing an HCV infection in a subject by administering, to a subject in need thereof, an effective amount of a compound provided herein, or a pharmaceutically acceptable salt thereof. The amount of the compound or composition which will be effective in the prevention or treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in certain embodiments, the dosage administered to a subject is 0.140 mg/kg to 3 mg/kg of the subject's body weight, based on weight of the active compound. In certain embodiments, the dosage administered to a subject is between 0.20 mg/kg and 2.00 mg/kg, or between 0.30 mg/kg and 1.50 mg/kg of the subject's body weight.

In certain embodiments, the recommended daily dose range of a composition provided herein for the conditions described herein lie within the range of from about 0.1 mg to about 1000 mg per day, given as a single once-a-day dose or as divided doses throughout a day. In certain embodiments, the daily dose is administered twice daily in equally divided doses. In certain embodiments, a daily dose range should be from about 10 mg to about 200 mg per day, in other embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiment, the dosage of the composition provided herein, based on weight of the active compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, treatment or prevention can be initiated with one or more loading doses of a compound or composition provided herein followed by one or more maintenance doses. In such embodiments, the loading dose can be, for instance, about 60 to about 400 mg per day, or about 100 to about 200 mg per day for one day to five weeks. The loading dose can be followed by one or more maintenance doses. In certain embodiments, each maintenance does is, independently, about from about 10 mg to about 200 mg per day, between about 25 mg and about 150 mg per day, or between about 25 and about 80 mg per day. Maintenance doses can be administered daily and can be administered as single doses, or as divided doses.

In certain embodiments, a dose of a compound or composition provided herein can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound or composition provided herein is administered to achieve a steady-state concentration in blood or serum of the subject of from about 300 to about 4000 ng/mL, from about 400 to about 1600 ng/mL, or from about 600 to about 1200 ng/mL. In some embodiments, loading doses can be administered to achieve steady-state blood or serum concentrations of about 1200 to about 8000 ng/mL, or about 2000 to about 4000 ng/mL for one to five days. In certain embodiments, maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, provided herein are unit dosages comprising a compound, or a pharmaceutically acceptable salt thereof, in a form suitable for administration. Such forms are described in detail herein. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

The dosages of the second agents are to be used in the combination therapies provided herein. In certain embodiments, dosages lower than those which have been or are currently being used to prevent or treat HCV infection are used in the combination therapies provided herein. The recommended dosages of second agents can be obtained from the knowledge of those of skill. For those second agents that are approved for clinical use, recommended dosages are described in, for example, Hardman et al., eds., 1996, Goodman & Gilman's The Pharmacological Basis Of Basis Of Therapeutics $9^{th}$ Ed, Mc-Graw-Hill, New York; Physician's Desk Reference (PDR) $57^{th}$ Ed., 2003, Medical Economics Co., Inc., Montvale, N.J., which are incorporated herein by reference in its entirety.

In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. In various embodiments, the therapies are administered no more than 24 hours apart or no more than 48 hours apart. In certain embodiments, two or more therapies are administered within the same patient visit. In other embodiments, the compound provided herein and the second agent are administered concurrently.

In other embodiments, the compound provided herein and the second agent are administered at about 2 to 4 days apart, at about 4 to 6 days apart, at about 1 week part, at about 1 to 2 weeks apart, or more than 2 weeks apart.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In certain embodiments, a compound provided herein and a second agent are administered to a patient, for example, a mammal, such as a human, in a sequence and within a time interval such that the compound provided herein can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In certain embodiments, the compound provided herein and the second active agent exert their effect at times which overlap. Each second active agent can be administered separately, in any appropriate form and by any suitable route. In other embodiments, the compound provided herein is administered before, concurrently or after administration of the second active agent.

In certain embodiments, the compound provided herein and the second agent are cyclically administered to a patient. Cycling therapy involves the administration of a first agent (e.g., a first prophylactic or therapeutic agents) for a period of time, followed by the administration of a second agent and/or third agent (e.g., a second and/or third prophylactic or therapeutic agents) for a period of time and repeating this sequential administration. Cycling therapy can reduce the development of resistance to one or more of the therapies, avoid or reduce the side effects of one of the therapies, and/or improve the efficacy of the treatment.

In certain embodiments, the compound provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the compound provided herein can work together with the second active agent. For example, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the compound provided herein. In certain embodiments, the compound provided herein is administered concurrently with one or more second agents in the same pharmaceutical composition. In another embodiment, a compound provided herein is administered concurrently with one or more second agents in separate pharmaceutical compositions. In still another embodiment, a compound provided herein is administered prior to or subsequent to administration of a second agent. Also contemplated are administration of a compound provided herein and a second agent by the same or different routes of administration, e.g., oral and parenteral. In certain embodiments, when the compound provided herein is administered concurrently with a second agent that potentially produces adverse side effects including, but not limited to, toxicity, the second active agent can advantageously be administered at a dose that falls below the threshold that the adverse side effect is elicited.

Kits

Also provided are kits for use in methods of treatment of a liver disorder such as HCV infections. The kits can include a compound or composition provided herein, a second agent or composition, and instructions providing information to a health care provider regarding usage for treating the disorder. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 days. In some embodiments, a compound or composition can be included as a sterile aqueous pharmaceutical composition or dry powder (e.g., lyophilized) composition.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Methods of Use

In certain embodiments, provided herein are methods for the treatment and/or prophylaxis of a host infected with Flaviviridae that includes the administration of an effective amount of a compounds provided herein, or a pharmaceutically acceptable salt thereof. In certain embodiments, provided herein are methods for treating an HCV infection in a subject. In certain embodiments, the methods encompass the step of administering to the subject in need thereof an amount of a compound effective for the treatment or prevention of an HCV infection in combination with a second agent effective for the treatment or prevention of the infection. The compound can be any compound as described herein, and the second agent can be any second agent described in the art or herein. In certain embodiments, the compound is in the form of a pharmaceutical composition or dosage form, as described elsewhere herein.

Flaviviridae that can be treated are discussed generally in *Fields Virology*, Editors: Fields, B. N., Knipe, D. M., and Howley, P. M., Lippincott-Raven Publishers, Philadelphia, Pa., Chapter 31, 1996. In a particular embodiment of the invention, the Flaviviridae is HCV. In an alternate embodiment of the invention, the Flaviviridae is a flavivirus or pestivirus. Specific flaviviruses include, without limitation: Absettarov, Alfuy, Apoi, Aroa, Bagaza, Banzi, Bouboui, Bussuquara, Cacipacore, Carey Island, Dakar bat, Dengue 1, Dengue 2, Dengue 3, Dengue 4, Edge Hill, Entebbe bat, Gadgets Gully, Hanzalova, Hypr, Ilheus, Israel turkey meningoencephalitis, Japanese encephalitis, Jugra, Jutiapa, Kadam, Karshi, Kedougou, Kokobera, Koutango, Kumlinge, Kunjin, Kyasanur Forest disease, Langat, Louping ill, Meaban, Modoc, Montana myotis leukoencephalitis, Murray valley encephalitis, Naranjal, Negishi, Ntaya, Omsk hemorrhagic fever, Phnom-Penh bat, Powassan, Rio Bravo, Rocio, Royal Farm, Russian spring-summer encephalitis, Saboya, St. Louis encephalitis, Sal Vieja, San Perlita, Saumarez Reef, Sepik, Sokuluk, Spondweni, Stratford, Tembusu, Tyuleniy, Uganda S, Usutu, Wesselsbron, West Nile, Yaounde, Yellow fever, and Zika.

Pestiviruses that can be treated are discussed generally in *Fields Virology*, Editors: Fields, B. N., Knipe, D. M., and Howley, P. M., Lippincott-Raven Publishers, Philadelphia, Pa., Chapter 33, 1996. Specific pestiviruses include, without limitation: bovine viral diarrhea virus ("BVDV"), classical swine fever virus ("CSFV," also called hog cholera virus), and border disease virus ("BDV").

In certain embodiments, the subject can be any subject infected with, or at risk for infection with, HCV. Infection or risk for infection can be determined according to any technique deemed suitable by the practitioner of skill in the art. In certain embodiments, subjects are humans infected with HCV.

In certain embodiments, the subject has never received therapy or prophylaxis for an HCV infection. In further embodiments, the subject has previously received therapy or prophylaxis for an HCV infection. For instance, in certain embodiments, the subject has not responded to an HCV therapy. For example, under current interferon therapy, up to 50% or more HCV subjects do not respond to therapy. In certain embodiments, the subject can be a subject that received therapy but continued to suffer from viral infection or one or more symptoms thereof. In certain embodiments, the subject can be a subject that received therapy but failed to achieve a sustained virologic response. In certain embodiments, the subject has received therapy for an HCV infection but has failed to show, for example, a 2 $\log_{10}$ decline in HCV RNA levels after 12 weeks of therapy. It is believed that subjects who have not shown more than 2 $\log_{10}$ reduction in serum HCV RNA after 12 weeks of therapy have a 97-100% chance of not responding.

In certain embodiments, the subject is a subject that discontinued an HCV therapy because of one or more adverse events associated with the therapy. In certain embodiments, the subject is a subject where current therapy is not indicated. For instance, certain therapies for HCV are associated with neuropsychiatric events. Interferon (IFN)-alfa plus ribavirin is associated with a high rate of depression. Depressive symptoms have been linked to a worse outcome in a number of medical disorders. Life-threatening or fatal neuropsychiatric events, including suicide, suicidal and homicidal ideation, depression, relapse of drug addiction/overdose, and aggressive behavior have occurred in subjects with and without a previous psychiatric disorder during HCV therapy. Interferon-induced depression is a limitation for the treatment of chronic hepatitis C, especially for subjects with psychiatric disorders. Psychiatric side effects are common with interferon therapy and responsible for about 10% to 20% of discontinuations of current therapy for HCV infection.

Accordingly, provided are methods of treating or preventing an HCV infection in subjects where the risk of neuropsychiatric events, such as depression, contraindicates treatment with current HCV therapy. In certain embodiments, provided are methods of treating or preventing HCV infection in subjects where a neuropsychiatric event, such as depression, or risk of such indicates discontinuation of treatment with current HCV therapy. Further provided are methods of treating or preventing HCV infection in subjects where a neuropsychiatric event, such as depression, or risk of such indicates dose reduction of current HCV therapy.

Current therapy is also contraindicated in subjects that are hypersensitive to interferon or ribavirin, or both, or any other component of a pharmaceutical product for administration of interferon or ribavirin. Current therapy is not indicated in subjects with hemoglobinopathies (e.g., thalassemia major, sickle-cell anemia) and other subjects at risk from the hematologic side effects of current therapy. Common hematologic side effects include bone marrow suppression, neutropenia and thrombocytopenia. Furthermore, ribavirin is toxic to red blood cells and is associated with hemolysis. Accordingly, in certain embodiments, provided are methods of treating or preventing HCV infection in subjects hypersensitive to interferon or ribavirin, or both, subjects with a hemoglobinopathy, for instance thalassemia major subjects and sickle-cell anemia subjects, and other subjects at risk from the hematologic side effects of current therapy.

In certain embodiments, the subject has received an HCV therapy and discontinued that therapy prior to administration of a method provided herein. In further embodiments, the subject has received therapy and continues to receive that therapy along with administration of a method provided herein. The methods can be co-administered with other therapy for HBC and/or HCV according to the judgment of one of skill in the art. In certain embodiments, the methods or compositions provided herein can be co-administered with a reduced dose of the other therapy for HBC and/or HCV.

In certain embodiments, provided are methods of treating a subject that is refractory to treatment with interferon. For instance, in some embodiments, the subject can be a subject that has failed to respond to treatment with one or more agents selected from the group consisting of interferon, interferon α, pegylated interferon α, interferon plus ribavirin, interferon α plus ribavirin and pegylated interferon α plus ribavirin. In some embodiments, the subject can be a subject that has responded poorly to treatment with one or more agents selected from the group consisting of interferon, interferon α, pegylated interferon α, interferon plus ribavirin, interferon α plus ribavirin and pegylated interferon α plus ribavirin. A pro-drug form of ribavirin, such as taribavirin, may also be used.

In certain embodiments, the subject has, or is at risk for, co-infection of HCV with HIV. For instance, in the United States, 30% of HIV subjects are co-infected with HCV and evidence indicates that people infected with HIV have a much more rapid course of their hepatitis C infection. Maier and Wu, 2002, *World J Gastroenterol* 8:577-57. The methods provided herein can be used to treat or prevent HCV infection in such subjects. It is believed that elimination of HCV in these subjects will lower mortality due to end-stage liver disease. Indeed, the risk of progressive liver disease is higher in subjects with severe AIDS-defining immunodeficiency than in those without. See, e.g., Lesens et al., 1999, *J Infect Dis* 179:1254-1258. In certain embodiments, compounds provided herein have been shown to suppress HIV in HIV subjects. Thus, in certain embodiments, provided are methods of treating or preventing HIV infection and HCV infection in subjects in need thereof.

In certain embodiments, the compounds or compositions are administered to a subject following liver transplant. Hepatitis C is a leading cause of liver transplantation in the U.S., and many subjects that undergo liver transplantation remain HCV positive following transplantation. In certain embodiments, provided are methods of treating such recurrent HCV subjects with a compound or composition provided herein. In certain embodiments, provided are methods of treating a subject before, during or following liver transplant to prevent recurrent HCV infection.

Assay Methods

Compounds can be assayed for HCV activity according to any assay known to those of skill in the art.

Further, compounds can be assayed for accumulation in liver cells of a subject according to any assay known to those of skill in the art. In certain embodiments, a compound can be administered to the subject, and a liver cell of the subject can be assayed for the compound or a derivative thereof, e.g. a nucleoside, nucleoside phosphate or nucleoside triphosphate derivative thereof.

In certain embodiments, a 2'-chloro nucleoside analog compound is administered to cells, such as liver cells, in vivo or in vitro, and the nucleoside triphosphate levels delivered intracellularly are measured, to indicate delivery of the compound and triphosphorylation in the cell. The levels of intracellular nucleoside triphosphate can be measured using analytical techniques known in the art. Methods of detecting ddATP are described herein below by way of example, but other nucleoside triphosphates can be readily detected using the appropriate controls, calibration samples and assay techniques.

In certain embodiments, ddATP concentrations are measured in a sample by comparison to calibration standards made from control samples. The ddATP concentrations in a sample can be measured using an analytical method such as HPLC LC MS. In certain embodiments, a test sample is compared to a calibration curve created with known concentrations of ddATP to thereby obtain the concentration of that sample.

In certain embodiments, the samples are manipulated to remove impurities such as salts ($Na^+$, $K^+$, etc.) before analysis. In certain embodiments, the lower limit of quantitation is about ~0.2 pmol/mL for hepatocyte cellular extracts particularly where reduced salt is present.

In certain embodiments, the method allows successfully measuring triphosphate nucleotides formed at levels of 1-10,000 pmol per million cells in e.g. cultured hepatocytes and HepG2 cells.

Second Therapeutic Agents

In certain embodiments, the compounds and compositions provided herein are useful in methods of treatment of a liver disorder, that comprise further administration of a second agent effective for the treatment of the disorder, such as HCV infection in a subject in need thereof. The second agent can be any agent known to those of skill in the art to be effective for the treatment of the disorder, including those currently approved by the FDA.

In certain embodiments, a compound provided herein is administered in combination with one second agent. In further embodiments, a second agent is administered in combination with two second agents. In still further embodiments, a second agent is administered in combination with two or more second agents.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" includes a combination of a compound provided herein and another therapy (e.g., a prophylactic or therapeutic agent) which has been or is currently being used to prevent, manage or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The active compounds provided herein can be administered in combination or alternation with another therapeutic agent, in particular an anti-HCV agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. In certain embodiments, an anti-HCV (or anti-pestivirus or anti-flavivirus) compound that exhibits an $EC_{50}$ of 10-15 µM. In certain embodiments, less than 1-5 µM, is desirable.

It has been recognized that drug-resistant variants of flaviviruses, pestiviruses or HCV can emerge after prolonged treatment with an antiviral agent. Drug resistance most typically occurs by mutation of a gene that encodes for an enzyme used in viral replication. The efficacy of a drug against the viral infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

Any of the viral treatments described in the Background of the Invention can be used in combination or alternation with the compounds described in this specification. Non-limiting examples of second agents include:

HCV Protease inhibitors: Examples include Medivir HCV Protease Inhibitor (HCV-PI or TMC435) (Medivir/Tibotec); MK-7009 (Merck), RG7227 (ITMN-191) (Roche/Pharmasset/InterMune), boceprevir (SCH 503034) (Schering), SCH 446211 (Schering), narlaprevir SCH900518 (Schering/Merck), ABT-450 (Abbott/Enanta), ACH-1625 (Achillion), BI 201335 (Boehringer Ingelheim), PHX1766 (Phenomix), VX-500 (Vertex) and telaprevir (VX-950) (Vertex). Further examples of protease inhibitors include substrate-based NS3 protease inhibitors (Attwood et al., Antiviral peptide derivatives, PCT WO 98/22496, 1998; Attwood et al., *Antiviral Chemistry and Chemotherapy* 1999, 10, 259-273; Attwood et al., Preparation and use of amino acid derivatives as anti-viral agents, German Patent Pub. DE 19914474; Tung et al., Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate (Llinas-Brunet et al, Hepatitis C inhibitor peptide analogues, PCT WO 99/07734); Non-substrate-based NS3 protease inhibitors such as 2,4,6-trihydroxy-3-nitro-benzamide derivatives (Sudo K. et al., *Biochemical and Biophysical Research Communications*, 1997, 238, 643-647; Sudo K. et al., *Antiviral Chemistry and Chemotherapy*, 1998, 9, 186), including RD3-4082 and RD3-4078, the former substituted on the amide with a 14 carbon chain and the latter processing a para-phenoxyphenyl group; and Sch 68631, a phenanthrenequinone, an HCV protease inhibitor (Chu M. et al., *Tetrahedron Letters* 37:7229-7232, 1996);

SCH 351633, isolated from the fungus *Penicillium griseofulvum*, was identified as a protease inhibitor (Chu M. et al., *Bioorganic and Medicinal Chemistry Letters* 9:1949-1952). Eglin c, isolated from leech, is a potent inhibitor of several serine proteases such as *S. griseus* proteases A and B, α-chymotrypsin, chymase and subtilisin. Qasim M. A. et al., *Biochemistry* 36:1598-1607, 1997;

U.S. patents disclosing protease inhibitors for the treatment of HCV include, for example, U.S. Pat. No. 6,004,933 to Spruce et al., which discloses a class of cysteine protease inhibitors for inhibiting HCV endopeptidase 2; U.S. Pat. No. 5,990,276 to Zhang et al., which discloses synthetic inhibitors of hepatitis C virus NS3 protease; U.S. Pat. No. 5,538,865 to Reyes et a; WO 02/008251 to Corvas International, Inc., and U.S. Pat. No. 7,169,760, US2005/176648, WO 02/08187 and WO 02/008256 to Schering Corporation. HCV inhibitor tripeptides are disclosed in U.S. Pat. Nos. 6,534,523, 6,410,531, and 6,420,380 to Boehringer Ingelheim and WO 02/060926 to Bristol Myers Squibb. Diaryl peptides as NS3 serine protease inhibitors of HCV are disclosed in WO 02/48172 and U.S. Pat. No. 6,911,428 to Schering Corporation. Imidazoleidinones as NS3 serine protease inhibitors of HCV are disclosed in WO 02/08198 and U.S. Pat. No. 6,838,475 to Schering Corporation and WO 02/48157 and U.S. Pat. No. 6,727,366 to Bristol Myers Squibb. WO 98/17679 and U.S. Pat. No. 6,265,380 to Vertex Pharmaceuticals and WO 02/48116 and U.S. Pat. No. 6,653,295 to Bristol Myers Squibb also disclose HCV protease inhibitors. Further examples of HCV serine protease inhibitors are provided in U.S. Pat. No. 6,872,805 (Bristol-Myers Squibb); WO 2006000085 (Boehringer Ingelheim); U.S. Pat. No. 7,208,600 (Vertex); US 2006/0046956 (Schering-Plough); WO 2007/001406 (Chiron); US 2005/0153877; WO 2006/119061 (Merck); WO 00/09543 (Boehringer Ingelheim), U.S. Pat. No. 6,323,180 (Boehringer Ingelheim) WO 03/064456 (Boehringer Ingelheim), U.S. Pat. No. 6,642,204 (Boehringer Ingelheim), WO 03/064416 (Boehringer Ingelheim), U.S. Pat. No. 7,091,184 (Boehringer Ingelheim), WO 03/053349 (Bristol-Myers Squibb), U.S. Pat. No. 6,867,185, WO 03/099316 (Bristol-Myers Squibb), U.S. Pat. No. 6,869,964, WO 03/099274 (Bristol-Myers Squibb), U.S. Pat. No. 6,995,174, WO 2004/032827 (Bristol-Myers Squibb), U.S. Pat. No. 7,041,698, WO 2004/043339 and U.S. Pat. No. 6,878,722 (Bristol-Myers Squibb);

Thiazolidine derivatives which show relevant inhibition in a reverse-phase HPLC assay with an NS3/4A fusion protein and NS5A/5B substrate (Sudo K. et al., *Antiviral Research*, 1996, 32, 9-18), especially compound RD-1-6250, possessing a fused cinnamoyl moiety substituted with a long alkyl chain, RD4 6205 and RD4 6193;

Thiazolidines and benzanilides identified in Kakiuchi N. et al., *J. EBS Letters* 421, 217-220; Takeshita N. et al., *Analytical Biochemistry*, 1997, 247, 242-246;

A phenanthrenequinone possessing activity against protease in a SDS-PAGE and autoradiography assay isolated from the fermentation culture broth of *Streptomyces* sp., SCH 68631 (Chu M. et al., *Tetrahedron Letters*, 1996, 37, 7229-7232), and SCH 351633, isolated from the fungus *Penicillium griseofulvum*, which demonstrates activity in a scintillation proximity assay (Chu M. et al., *Bioorganic and Medicinal Chemistry Letters* 9, 1949-1952);

Helicase inhibitors (Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);

HCV polymerase inhibitors, including nucleoside and non-nucleoside polymerase inhibitors, such as ribavirin, viramidine, clemizole, filibuvir (PF-00868554), HCV POL, NM 283 (valopicitabine), MK-0608, 7-Fluoro-MK-0608, MK-3281, IDX-375, ABT-072, ABT-333, ANA598, BI 207127, GS 9190, PSI-6130, R1626, PSI-6206, PSI-938, PSI-7851, sofosbuvir (Gilead Sciences, formerly PSI-7977 and GS-7977), RG1479, RG7128, HCV-796 VCH-759 or VCH-916;

Gliotoxin (Ferrari R. et al., *Journal of Virology*, 1999, 73, 1649-1654), and the natural product cerulenin (Lohmann V. et al., *Virology*, 1998, 249, 108-118);

Interfering RNA (iRNA) based antivirals, including short interfering RNA (siRNA) based antivirals, such as Sirna-034 and others described in International Patent Publication Nos. WO/03/070750 and WO 2005/012525, and US Patent Publication No. US 2004/0209831;

Antisense phosphorothioate oligodeoxynucleotides (S-ODN) complementary to sequence stretches in the 5' non-coding region (NCR) of the virus (Alt M. et al., *Hepatology*, 1995, 22, 707-717), or nucleotides 326-348 comprising the 3' end of the NCR and nucleotides 371-388 located in the core coding region of the HCV RNA (Alt M. et al., *Archives of Virology*, 1997, 142, 589-599; Galderisi U. et al., *Journal of Cellular Physiology*, 1999, 181, 251-257);

Inhibitors of IRES-dependent translation (Ikeda N et al., Agent for the prevention and treatment of hepatitis C, Japanese Patent Pub. JP-08268890; Kai Y. et al., Prevention and treatment of viral diseases, Japanese Patent Pub. JP-10101591);

HCV NS5A inhibitors, such as BMS-790052 (daclatasvir, Bristol-Myers Squibb), PPI-461 (Presidio Pharmaceuticals), PPI-1301 (Presidio Pharmaceuticals), IDX-719 (Idenix Pharmaceuticals), AZD7295 (Arrow Therapeutics, AstraZeneca), EDP-239 (Enanta), ACH-2928 (Achillion), ACH-3102 (Achillion), ABT-267 (Abbott), or GS-5885 (Gilead);

HCV entry inhibitors, such as celgosivir (MK-3253) (MIGENIX Inc.), SP-30 (Samaritan Pharmaceuticals), ITX4520 (iTherX), ITX5061 (iTherX), PRO-206 (Progenics Pharmaceuticals) and other entry inhibitors by Progenics Pharmaceuticals, e.g., as disclosed in U.S. Patent Publication No. 2006/0198855;

Ribozymes, such as nuclease-resistant ribozymes (Maccjak, D. J. et al., *Hepatology* 1999, 30, abstract 995) and those disclosed in U.S. Pat. No. 6,043,077 to Barber et al., and U.S. Pat. Nos. 5,869,253 and 5,610,054 to Draper et al.; and Nucleoside analogs have also been developed for the treatment of Flaviviridae infections.

In certain embodiments, the compounds provided herein can be administered in combination with any of the compounds described by Idenix Pharmaceuticals in International Publication Nos. WO 01/90121, WO 01/92282, WO 2004/003000, 2004/002422 and WO 2004/002999.

Other patent applications disclosing the use of certain nucleoside analogs that can be used as second agents to treat hepatitis C virus include: PCT/CA00/01316 (WO 01/32153; filed Nov. 3, 2000) and PCT/CA01/00197 (WO 01/60315; filed Feb. 19, 2001) filed by BioChem Pharma, Inc. (now Shire Biochem, Inc.); PCT/US02/01531 (WO 02/057425; filed Jan. 18, 2002); PCT/US02/03086 (WO 02/057287; filed Jan. 18, 2002); U.S. Pat. Nos. 7,202,224; 7,125,855; 7,105,499 and 6,777,395 by Merck & Co., Inc.; PCT/EP01/09633 (WO 02/18404; published Aug. 21, 2001); US 2006/0040890; 2005/0038240; 2004/0121980; U.S. Pat. Nos. 6,846,810; 6,784,166 and 6,660,721 by Roche; PCT Publication Nos. WO 01/79246 (filed Apr. 13, 2001), WO 02/32920 (filed Oct. 18, 2001) and WO 02/48165; US 2005/0009737; US 2005/0009737; U.S. Pat. Nos. 7,094,770 and 6,927,291 by Pharmasset, Ltd.

Further compounds that can be used as second agents to treat hepatitis C virus are disclosed in PCT Publication No. WO 99/43691 to Emory University, entitled "2'-Fluoronucleosides". The use of certain 2'-fluoronucleosides to treat HCV is disclosed.

Other compounds that can be used as second agents include 1-amino-alkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), benzimidazoles (U.S. Pat. No. 5,891,874 to Colacino et al.), plant extracts (U.S. Pat. No. 5,837,257 to Tsai et al., U.S. Pat. No. 5,725,859 to Omer et al., and U.S. Pat. No. 6,056,961), and piperidines (U.S. Pat. No. 5,830,905 to Diana et al.).

In certain embodiments, a compound of Formula 1001, 2001-2003, I-XXVII, 1-104iib, 201-213iib, 301-315, 401-415, or i-ivH, or a composition comprising a compound of Formula 1001, 2001-2003, I-XXVII, 1-104iib, 201-213iib, 301-315, 401-415, or i-ivH, is administered in combination or alternation with a second anti-viral agent selected from the group consisting of an interferon, a nucleotide analogue, a polymerase inhibitor, an NS3 protease inhibitor, an NS5A inhibitor, an entry inhibitor, a non-nucleoside polymerase inhibitor, a cyclosporine immune inhibitor, an NS4A antagonist, an NS4B-RNA binding inhibitor, a locked nucleic acid mRNA inhibitor, a cyclophilin inhibitor, and combinations thereof.

Exemplary Second Therapeutic Agents for Treatment of HCV

In certain embodiments, one or more compounds provided herein can be administered in combination or alternation with an anti-hepatitis C virus interferon, such as Intron A® (interferon alfa-2b) and; Roferon A® (Recombinant interferon alfa-2a), Infergen® (consensus interferon; interferon alfacon-1), PEG-Intron® (pegylated interferon alfa-2b), and Pegasys® (pegylated interferon alfa-2a). In certain embodiments, one or more compounds provided herein can be administered in combination or alternation with ribavirin and in combination or alternation with an anti-hepatitis C virus interferon. In certain embodiments, one or more compounds provided herein can be administered in combination or alternation with ribavirin, in combination or alternation with an anti-hepatitis C virus interferon, and in combination or alternation with an anti-hepatitis C virus protease inhibitor. In certain embodiments, one or more compounds provided herein can be administered in combination or alternation with ribavirin. In certain embodiments, one or more compounds provided herein can be administered in combination or alternation with an anti-hepatitis C virus interferon and without ribavirin. In certain embodiments, one or more compounds provided herein can be administered in combination or alternation with an anti-hepatitis C virus interferon, in combination or alternation with an anti-hepatitis C virus protease inhibitor, and without ribavirin.

In certain embodiments, the anti-hepatitis C virus interferon is infergen, IL-29 (PEG-Interferon lambda), R7025 (Maxy-alpha), Belerofon, Oral Interferon alpha, BLX-883 (Locteron), omega interferon, multiferon, medusa interferon, Albuferon or REBIF®.

In certain embodiments, one or more compounds provided herein can be administered in combination or alternation with an anti-hepatitis C virus polymerase inhibitor, such as ribavirin, viramidine, HCV POL, NM 283 (valopicitabine), MK-0608, 7-Fluoro-MK-0608, PSI-6130, R1626, PSI-6206, PSI-938, R1479, HCV-796, VX-950 (Telaprevir, Vertex), GS 9190 NN (Gilead), GS 9256 (Gilead), PSI-7792 (BMS), BI 207127 (BI), R7128 (Roche), sofosbuvir (Gilead Sciences, formerly PSI-7977 and GS-7977), PSI-938 (Pharmasset), VX-222 (Vertex), ALS-2200 (Vertex), ALS-2158 (Vertex), MK-0608 (Merck), TMC649128 (Medivir), PF-868554 (Pfizer), PF-4878691 (Pfizer), ANA598 (Roche), VCH-759 (Vertex), IDX184 (Idenix), IDX375 (Idenix), A-837093 (Abbott), GS 9190 (Gilead), GSK625433 (GlaxoSmithKline), ABT-072 (Abbott), ABT-333 (Abbott), INX-189 (Inhibitex), or EDP-239 (Enanta).

In certain embodiments, the one or more compounds provided herein can be administered in combination with ribavarin and an anti-hepatitis C virus interferon, such as Intron A® (interferon alfa-2b) and Pegasys® (Peginterferon alfa-2a); Roferon A® (Recombinant interferon alfa-2a), Infergen® (consensus interferon; interferon alfacon-1), PEG-Intron® (pegylated interferon alfa-2b), Zalbin (albinterferon alfa-2b), omega interferon, pegylated interferon lambda, and Pegasys® (pegylated interferon alfa-2a).

In certain embodiments, one or more compounds provided herein can be administered in combination or alternation with an anti-hepatitis C virus protease inhibitor such as ITMN-191, SCH 503034 (bocepravir), VX950 (telaprevir), VX985, VX500, VX813, PHX1766, BMS-650032, GS 9256, BI 201335, IDX320, R7227, MK-7009 (vaniprevir), TMC435, BMS-791325, ACH-1625, ACH-2684, ABT-450, or AVL-181.

In certain embodiments, one or more compounds provided herein can be administered in combination or alternation with an HCV NS5A inhibitor, such as BMS-790052 (daclatasvir, Bristol-Myers Squibb), PPI-461 (Presidio Pharmaceuticals), PPI-1301 (Presidio Pharmaceuticals), IDX-719 (Idenix Pharmaceuticals), AZD7295 (Arrow Therapeutics, AstraZeneca), EDP-239 (Enanta), ACH-2928 (Achillion), ACH-3102 (Achillion), ABT-267 (Abbott), or GS-5885 (Gilead).

In certain embodiments, one or more compounds provided herein can be administered in combination or alternation with an anti-hepatitis C virus vaccine, such as TG4040, PeviPRO™, CGI-5005, HCV/MF59, GV1001, IC41, GNI-103, GenPhar HCV vaccine, C-Vaxin, CSL123, Hepavaxx C, ChronVac-C® or INNO0101 (E1).

In certain embodiments, one or more compounds provided herein can be administered in combination or alternation with an anti-hepatitis C virus monoclonal antibody, such as MBL-HCV1, AB68 or XTL-6865 (formerly HepX-C); or an anti-hepatitis C virus polyclonal antibody, such as cicavir.

In certain embodiments, one or more compounds provided herein can be administered in combination or alternation with an anti-hepatitis C virus immunomodulator, such as Zadaxin® (thymalfasin), SCV-07, NOV-205 or Oglufanide.

In certain embodiments, one or more compounds provided herein can be administered in combination or alternation with cyclophilin inhibitor, such as Enanta cyclophilin binder, SCY-635, or Debio-025.

In certain embodiments, one or more compounds provided herein can be administered in combination or alternation with Nexavar, doxorubicin, PI-88, amantadine, JBK-122, VGX-410C, MX-3253 (Ceglosivir), Suvus (BIVN-401 or virostat), PF-03491390 (formerly IDN-6556), G126270, UT-231B, DEBIO-025, EMZ702, ACH-0137171, MitoQ, ANA975, AVI-4065, Bavituxinab (Tarvacin), Alinia (nitrazoxanide) or PYN17.

In certain embodiments, one or more compounds provided herein can be administered in combination or alternation with telaprevir, bocepravir, interferon alfacon-1, interferon alfa-2b, pegylated interferon alpha 2a, pegylated interferon alpha 2b, ribavirin, or combinations thereof.

In certain embodiments, one or more compounds provided herein can be administered in combination or alternation with a protease inhibitor. In certain embodiments, one or more compounds provided herein can be administered in combination or alternation with telaprevir. In certain embodiments, one or more compounds provided herein can be administered in combination or alternation with bocepravir.

In certain embodiments, one or more compounds provided herein can be administered in combination or alternation with a protease inhibitor and in combination or alternation with ribavirin. In certain embodiments, one or more compounds provided herein can be administered in combination or alternation with telaprevir and in combination or alternation with ribavirin. In certain embodiments, one or more compounds provided herein can be administered in combination or alternation with bocepravir and in combination or alternation with ribavirin.

In certain embodiments, one or more compounds provided herein can be administered in combination or alternation with a protease inhibitor and not in combination or alternation with ribavirin. In certain embodiments, one or more compounds provided herein can be administered in combination or alternation with telaprevir and not in combination or alternation with ribavirin. In certain embodiments, one or more compounds provided herein can be administered in combination or alternation with bocepravir and not in combination or alternation with ribavirin.

In certain embodiments, one or more compounds provided herein can be administered in combination or alternation with an interferon. In certain embodiments, one or more compounds provided herein can be administered in combination or alternation with interferon alfacon-1. In certain embodiments, one or more compounds provided herein can be administered in combination or alternation with interferon alfa-2b. In certain embodiments, one or more compounds provided herein can be administered in combination or alternation with pegylated interferon alpha 2a. In certain embodiments, one or more compounds provided herein can be administered in combination or alternation with pegylated interferon alpha 2b.

In certain embodiments, one or more compounds provided herein can be administered in combination or alternation with an interferon and in combination or alternation with ribavirin. In certain embodiments, one or more compounds provided herein can be administered in combination or alternation with interferon alfacon-1and in combination or alternation with ribavirin. In certain embodiments, one or more compounds provided herein can be administered in combination or alternation with interferon alfa-2b and in combination or alternation with ribavirin. In certain embodiments, one or more compounds provided herein can be administered in combination or alternation with pegylated interferon alpha 2a and in combination or alternation with ribavirin. In certain embodiments, one or more compounds provided herein can be administered in combination or alternation with pegylated interferon alpha 2b and in combination or alternation with ribavirin.

In certain embodiments, one or more compounds can be administered in combination or alternation with one or more of the second agents provided herein and not in combination or alternation with ribavirin. In certain embodiments, one or more compounds provided herein can be administered in combination or alternation with an interferon and not in combination or alternation with ribavirin. In certain embodiments, one or more compounds provided herein can be administered in combination or alternation with interferon alfacon-land not in combination or alternation with ribavirin. In certain embodiments, one or more compounds provided herein can be administered in combination or alternation with interferon alfa-2b and not in combination or alternation with ribavirin. In certain embodiments, one or more compounds provided herein can be administered in combination or alternation with pegylated interferon alpha 2a and not in combination or alternation with ribavirin. In certain embodiments, one or more compounds provided herein can be administered in combination or alternation with pegylated interferon alpha 2b and not in combination or alternation with ribavirin.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); mM (millimolar); μM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); THF (tetrahydrofuran); $CDCl_3$ (deuterated chloroform); AcOH (acetic acid); DCM (dichloromethane); DMSO (dimethylsulfoxide); $DMSO-d_6$ (deuterated dimethylsulfoxide); EtOAc (ethyl acetate); MeOH (methanol); and BOC (t-butyloxycarbonyl).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Example 1

Preparation of 2'-Chloro Nucleoside Analogs

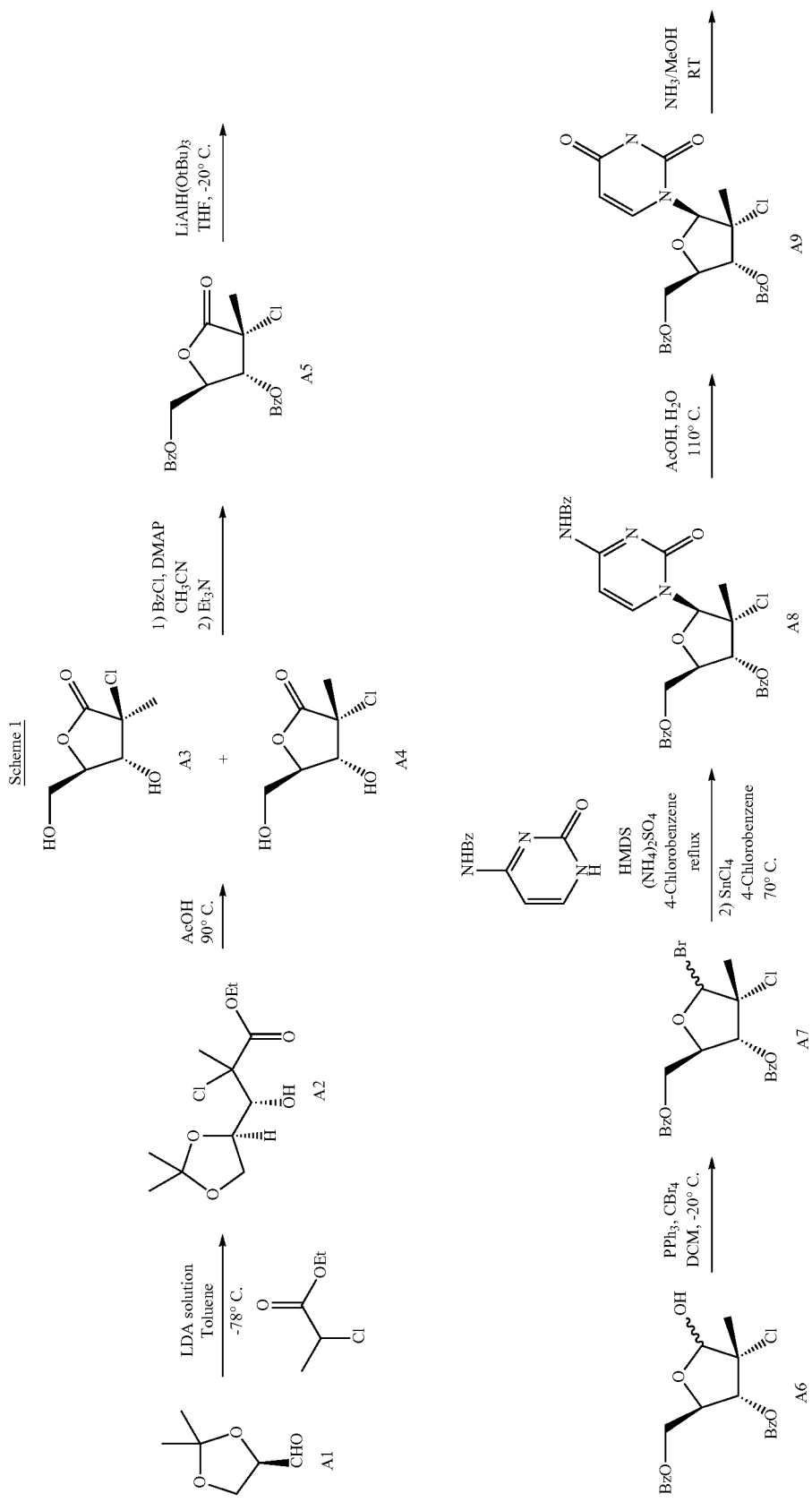

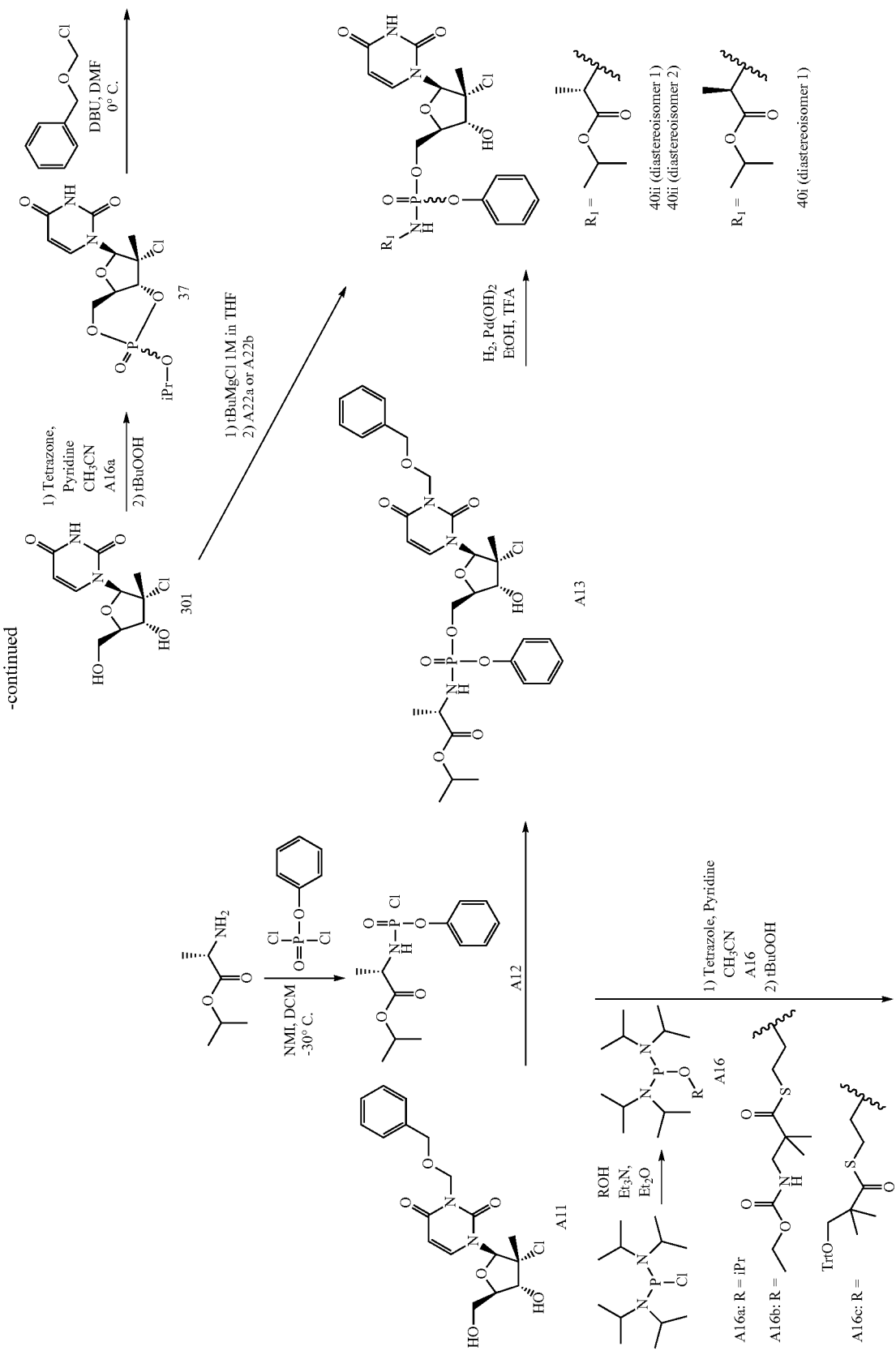

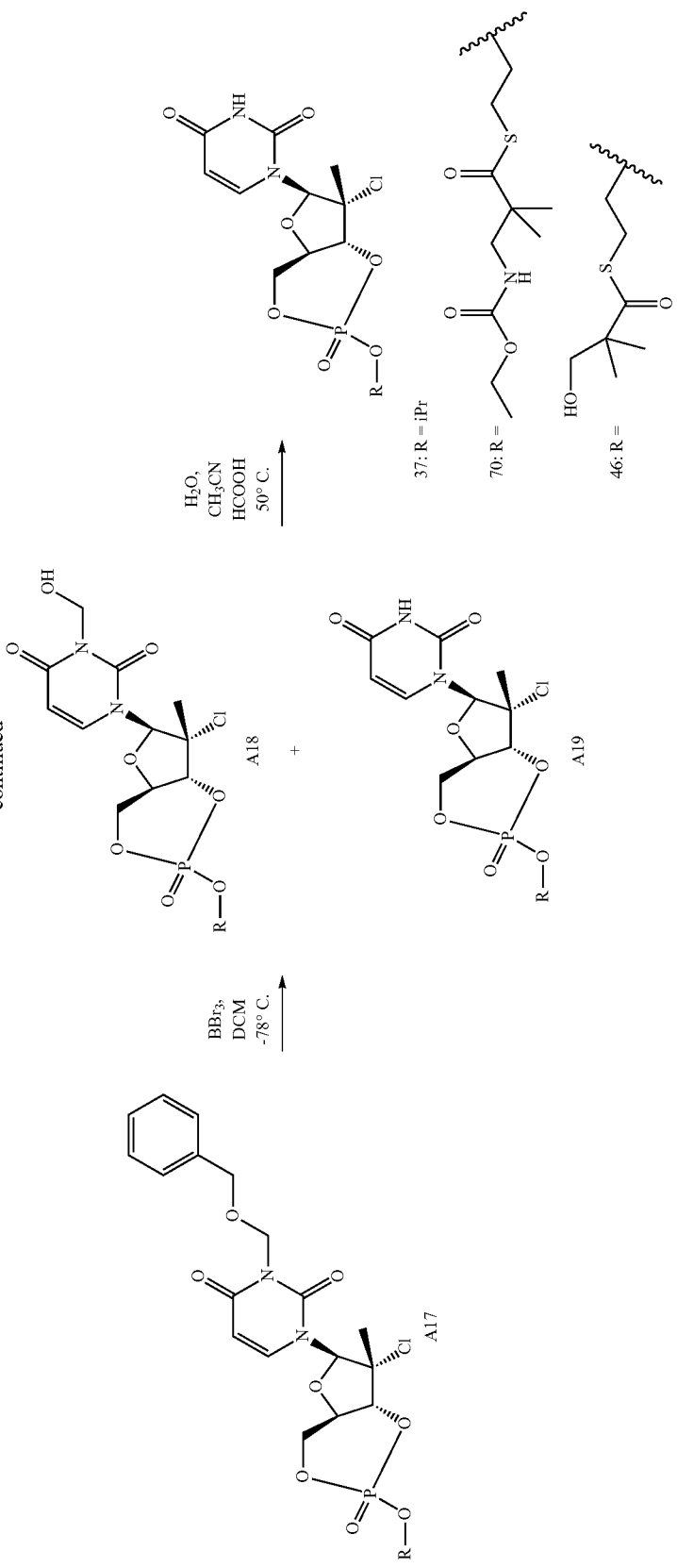

Ethyl (3R)-2-chloro-3-[(4R)-2,2-dimethyl-1,3-dioxolan-4-yl]-3-hydroxy-2-methylpropanoate (A2)

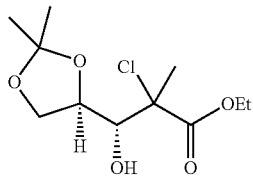 [SMILES: CCOC(=O)C(C)(Cl)[C@H](O)[C@H]1COC(C)(C)O1]

A 5 L flange flask was fitted with a thermometer, nitrogen inlet, pressure equalizing dropping funnel, bubbler, and a suba•seal. Methyl lithium solution (1.06 L, 1.6 M in diethylether, 1.7 equiv.) was added, and the solution was cooled to about −25° C. Diisopropyl amine (238 ml, 1.7 equiv.) was added using the dropping funnel over about 40 minutes. The reaction was left stirring, allowing to warm to ambient temperature overnight. $CO_{2(s)}$/acetone cooling was applied to the LDA solution, cooling to about −70° C.

R-Glyceraldehyde dimethylacetal solution (50% in DCM) was evaporated down to ~100 mbar at a bath temp of 35° C., to remove the DCM, then azeotroped with anhydrous hexane (200 ml), under the same Büchi conditions. $^1$H NMR was used to confirm that all but a trace of DCM remained.

The fresh aldehyde (130 g, 1 mol) and ethyl 2-chloropropionate (191 ml, 1.5 equiv.) were placed in a 1 L round bottom flask, which was filled with toluene (800 ml). This solution was cooled in a $CO_{2(s)}$/acetone bath, and added via cannula to the LDA solution over about 50 minutes, keeping the internal temperature of the reaction mixture cooler than −60° C. The mixture was stirred with cooling (internal temp. slowly fell to ~−72° C.) for 90 min, then warmed to room temperature over 30 minutes using a water bath. This solution was added to a sodium dihydrogen phosphate solution equivalent to 360 g of $NaH_2PO_4$ in 1.5 L of ice/water, over about 10 minutes, with ice-bath cooling. The mixture was stirred for 20 minutes, then transferred to a sep. funnel, and partitioned. The aqueous layer was further extracted with EtOAc (2×1 L), and the combined organic extracts were dried over sodium sulfate. The volatiles were removed in vacuo (down to 20 mbar). The resultant oil was hydrolyzed crude.

(3R,4R,5R)-3-chloro-4-hydroxy-5-(hydroxymethyl)-3-methyloxolan-2-one (A4)

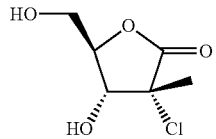

The crude oil A2 was taken up in acetic acid (1.5 L, 66% in water) and heated to 90° C. over one hour, then at held at that temperature for one hour. Once the mixture had cooled to room temperature, the volatiles were removed in vacuo, and azeotroped with toluene (500 ml). The resultant oil was combined with some mixed material from an earlier synthesis and columned in two portions (each ~1.25 L of silica, 38→75% EtOAc in DCM). The lower of the two main spots is the desired material; fractions containing this material as the major component were combined and the solvent removed in vacuo to give 82 g of orange solid whose $^1$H NMR showed the material to be of about 57% purity (of the remainder 29% was the indicated epimer). This material was recrystallized from toluene/butanone (600 ml/~185 ml), the butanone being the 'good' solvent. The resultant solid was filtered washing with toluene and hexane, and dried in vacuo to give product of about 92% purity (30 g).

(2R,3R,4R)-2-[(benzoyloxy)methyl]-4-chloro-4-methyl-5-oxooxolan-3-yl benzoate (A5)

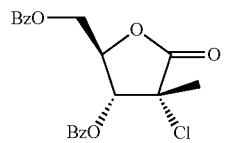

A 2 L 3-neck round bottom flask was fitted with an overhead stirrer, thermometer and pressure equalizing dropping funnel (→$N_2$). The intermediate A4 (160 mmol) in acetonitrile (1 L) was added, followed by 4-dimethylaminopyridine (3.2 mmol) and benzoyl chloride (352 mmol). Finally triethylamine (384 mmol) was added over 10 minutes using the dropping funnel. The addition of the triethylamine is accompanied by a mild exotherm, which obviated the addition of a cold water bath to keep the internal temperature below 25° C. The reaction was stirred at ambient temperature for 2.5 hours. The reaction mixture was transferred to a sep. funnel with EtOAc (2 L) and half saturated brine (2 L), and partitioned. The aqueous layer was re-extracted with EtOAc (1 L). The combined organic layers were washed with 50% sodium bicarbonate/25% brine (1.5 L) and dried over sodium sulfate, to give 62 g of solid. This was recrystallized from 1.8 L of 1:1 toluene/trimethylpentane (95° C.), to give 52.4 g of product.

$^1$H NMR (CDCl$_3$, 400 MHz): δ (ppm) 1.91 (s, 3H), 4.57 (dd, J=5.12 Hz and J=12.57 Hz, 1H), 4.77 (dd, J=3.29 Hz and J=12.68 Hz, 1H), 4.92-4.96 (m, 1H), 5.60 (d, J=8.36 Hz, 1H), 7.38-7.66 (m, 6H), 7.97-7.99 (m, 2H), 8.08-8.10 (m, 2H); MS (ESI) m/z=411.1 (MNa$^+$).

3,5-Di-O-benzoyl-2-C-chloro-2-C-methyl-D-ribofuranose (A6)

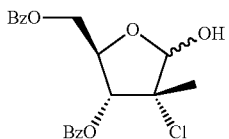

To a solution of A5 (14.48 mmol) in anhydrous tetrahydrofurane (70 ml) was added under inert atmosphere at −35° C., LiAlH(OtBu)$_3$ (1M in tetrahydrofurane, 21.7 mmol) over a 30 min period. The reaction mixture was stirred for 1 hour at −20° C. and quenched by addition of a saturated NH$_4$Cl solution, keeping the temperature bellow 0° C. Ethyl acetate was added and the white suspension was filtered through a pad of celite and washed with ethyl acetate. The filtrate was extracted with ethyl acetate twice. The combined organic layers were dried over anhydrous sodium sulfate, filtered and evaporated under reduced pressure. The residue was purified by chromatography on silica gel (eluent: petroleum ether/ethyl acetate 0 to 20%). The product was dried in vacuum (50° C.) overnight to afford expected intermediate as a colorless oil in 96% yield (mixture α/β: 45/55).

$^1$H NMR (CDCl$_3$, 400 MHz): δ (ppm) 1.74 (s, 1.75H$_\beta$), 1.76 (s, 1.25H$_\alpha$), 4.42-4.69 (m, 3H), 5.30 (d, J=12.8 Hz, 0.55H$_\beta$), 5.43-5.47 (m, 0.45H$_\alpha$), 5.60 (d, J=7.0 Hz, 0.55H$_\beta$), 5.78 (d, J=7.0 Hz, 0.45H$_\alpha$), 7.35-7.41 (m, 2H), 7.45-7.56 (m, 3H), 7.59-7.65 (m, 1H), 7.96-8.04 (m, 2H), 8.06-8.14 (m, 2H); MS (ESI) m/z=413 (MNa$^+$).

3,5-Di-O-benzoyl-2-C-chloro-2-C-methyl-D-arabinofuranosyl bromide (A7)

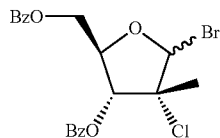

To a solution of A6 (12.80 mmol) in anhydrous dichloromethane (80 ml) was added under inert atmosphere at −20° C., triphenylphosphine (18.0 mmol). The reaction mixture was stirred for 15 minutes at −20° C. and CBr$_4$ (19.20 mmol) was added. The reaction mixture was then stirred for 1 hour at −20° C. The crude was partially concentrated under reduced pressure (bath temperature bellow 30° C.) and directly purified by chromatography on silica gel (eluent: petroleum ether/ethyl acetate 0 to 30%) to afford a mixture of θ sugar A7a (1.67 g) and α sugar A7b (2.15 g) as a colorless gum in 66% global yield.

$^1$H NMR (CDCl$_3$, 400 MHz): β sugar δ (ppm) 1.93 (s, 3H), 4.60-4.88 (m, 3H), 6.08 (d, J=7.9 Hz, 1H), 6.62 (s, 1H), 7.31-7.38 (m, 2H), 7.41-7.55 (m, 3H), 7.59-7.65 (m, 1H), 8.00-8.05 (m, 2H), 8.06-8.12 (m, 2H); α sugar δ (ppm) 1.88 (s, 3H), 4.66-4.89 (m, 3H), 5.37 (d, J=4.88 Hz, 1H), 6.44 (s, 1H), 7.41-7.55 (m, 4H), 7.54-7.65 (m, 2H), 8.00-8.05 (m, 2H), 8.14-8.20 (m, 2H); MS (ESI) m/z=476/478 (MNa$^+$).

3',5'-Di-O-benzoyl-2'-C-chloro-2'-C-methyl-4-benzoyl-cytidine (A8)

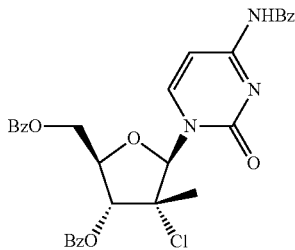

To a suspension of N-benzoyl cytosine (9.48 mmol), and a catalytic amount of ammonium sulfate in 4-chlorobenzene (24 ml) was added HMDS (28.44 mmol). The reaction mixture was heated during 2 hours at 140° C. The solvent was removed under inert atmosphere and the residue was taken in 4-chlorobenzene (15 ml). Then, A7b (4.74 mmol) in chlorobenzene (10 ml) was added dropwise to the reaction mixture followed by SnCl$_4$ (14.22 mmol) dropwise. The reaction mixture was stirred at 70° C. overnight, cooled to room temperature and diluted with dichloromethane and a saturated NaHCO$_3$ solution. The white suspension was filtered through a pad of celite and washed with dichloromethane. The filtrate was extracted with dichloromethane twice. The combined organic layers were dried over anhydrous Na$_2$SO$_4$, filtered and evaporated under reduced pressure to afford expected intermediate as a white solid in 89% yield.

$^1$H NMR (DMSO, 400 MHz): δ (ppm) 1.58 (s, 3H), 4.68-4.81 (m, 3H), 5.68 (brs, 1H), 6.55 (brs, 1H), 7.36 (d, J=7.84 Hz, 1H), 7.39-7.76 (m, 9H), 7.88-8.07 (m, 6H), 8.30 (d, J=7.84 Hz, 1H); MS (ESI) m/z=588 (MH$^+$).

3',5'-Di-O-benzoyl-2'-C-chloro-2'-C-methyluridine (A9)

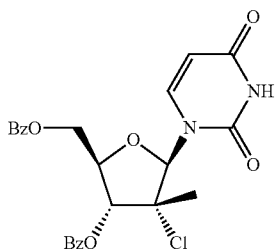

A suspension of A8 (4.19 mmol) in an acetic acid/water mixture (67 ml/17 ml, v/v), was heated at 110° C. for 3 hours. The reaction mixture was evaporated to dryness and co-evaporated with toluene (three times) to afford expected intermediate in quantitative yield as an oil which was directly used for the next step; MS (ESI) m/z=485 (MH$^+$).

2'-C-Chloro-2'-C-methyluridine (301)

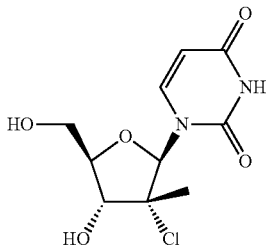 [SMILES: C[C@@]1(Cl)[C@H](O)[C@@H](CO)O[C@H]1n1ccc(=O)[nH]c1=O]

Intermediate A9 (4.19 mmol) in 7 N methanolic ammonia (80 ml) was stirred at room temperature for 24 hours. The mixture was evaporated to dryness, diluted with water and transferred into a separatory funnel. The aqueous layer was extracted with dichloromethane and water was removed under reduced pressure. The residue was purified by flash RP18 gel chromatography (eluent: water/acetonitrile 0 to 40%) to afford pure expected compound as a white foam in 79% yield.

$^1$H NMR (DMSO, 400 MHz): δ (ppm) 1.44 (s, 3H), 3.60-3.68 (m, 1H), 3.80-3.94 (m, 3H), 5.39 (t, J=4.45 Hz, 1H), 5.63 (d, J=8.26 Hz, 1H), 5.93 (d, J=5.72 Hz, 1H), 6.21 (s, 1H), 8.16 (d, J=8.90 Hz, 1H), 11.44 (m, 1H); MS (ESI) m/z=277 (MH$^+$).

2'-C-Chloro-2'-C-methyl-3-benzyloxymethyluridine (A11)

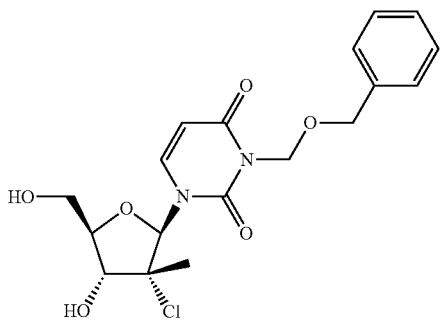 [SMILES: C[C@@]1(Cl)[C@H](O)[C@@H](CO)O[C@H]1n1ccc(=O)n(COCc2ccccc2)c1=O]

To a solution of 301 (0.361 mmol) in anhydrous DMF (4 ml) was added at −5° C., DBU (0.723 mmol) followed by benzyloxymethylchloride (0.542 mmol). The reaction mixture was stirred for 45 minutes between −5° C. and 5° C. The solvent was evaporated under reduced pressure and the residue was purified by chromatography on silica gel (eluent: dichloromethane/methanol 0 to 10%) to afford pure expected intermediate as a white solid in 80% yield.

$^1$H NMR (DMSO, 400 MHz): δ (ppm) 1.41 (s, 3H), 3.61-3.69 (m, 1H), 3.82-3.95 (m, 3H), 4.57 (s, 2H), 5.32 (s, 2H), 5.43 (t, J=4.46 Hz, 1H), 5.80 (d, J=8.08 Hz, 1H), 5.96 (d, J=4.46 Hz, 1H), 6.23 (s, 1H), 7.22-7.36 (m, 5H), 8.25 (d, J=8.22 Hz, 1H); MS (ESI) m/z=397 (MH$^+$).

Isopropyl (2S)-2-[[chloro(phenoxy)phosphoryl]amino]propanoate (A12a)

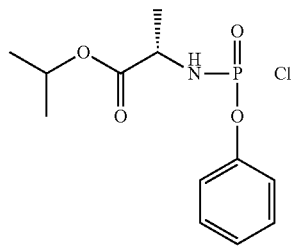

2,2-Dimethylpropyl (2S)-2-[[chloro(phenoxy)phosphoryl]amino]propanoate (A12b)

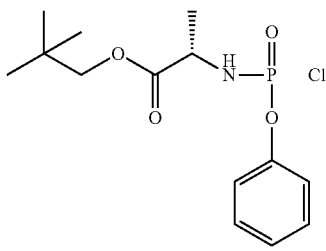

To a solution of aminoester, HCl salt (0.434 mmol) in anhydrous dichloromethane (or acetonitrile) (4 ml) (3 times vacuo/nitrogen) under nitrogen was added at −30° C. phenyldichlorophosphate (0.434 mmol) followed by N-methylimidazole (2.90 mmol)(or only 1.45 mmol for A12b). The reaction mixture was stirred at −30° C. during 1 hour. The reaction was monitored by LC/MS (the sample was quenched by methanol or water) to check the complete formation of expected intermediate A12a [MS (ESI) m/z=302 (MH$^+$)(—OMe compound)] or A12b [MS (ESI) m/z=314 (MH$^-$)].

Compound (A13a), (A13b) or (83ii)

To the previous reaction mixture containing A12 was added A11 (or 302) (0.29 mmol) at −25° C. under nitrogen. The reaction mixture was allowed to warm up slowly to room temperature overnight, and then diluted with dichloromethane and water (or with NaHCO$_3$ and EtOAc). The organic layer was extracted, dried, filtered and evaporated under reduced pressure. The crude residue was purified by chromatography on silica gel (eluent: dichloromethane/methanol 0 to 10%) (followed by preparative HPLC for A29).

Compound (A13a)

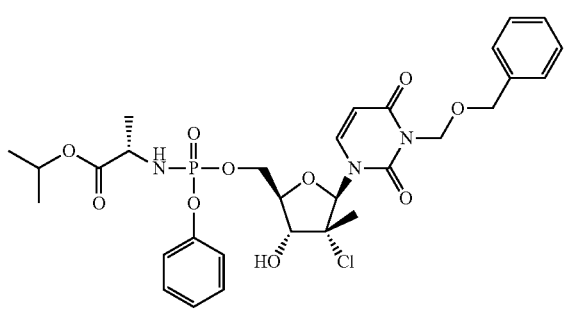

Mixture of diastereoisomers; MS (ESI) m/z=666 (MH$^+$).

Compound (A13b)

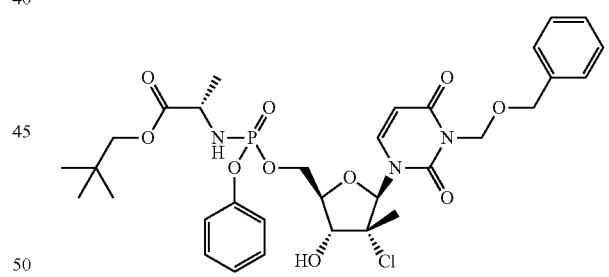

Mixture of diastereoisomers; MS (ESI) m/z=692.3 (MH$^+$).

Compound (83ii)

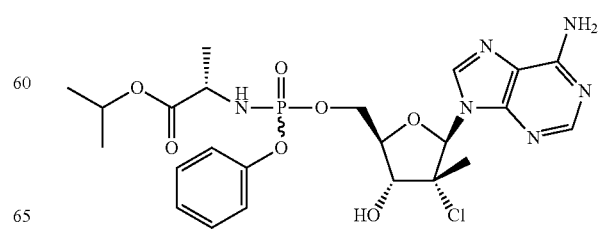

Glassy solid; $^1$H NMR (CDCl$_3$, 400 MHz): δ (ppm) 1.19-1.24 (m, 9H), 1.35 (d, J=7.1 Hz, 3H), 3.95-4.05 (m, 1H), 4.31 (d, J=8.1 Hz, 2H), 4.41 (d, J=9.0 Hz, 1H), 4.59 (d, J=7.1 Hz, 2H), 4.98 (heptuplet, J=6.28 Hz, 1H), 6.38 (brs, 1H), 6.52 (s, 1H), 7.08-7.15 (m, 1H), 7.23-7.30 (m, 4H), 8.07 (s, 1H), 8.31 (s, 1H); $^{31}$P NMR (CDCl$_3$, 161.98 MHz): δ (ppm) 3.96 (s, 1P); MS (ESI) m/z=569.20 (MH$^+$).

Compounds (40iia) and (40iib)

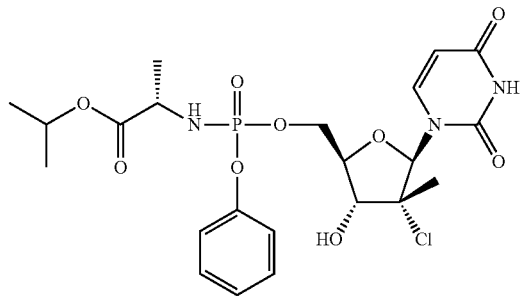

To a solution of A13 (0.29 mmol) in anhydrous ethanol (6 ml) was added trifluoroacetic acid (2.9 mmol) dropwise (then 3 times vacuo/nitrogen purges), followed by Palladium hydroxide (20% on Carbon). The reaction mixture was purged 3 times vacuo/nitrogen, and 3 times vacuo/hydrogen and then stirred under hydrogen for 5 hours. The reaction mixture was diluted with ethyl acetate and filtered through a pad of celite. The filtrate was evaporated under reduced pressure, and the crude compound was purified by preparative MS/HPLC to afford two pure compounds in 48% global yield.

Compound 40ii (diastereoisomer 1): white solid; $^1$H NMR (CDCl$_3$, 400 MHz): δ (ppm) 1.22-1.26 (m, 6H), 1.37 (d, J=7.08 Hz, 3H), 1.51 (s, 3H), 3.71-3.88 (m, 2H), 3.97-4.06 (m, 1H), 4.16-4.18 (m, 1H), 4.45-4.57 (m, 2H), 4.97-5.07 (m, 1H), 5.57 (d, J=8.20 Hz, 1H), 6.39 (s, 1H), 7.18-7.37 (m, 5H), 7.44 (d, J=8.20 Hz, 1H), 8.40 (s, 1H); $^{31}$P NMR (CDCl$_3$, 161.98 MHz): δ (ppm) 4.20 (s, 1P); MS (ESI, E1$^+$) m/z=546 (MH$^+$).

Compound 40ii (diastereoisomer 2): white solid; $^1$H NMR (CDCl$_3$, 400 MHz): δ (ppm) 1.24-1.26 (m, 6H), 1.36 (d, J=7.04 Hz, 3H), 1.59 (s, 3H), 3.69-3.77 (m, 1H), 3.91-3.99 (m, 2H), 4.17-4.19 (m, 1H), 4.43-4.59 (m, 2H), 5.01-5.06 (m, 1H), 5.68 (d, J=8.20 Hz, 1H), 6.42 (s, 1H), 7.21-7.39 (m, 5H), 7.60 (d, J=8.20 Hz, 1H), 8.14 (s, 1H); $^{31}$P NMR (CDCl$_3$, 161.98 MHz): δ (ppm) 3.47 (s, 1P); MS (ESI) m/z=546 (MH$^+$).

Compound 42iii

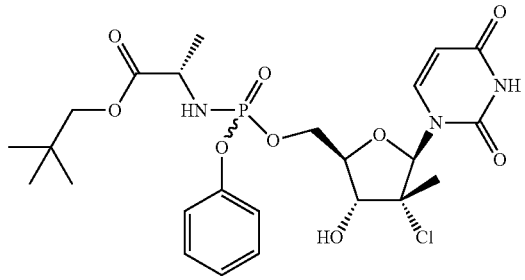

Compound 42ii was synthesized from compound A13b (0.144 mmol) as described for compound 40ii.

White solid; $^1$H NMR (MeOD, 400 MHz) δ (ppm) 0.94 (s, 9H), 1.40 (d, J=7.10 Hz, 3H), 1.53 (s, 3H), 3.76 (d, J=10.43H, 1H), 3.86 (d, J=10.44H, 1H), 3.98-4.06 (m, 2H), 4.18-4.22 (m, 1H), 4.39-4.44 (m, 1H), 4.52-4.57 (m, 1H), 5.62 (d, J=8.18 Hz, 1H), 6.40 (s, 1H), 7.20-7.29 (m, 3H), 7.36-7.41 (m, 2H), 7.74 (d, J=8.18 Hz, 1H); $^{31}$P NMR (MeOD, 161.98 MHz) δ (ppm) 3.68 (s, 1P); MS (ESI) m/z=574.08 (MH$^+$).

General Method A

The following procedure was used to obtain intermediates A16a, A16b, A16c and A16d.

To a solution of 2-bis(diisopropylamino)chlorophosphine (4.25 mmol) in anhydrous diethyl ether (5 mL/mmol) (3 times vacuo/nitrogen) under nitrogen was added at −15° C. triethylamine (12.70 mmol) followed by a solution of an appropriate alcohol (5.08 mmol) in anhydrous ether (2.5 mL/mmol). The reaction mixture was stirred at −15° C. for 1.5 hours then allowed to warm up to room temperature, and stirred at room temperature for 3.5 hours. The reaction mixture was filtered through an autocup (0.45 μm) to remove salts and washed with diethyl ether. The filtrate was evaporated under reduced pressure under nitrogen to give the expected intermediate.

2-Bis(diisopropylamino)isopropoxyphosphine (A16a)

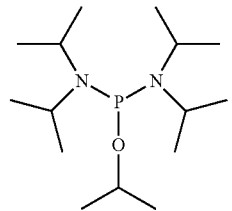 [SMILES: CC(C)OP(N(C(C)C)C(C)C)N(C(C)C)C(C)C]

Colorless oil; 94% yield; $^{31}$P NMR (CDCl$_3$, 161.98 MHz): δ (ppm) 114.98 (s, 1P).

S-[2-bis(diisopropylamino)phosphanyloxyethyl]-3-(ethoxycarbonylamino)-2,2-dimethyl-propanethioate (A16b)

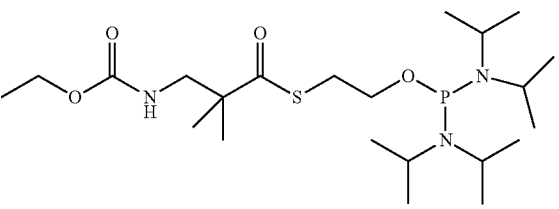 [SMILES: CCOC(=O)NCC(C)(C)C(=O)SCCOP(N(C(C)C)C(C)C)N(C(C)C)C(C)C]

Yellow oil; quantitative yield; $^{31}$P NMR (CDCl$_3$, 161.98 MHz) δ 124.62 (s, 1P).

S-[2-bis(diisopropylamino)phosphanyloxyethyl]-2,2-dimethyl-3-trityloxy-propanethioate (A16c)

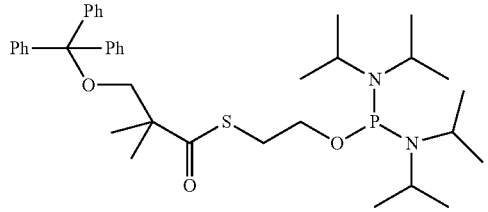 [SMILES: CC(C)N(C(C)C)P(OCCSC(=O)C(C)(C)COC(c1ccccc1)(c1ccccc1)c1ccccc1)N(C(C)C)C(C)C]

Quantitative yield; $^{31}$P NMR (CDCl$_3$, 161.98 MHz) δ 124.79 (s, 1P).

S-[2-bis(diisopropylamino)phosphanyloxyethyl]2,2-dimethylpropanethioate (16d)

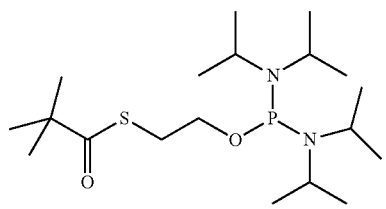 [SMILES: CC(C)N(C(C)C)P(OCCSC(=O)C(C)(C)C)N(C(C)C)C(C)C]

Quantitative yield; $^{31}$P NMR (CDCl$_3$, 161.98 MHz) δ 124.83 (s, 1P).

General Method B

The following procedure was used to obtain intermediates A17a, A17b, A17c, 37 and A60.

Scheme 6

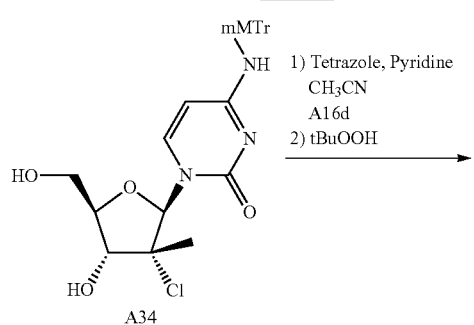

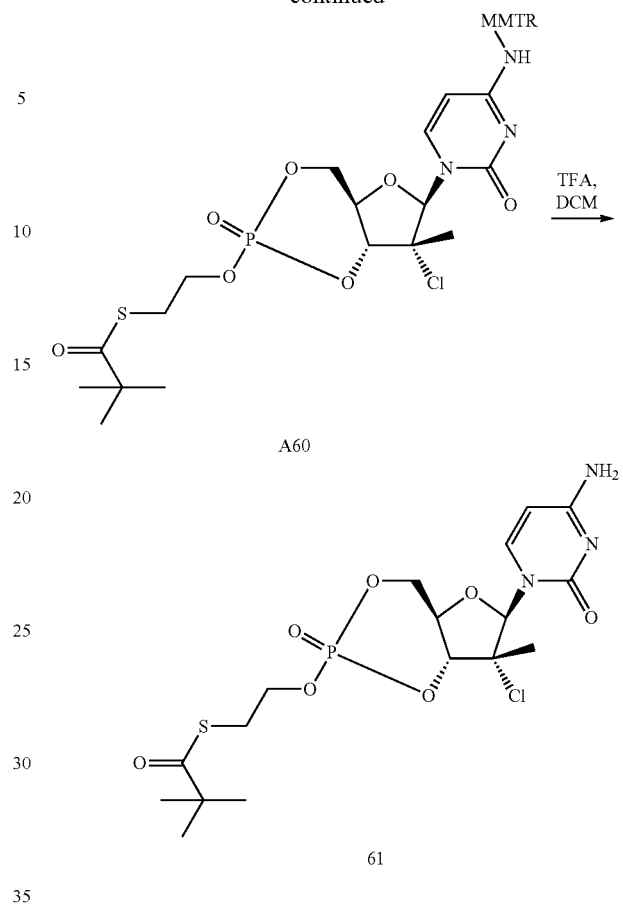

To a solution of A11 (or A34)(1.41 mmol) in anhydrous pyridine (6.5 mL/mmol) was added tetrazole (0.45M in acetonitrile) (6.5 mL/mmol). The solution was cooled to −5° C., and a solution of A16 (2.12 mmol) in anhydrous acetonitrile (3.2 mL/mmol) was added. The reaction mixture was stirred at −5° C. during 1 hour, then allowed to warm up to room temperature, and stirred at room temperature during 2.5 hours. Tert-butylhydroperoxide (5-6 M in decane) (0.5 mL/mmol) was added, and the reaction mixture was stirred at room temperature during 2 hours. The reaction mixture was evaporated under reduced pressure, and the crude compound was purified by chromatography on silica gel to give the expected mixture of corresponding intermediates.

Compound (A17a)

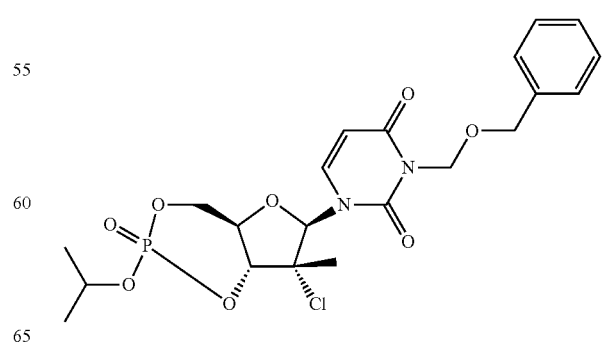

Colorless gum; 90%; MS (ESI) m/z=501 (MH$^+$).

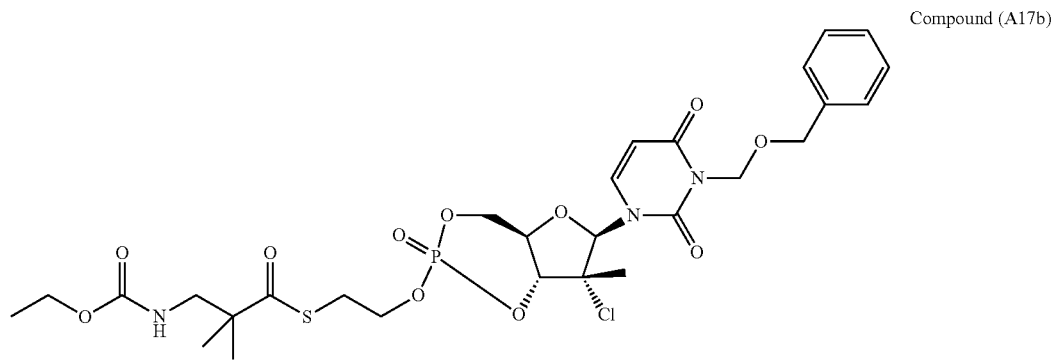

Compound (A17b)

Colorless oil; quantitative yield; MS (ESI) m/z=690 (MH+).

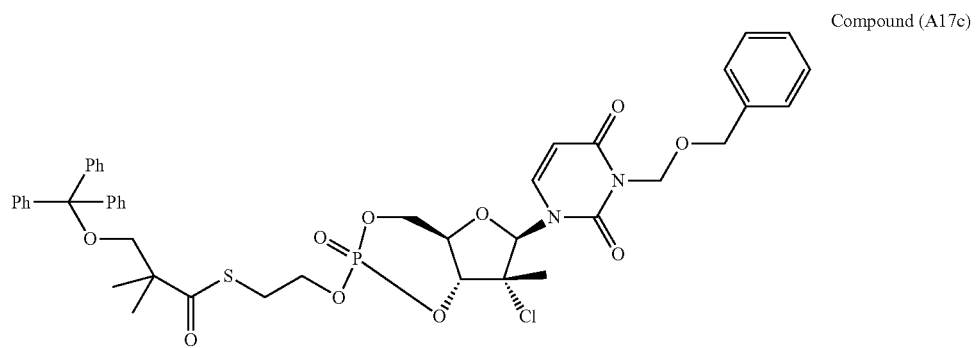

Compound (A17c)

Colorless gum; 11%; MS (ESI) m/z=859 (MH−).

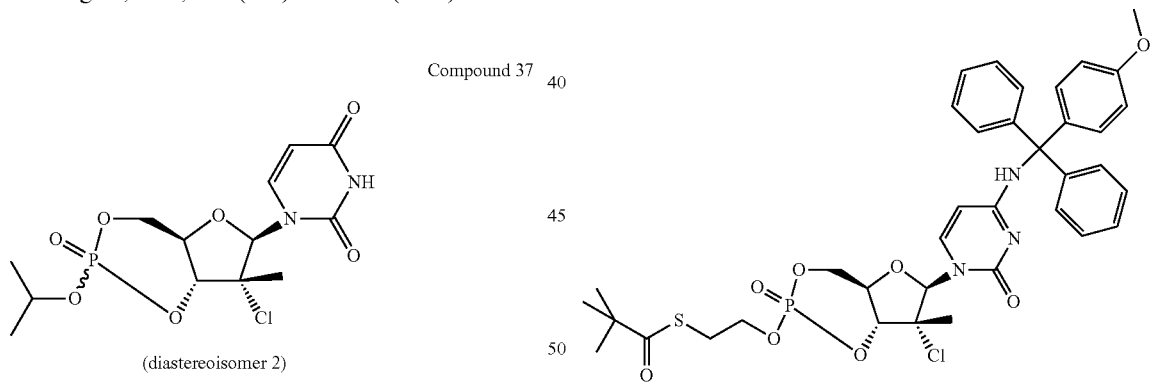

Compound 37 (diastereoisomer 2)

In this case, tert-butylhydroperoxide was added at 0° C. and the reaction mixture was stirred 30 minutes at this temperature. After concentration, the crude was dissolved in DCM and washed with a 1N HCl solution. The crude was purified by chromatography on silica gel and by flash RP18 gel chromatography to separate the 2 diastereoisomers. White solid; 19% yield.

$^1$H NMR (MeOD, 400 MHz): δ (ppm) 1.39-1.42 (m, 6H), 1.61 (s, 3H), 4.50-4.82 (m, 5H), 5.78 (d, J=8.12 Hz, 1H), 6.57 (s, 1H), 7.64 (d, J=8.20 Hz, 1H); $^{31}$P NMR (MeOD, 161.98 MHz): δ (ppm)-5.55 (s, 1P); MS (ESI) m/z=381 (MH+).

After concentration, the crude was dissolved in EtOAc and washed with a 1N solution of HCl, H$_2$O and brine. The crude was purified by chromatography on silica gel column (eluent: CH$_2$Cl$_2$/ethanol 0 to 2%). 52% yield; MS (ESI) m/z=754 (MH+).

General Method C

The following procedure was used to obtain intermediates A18a (mixture of diastereoisomers) and 37 (mixture of diastereoisomers), 70 (pure diastereoisomer) and 46 (pure diastereoisomer).

To a solution of intermediate A17 (1.71 mmol) in anhydrous dichloromethane (50 ml) under nitrogen was added dropwise at −78° C. a solution of boron tribromide (1.0 M)

in dichloromethane (5.12 mmol). The reaction mixture was stirred at −78° C. for 1 hour. Then, a solution of boron tribromide (1.0 M) in anhydrous dichloromethane (5.12 mmol) was added dropwise a second time, and the reaction mixture was stirred at −78° C. for 3 hours. Then, the reaction mixture was quenched with an aqueous saturated solution of NaHCO$_3$ added at −78° C., and allowed to warm to room temperature. The aqueous layer was extracted twice with dichloromethane, and the combined organic layers were dried, filtered and evaporated under reduced pressure to give a crude mixture.

Compounds (A18a) and (37):

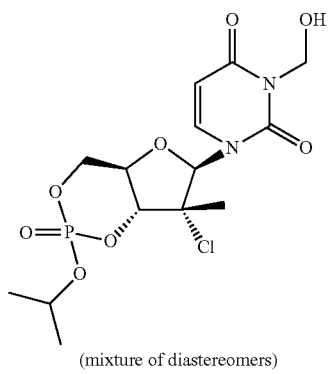

A18a (mixture of diastereomers)

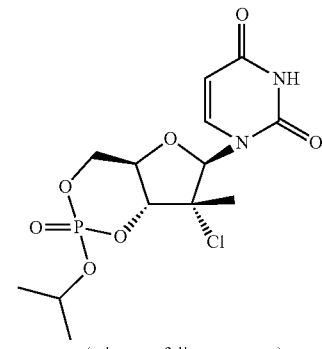

37

(mixture of diastereomers)

The crude was purified by chromatography on silica gel (eluent: dichloromethane/methanol 0 to 10%) to afford a yellowish solid in 20% global yield, corresponding in a mixture of 4 compounds; MS (ESI) m/z=411 (MH$^+$); MS (ESI) m/z=381 (MH$^+$).

Compound (70)

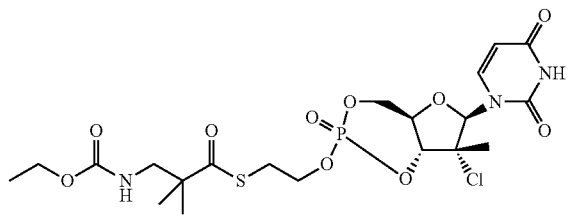

The crude mixture was purified by chromatography on silica gel and preparative HPLC to give the pure expected diastereoisomer as a white solid; $^1$H NMR (CDCl$_3$, 400 MHz) δ (ppm) 1.24 (t, J=7.03 Hz, 3H), 1.26 (s, 6H), 1.62 (s, 3H), 3.20 (t, J=6.26 Hz, 2H), 3.34 (d, J=6.65 Hz, 2H), 4.11 (q, J=7.03 Hz, 2H), 4.23-4.30 (m, 3H), 4.44-4.61 (m, 2H), 4.68-4.77 (m, 1H), 5.07 (brs, 1H), 5.82 (d, J=7.66 Hz, 1H), 6.57 (s, 1H), 7.21 (d, J=7.66 Hz, 1H), 8.42 (s, 1H); $^{31}$P NMR (CDCl$_3$, 161.98 MHz) δ (ppm)-4.56 (s, 1P); MS (ESI) m/z=570 (MH$^+$).

Compound (46)

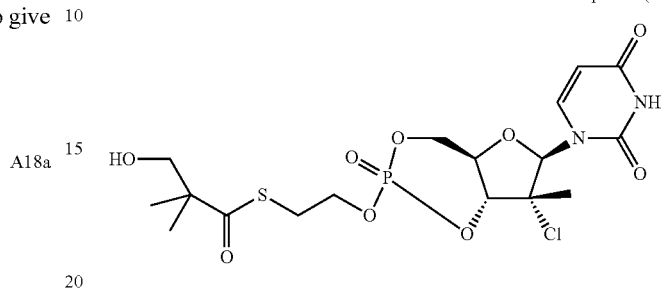

The crude was directly purified by preparative HPLC to give the pure expected diastereoisomer as a white solid in 15% yield; $^1$H NMR (MeOD, 400 MHz) δ (ppm) 1.23 (s, 6H), 1.61 (s, 3H), 3.24 (t, J=6.49 Hz, 2H), 3.6 (s, 2H), 4.22-4.27 (m, 2H), 4.59-4.75 (m, 3H), 4.79-4.86 (m, 1H), 5.78 (d, J=8.08 Hz, 1H), 6.58 (s, 1H), 7.63 (d, J=8.08 Hz, 1H); $^{31}$P NMR (MeOD, 161.98 MHz) δ (ppm)-5.44 (s, 1P); MS (ESI) m/z=499 (MH$^+$).

Compounds (37a) and (37b)

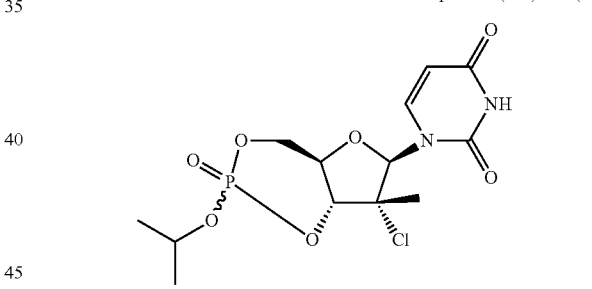

To a solution of A18a (0.24 mmol) in a mixture of water/acetonitrile (1/1:6 ml) was added formic acid (0.5 ml+0.3 ml). The reaction mixture was stirred at 50° C. during 24 hours and at 55° C. during 6 hours. The reaction mixture was evaporated under reduced pressure, and the crude compound was purified by chromatography on silica gel (eluent: dichloromethane/methanol 4 to 10%) to afford two pure diastereoisomers in 63% global yield.

Compound 37 (diastereoisomer 1): white solid; $^1$H NMR (MeOD, 400 MHz): δ (ppm) 1.42-1.46 (m, 6H), 1.61 (s, 3H), 4.30-4.43 (m, 2H), 4.62-4.82 (m 3H), 5.78 (d, J=7.88 Hz, 1H), 6.56 (s, 1H), 7.69 (d, J=8.08 Hz, 1H); $^{31}$P NMR (MeOD, 161.98 MHz): δ (ppm)-7.37 (s, 1P); MS (ESI) m/z=381, (MH$^+$).

Compound 37 (diastereoisomer 2): white solid; $^1$H NMR (MeOD, 400 MHz): δ (ppm) 1.39-1.42 (m, 6H), 1.61 (s, 3H), 4.50-4.82 (m, 5H), 5.78 (d, J=8.12 Hz, 1H), 6.57 (s, 1H), 7.64 (d, J=8.20 Hz, 1H); $^{31}$P NMR (MeOD, 161.98 MHz): δ (ppm)-5.55 (s, 1P); MS (ESI) m/z=381, (MH$^+$).

Scheme 2

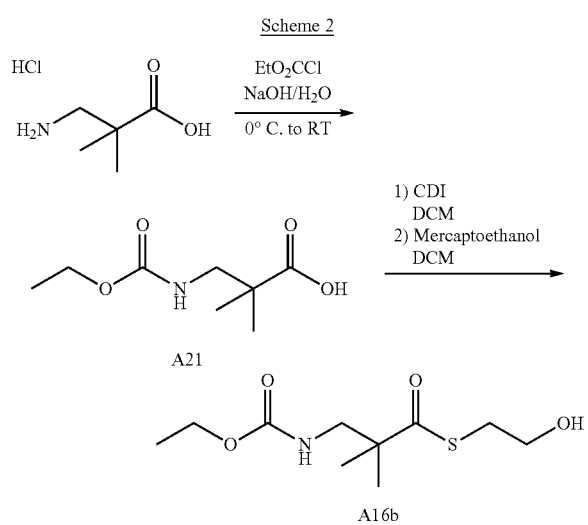

A21

A16b

3-(ethoxycarbonylamino)-2,2-dimethyl-propanoic acid (A21)

To a solution of 3-amino-2,2-dimethylpropanoic acid hydrochloride (65.10 mmol) in NaOH 2 N (60 mL) at 0° C. were added in the same time ethylchloroformate (65.10 mmol) and NaOH 2 N (130 mmol). The reaction mixture was stirred at 0° C. during 30 minutes and allowed to warm up to room temperature. The reaction was stirred 1 hour at room temperature. The reaction was not complete so ethylchloroformate (65.10 mmol) and NaOH 2 N (130 mmol) were added again at 0° C. and the mixture was stirred at 0° C. during 45 minutes. The aqueous layer was extracted two times with diethyl ether and acidified at 0° C. with HCl 2 N. The aqueous layer was extracted with DCM and the organic layer was dried, filtered and concentrated under reduced pressure to give the title intermediate as a yellow oil in 73% yield. $^1$H NMR (CDCl$_3$, 400 MHz) δ 1.20-1.26 (m, 9H), 3.29-3.32 (m, 2H), 4.09-4.14 (m, 2H), 5.15 (brs, 1H); MS (ESI) m/z=190 (MH$^+$).

S-(2-hydroxyethyl) 3-(ethoxycarbonylamino)-2,2-dimethyl-propanethioate (A16b)

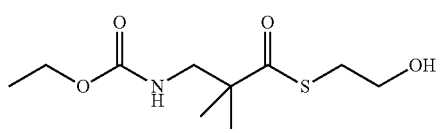 [SMILES: CCOC(=O)NCC(C)(C)C(=O)SCCO]

To a solution of intermediate A21 (47.5 mmol) in DCM (1 mL/mmol) at room temperature was added portionwise CDI (61.8 mmol) and the reaction mixture was stirred during 30 minutes. DCM (5 mL/mmol) was added and the mixture was cooled down to 0° C. before addition of 2-mercaptoethanol (61.8 mmol). The reaction mixture was stirred at room temperature during 1 hour. A saturated solution of NaHCO$_3$ was added and the mixture was extracted with DCM. The organic layer was dried, filtered and concentrated under reduced pressure. The crude was purified by chromatography on silica gel (eluent: DCM/CH$_3$OH 0 to 10%) to give expected intermediate as a colorless oil in 94% yield.

$^1$H NMR (CDCl$_3$, 400 MHz) δ 1.23 (t, J=7.10 Hz, 3H), 1.27 (s, 6H), 3.08 (t, J=5.90 Hz, 2H), 3.35 (d, J=6.70 Hz, 2H), 3.76 (t, J=5.90 Hz, 2H), 4.10 (q, J=7.10 Hz, 2H), 5 (brs, 1H); MS (ESI) m/z=272 (MNa$^+$).

General Method D

The following procedure was used to obtain intermediates A22a, A22b, A22c and A22d.

Scheme 3

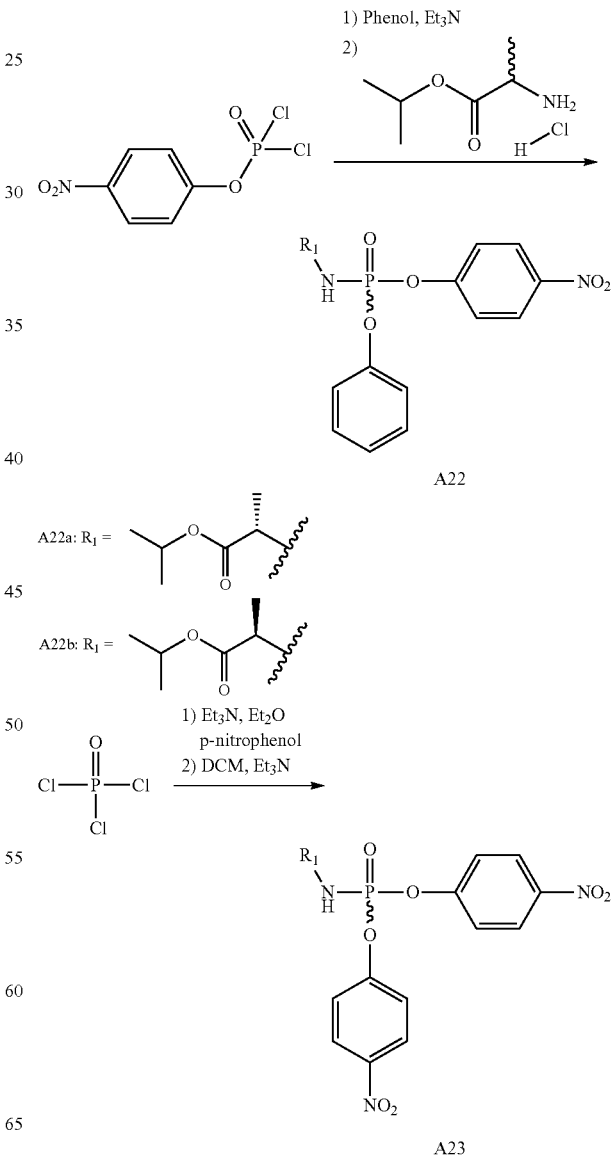

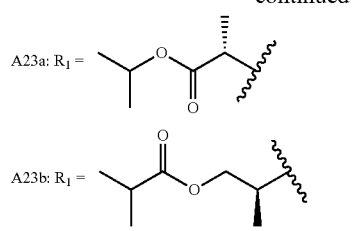

A23a: R₁ =

A23b: R₁ =

Scheme 3A

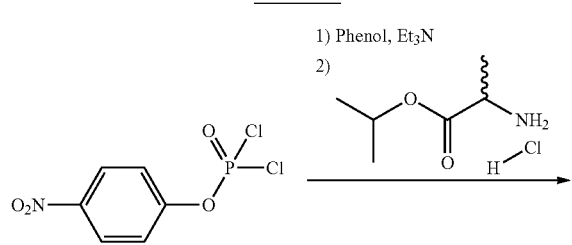

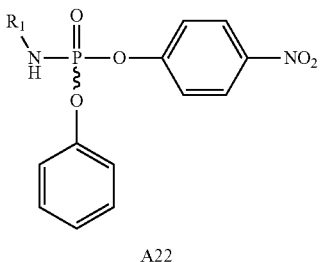

A22

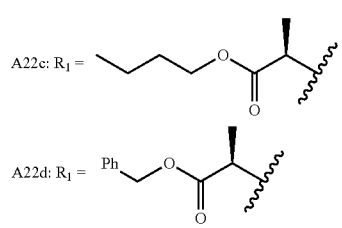

A22c: R₁ =

A22d: R₁ =

To a stirred solution of 4-nitrophenyl dichlorophosphate (Aldrich) (14.91 mmol) in DCM (30 mL) was added a solution of phenol (Aldrich) (14.91 mmol) and TEA (16.40 mmol) in DCM (30 mL) at −78° C. over a period of 20 minutes. The reaction mixture was stirred at −78° C. during 30 minutes and then, transferred into another round-bottom flask containing L- or D-alanine isopropyl ethyl ester hydrochloride (14.91 mmol) in DCM (30 mL) at 0° C. To the mixture was added TEA (31.31 mmol) over a period of 15 minutes. The reaction mixture was stirred at 0° C. during 1 hour and then, the solvent was evaporated. The residue was triturated with ethyl acetate (45 mL) and the white solid was filtered-off. The filtrate was concentrated under reduced pressure and the residue was purified by chromatography on silica gel (eluent: petroleum ether-petroleum ether/ethyl acetate 20%) to give the expected intermediate.

Isopropyl (2S)-2-[[(4-nitrophenoxy)-phenoxy-phosphoryl]amino]propanoate (A22a)

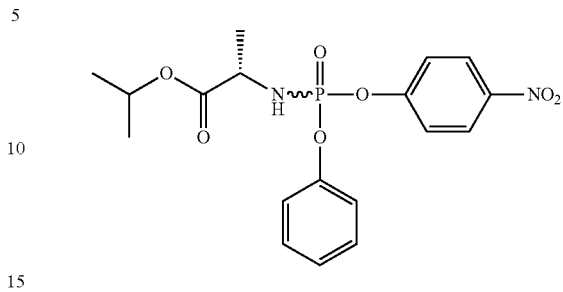

60% yield; ¹H NMR (CDCl₃, 400 MHz) δ (ppm) 1.15 (d, J=6.26 Hz, 3H), 1.16 (d, J=6.26 Hz, 3H), 1.33 (m, 3H), 3.83 (dd, J=9.7 and 11.76 Hz, 1H), 3.97-4.08 (m, 1H), 4.94 (heptuplet, J=6.26 Hz, 1H), 7.11-7.19 (m, 3H), 7.27-7.35 (m, 4H), 8.16 (dd, J=1.72 and 9.07 Hz, 2H); ³¹P NMR (CDCl₃, 161.98 MHz): δ (ppm)-3.21 (s, 0.45P), −3.18 (s, 0.55P); MS (ESI) m/z=409.14 (MH⁺).

Isopropyl (2R)-2-[[(4-nitrophenoxy)-phenoxy-phosphoryl]amino]propanoate (A22b)

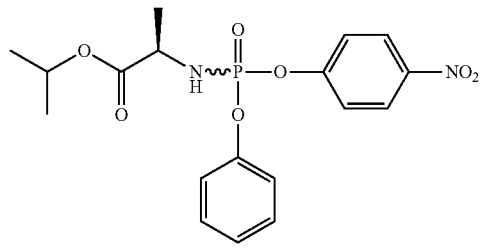 [SMILES: CC(C)OC(=O)[C@@H](C)NP(=O)(Oc1ccccc1)Oc1ccc([N+](=O)[O-])cc1]

80% yield; ¹H NMR (CDCl₃, 400 MHz) δ (ppm) 1.22 (d, J=6.28 Hz, 3H), 1.23 (d, J=6.28 Hz, 3H), 1.40 (m, 3H), 3.91-3.96 (m, 1H), 4.05-4.13 (m, 1H), 5.01 (heptuplet, J=6.30 Hz, 1H), 7.19-7.25 (m, 3H), 7.33-7.41 (m, 4H), 8.22 (dd, J=1.74 Hz and 8.95 Hz, 2H); ³¹P NMR (CDCl₃, 161.98 MHz): δ (ppm)-3.21 (s, 0.45P), −3.18 (s, 0.55P); MS (ESI) m/z=409.14 (MH⁺).

Butyl (2R)-2-[[(4-nitrophenoxy)-phenoxy-phosphoryl]amino]propanoate (A22c)

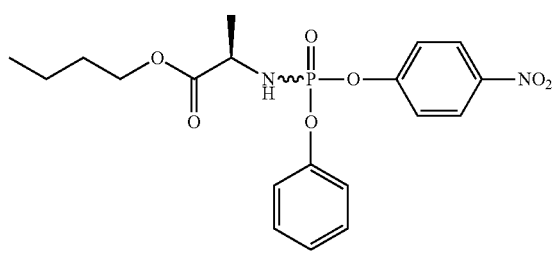 [SMILES: CCCCOC(=O)[C@@H](C)NP(=O)(Oc1ccccc1)Oc1ccc([N+](=O)[O-])cc1]

72% yield; yellow oil; ¹H NMR (CDCl₃, 400 MHz) δ (ppm) 0.92 (t, J=7.35 Hz, 3H), 1.30-1.39 (m, 2H), 1.40-1.43 (m, 3H), 1.56-1.63 (m, 2H), 3.84-3.89 (m, 1H), 4.08-4.18

(m, 3H), 7.18-7.26 (m, 3H), 7.33-7.41 (m, 4H), 8.23 (dd, J=1.77 Hz and 9.01 Hz, 2H); MS (ESI) m/z=423 (MH⁺).

Benzyl (2R)-2-[[(4-nitrophenoxy)-phenoxy-phosphoryl]amino]propanoate (A22d)

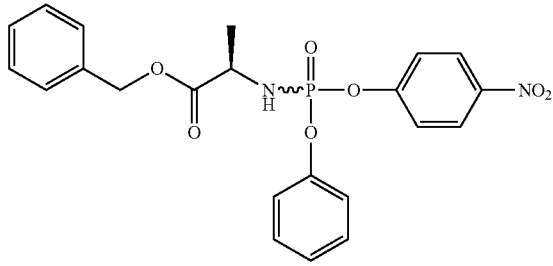 [SMILES: C[C@@H](NP(=O)(Oc1ccccc1)Oc1ccc([N+](=O)[O-])cc1)C(=O)OCc1ccccc1]

89% yield; yellow oil; ¹H NMR (CDCl₃, 400 MHz) δ (ppm) 1.41-1.44 (m, 3H), 3.82-3.88 (m, 1H), 4.13-4.25 (m, 1H), 5.14-5.15 (m, 2H), 7.18-7.24 (m, 3H), 7.28-7.38 (m, 9H), 8.16-8.21 (m, 2H); MS (ESI) m/z=457 (MH⁺).

General Method E

The following procedure was used to obtain intermediates A23a and A23b.

To a stirred solution of p-nitrophenol (20.2 mmol) in Et₂O (100 mL) at −10° C. (or -80° C.) under nitrogen was added phosphoryl chloride (10.1 mmol) followed by TEA (20.2 mmol) dropwise. The reaction mixture was allowed to warm up to room temperature and stirred at this temperature during 2 hours. The solvent was evaporated and the crude was dissolved in DCM (100 mL) and cooled down to 0° C. The amino compound (10.1 mmol) was added followed by TEA (20.2 mmol) dropwise. The reaction mixture was stirred at room temperature during 2 hours. The mixture was evaporated and purified directly by chromatography on silica gel (eluent: petroleum ether/ethyl acetate 0 to 70%) to give the expected intermediate.

Isopropyl (2S)-2-[bis(4-nitrophenoxy)phosphorylamino]propanoate (A23a)

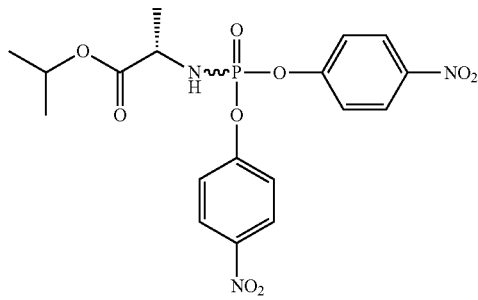 [SMILES: CC(C)OC(=O)[C@H](C)NP(=O)(Oc1ccc([N+](=O)[O-])cc1)Oc1ccc([N+](=O)[O-])cc1]

Yellowish oil; 31% yield; ¹H NMR (CDCl₃, 400 MHz) δ (ppm) 1.23-1.25 (m, 6H), 1.42 (d, J=6.6 Hz, 3H), 4.03-4.15 (m, 2H), 5.02 (heptuplet, J=6.23 Hz, 1H), 7.39-7.46 (m, 4H), 8.25 (d, J=7.8 Hz, 4H); ³¹P NMR (CDCl₃, 161.98 MHz) δ (ppm)-3.60 (s, 1P).

[(2S)-2-[bis(4-nitrophenoxy)phosphorylamino]propyl]2-methylpropanoate (A23b)

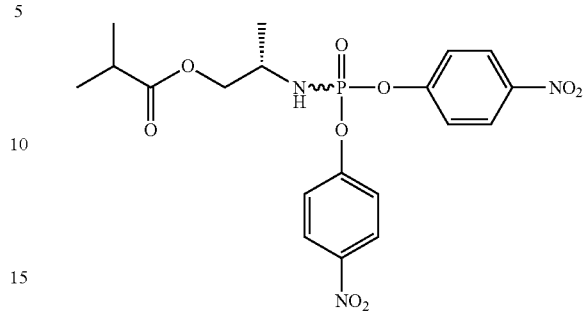

Beige-yellow solid; 50% yield; ¹H NMR (CDCl₃, 400 MHz) δ 1.15 (d, J=6.93 Hz, 6H), 1.24 (d, J=6.73 Hz, 3H), 2.51 (heptuplet, J=6.99 Hz, 1H), 3.37 (dd, J=9.88 and 12.40 Hz, 1H), 3.74-3.83 (m, 1H), 3.97-4 (m, 1H), 4.12 (dd, J=5.55 and 11.31 Hz, 1H), 7.40-7.45 (m, 4H), 8.26 (d, J=9.07 Hz, 4H); ³¹P NMR (CDCl₃, 161.98 MHz) δ (ppm)-3.07 (s, 1P); MS (ESI) m/z=468 (MH⁺).

General Method F

The following procedure was used to obtain compounds 40i and 40ii.

To a solution of compound 301 (15 mmol) in THF (5 mL/mmol) was added tert-butylmagnesium chloride (1M in THF) (31 mmol) over a period of 10 minutes. Appropriate intermediate A22 (18 mmol) in THF (20 mL) was added and the reaction mixture was stirred at room temperature during 3 days. The reaction mixture was quenched with saturated aqueous solution of ammonium chloride. The residue was suspended in ethyl acetate and washed with water. The organic layer was washed with aqueous sodium bicarbonate and brine, dried over MgSO₄, filtered and concentrated under reduced pressure. The residue was purified by chromatography on silica gel (eluent: DCM-DCM/MeOH 2%) to separate the diastereoisomers.

Compound 40ii

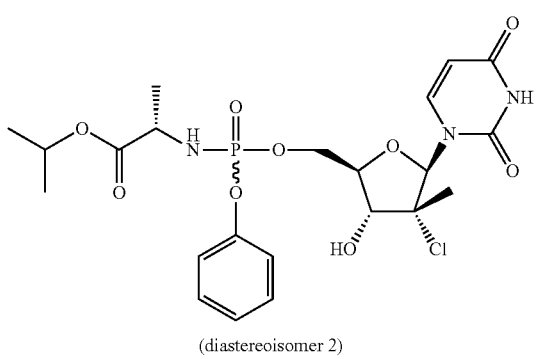

(diastereoisomer 2)

White solid; 13% yield; ¹H NMR (CDCl₃, 400 MHz): δ (ppm) 1.24-1.26 (m, 6H), 1.36 (d, J=7.04 Hz, 3H), 1.59 (s, 3H), 3.69-3.77 (m, 1H), 3.91-3.99 (m, 2H), 4.17-4.19 (m, 1H), 4.43-4.59 (m, 2H), 5.01-5.06 (m, 1H), 5.68 (d, J=8.20 Hz, 1H), 6.42 (s, 1H), 7.21-7.39 (m, 5H), 7.60 (d, J=8.20 Hz, 1H), 8.14 (s, 1H); ³¹P NMR (CDCl₃, 161.98 MHz): δ (ppm) 3.47 (s, 1P); MS (ESI) m/z=546.2 (MH⁺).

Compound 40i

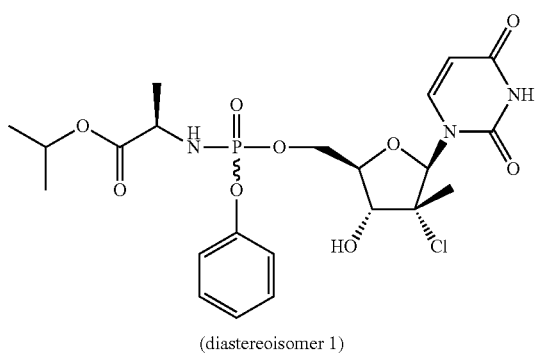

(diastereoisomer 1)

In this case, after chromatography on silica gel, the mixture of diastereoisomers was purified by preparative HPLC.

White solid; 3% yield; $^1$H NMR (CDCl$_3$, 400 MHz) δ 1.25 (d, J=6.25 Hz, 6H), 1.38 (d, J=7.04 Hz, 3H), 1.51 (s, 3H), 3.66-3.74 (m, 2H), 3.82-3.96 (m, 2H), 4.15 (dd, J=1.62 and 9.24 Hz, 1H), 4.39-4.53 (m, 2H), 5.03 (heptuplet, J=6.26 Hz, 1H), 5.56 (dd, J=2.29 and 8.18 Hz, 1H), 6.39 (s, 1H), 7.19-7.26 (m, 3H), 7.34-7.43 (m, 3H), 8.06 (s, 1H); $^{31}$P NMR (CDCl$_3$, 161.98 MHz): δ (ppm) 3.35 (s, 1P); MS (ESI) m/z=546.20 (MH$^+$).

3,5-Di-O-benzoyl-2-C-chloro-2-C-methylarabinofuranosyl acetate (A25)

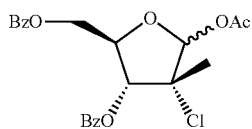

To a solution of compound A6 (84.44 mmol) in pyridine (400 mL) was added under nitrogen DMAP (0.06 g/mmol) followed by the addition at 0° C. of Ac$_2$O (844.4 mmol). The reaction mixture was stirred during 2 hours. The reaction mixture was concentrated and co-evaporated with toluene under reduced pressure. The residue was diluted with DCM and washed with a 1N HCl solution and saturated solution of NaHCO$_3$. The organic layer was dried over Na$_2$SO$_4$, filtered and concentrated. The crude was purified by chromatography on silica gel (PE to PE/EtOAc 60/40) to give the expected intermediate in 82% yield.

$^1$H NMR (CDCl$_3$, 400 MHz): δ (ppm) 1.69 (s, 3H), 1.97 (s, 3H), 4.43 (dd, J=4.30 and 11.7 Hz, 1H), 4.65-4.74 (m, 2H), 5.78 (d, J=7.89 Hz, 1H), 6.35 (s, 1H), 7.34-7.38 (m, 2H), 7.46-7.55 (m, 3H), 7.61-7.65 (m, 1H), 8.01-8.03 (m, 2H), 8.09-8.11 (m, 2H).

Compound (A26)

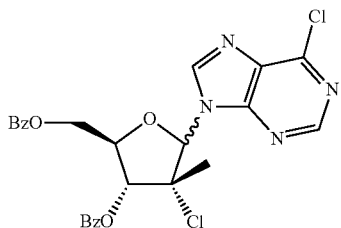

First Procedure:

A solution of 6-chloropurine (99.3 mmol), BSA (66.2 mmol) in toluene (150 mL) was heated at 110° C. under nitrogen during 45 minutes. A solution of compound A7 (33.1 mmol) in toluene (150 mL) was added at room temperature under nitrogen, followed by addition of TMSOTf (115.8 mmol). The reaction mixture was stirred at 110° C. under nitrogen overnight. After cooling, the reaction mixture was added to a solution of 300 mL of saturated bicarbonate solution and 200 mL of EtOAc. The aqueous layer was extracted 2 times with EtOAc and the organic layer was dried by filtration through a phase separator and concentrated under reduced pressure. The residue was purified by chromatography on silica gel (eluent: DCM to DCM/MeOH 95/5) to give a mixture of α and β compounds as a white solid in 24% yield.

Second Procedure:

To a solution of compound A25 (11.55 mmol) and 6-chloropurine (12.68 mmol) in acetonitrile (115 mL) was added under nitrogen DBU (34.65 mmol), followed by addition at 0° C. of TMSOTf (46.2 mmol). The reaction mixture was heated at 60° C. during 2 hours and then, added slowly to a saturated solution of NaHCO$_3$ at 0° C. EtOAc was added and the aqueous layer was extracted three times. The combined organic layers were filtered and concentrated under reduced pressure. The crude was purified by chromatography on silica gel (eluent: DCM to DCM/MeOH 98/2) to give a mixture of a and (3 compounds as a white foam in 50% yield.); MS (ESI) m/z=527 (MH$^+$).

2'-C-Chloro-2'-C-methyladenosine (302)

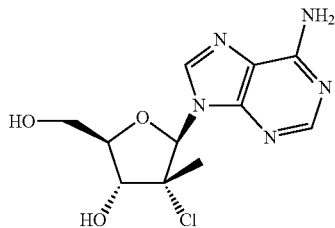 [SMILES: C[C@@]1(Cl)[C@H](O)[C@@H](CO)O[C@H]1n1cnc2c(N)ncnc21]

A solution of compound A26 (14.9 mmol) in 7N ammonia solution in methanol was saturated at 0° C. with ammoniac gas. The reaction mixture in sealed steel cylinder was heated at 100° C. during 3 hours. The reaction mixture was concentrated and diluted with EtOAc. The white solid was filtered, washed with EtOAc and dried. The solid was purified by flash RP 18 gel chromatography to give the pure β compound as a white solid in 18% yield.

$^1$H NMR (DMSO-d$_6$, 400 MHz): δ (ppm) 1.18 (s, 3H), 3.70-3.75 (m, 1H), 3.86-3.90 (m, 1H), 3.95-3.99 (m, 1H), 4.36 (dd, J=6.27 and 8.77 Hz, 1H), 5.38-5.40 (m, 1H), 5.96 (d, J=6.04 Hz, 1H), 6.41 (s, 1H), 7.37 (brs, 2H), 8.16 (s, 1H), 8.56 (s, 1H); MS (ESI) m/z=300 (MH$^+$).

Compound (93)

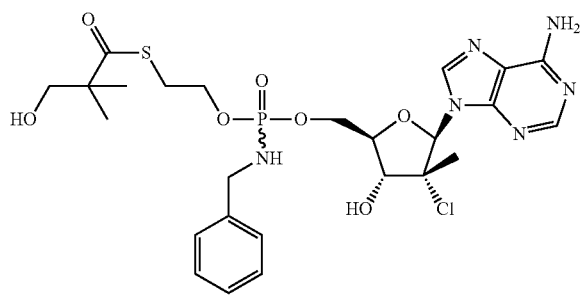

To a solution of compound 302 (1 mmol) and H-phosphonate (1.5 mmol) in pyridine (12 mL/mmol) at 0° C. under nitrogen was added dropwise pivaloyl chloride (2 mmol). The reaction mixture was stirred at 0° C. during 1 hour. The mixture was added to a stirring 0.5M NH₄Cl solution (25 mL) and EtOAc (25 mL). The aqueous layer was extracted with EtOAc and the combined organic layers were washed with 0.5M NH₄Cl, dried over Na₂SO₄, filtered and concentrated under reduced pressure. The crude was dissolved with DCM (12 mL) and CCl₄ (6 mL). Benzylamine (5 mmol) was added and the reaction mixture was stirred at room temperature during 1.5 hours. The reaction mixture was purified by chromatography on silica gel (eluent: DCM to DCM/MeOH 95/5) to give colorless solid. The product was dissolved in DCM (12 mL) and TFA (0.3 mL) was added at 0° C. under nitrogen. The reaction mixture was stirred at 0° C. during 1 hour and purified by chromatography on silica gel (DCM to DCM/MeOH 90/10) and by preparative HPLC to give the pure compound as a white solid in 26% yield.

$^1$H NMR (DMSO-$d_6$, 400 MHz): δ (ppm) 1.08 (s, 6H), 1.22 (s, 3H), 2.99-3.03 (m, 2H), 3.41 (d, J=4.85 Hz, 2H), 3.80-3.98 (m, 4H), 4.12-4.16 (m, 1H), 4.26-4.31 (m, 2H), 4.51-4.54 (m, 1H), 4.90-4.93 (m, 1H), 5.67-5.74 (m, 1H), 6.15 (d, J=5.8 Hz, 1H), 6.47 (s, 1H), 7.26-7.30 (m, 5H), 7.38 (brs, 2H), 8.17 (s, 1H), 8.28 (s, 1H); $^{31}$P NMR (DMSO-$d_6$, 161.98 MHz): δ (ppm) 9.74 (s, 1P); MS (ESI) m/z=629.24 (MH$^+$).

Scheme 4

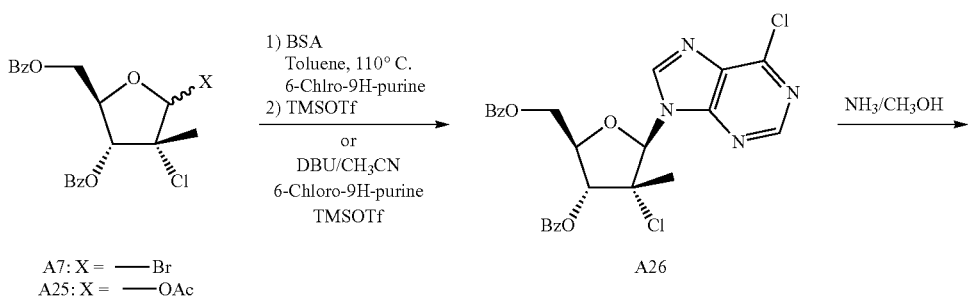

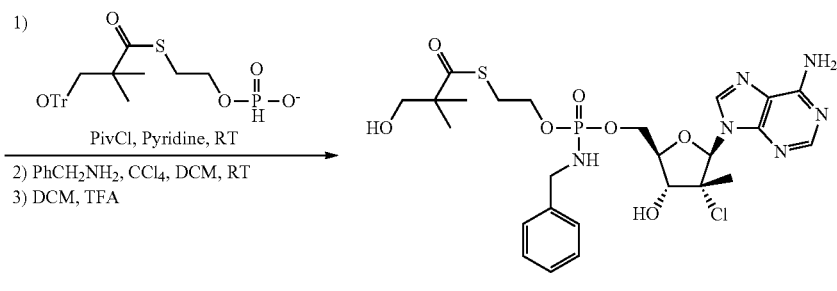

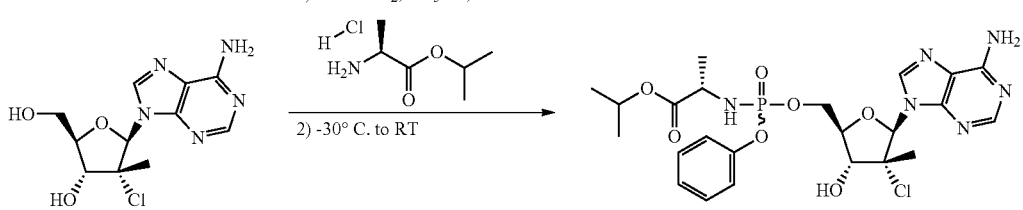

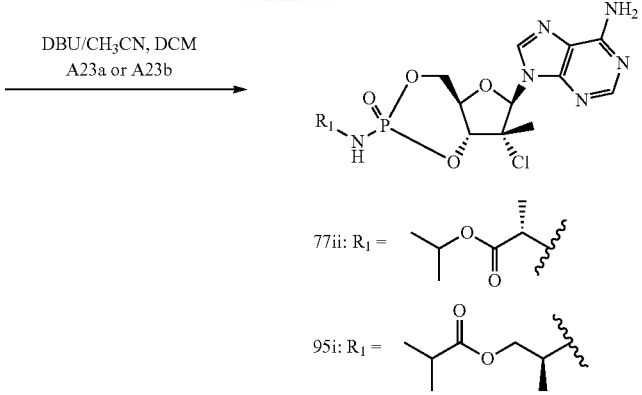

General Method G

The following procedure was used to obtain compounds 77ii and 95i.

To a solution of compound 302 (0.67 mmol) and DBU (1.53 mmol) in CH$_3$CN (25 mL/mmol) was added under nitrogen the appropriate compound A23 (0.80 mmol) dissolved in DCM (25 mL/mmol). The reaction mixture was stirred at room temperature during 3 hours and concentrated under reduced pressure. The crude (mixture of diastereoisomers) was purified by chromatography on silica gel (eluent: DCM to DCM/MeOH 90/10) to give the pure expected compound.

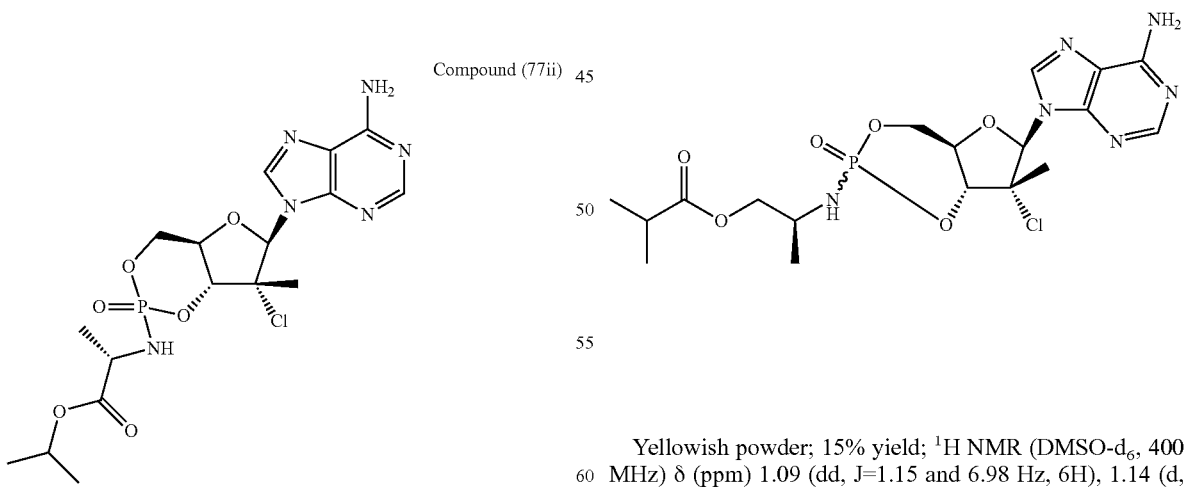

In this case, the pure expected compound was obtained after purification by chromatography on silica gel and preparative HPLC; white solid; 21% yield; $^1$H NMR (CDCl$_3$, 400 MHz): δ (ppm) 1.28 (d, J=6.25 Hz, 3H), 1.29 (d, J=6.25 Hz, 3H), 1.44 (s, 3H), 1.47 (d, J=6.93 Hz, 3H), 3.94-4.10 (m, 2H), 4.58-4.70 (m, 3H), 5.09 (heptuplet, J=6.23 Hz, 1H), 5.68 (s, 2H), 5.89 (brs, 1H), 6.33 (s, 1H), 7.83 (s, 1H), 8.38 (s, 1H); $^{31}$P NMR (CDCl$_3$, 161.98 MHz): δ (ppm) 2.96 (s, 1P); MS (ESI) m/z=475.20 (MH$^+$).

Yellowish powder; 15% yield; $^1$H NMR (DMSO-d$_6$, 400 MHz) δ (ppm) 1.09 (dd, J=1.15 and 6.98 Hz, 6H), 1.14 (d, J=6.62 Hz, 3H), 1.34 (s, 3H), 2.51-2.58 (m, 1H), 3.30 (s, 1H), 3.34-3.42 (m, 1H), 3.88 (dd, J=6.27 and 10.71 Hz, 1H), 4.03 (dd, J=6.26 and 10.74 Hz, 1H), 4.28-4.35 (m, 1H), 4.54-4.64 (m, 2H), 5.63-5.69 (m, 1H), 6.62 (s, 1H), 7.45 (brs, 2H), 8.16 (s, 1H), 8.34 (s, 1H); $^{31}$P NMR (DMSO-d$_6$, 161.98 MHz): δ (ppm) 3.63 (s, 1P); MS (ESI) m/z=489.1 (MH$^+$).

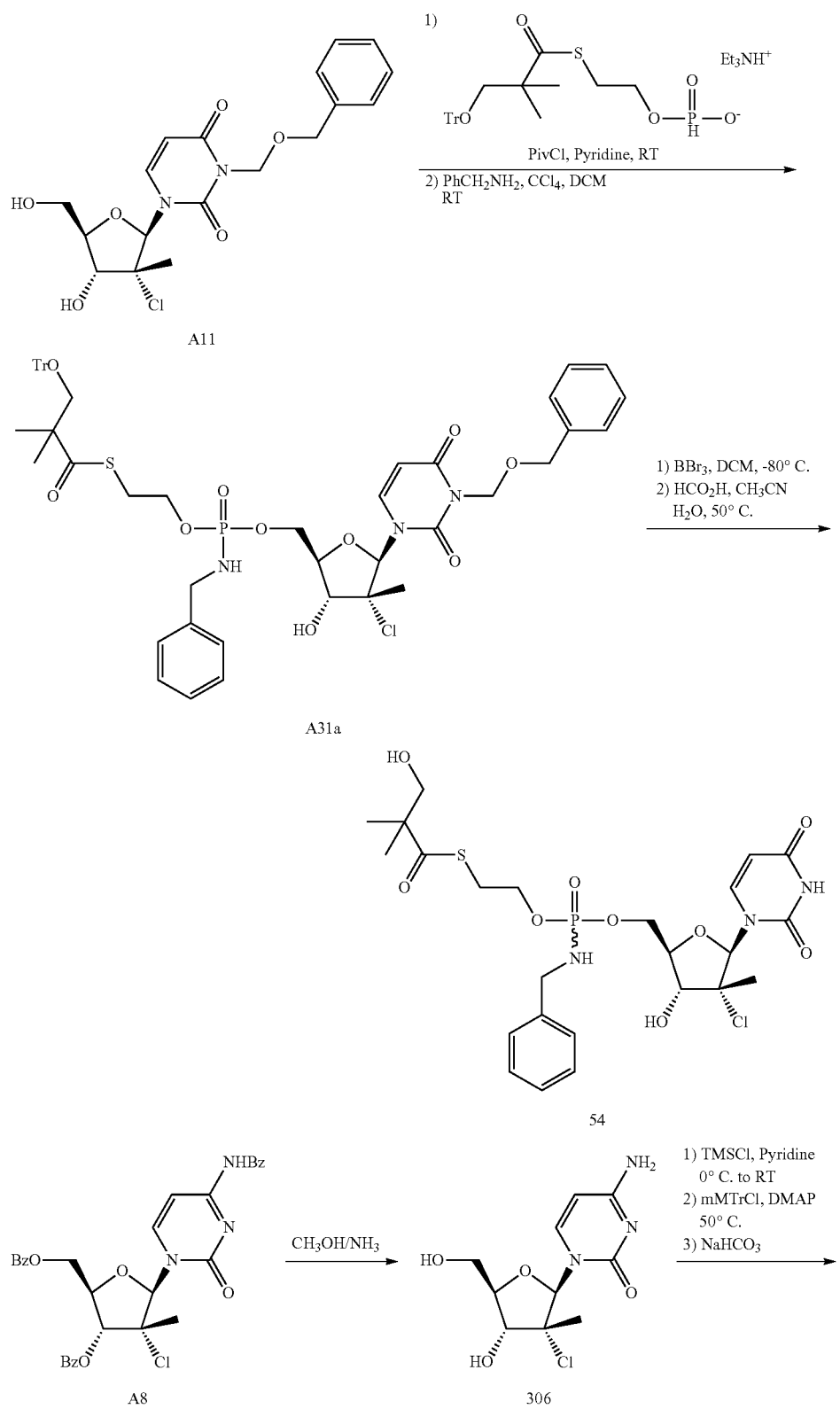

-continued
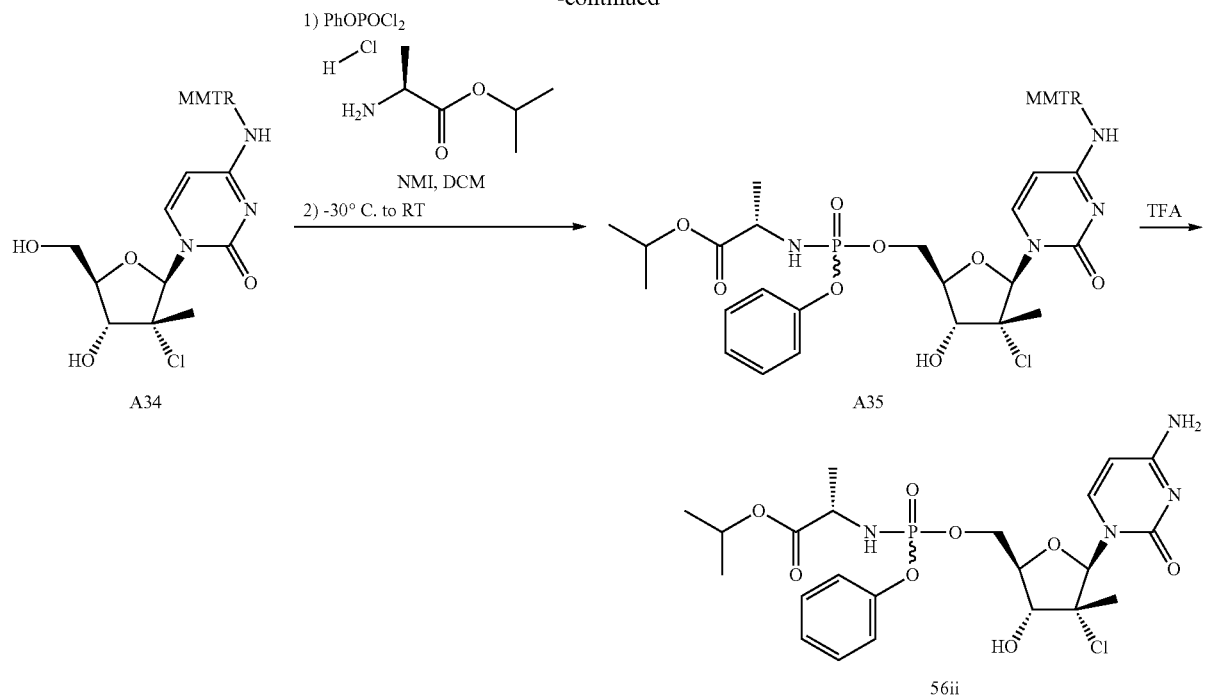
Scheme 5A
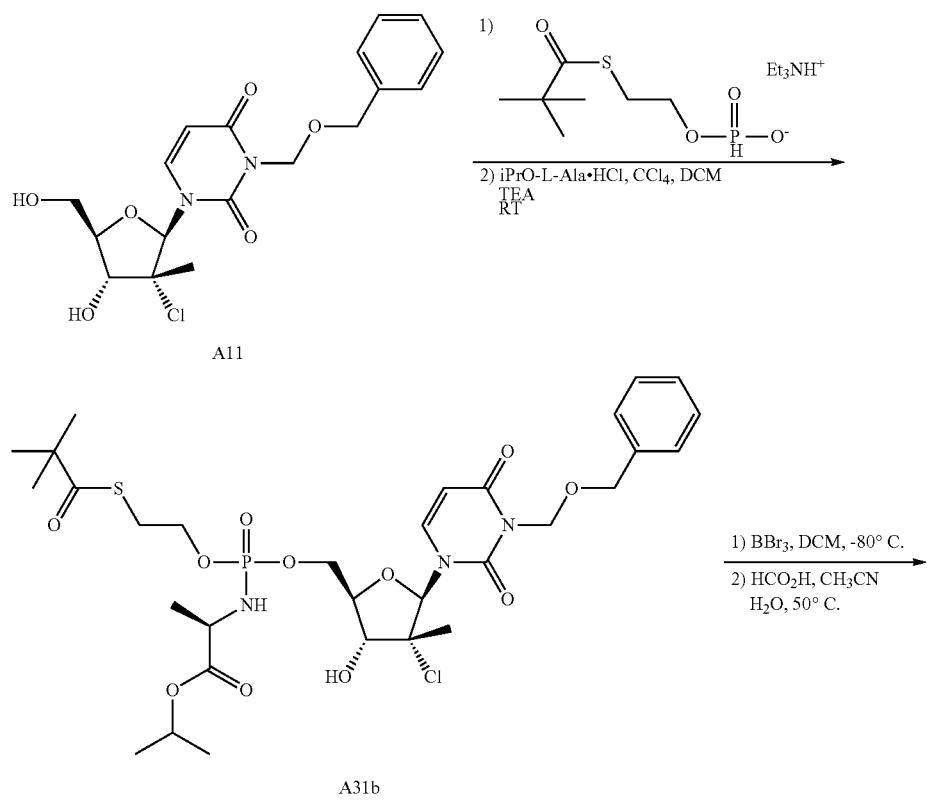

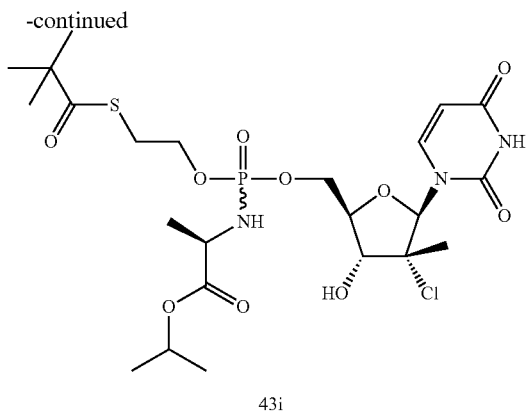
43i

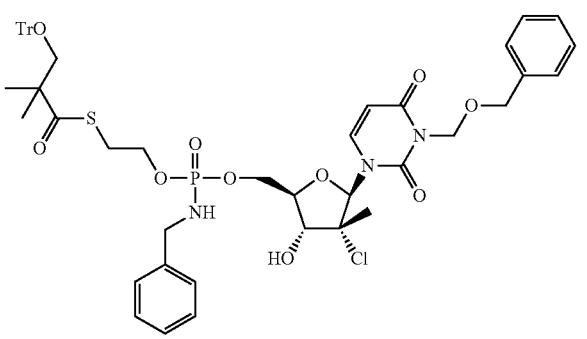

Compound (A31a)

Compound A31a (mixture of diastereoisomers) was synthesized from intermediate A11 (0.63 mmol) and appropriate H-phosphonate (0.954 mmol) as described for compound 88 but without the step of deprotection (DCM/TFA). 63% yield; MS (ESI) m/z=966.9 (MH⁻).

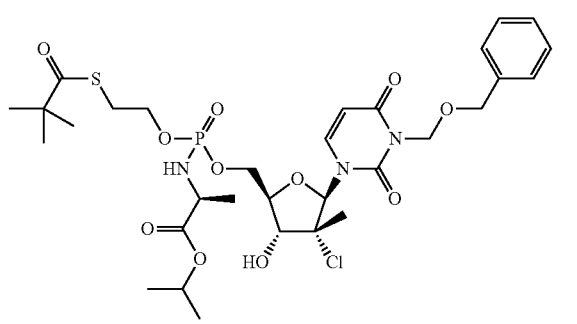

Compound (A31b)

To a solution of compound A11 (0.302 mmol) and H-phosphonate (0.454 mmol) in pyridine (10 mL/mmol) at 0° C. under nitrogen was added dropwise pivaloyl chloride (0.604 mmol). The reaction mixture was allowed to warm up at room temperature and stirred during 3 hours. The reaction mixture was neutralized with NH₄Cl solution and diluted with EtOAc. The aqueous layer was extracted with EtOAc and the combined organic layers were dried over Na₂SO₄, filtered and concentrated under reduced pressure. The crude was dissolved with DCM (6 mL/mmol) and CCl₄ (3 mL/mmol). L-alanine isopropyl ester hydrochloride salt (1.512 mmol) and Et₃N (1.512 mmol) were added and the reaction mixture was stirred at room temperature overnight. The reaction mixture was purified by chromatography on silica gel (eluent: DCM/MeOH 0 to 10%) to give a mixture of diastereoisomers in 59% yield; MS (ESI) m/z=734 (MH⁺).

General Method H

The following procedure was used to obtain compounds 54 and 43i.

To a solution of compound A31a or A31b (0.397 mmol) in dry DCM (38 mL/mmol) at −80° C. under nitrogen was added a 1M BBr₃ solution in DCM (1.988 mmol). The reaction mixture was stirred under nitrogen between −80° C. and −60° C. during 1 h45. CH₃CN (10 mL) was added at −80° C. followed by addition of water (1 mL) and saturated solution of NaHCO₃. The pH was adjusted to 4-5 with acetic acid. The salts were removed by filtration over autocup PTFE. The filtrate was transferred into a separatory funnel and extracted with DCM. The organic layer was dried, filtered and concentrated under reduced pressure. The crude was purified by chromatography on silica gel (eluent: DCM to DCM/MeOH 90/10) to give the intermediate. This intermediate was dissolved in CH₃CN (5 mL) and water (4 mL). Formic acid (0.8 mL) was added dropwise and the reaction mixture was heated at 50° C. overnight. The solvents were removed and the crude material was purified by one or two preparative HPLC to give the pure diastereoisomer.

Compound (54)

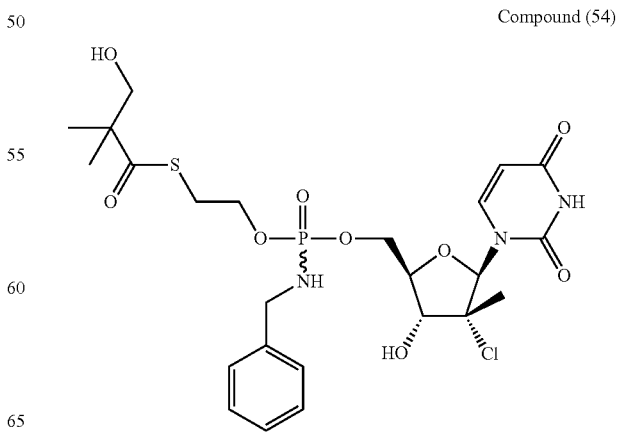

Diastereoisomer 1:

White powder; $^1$H NMR (CDCl$_3$, 400 MHz) δ (ppm) 1.16 (s, 3H), 1.31 (s, 3H), 1.57 (s, 3H), 3-3.09 (m, 1H), 3.21 (d, J=14.10 Hz, 1H), 3.30-3.38 (m, 1H), 3.49 (d, J=11.30 Hz, 1H), 3.74 (d, J=11.48 Hz, 1H), 3.91-4.02 (m, 2H), 4.09-4.18 (m, 3H), 4.22-4.31 (m, 1H), 4.40-4.58 (m, 2H), 5.50 (d, J=8.12 Hz, 1H), 6.42 (s, 1H), 7.26-7.38 (m, 6H), 7.68 (d, J=7.97 Hz, 1H), 8.21 (m, 1H); $^{31}$P NMR (CDCl$_3$, 161.98 MHz): δ (ppm) 9.49 (s, 1P); MS (ESI) m/z=605.9 (MH$^+$).

Compound (43ii)

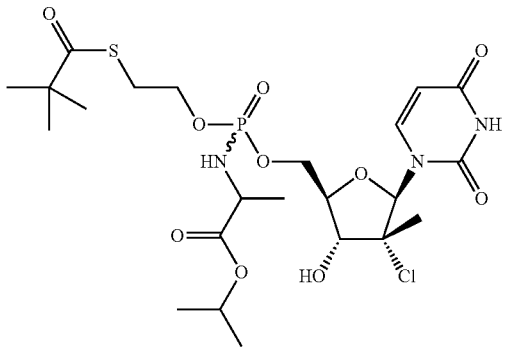

Diastereoisomer 2:

White powder; 14% yield; $^1$H NMR (CDCl$_3$, 400 MHz) δ (ppm) 1.25-1.26 (m, 15H), 1.42 (d, J=7.11 Hz, 3H), 1.59 (s, 3H), 3.15-3.19 (m, 2H), 3.65 (t, J=10.40 Hz, 1H), 3.82-3.92 (m, 2H), 3.95-3.99 (m, 1H), 4.04-4.19 (m, 3H), 4.32-4.45 (m, 2H), 5.03 (heptuplet, J=6.27 Hz, 1H), 5.84-5.87 (m, 1H), 6.42 (s, 1H), 7.61 (d, J=8.16 Hz, 1H), 8.49 (s, 1H); $^{31}$P NMR (CDCl$_3$, 161.98 MHz) δ (ppm) 8.47 (s, 1P); MS (ESI) m/z=614 (MH$^+$).

Compound (306)

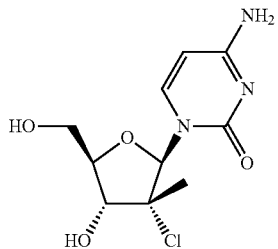

Compound A8 (1.5 mmol) was diluted in a 7N ammonia solution in methanol (20 mL/mmol) and the reaction mixture was stirred at room temperature overnight. The solvent was removed and the residue was precipitated in DCM (30 mL). The solid was filtered, washed with DCM and dried under vacuum to give the expected compound as a white solid in quantitative yield. $^1$H NMR (DMSO-d$_6$, 400 MHz) δ (ppm) 1.35 (s, 3H), 3.61-3.66 (m, 1H), 3.82-3.86 (m, 3H), 5.29-5.31 (m, 1H), 5.70 (d, J=7.54 Hz, 1H), 5.82 (d, J=5.5 Hz, 1H), 6.30 (s, 1H), 7.20 (s, 1H), 7.26 (s, 1H), 8.07 (d, J=7.47 Hz, 1H); MS (ESI) m/z=276 (MH$^+$).

Compound (A34)

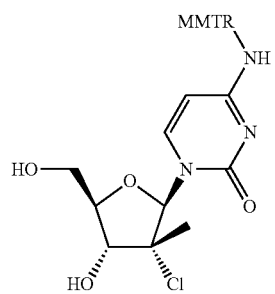

To a solution of compound 306 (0.725 mmol) in pyridine (5 mL) at 0° C. under nitrogen was added dropwise TMSCl (4.35 mmol). The reaction was allowed to warm up to room temperature and stirred at this temperature during 4 hours. Then, DMAP (0.725 mmol) and mMTrCl (1.45 mmol) were added at room temperature and the reaction mixture was stirred at 50° C. overnight. The reaction mixture was slowly added to a saturated solution of NaHCO$_3$. The aqueous layer was extracted with DCM and the combined organic layers were dried over Na$_2$SO$_4$, filtered and concentrated under reduced pressure. The crude was diluted in MeOH (10 mL) and NH$_4$F (3.63 mmol) was added. The reaction mixture was stirred at 75° C. during 1 hour and concentrated under reduced pressure. The residue was purified by chromatography on silica gel (eluent: DCM to DCM/MeOH 90/10) to give the expected compound as beige solid. MS (ESI) m/z=548 (MH$^+$).

Compound (A35)

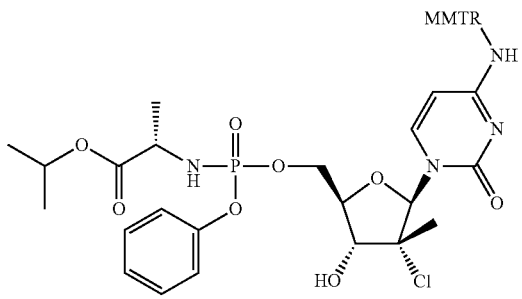

Compound A35 was synthesized from intermediate A12 and intermediate A34 as described for compound A13 but without purification. MS (ESI) m/z=817.1 (MH$^+$).

General Method I

The following procedure was used to obtain compounds 56ii and 61.

To a solution of compound A35 or A60 (0.12 mmol) in dichloromethane (2 mL) was added dropwise TFA (2.4 mmol) under nitrogen. The reaction mixture was stirred at room temperature overnight. The reaction mixture was purified directly by chromatography on silica gel and by preparative HPLC to give the expected compound.

233

Compound (56ii)

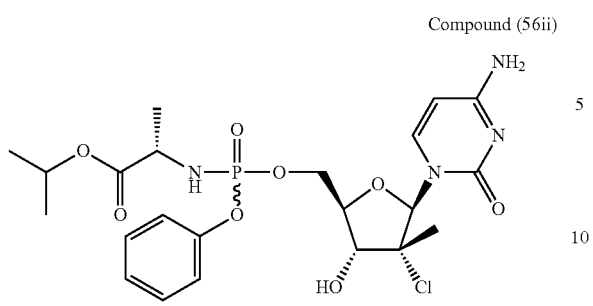

White powder. $^1$H NMR (MeOD, 400 MHz) δ (ppm) 1.23 (d, J=6.25 Hz, 3H), 1.24 (d, J=6.25 Hz, 3H), 1.33 (dd, J=1.06 and 7.16 Hz, 3H), 1.46 (s, 3H), 3.88-3.95 (m, 2H), 4.19-4.23 (m, 1H), 4.45 (ddd, J=2.53 and 5.40 and 11.91 Hz, 1H), 4.63 (ddd, J=1.96 and 4.66 and 11.95 Hz, 1H), 4.99 (heptuplet, J=6.20 Hz, 1H), 5.86 (d, J=7.60 Hz, 1H), 6.49 (s, 1H), 7.19-7.28 (m, 3H), 7.36-7.40 (m, 2H), 7.79 (d, J=7.56 Hz, 1H); $^{31}$P NMR (MeOD, 161.98 MHz): δ (ppm) 3.86 (s, 1P); MS (ESI) m/z=543.03 (MH$^-$).

Scheme 6

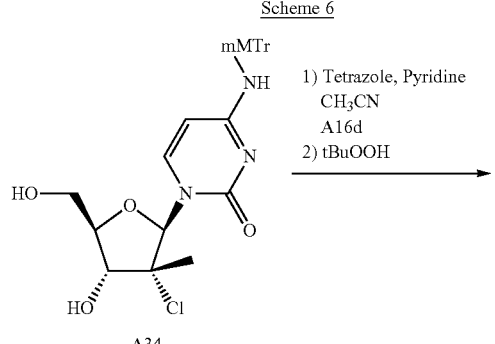

A34

1) Tetrazole, Pyridine
   CH$_3$CN
   A16d
2) tBuOOH

→

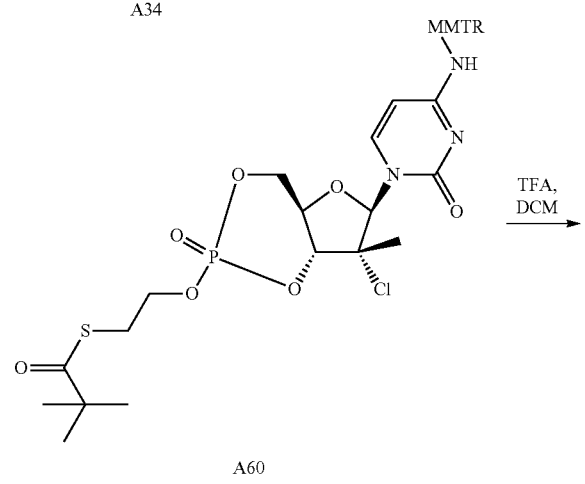

A60

TFA, DCM

234

-continued

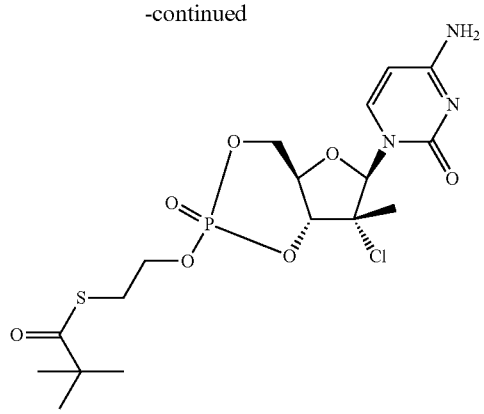

61

Compound (61)

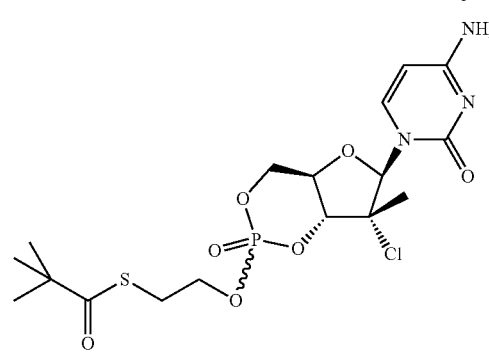

(Mixture of P-Diastereoeisomers)

61 P-Diastereoisomer 1:

White solid; 23% yield; $^1$H NMR (MeOD, 400 MHz) δ (ppm) 1.26 (s, 9H), 1.59 (s, 3H), 3.25 (t, J=6.38 Hz, 2H), 4.21-4.26 (m, 2H), 4.40-4.47 (m, 2H), 4.62-4.68 (m, 1H), 4.72-4.82 (m, 1H), 5.98 (d, J=7.57 Hz, 1H), 6.64 (s, 1H), 7.7 (d, J=7.59 Hz, 1H); $^{31}$P NMR (MeOD, 161.98 MHz) δ (ppm)-6.64 (s, 1P); MS (ESI) m/z=480.1 (MH$^-$).

61 P-Diastereoisomer 2:

White solid; 32% yield; $^1$H NMR (MeOD, 400 MHz) δ (ppm) 1.26 (s, 9H), 1.56 (s, 3H), 3.22 (t, J=6.39 Hz, 2H), 4.21-4.26 (m, 2H), 4.58-4.65 (m, 2H), 4.69-4.85 (m, 2H), 5.98 (d, J=7.57 Hz, 1H), 6.64 (s, 1H), 7.62 (d, J=7.61 Hz, 1H); $^{31}$P NMR (MeOD, 161.98 MHz) δ (ppm)-5.39 (s, 1P); MS (ESI) m/z=482.0 (MH$^+$).

Scheme 7

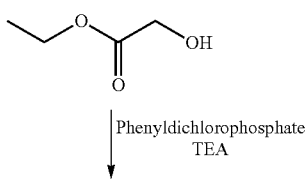

Phenyldichlorophosphate
TEA
↓

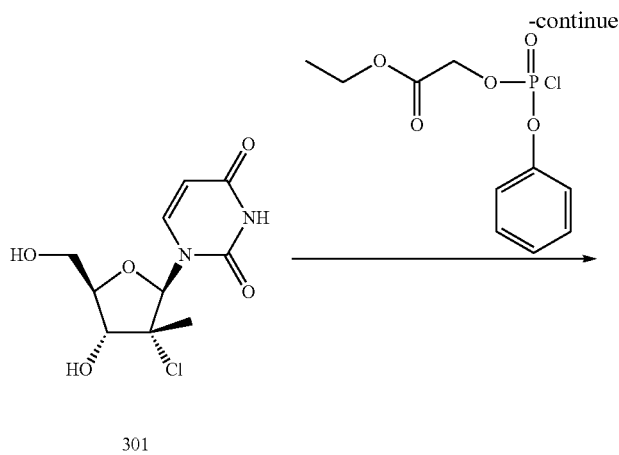

Compound 72

[Structure of compound 72]

To a solution of phenyldichlorophosphate (7.22 mmol) and Et₃N (21.69 mmol) in dichloromethane (5 mL/mmol) was added dropwise under nitrogen at −15° C. ethyl glycolate (7.22 mmol). The reaction mixture was stirred at −15° C. during 40 minutes. Compound 301 (1.81 mmol) was added at −10° C. and the reaction mixture was stirred at room temperature. The mixture was quenched with phosphate buffer solution and extracted with dichloromethane. The organic layer was dried over Na₂SO₄, filtered and concentrated under reduced pressure. The crude was purified by chromatography on silica gel (eluent: DCM/CH₃OH 0 to 50%) and by preparative HPLC to give a mixture of diastereoisomers as white lyophilized solid in 20% yield.

72: Mixture of P-Diastereoisomers:
$^1$H NMR (DMSO-d$_6$, 400 MHz) □□ (ppm) 1.20 (t, J=7.07 Hz, 3H), 1.41 (s, 1.44H), 1.43 (s, 1.56H), 3.83-3.97 (m, 1H), 4.06-4.12 (m, 1H), 4.16 (q, J=7.09 Hz, 1.04H), 4.17 (q, J=7.09 Hz, 0.96H), 4.45-4.58 (m, 2H), 4.80 (d, J=11.60 Hz, 2H), 5.50 (d, J=8.12 Hz, 0.52H), 5.54 (d, J=8.12 Hz, 0.48H), 6.24 (brs, 1.04H), 6.27 (brs, 0.96H), 7.23-7.28 (m, 3H), 7.40-7.44 (m, 2H), 7.50-7.57 (m, 1H), 11.53 (brs, 1H); $^{31}$P NMR (DMSO-d$_6$, 161.98 MHz): δ (ppm)-6.57 (s, 0.48P), −6.46 (s, 0.52P); MS (ESI) m/z=519 (MH$^+$).

The mixture was purified by chiral chromatography (eluent: heptane 40/isopropanol 60; run: 100 minutes) to give the separated P-diastereoisomers.

72: P-Diastereoisomer 1
(RT=50.5 minutes): White solid; $^1$H NMR (DMSO-d$_6$, 400 MHz) δ (ppm) 1.19 (t, J=7.10 Hz, 3H), 1.42 (s, 3H), 3.88-3.96 (m, 1H), 4.05-4.10 (m, 1H), 4.15 (q, J=7.09 Hz, 2H), 4.45-4.55 (m, 2H), 4.79 (d, J=11.46 Hz, 2H), 5.49 (d, J=8.07 Hz, 1H), 6.22 (d, J=4.75 Hz, 1H), 6.27 (brs, 1H), 7.22-7.26 (m, 3H), 7.38-7.43 (m, 2H), 7.55 (d, J=8.08 Hz, 1H), 11.51 (s, 1H); $^{31}$P NMR (DMSO-d$_6$, 161.98 MHz): δ (ppm)-6.47 (s, 1P).

72: P-Diastereoisomer 2
(RT=57.2 minutes): White solid; $^1$H NMR (DMSO-d$_6$, 400 MHz) δ (ppm) 1.19 (t, J=7.07 Hz, 3H), 1.41 (s, 3H), 3.83-3.92 (m, 1H), 4.06-4.11 (m, 1H), 4.16 (q, J=7.10 Hz, 2H), 4.44-4.49 (m, 1H), 4.53-4.57 (m, 1H), 4.79 (d, J=11.52 Hz, 2H), 5.53 (d, J=8.11 Hz, 1H), 6.22 (d, J=4.98 Hz, 1H), 6.26 (brs, 1H), 7.22-7.27 (m, 3H), 7.38-7.42 (m, 2H), 7.50 (d, J=8.0 Hz, 1H), 11.51 (s, 1H); $^{31}$P NMR (DMSO-d$_6$, 161.98 MHz): δ (ppm)-6.58 (s, 1P).

Scheme 8

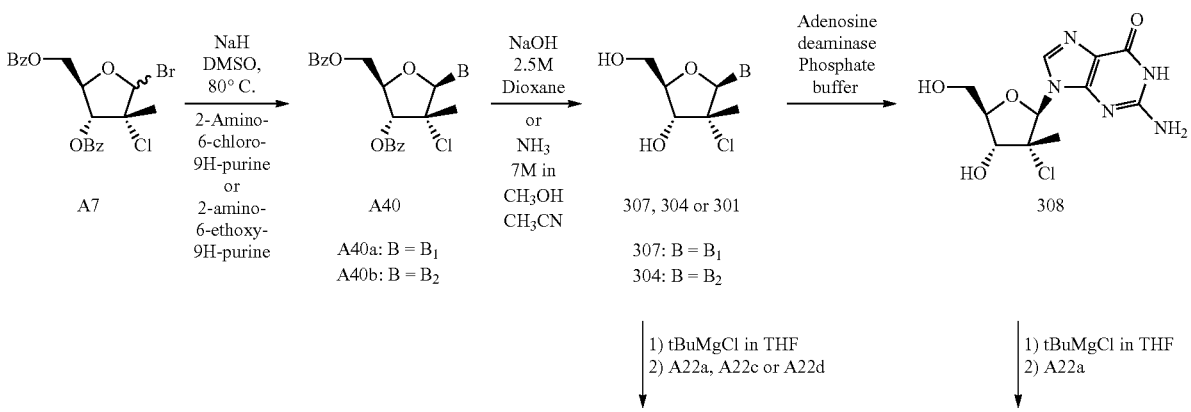

-continued

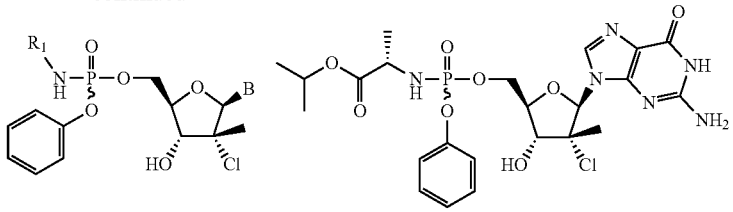

17ii, 202i and 205i

21ii
(Mixture of P-diastereoisomers)

The following abbreviations are used in Scheme 8:

B=B₁:

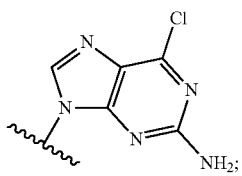 [SMILES: *n1cnc2c(Cl)nc(N)nc21]

B=B₂:

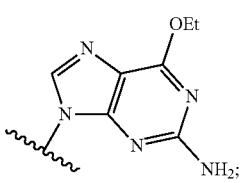 [SMILES: *n1cnc2c(OCC)nc(N)nc21]

B=B₃:

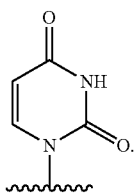 [SMILES: *n1ccc(=O)[nH]c1=O]

17ii: B=B₂ and

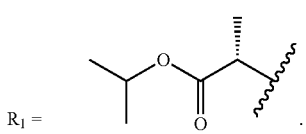 [SMILES: *[C@@H](C)C(=O)OC(C)C]

202i: B=B₃ and

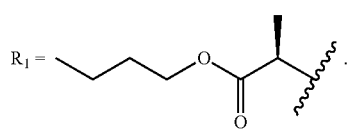 [SMILES: *[C@H](C)C(=O)OCCCC]

205i: B=B₃ and

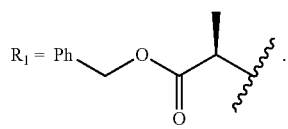 [SMILES: *[C@H](C)C(=O)OCc1ccccc1]

Compounds (A40a) and (A40b)

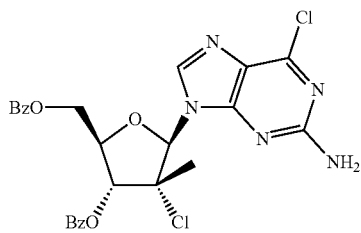

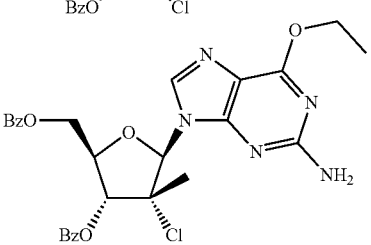

To a solution of 2-Amino-6-chloro-9H-purine (or 2-amino-6-ethoxy-9H-purine) (22.04 mmol) in dimethyl sulfoxide (141 mmol) was added sodium hydride (22.04 mmol) and the reaction mixture was stirred at 80° C., under nitrogen during 30 minutes. Compound A7 (4.41 mmol) was added and the mixture was stirred under nitrogen at 80° C. during 15 minutes. The reaction mixture was cooled down to room temperature.

For the compound A40a, EtOAc and water were added and the aqueous layer was acidified to pH=6 by addition of HCl 2.5N. The organic layer was washed with water (3 times), brine, dried and concentrated under reduced pressure. The residue was purified by chromatography on silica gel (eluent: DCM/MeOH 0 to 15%) to give the expected compound.

For the compound A40b, the mixture was quenched with a saturated solution of NH₄Cl and extracted with EtOAc. The organic layer was washed with water, brine, dried and concentrated under reduced pressure. The residue was purified by chromatography on silica gel (eluent: DCM/MeOH 0 to 3%) to give the expected compound.

A40a: 22% yield; white foam; MS (ESI) m/z=540 (MH⁻).
A40b: 12% yield; beige solid; ¹H NMR (DMSO-d₆, 400 MHz) δ (ppm) 1.37 (t, J=7.08 Hz, 3H), 1.42 (s, 3H), 4.47 (q, J=7.07 Hz, 2H), 4.72-4.79 (m, 2H), 4.86-4.92 (m, 1H), 6.37 (brs, 1H), 6.52 (s, 1H), 6.61 (brs, 2H), 7.10 (s, 2H), 8.59 (s, 1H); MS (ESI) m/z=552.2 (MH+).

Compound (307)

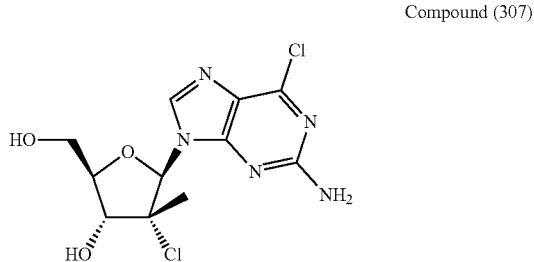 [SMILES: C[C@@]1(Cl)[C@H](O)[C@@H](CO)O[C@H]1n1cnc2c(Cl)nc(N)nc21]

To a solution of compound A40a (0.92 mmol) in 1,4-dioxane (117 mmol) was added NaOH 2.5 M (1.84 mmol) and the reaction mixture was stirred at room temperature during 1 hour. The reaction mixture was acidified to pH=6 by addition of HCl 1N and concentrated under reduced pressure. The residue was purified by chromatography on silica gel (eluent: DCM/MeOH 0 to 5%) to give the expected pure anomer β as white solid in 15% yield.

$^1$H NMR (DMSO-d$_6$, 400 MHz) δ (ppm) 1.25 (s, 3H), 3.69-3.74 (m, 1H), 3.85-3.90 (m, 1H), 3.94-3.98 (m, 1H), 4.27-4.30 (m, 1H), 5.41-5.44 (m, 1H), 6.00 (d, J=5.70 Hz, 1H), 6.29 (s, 1H), 7.10 (s, 2H), 8.59 (s, 1H); MS (ESI) m/z=334 (MH+).

Compound 304

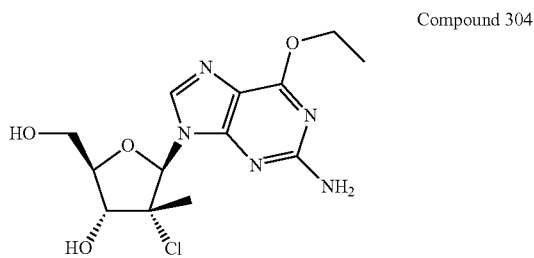 [SMILES: CCOc1nc(N)nc2c1ncn2[C@@H]1O[C@H](CO)[C@@H](O)[C@@]1(C)Cl]

To a solution of compound A40b (0.12 mmol) in acetonitrile (3 mL) was added ammonia solution (7M in methanol) (21 mmol) and the reaction mixture was stirred at room temperature during 72 hours. The reaction mixture was acidified to pH=6 by addition of acetic acid and concentrated under reduced pressure. The residue was purified by C18 chromatography to give the expected compound as a white solid in 25% yield.

$^1$H NMR (DMSO-d$_6$, 400 MHz) δ (ppm) 1.20 (s, 3H), 1.36 (t, J=7.11 Hz, 3H), 3.69-3.74 (m, 1H), 3.84-3.90 (m, 1H), 3.93-3.96 (m, 1H), 4.26-4.29 (m, 1H), 4.44 (q, J=7.11 Hz, 2H), 5.38-5.40 (m, 1H), 5.96 (d, J=5.91 Hz, 1H), 6.28 (s, 1H), 6.58 (brs, 2H), 8.32 (s, 1H); MS (ESI) m/z=344 (MH+).

Compound (309)

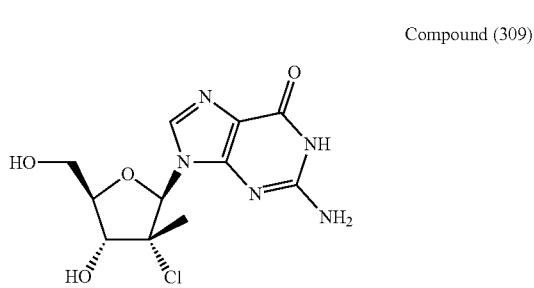 [SMILES: C[C@@]1(Cl)[C@H](O)[C@@H](CO)O[C@H]1n1cnc2c(=O)[nH]c(N)nc21]

To a solution of compound 307 (0.024 mmol) in phosphate buffer (5 mL) was added adenosine deaminase (0.05 mL). The reaction mixture was stirred at 30° C. during 1 hour. The solution was concentrated under reduced pressure and the residue was purified by C18 chromatography to give the expected compound as white solid in 66% yield.

$^1$H NMR (DMSO-d$_6$, 400 MHz) δ (ppm) 1.21 (s, 3H), 3.66-3.72 (m, 1H), 3.82-3.88 (m, 1H), 3.89-3.93 (m, 1H), 4.24 (d, J=9.02 Hz, 1H), 5.38 (s, 1H), 5.95 (brs, 1H), 6.17 (s, 1H), 6.79 (brs, 2H), 8.11 (s, 1H); MS (ESI) m/z=316 (MH+).

General Method J

The following procedure was used to obtain compounds 21ii and 17ii.

To as solution of compound 308 (or 304) (0.25 mmol) in THF (31.2 mmol) under nitrogen at room temperature was added tert-butylmagnesium chloride (1M in THF) (0.53 mmol) and the reaction mixture was stirred 15 minutes at room temperature. Compound A22a (0.30 mmol) solubilized in THF (18 mmol) was added. The resulting mixture was stirred at room temperature overnight. The reaction wasn't complete so DMSO (1.5 mL) was added and the mixture was further stirred during 48 hours. The reaction mixture was quenched by addition of saturated solution of NH$_4$Cl. EtOAc and NaHCO$_3$ 5% were added and the layers were separated. The organic phase was washed with NaHCO$_3$ 5% and brine, dried and concentrated under reduced pressure. The residue was purified by chromatography on silica gel (eluent: DCM/MeOH 0 to 10%) followed by purification by preparative HPLC to give the expected pure diastereoisomers.

Compound 21ii

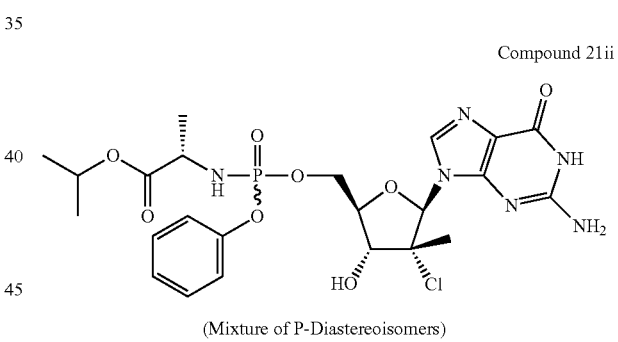

(Mixture of P-Diastereoisomers)

21ii P-Diastereoisomer 1:

2% yield; White solid; $^1$H NMR (DMSO-d$_6$, 400 MHz) δ (ppm) 1.11 (d, J=6 Hz, 3H), 1.12 (d, J=6 Hz, 3H), 1.19 (d, J=7.07 Hz, 3H), 1.22 (s, 3H), 3.69-3.78 (m, 1H), 4.13-4.17 (m, 1H), 4.22-4.31 (m, 1H), 4.30-4.37 (m, 1H), 4.40-4.47 (m, 1H), 4.78-4.84 (m, 1H), 6.06-6.11 (m, 1H), 6.16-6.20 (m, 1H), 6.25 (s, 1H), 6.68 (brs, 2H), 7.13-7.21 (m, 3H), 7.33-7.37 (m, 2H), 7.84 (s, 1H), 10.80 (brs, 1H); $^{31}$P NMR (DMSO-d$_6$, 161.98 MHz): δ (ppm) 3.62 (s, 1P); MS (ESI) m/z=585.2 (MH+).

21ii P-Diastereoisomer 2:

3% yield; $^1$H NMR (DMSO-d$_6$, 400 MHz) δ (ppm) 1.09-1.12 (m, 6H), 1.21 (d, J=7.11 Hz, 3H), 1.23 (s, 3H), 3.76-3.84 (m, 1H), 4.08-4.13 (m, 1H), 4.26-4.41 (m, 3H), 4.76-4.83 (m, 1H), 6.0-6.05 (m, 1H), 6.06-6.10 (m, 1H), 6.24 (s, 1H), 6.64 (brs, 2H), 7.15-7.23 (m, 3H), 7.34-7.38 (m, 2H), 7.85 (s, 1H), 10.73 (brs, 1H); $^{31}$P NMR (DMSO-d$_6$, 161.98 MHz): δ (ppm) 3.84 (s, 1P); MS (ESI) m/z=585.2 (MH+).

Compound 17ii

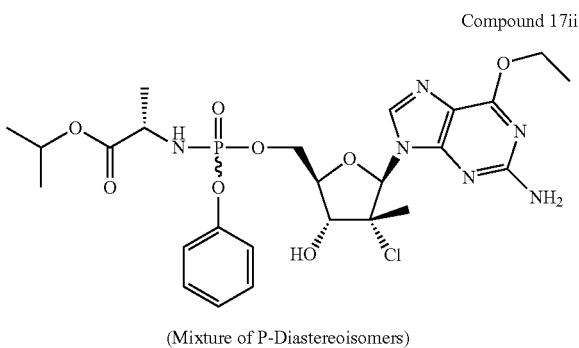 [SMILES: CCOc1nc(N)nc2c1ncn2[C@@H]1O[C@H](COP(=O)(N[C@@H](C)C(=O)OC(C)C)Oc2ccccc2)[C@@H](O)[C@@]1(C)Cl]

(Mixture of P-Diastereoisomers)

For these compounds, the addition of DMSO was not necessary.

17ii P-Diastereoisomer 1:

4% yield; White solid; $^1$H NMR (DMSO-$d_6$, 400 MHz) δ (ppm) 1.11-1.14 (m, 6H), 1.20 (d, J=7.11 Hz, 3H), 1.22 (s, 3H), 1.36 (t, J=7.08 Hz, 3H), 3.72-3.79 (m, 1H), 4.15-4.21 (m, 1H), 4.35-4.45 (m, 3H), 4.45 (q, J=7.05 Hz, 2H), 4.82 (heptuplet, J=6.23 Hz, 1H), 6.03-6.09 (m, 1H), 6.16 (d, J=5.63 Hz, 1H), 6.36 (s, 1H), 6.59 (brs, 2H), 7.14-7.21 (m, 3H), 7.33-7.37 (m, 2H), 7.99 (s, 1H); $^{31}$P NMR (DMSO-$d_6$, 161.98 MHz): δ (ppm) 3.63 (s, 1P); MS (ESI) m/z=613.2 (MH$^+$).

17ii P-Diastereoisomer 2:

5% yield; White solid; $^1$H NMR (DMSO-$d_6$, 400 MHz) δ (ppm) 1.09-1.12 (m, 6H), 1.21 (d, J=7.10 Hz, 3H), 1.23 (s, 3H), 1.36 (t, J=7.11 Hz, 3H), 3.76-3.84 (m, 1H), 4.10-4.15 (m, 1H), 4.33-4.48 (m, 5H), 4.79 (heptuplet, J=6.22 Hz, 1H), 5.98-6.04 (m, 1H), 6.08-6.10 (m, 1H), 6.34 (s, 1H), 6.58 (brs, 2H), 7.15-7.23 (m, 3H), 7.34-7.38 (m, 2H), 8.01 (s, 1H); $^{31}$P NMR (DMSO-$d_6$, 161.98 MHz): δ (ppm) 3.80 (s, 1P); MS (ESI) m/z=613.2 (MH$^+$).

General Method K

The following procedure was used to obtain compounds 202i and 205i.

To as solution of compound 301 (0.72 mmol) in anhydrous THF (7 mL/mmol) under nitrogen at room temperature was added tert-butylmagnesium chloride (1M in THF) (1.52 mmol) followed by compound A22c or A22d (0.795 mmol) solubilized in THF (4 mL/mmol). DMSO (4 mL/mmol) was added and the mixture was stirred at room temperature overnight. The reaction mixture was diluted with dichloromethane and washed with H$_2$O. The organic phase was dried, filtered and concentrated under reduced pressure. The residue was purified by chromatography on silica gel (eluent: DCM/MeOH 0 to 2%) followed by purification by preparative HPLC to give the expected pure diastereoisomers.

Compound 202i

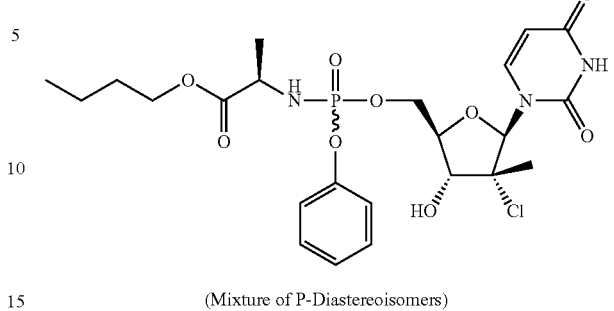

(Mixture of P-Diastereoisomers)

202i P-Diastereoisomer 1:

15% yield; white solid; $^1$H NMR (CDCl$_3$, 400 MHz): δ (ppm) 0.93 (t, J=7.37 Hz, 3H), 1.32-1.40 (m, 2H), 1.40 (d, J=7.04 Hz, 3H), 1.51 (s, 3H), 1.56-1.65 (m, 2H), 3.63 (d, J=7.70 Hz, 1H), 3.70-3.75 (m, 1H), 3.82-3.86 (m, 1H), 3.92-4.02 (m, 1H), 4.08-4.19 (m, 3H), 4.39-4.52 (m, 2H), 5.56 (d, J=8.20 Hz, 1H), 6.39 (s, 1H), 7.19-7.26 (m, 3H), 7.34-7.38 (m, 2H), 7.41 (d, J=8.21 Hz, 1H), 8.10 (s, 1H); $^{31}$P NMR (CDCl$_3$, 161.98 MHz): δ (ppm) 4.27 (s, 1P); MS (ESI, E1$^+$) m/z=560 (MH$^+$).

202i P-Diastereoisomer 2:

18% yield; white solid; $^1$H NMR (CDCl$_3$, 400 MHz): δ (ppm) 0.92 (t, J=7.35 Hz, 3H), 1.30-1.38 (m, 2H), 1.37 (d, J=7.13 Hz, 3H), 1.57-1.62 (m, 2H), 1.61 (s, 3H), 3.45-3.53 (m, 2H), 4.00-4.20 (m, 5H), 4.46-4.59 (m, 2H), 5.63 (d, J=8.26 Hz, 1H), 6.44 (s, 1H), 7.19-7.22 (m, 3H), 7.34-7.38 (m, 2H), 7.66 (d, J=8.18 Hz, 1H), 8.04 (s, 1H); $^{31}$P NMR (CDCl$_3$, 161.98 MHz): δ (ppm) 3.84 (s, 1P); MS (ESI, E1$^+$) m/z=560 (MH$^+$).

Compound 205i

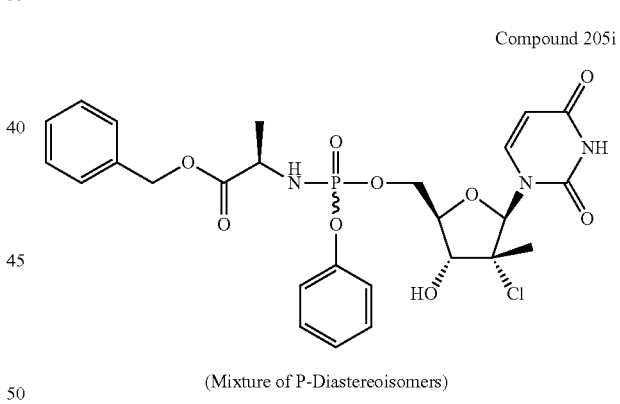

(Mixture of P-Diastereoisomers)

205i P-Diastereoisomer 1:

12% yield; white solid; $^1$H NMR (CDCl$_3$, 400 MHz): δ (ppm) 1.40 (d, J=7.08 Hz, 3H), 1.49 (s, 3H), 3.55 (d, J=7.83 Hz, 1H), 3.65-3.70 (m, 1H), 3.77-3.81 (m, 1H), 3.97-4.04 (m, 1H), 4.07-4.10 (m, 1H), 4.28-4.45 (m, 2H), 5.16 (s, 2H), 5.54 (d, J=8.22 Hz, 1H), 6.36 (s, 1H), 7.18-7.23 (m, 3H), 7.31-7.38 (m, 8H), 7.99 (s, 1H); $^{31}$P NMR (CDCl$_3$, 161.98 MHz): δ (ppm) 4.07 (s, 1P); MS (ESI, E1$^+$) m/z=594 (MH$^+$).

205i P-Diastereoisomer 2:

19% yield; white solid; $^1$H NMR (CDCl$_3$, 400 MHz): δ (ppm) 1.38 (d, J=7.11 Hz, 3H), 1.59 (s, 3H), 3.41 (d, J=7.94 Hz, 1H), 3.51-3.56 (m, 1H), 3.98-4.02 (m, 1H), 4.09-4.19 (m, 2H), 4.43-4.57 (m, 2H), 5.13 (s, 2H), 5.61 (d, J=8.27 Hz, 1H), 6.43 (s, 1H), 7.18-7.22 (m, 3H), 7.28-7.39 (m, 7H), 7.63 (d, J=8.16 Hz, 1H), 8.16 (s, 1H); $^{31}$P NMR (CDCl$_3$, 161.98 MHz): δ (ppm) 3.69 (s, 1P); MS (ESI, E1$^+$) m/z=594 (MH$^+$).

Scheme 9

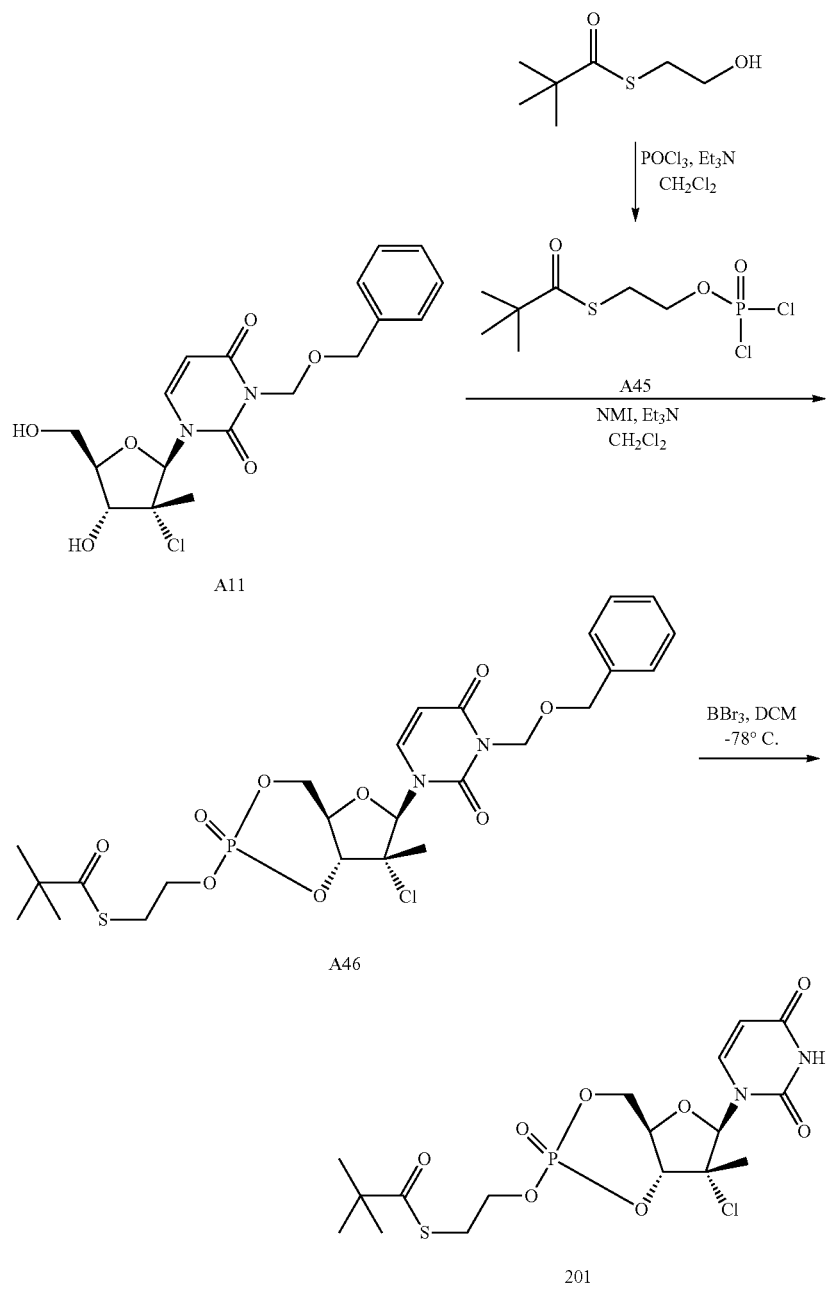

S-(2-dichlorophosphoryloxyethyl) 2,2-dimethylpropanethioate (A45)

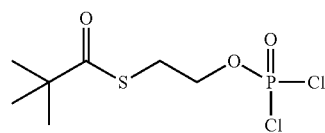

S-(2-hydroxyethyl) 2,2-dimethylpropanethioate (6.38 mmol) was dissolved in dichloromethane (2.5 mL/mmol) and $Et_3N$ (7.02 mmol) was added under nitrogen. The reaction mixture was cooled down to −15° C. and $POCl_3$ (7.02 mmol) was added dropwise. The reaction mixture was stirred at this temperature during 1 hour. The solvent was concentrated under reduced pressure, $Et_2O$ was added and the salts were filtered under nitrogen to give, after concentration the expected compound as a colorless oil used crude.

Compound A46

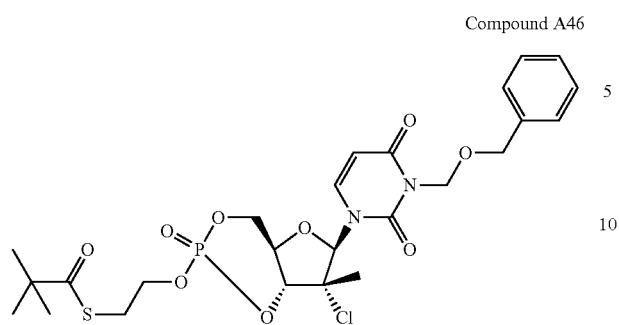

To a solution of compound A11 (1.51 mmol) in dichloromethane (10 mL/mmol) and Et₃N (6.04 mmol) under nitrogen was added at 0° C. the compound A45 (2.27 mmol). The reaction mixture was stirred at 0° C. during 15 minutes and NMI (3.17 mmol) was added dropwise. The reaction was stirred at 0° C. during 1 hour. The reaction was diluted with dichloromethane and washed with H₂O. The organic layer was dried over Na₂SO₄, filtered and concentrated under reduced pressure. The crude was purified by chromatography on a silica gel (eluent: DCM/MeOH 0 to 7%) to give the pure diastereoisomers in 52% yield. MS (ESI) m/z=603.2 (MH⁺).

Compound 201

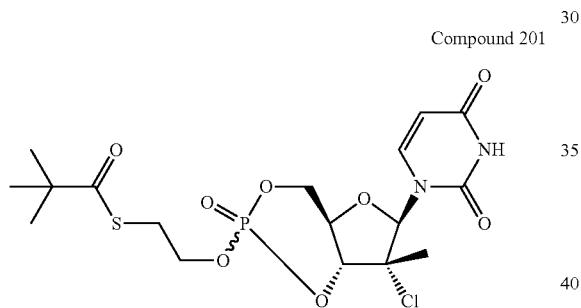

Compound 201 was synthesized from intermediate A46 (0.61 mmol) as described in general method C (with only one addition of BBr₃). The crude was purified by chromatography on silica gel (eluent: DCM/CH₃OH 0 to 5%) and C18 chromatography to give the pure diastereoisomer as white foam in 82% yield.

¹H NMR (DMSO-d₆, 400 MHz) δ (ppm) 1.18 (s, 9H), 1.53 (s, 3H), 3.19 (t, J=6.56 Hz, 2H), 4.11-4.17 (m, 2H), 4.20-4.26 (m, 1H), 4.48 (d, J=9.39 Hz, 1H), 4.63-4.75 (m, 2H), 5.70 (d, J=8.15 Hz, 1H), 6.43 (s, 1H), 7.76 (d, J=8.13 Hz, 1H), 11.63 (s, 1H); ³¹P NMR (DMSO-d₆, 161.98 MHz) δ (ppm)-7.33 (s, 1P); MS (ESI) m/z=481 (MH⁻).

Scheme 10

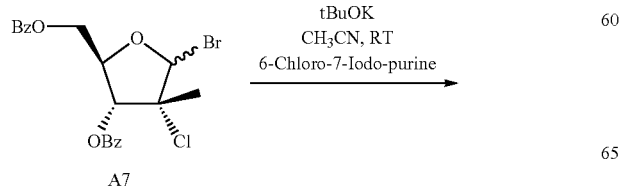

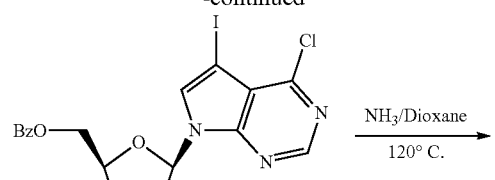

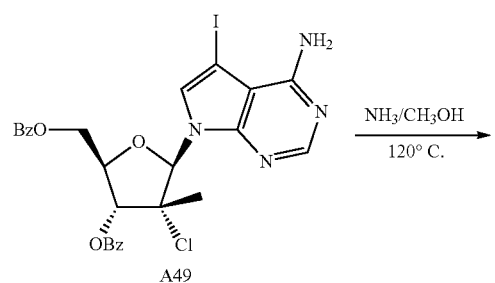

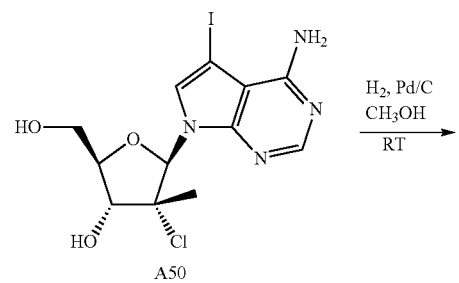

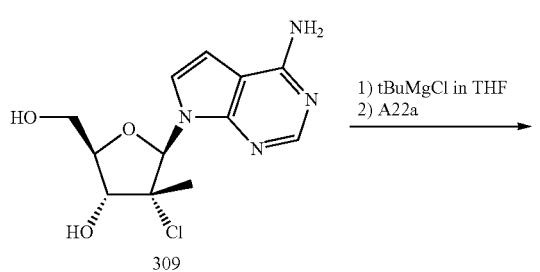

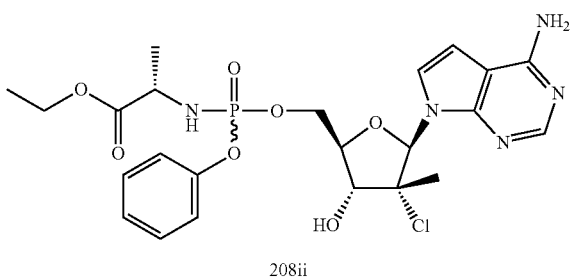

Compounds 309 and 208ii were synthesized according to Scheme 10.

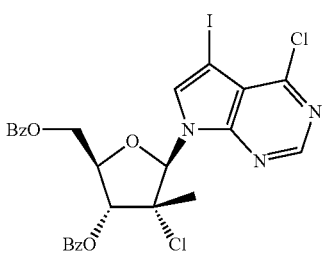

Compound A48

To a solution of 6-chloro-7-iodo-7deazapurine (15.38 mmol) in acetonitrile (7 mL/mmol) was added potassium tert-butoxide (15.38 mmol) at room temperature under nitrogen. The reaction mixture was stirred for 40 minutes and compound A7 (15.38 mmol) was added. The reaction mixture was stirred for a week-end. The mixture was then diluted with ethyl acetate, extracted, washed with brine. The aqueous layer was extracted with ethyl acetate and the combined organic layers were dried, filtrated and concentrated under reduced pressure. The residue was purified by flash chromatography (eluent: petroleum ether/ethyl acetate 0 to 30%) to give the β anomer as a white solid in 23% yield.

$^1$H NMR (CDCl$_3$, 400 MHz) δ (ppm) 1.37 (s, 3H), 4.65 (dd, J=3.88 Hz and 12.75 Hz, 1H), 4.82-4.86 (m, 1H), 4.94 (dd, J=2.81 Hz and 12.75 Hz, 1H), 5.92 (d, J=8.92 Hz, 1H), 6.91 (s, 1H), 7.48-7.54 (m, 4H), 7.60-7.67 (m, 2H), 7.70 (s, 1H), 8.11-8.14 (m, 4H), 8.68 (s, 1H); MS (ESI) m/z=652 (MH$^+$).

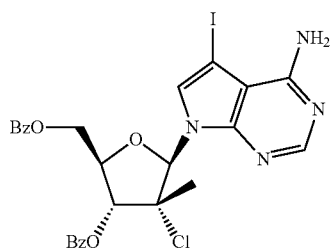

Compound A49

Compound A48 (1.07 mmol) was dissolved in a 0.5M ammonia solution in dioxane (20 mL/mmol) in a sealed vial and the reaction mixture was stirred at 110° C. during 24 hours. The reaction wasn't completed so 0.5M ammonia solution in dioxane (10 mL/mmol) was added and the reaction mixture was saturated twice with ammonia gas. After 3 days of reaction at 110° C., the mixture was concentrated under reduced pressure to give a mixture of expected compound and partially deprotected compound. This crude mixture was used in the next step without purification.

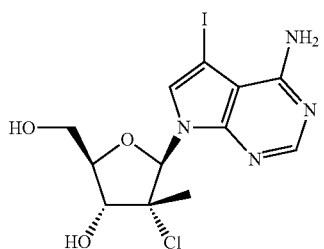

Compound A50

Compound A49 (1.07 mmol) was dissolved in a 7N ammonia solution in methanol (30 mL) in a sealed vial and the reaction mixture was stirred at room temperature for a week-end. The mixture was concentrated under reduced pressure to give crude compound. This crude residue was diluted with dichloromethane and water, a precipitate appeared. The organic layer was extracted twice, and the aqueous layer was filtered and purified by flash C18 chromatography to give, combined with precipitate, the expected compound as beige solid in 74% yield (2 steps).

$^1$H NMR (DMSO-d$_6$, 400 MHz) δ (ppm) 1.06 (s, 3H), 3.66-3.71 (m, 1H), 3.84-3.93 (m, 2H), 4.18-4.21 (m, 1H), 5.38 (t, J=4.70 Hz, 1H), 5.87 (d, J=6.07 Hz, 1H), 6.56 (s, 1H), 6.73 (brs, 2H), 7.94 (s, 1H), 8.13 (s, 1H); MS (ESI) m/z=425 (MH$^+$).

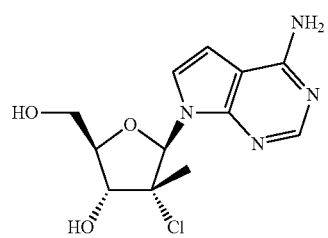

Compound 309

To a solution of A50 (0.79 mmol) in anhydrous methanol (25 mL/mmol) was added Palladium (10% on Carbon, 68 mg). The reaction mixture was purged 3 times vacuo/nitrogen, then 3 times vacuo/hydrogen and stirred under hydrogen atmosphere overnight at room temperature. The mixture was filtered through a pad of celite, and the filtrate was concentrated under reduced pressure. The crude compound was purified by flash C18 chromatography to give the expected compound as a white foam in 81% yield.

$^1$H NMR (DMSO-d$_6$, 400 MHz) δ (ppm) 1.02 (s, 3H), 3.67-3.72 (m, 1H), 3.84-3.93 (m, 2H), 4.19-4.23 (m, 1H), 5.27 (t, J=4.68 Hz, 1H), 5.84 (d, J=5.98 Hz, 1H), 6.59 (s, 1H), 6.60 (d, J=3.70 Hz, 1H), 7.08 (s, 2H), 7.59 (d, J=3.70 Hz, 1H), 8.07 (s, 1H); MS (ESI) m/z=299 (MH$^+$).

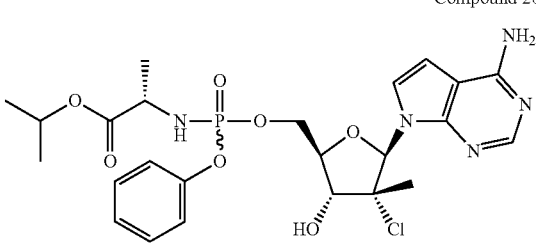

Compound 208ii (Two Diastereoisomers)

Compound 208ii was synthesized from compound 309 (0.30 mmol) as described for compound 17ii.

208ii: Diastereoisomer 1:

white solid; $^1$H NMR (MeOD, 400 MHz): δ (ppm) 1.16 (s, 3H), 1.22-1.25 (m, 6H), 1.33 (d, J=7.04 Hz, 3H), 3.89-3.97 (m, 1H), 4.28-4.33 (m, 2H), 4.48-4.53 (m, 1H), 4.63-4.68 (m, 1H), 4.95-5.02 (m, 1H), 6.66 (d, J=3.73 Hz, 1H), 6.76 (s, 1H), 7.20-7.42 (m, 6H), 8.14 (s, 1H); $^{31}$P NMR (MeOD, 161.98 MHz): δ (ppm) 3.83 (s, 1P); MS (ESI, E1$^+$) m/z=568.3 (MH$^+$).

208ii: Diastereoisomer 2:

white solid; $^1$H NMR (MeOD, 400 MHz): δ (ppm) 1.17-1.22 (m, 9H), 1.35 (d, J=7.04 Hz, 3H), 3.91-3.99 (m, 1H), 4.26-4.37 (m, 2H), 4.46-4.52 (m, 1H), 4.56-4.61 (m, 1H), 4.91-4.96 (m, 1H), 6.65 (d, J=3.79 Hz, 1H), 6.75 (s, 1H), 7.21-7.25 (m, 1H), 7.30-7.34 (m, 3H), 7.38-7.42 (m, 2H), 8.14 (s, 1H); $^{31}$P NMR (MeOD, 161.98 MHz): δ (ppm) 3.67 (s, 1P); MS (ESI, E1$^+$) m/z=568.3 (MH$^+$).

Scheme 11

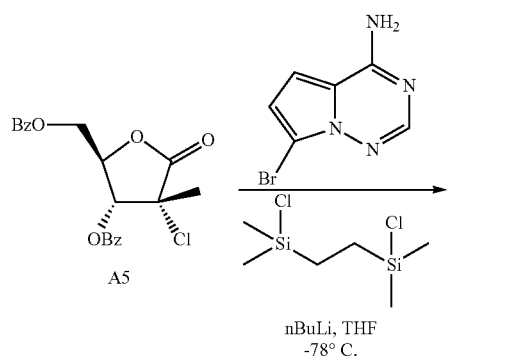

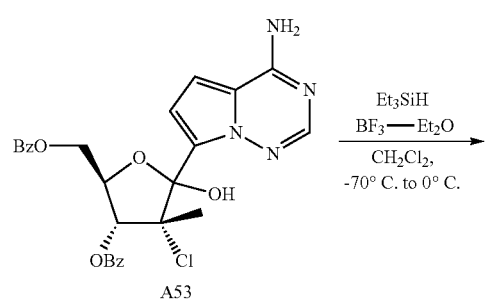

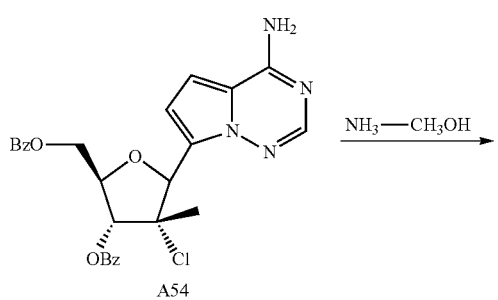

Compound 305 was synthesized according to Scheme 11.

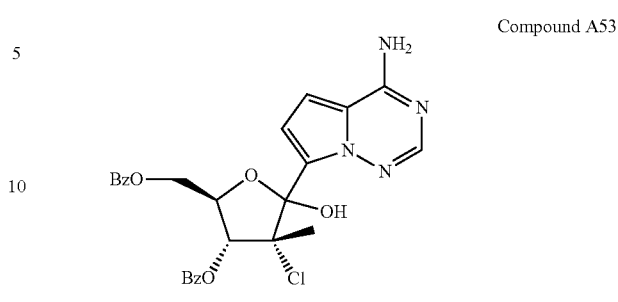

Compound A53

To a suspension of 7-bromo-pyrrolo[2,1-f][1,2,4]triazin-4-ylamine (2.35 mmol) in THF (6.5 mL) was added nBuLi (2.5M in hexane) (2.56 mmol) at −78° C. After 30 minutes, a solution of 1,2-bis-[(chlorodimethyl)silanyl)]ethane (2.49 mmol) was added. After 45 minutes, nBuli (2.56 mmol) was added. And after additional 30 minutes, nBuli (2.56 mmol) was added again. After 30 minutes, a solution of compound A5 (1.88 mmol) in THF (2 mL) was added dropwise. The reaction mixture was stirred at −78° C. during 2 hours under argon. Acetic acid (0.7 mL) was added dropwise to quench the reaction, followed by addition of saturated NH$_4$Cl solution. The mixture was extracted with ethyl acetate and the organic layer was dried, filtered and concentrated under reduced pressure. The crude was purified by chromatography on silica gel column (eluent: CH$_2$Cl$_2$/CH$_3$OH 0 to 10%) to give the expected compound in 53% yield. MS (ESI) m/z=522.89 (MH$^+$).

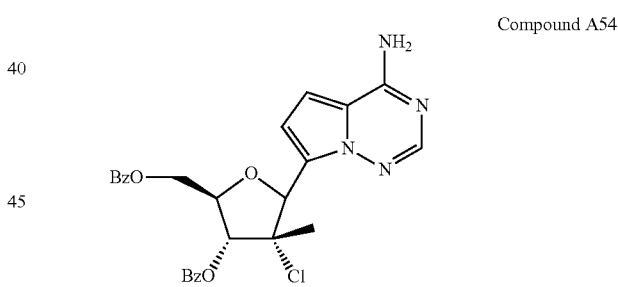

Compound A54

To a solution of compound A53 (0.99 mmol) in dry dichloromethane (20 mL) at −78° C. under nitrogen was added Et$_3$SiH (3.96 mmol) followed by addition of BF$_3$-Et$_2$O (1.98 mmol). The reaction mixture was stirred at −78° C. to 0° C. during 2 hours. After control, the starting material was always present so Et$_3$SiH (3.96 mmol) and BF$_3$-Et$_2$O (1.98 mmol) were added again and the reaction mixture was allowed to warm up from −10° C. to 0° C. during 2 hours. The mixture was washed with water and the organic layer was dried, filtered and concentrated under reduced pressure. The crude was purified by chromatography on silica gel column (eluent: CH$_2$Cl$_2$/CH$_3$OH 0 to 10%) to give a mixture of diastereoisomers in 73% yield. MS (ESI) m/z=507.2 (MH$^+$).

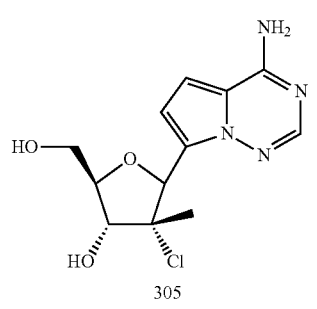

Compound 305

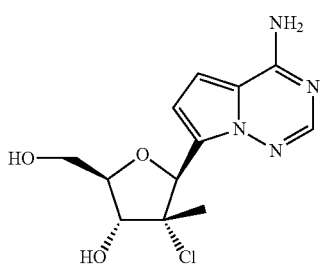

Compound 305 was synthesized from compound A54 (0.604 mmol) as described for compound 301. The crude was purified by RP18 chromatography followed by preparative HPLC to give the expected compound as a white powder.

$^1$H NMR (MeOD, 400 MHz) δ (ppm) 1.28 (s, 3H), 3.82-3.86 (m, 1H), 3.97-4.0 (m, 1H), 4.03-4.07 (m, 1H), 4.11-4.14 (m, 1H), 6.04 (s, 1H), 6.87-6.90 (m, 2H), 7.81 (s, 1H); MS (ESI) m/z=299 (MH$^+$).

Scheme 12

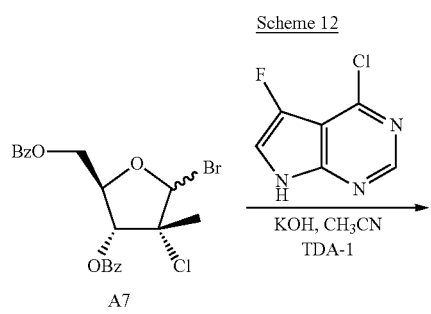

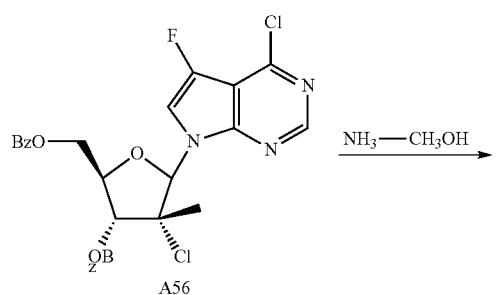

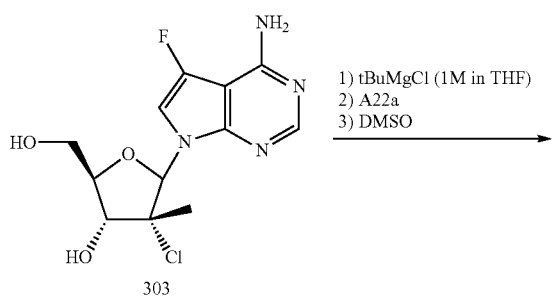

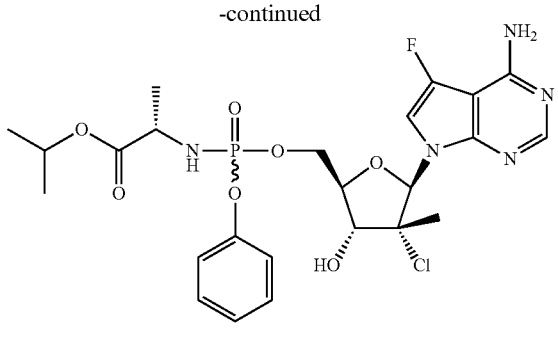

207ii

Compounds 303 and 207ii were synthesized according to Scheme 12.

Compound A56

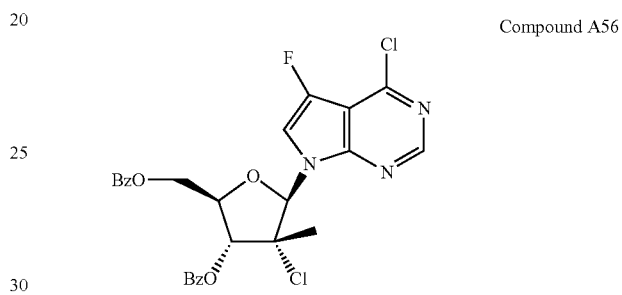

A solution of 4-chloro-5-fluoropyrrolo[2,3-d]pyrimidine (11.66 mmol), potassium hydroxide (40 mmol) and tris[2-(2-methoxyethoxy)ethyl]amine (TDA-1)(3.50 mmol) in acetonitrile (140 ml) was stirred at room temperature during 15 minutes. A solution of compound A7 (15.16 mmol) in acetonitrile (40 mL) was added dropwise at room temperature under nitrogen and the reaction mixture was stirred overnight. Acetonitrile (200 mL) was added and the reaction mixture was filtered. The filtrate was concentrated under reduced pressure and purified by chromatography on a silica gel column (CH$_2$Cl$_2$/CH$_3$OH 0 to 10%) to give impure expected compound as an oil in 23% yield. MS (ESI) m/z=567.3 (MNa$^+$).

Compound 303

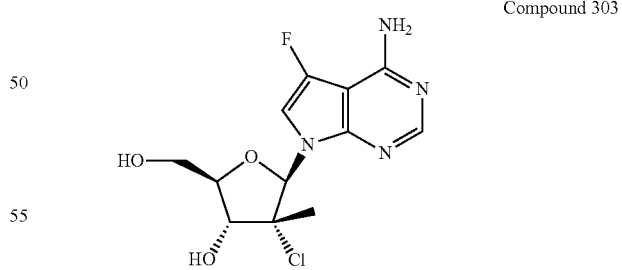

Compound 303 was synthesized from compound A56 (2.57 mmol) as described for compound 302. After concentration, the crude was directly purified by RP18 chromatography to give the expected compound as a white solid in 52% yield.

$^1$H NMR (DMSO-d$_6$, 400 MHz) δ (ppm) 1.07 (s, 3H), 3.66-3.71 (m, 1H), 3.84-3.92 (m, 2H), 4.18 (dd, J=5.71 Hz and 8.84 Hz, 1H), 5.36-5.38 (m, 1H), 5.86 (d, J=5.71 Hz, 1H), 6.62 (d, J=1.26 Hz, 1H), 7.08 (brs, 2H), 7.61 (d, J=1.44

Hz, 1H), 8.09 (s, 1H); $^{19}$F NMR (DMSO-d$_6$, 376.5 MHz) δ (ppm)-166.64 (1F); MS (ESI) m/z=317 (MH$^+$).

Compound 207ii

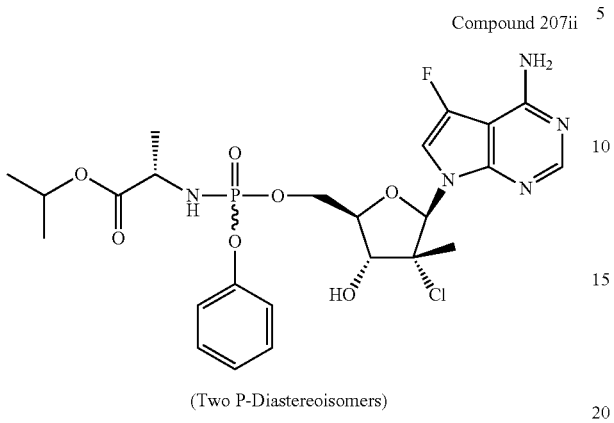

(Two P-Diastereoisomers)

Compound 207ii was synthesized from compound 303 (1 mmol) as described in General Method J. For this reaction, the additions of reactants were realized at 0° C. and DMSO was added 15 minutes after the compound A22a.

207ii P-Diastereoisomer 1:

White solid; 6% yield; $^1$H NMR (DMSO-d$_6$, 400 MHz) δ (ppm) 1.09-1.13 (m, 9H), 1.19 (d, J=7.08 Hz, 3H), 3.70-3.80 (m, 1H), 4.11-4.18 (m, 2H), 4.30-4.35 (m, 1H), 4.41-4.45 (m, 1H), 4.81 (heptuplet, J=6.26 Hz, 1H), 6.11 (dd, J=10.13 Hz and 13.18 Hz, 1H), 6.18 (brs, 1H), 6.69 (s, 1H), 7.12 (brs, 2H), 7.14-7.21 (m, 4H), 7.33-7.37 (m, 2H), 8.11 (s, 1H); $^{19}$F NMR (DMSO-d$_6$, 376.5 MHz) δ (ppm)-165.79 (s, 1F); $^{31}$P NMR (DMSO-d$_6$, 161.98 MHz) δ (ppm) 3.67 (s, 1P); MS (ESI) m/z=586.29 (MH$^+$).

207ii P-Diastereoisomer 2:

White solid; 7% yield; $^1$H NMR (DMSO-d$_6$, 400 MHz) δ (ppm) 1.08-1.12 (m, 9H), 1.21 (d, J=7.07 Hz, 3H), 3.76-3.86 (m, 1H), 4.07-4.11 (m, 1H), 4.19-4.23 (m, 1H), 4.28-4.33 (m, 1H), 4.37-4.42 (m, 1H), 4.80 (heptuplet, J=6.22 Hz, 1H), 6.06 (dd, J=10.15 Hz and 12.97 Hz, 1H), 6.11 (brs, 1H), 6.67 (s, 1H), 7.10 (brs, 2H), 7.15-7.24 (m, 4H), 7.34-7.38 (m, 2H), 8.10 (s, 1H); $^{19}$F NMR (DMSO-d$_6$, 376.5 MHz) δ (ppm)-166 (s, 1F); $^{31}$P NMR (DMSO-d$_6$, 161.98 MHz) δ (ppm) 3.79 (s, 1P); MS (ESI) m/z=586.29 (MH$^+$).

General Method L

The following procedure was used to obtain compounds 401-411.

Scheme 13

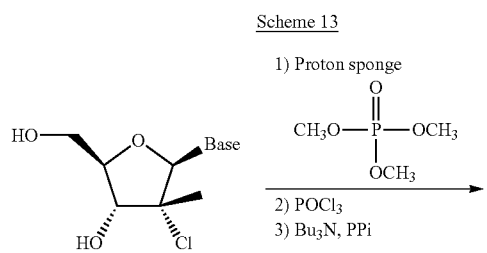

1) Proton sponge
2) POCl$_3$
3) Bu$_3$N, PPi

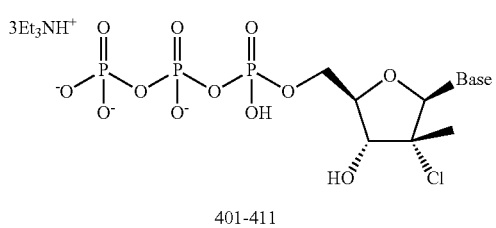

401-411

The appropriate nucleoside (100 mg) was dried in a flask under vacuum overnight. Trimethylphosphate (1.9 ml) and Proton Sponge (100 mg) were added to the flask and the reaction mixture was stirred under nitrogen cooled by an ice/water bath. Distilled phosphorus oxychloride (45 μl) was added and the reaction mixture was stirred during 4 hours with cooling. Tributylamine (0.32 ml) and tributylamine pyrophosphate (4.0 ml of a 0.5 M solution in DMF) were added and the reaction was allowed to stir for an additional 45 min with cooling. The reaction was quenched with triethylammonium bicarbonate (0.5 M, 20 ml) and the solvents were concentrated under reduced pressure. The crude was dissolved in 10 ml of water and purified using a Sephadex DEAE A-25 column with a linear gradient of 0-1 M NaCl buffered with 20 mM Tris-HCl (pH 7.0) (triphosphates eluted at ~0.4 M NaCl) and desalted on a C18 column to give the expected compound.

Compound 401

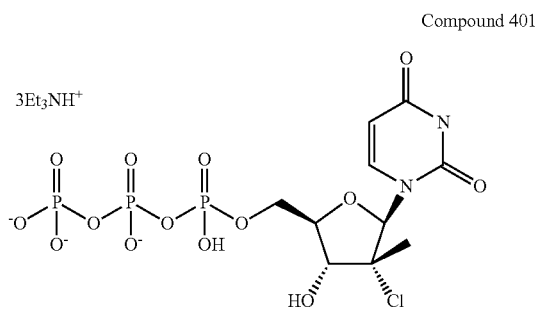

MS (ESI) m/z=515.0 (MH$^-$).

Compound 402

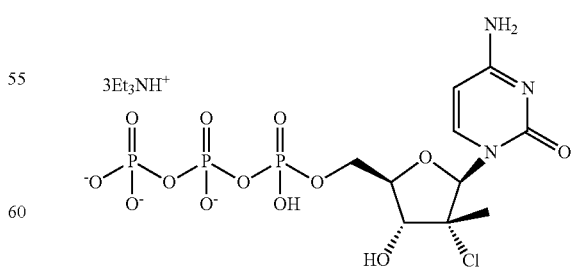

MS (ESI) m/z=514.0 (MH$^-$).

Compound 405
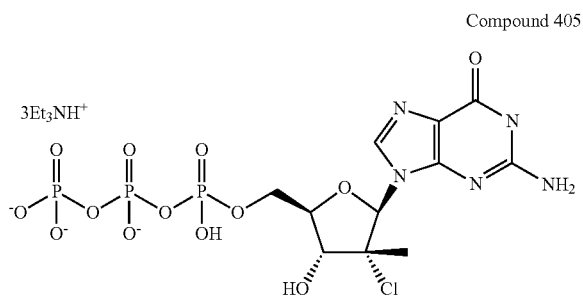
Colorless solid; MS (ESI) m/z=554.0 (MH⁻).
Compound 406
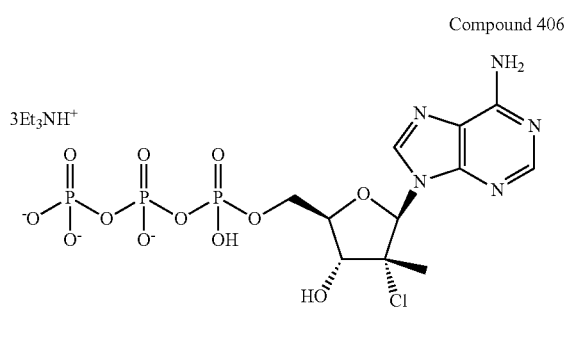
MS (ESI) m/z=538.0 (MH⁻).
Compound 403
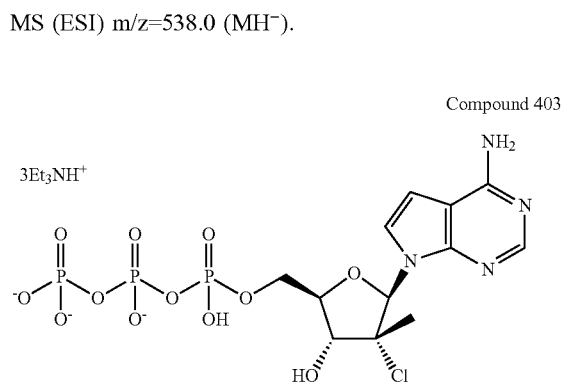
Colorless solid; MS (ESI) m/z=537.0 (MH⁻).
Compound 407
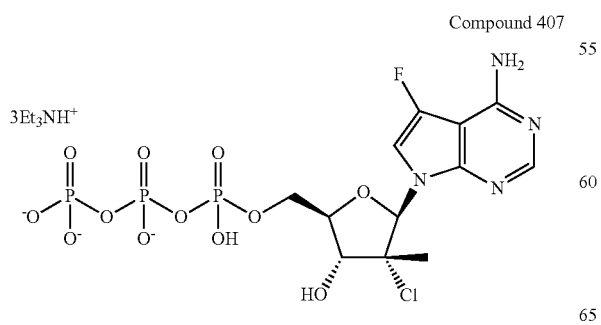
White powder; MS (ESI) m/z=555.0 (MH⁻).
Compound 404
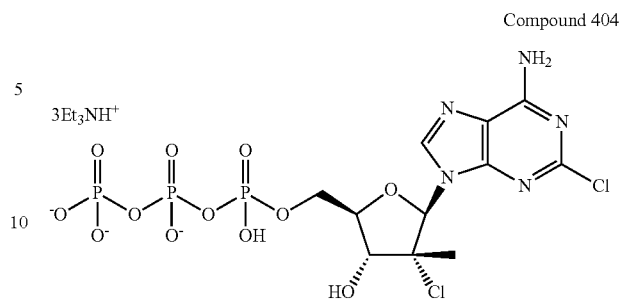
White powder; MS (ESI) m/z=572.0 (MH⁻).
Compound 410
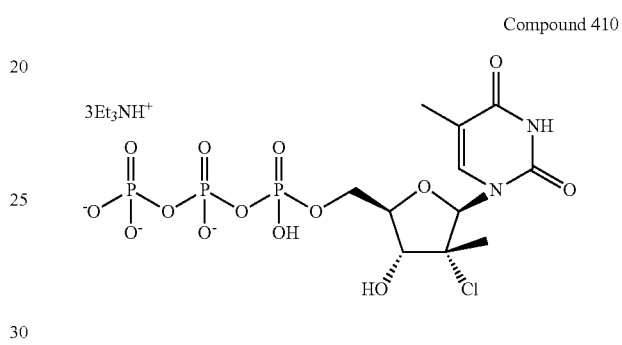
White solid; MS (ESI) m/z=529.0 (MH⁻).
Compound 411
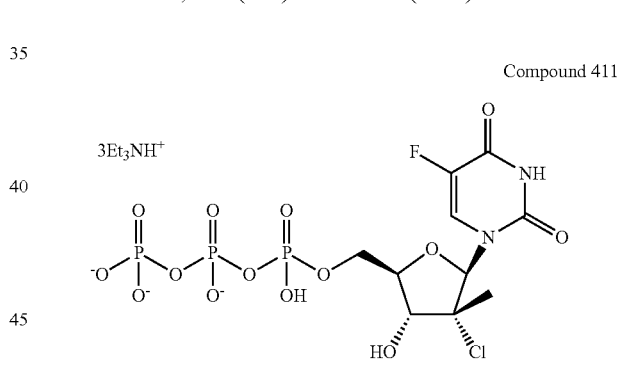
Colorless solid; MS (ESI) m/z=533.0 (MH⁻).
Compound 408
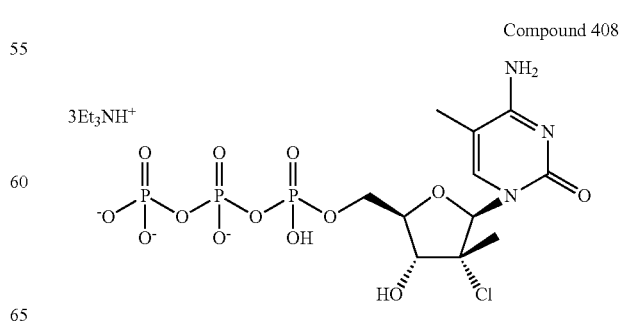
White solid; MS (ESI) m/z=528.0 (MH⁻).

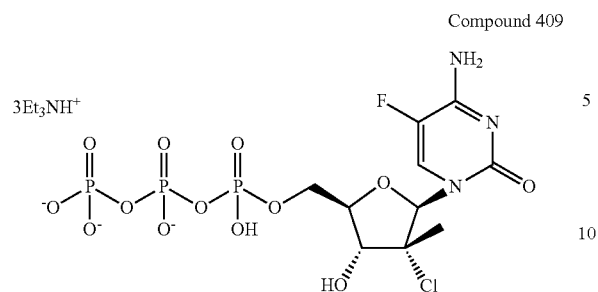
Compound 409
White solid; MS (ESI) m/z=532.0 (MH⁻).
Scheme 14
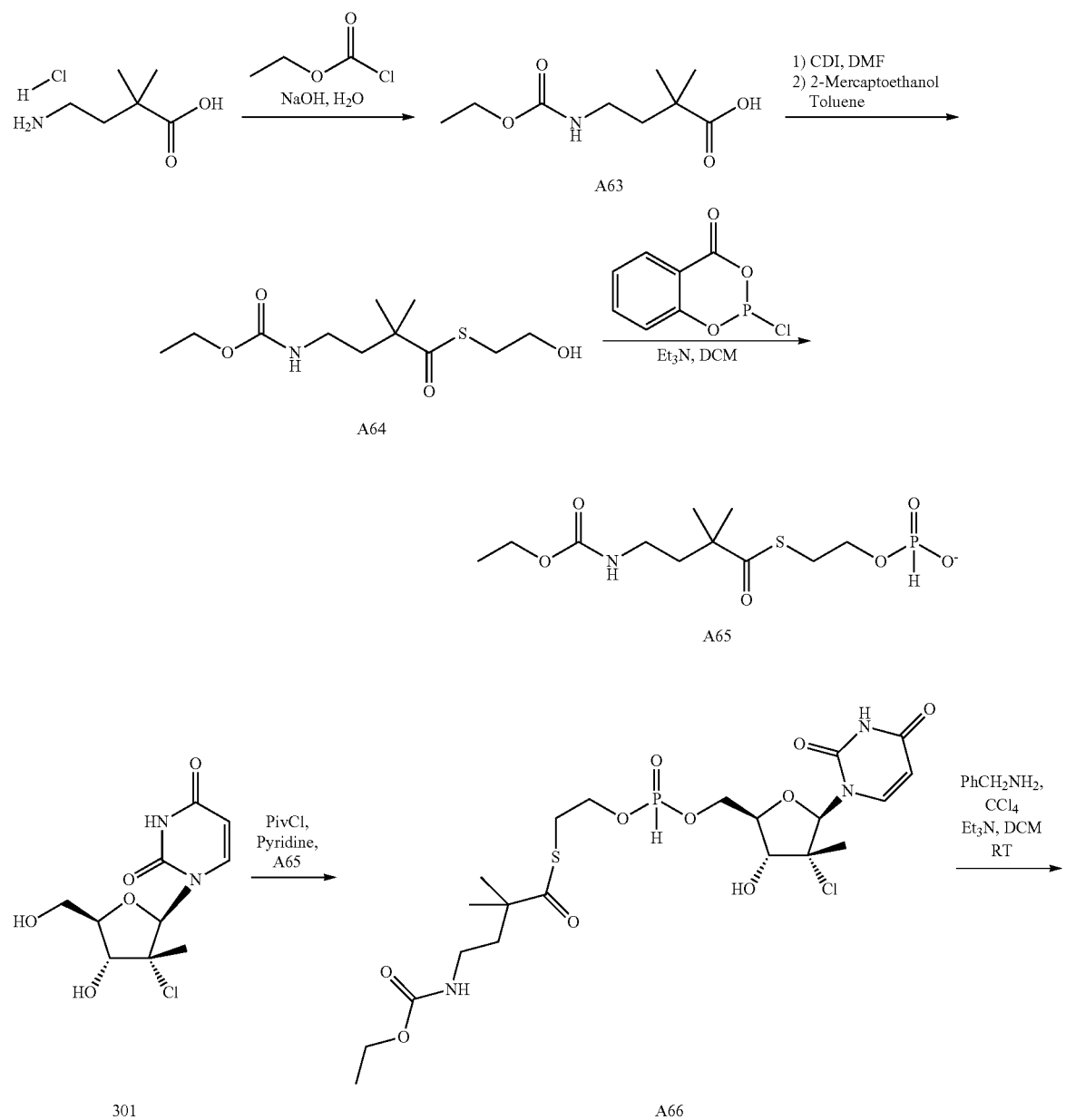

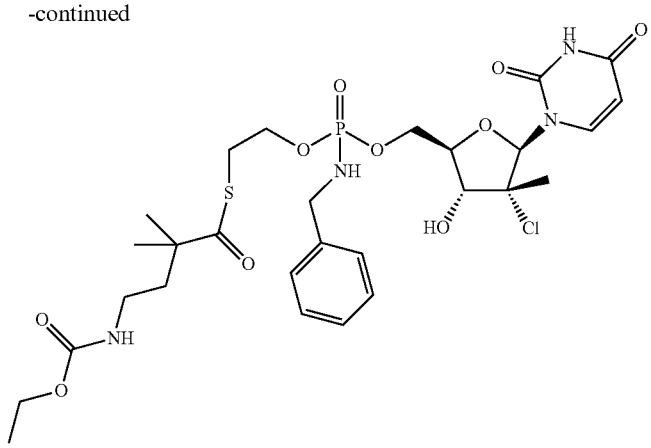

51

Compound 51 was synthesized according to Scheme 14.

4-(Ethoxycarbonylamino)-2,2-dimethyl-butanoic acid (A63)

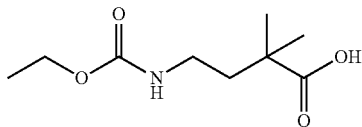

A solution of 4-amino-2,2-dimethylbutanoic acid hydrochloride (14.91 mmol) and NaOH (29.83 mmol) in 30 mL of H$_2$O was stirred at room temperature. A solution of NaOH (14.91 mmol) in 15 mL of H$_2$O and ethyl chloroformate (14.91 mmol) were added simultaneously dropwise at 0° C. to the reaction mixture. The reaction mixture was stirred at 0° C. during 1 hour and was washed with dichloromethane (30 mL). The aqueous layer was stirred at 0° C. and a solution of HCl 1N was added until pH≥2. The mixture was extracted with EtOAc and the organic layer was dried over Na$_2$SO$_4$, filtered and concentrated under reduced pressure to give the expected compound as colorless oil in 99% yield.

$^1$H NMR (CDCl$_3$, 400 MHz) δ (ppm) 1.21-1.28 (m, 9H), 1.78-1.82 (m, 2H), 3.21-3.26 (m, 2H), 4.10-4.15 (m, 2H), 10.96 (brs, 1H).

S-(2-hydroxyethyl) 4-(ethoxycarbonylamino)-2,2-dimethyl-butanethioate (A64)

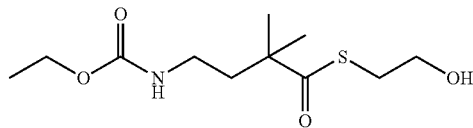 [SMILES: CCOC(=O)NCCC(C)(C)C(=O)SCCO]

To a solution of compound A63 (14.76 mmol) in DMF (1 mL/mmol) was added CDI (19.2 mmol) at room temperature under nitrogen. The reaction mixture was stirred at room temperature during 30 minutes. Toluene (5 mL/mmol) and 2-mercaptoethanol (19.2 mmol) were added dropwise at 0° C. and the reaction mixture was stirred at room temperature overnight. The mixture was neutralized with a saturated solution of NaHCO$_3$ and extracted with dichloromethane (2×100 mL). The organic layer was dried, filtered and concentrated under reduced pressure. The crude was purified by chromatography on silica gel column (eluent: CH$_2$Cl$_2$/CH$_3$OH 0 to 10%) to give the expected compound as colorless oil in 36% yield.

$^1$H NMR (CDCl$_3$, 400 MHz) δ (ppm) 1.20-1.26 (m, 9H), 1.82-1.86 (m, 2H), 2.59 (brs, 1H), 3.08 (t, J=5.78 Hz, 2H), 3.13-3.18 (m, 2H), 3.76 (t, J=5.77 Hz, 2H), 4.07-4.14 (m, 2H), 4.75 (brs, 1H).

Compound A65

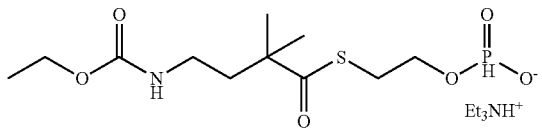

To a solution of compound A64 (1.90 mmol) and Et$_3$N (7.59 mmol) in anhydrous dichloromethane (50 mL) at 0° C. under nitrogen was added dropwise over 25 minutes a solution of 2-chloro-1,3,2-benzodioxaphosphinin-4-one (2.85 mmol) in anhydrous dichloromethane (7 mL) over 30 minutes. The reaction mixture was stirred at room temperature overnight. A solution 1M of TEAB (20 mL) was added. The organic layer was dried, filtered and concentrated under reduced pressure. The crude was purified by chromatography on silica gel column (eluent: CH$_2$Cl$_2$/CH$_3$OH 0 to 20% with 2.5% of Et$_3$N) to give the expected compound as off-white solid in 78% yield.

$^1$H NMR (CDCl$_3$, 400 MHz) δ (ppm) 1.19-1.25 (m, 3H), 1.24 (s, 6H), 1.33 (t, J=7.34 Hz, 9H), 1.80-1.84 (m, 2H), 3.05 (q, J=7.33 Hz, 6H), 3.14 (t, J=6.40 Hz, 4H), 3.44 (s, 1H), 3.92-3.97 (m, 2H), 4.08 (q, J=7.04 Hz, 2H), 5.31 (brs, 1H), 6.1 (s, 0.5H), 7.64 (s, 0.5H); $^{31}$P NMR (CDCl$_3$, 161.98 MHz) δ (ppm) 4.31 (s, 1P).

Compound A66

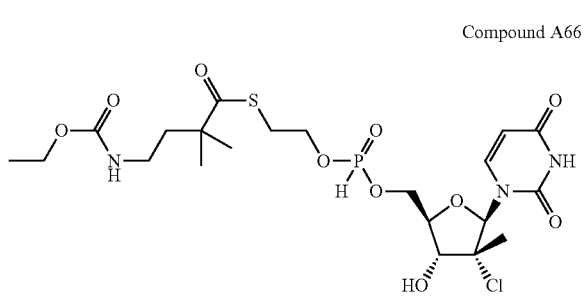 [SMILES: CCOC(=O)NCCC(C)(C)C(=O)SCCO[PH](=O)OC[C@H]1O[C@@H](n2ccc(=O)[nH]c2=O)[C@](C)(Cl)[C@@H]1O]

To a solution of compound 301 (0.97 mmol) and compound A65 (1.26 mmol) in pyridine (10 mL/mmol) at 0° C. under nitrogen was added dropwise pivaloyl chloride (1.94 mmol). The reaction mixture was stirred at 0° C. during 1 hour. A solution 1M of NH$_4$Cl (35 mL) was added. The aqueous layer was extracted with EtOAc and the combined organic layers were dried over MgSO$_4$, filtered and concentrated under reduced pressure and evaporated with toluene to give the expected compound as oil in quantitative yield. MS (ESI) m/z=586.2 (MH$^+$).

Compound 51

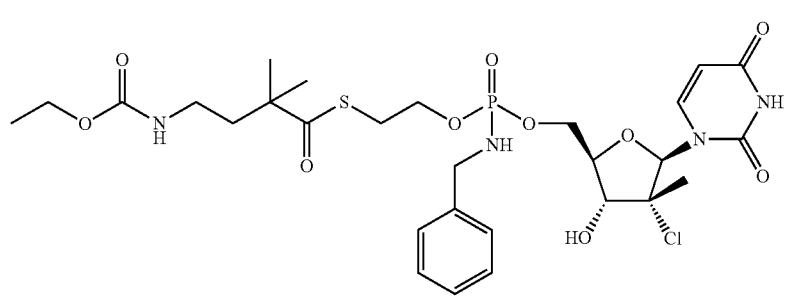

To a solution of compound A66 (0.97 mmol) in dichloromethane (10 mL/mmol) under nitrogen were added benzylamine (4.85 mmol) and Et$_3$N (5.82 mmol). CCl$_4$ (10 mL/mmol) was added and the reaction mixture was stirred at room temperature during 4 hours. The solvents were removed and the crude was purified by chromatography on silica gel (eluent: CH$_2$Cl$_2$/CH$_3$OH 0 to 5%) to give a mixture of two diastereoisomers.

$^1$H NMR (DMSO-d$_6$, 400 MHz): δ (ppm) 1.12 (t, J=7.08 Hz, 3H), 1.15 (s, 6H), 1.41 (s, 3H), 1.65-1.69 (m, 2H), 2.87-2.93 (m, 2H), 3.06 (t, J=6.45 Hz, 2H), 3.83-4.06 (m, 8H), 4.11-4.17 (m, 1H), 4.23-4.30 (m, 1H), 5.53-5.56 (m, 1H), 5.75 (s, 2H), 6.11-6.15 (m, 1H), 6.25 (s, 1H), 6.96-7.01 (m, 1H), 7.19-7.24 (m, 1H), 7.27-7.34 (m, 4H), 7.59-7.66 (m, 1H); $^{31}$P NMR (DMSO-d$_6$, 161.98 MHz) δ (ppm) 9.69 (s, 0.15P), 10.02 (s, 0.85P); MS (ESI) m/z=691.24 (MH$^+$).

Example 2

HCV Polymerase Enzyme Assay

Test compounds in the form of nucleoside triphosphates were examined for inhibitory activity against purified HCV polymerase in a standard assay. Bacterial expression constructs encoding the approximately 65 kDa HCV genotype 1b NS5B protein were used to generate recombinant HCV polymerases (with a deletion of the 21 carboxy terminal amino acids). Both the wild-type genotype 1b protein and protein containing the S282T mutation were expressed and purified for use in the enzymatic activity assay.

The enzymatic activity assay measured the inhibitory effect of increasing concentrations of test compound on the incorporation of α-[$^{33}$P]-labeled nucleotide into trichloroacetic acid-precipitable material. Recombinant polymerase and synthetic RNA template were combined in reaction buffer containing ribonucleoside triphosphates, α-[$^{33}$P]-labeled nucleotide and eight concentrations of test compound in three-fold dilutions. Reactions were incubated for two hours at 30° C.

Reactions were terminated by the addition of ice-cold trichloroacetic acid and sodium pyrophosphate to promote precipitation of newly-synthesized ribonucleic acid. Precipitable material from the reactions was collected by filtration onto 96-well filter plates, washed extensively with water, and quantified by liquid scintillation.

The inhibitory activity of test compounds was determined by fitting results to dose-response curves using XLfit software.

Results are provided in Table 1.

TABLE 1

| HCV Polymerase Enzyme Activity | | |
|---|---|---|
| Compound | Wild-Type IC$_{50}$ (µM) | S282T IC$_{50}$ (µM) |
| 401 | ++++ | +++ |
| 402 | ++ | ND |
| 403 | +++ | ++++ |
| 404 | + | + |
| 405 | +++ | ++++ |
| 406 | ++++ | +++ |
| 407 | +++ | ++++ |
| 408 | +++ | ND |
| 409 | +++ | ND |
| 410 | +++ | ND |
| 411 | +++ | ND |

$^a$ ND = not determined
IC$_{50}$ is provided as follows:
++++ ≤ 250 nM, 250 nM < +++ ≤ 1 µM, 1 µM < ++ ≤ 10 µM, and + > 10 µM.

Example 3

HCV Replicon Assay

Huh-7-derived cell line (Zluc) that harbors an HCV genotype 1b replicon and a luciferase reporter gene was grown in Dulbecco's Modified Eagle Medium (DMEM) supplemented with 10% fetal bovine serum, 2 mM Gluta-MAX, 1% MEM nonessential amino acids, 100 IU/mL penicillin, 100 µg/mL streptomycin, and 0.5 mg/mL Geneticin® (G418). For dose response testing the cells were seeded in 96-well plates at $7.5 \times 10^3$ cells per well in a volume of 50 µL, and incubated at 37° C./5% $CO_2$. Drug solutions were made up freshly in Huh-7 media as 2× stocks. Ten additional 5-fold dilutions were prepared from these stocks in DMEM without G418. At least three hours after Zluc cells were seeded, drug treatment was initiated by adding 50 µL of drug dilutions to the plates in duplicate. Final concentrations of drug ranged from 100 µM to 0.0000512 µM. Cells were then incubated at 37° C./5% $CO_2$. Alternatively, compounds were tested at two concentrations (1 µM and 10 µM). In all cases, Huh-7 (which do not harbors the HCV replicon) served as negative control. After 72 hours of incubation, the inhibition of HCV replication was measured by quantification of photons emitted after mono-oxygenation of 5'-fluoroluciferin to oxyfluoroluciferin by firefly luciferase. For this, media was removed from the plates via gentle tapping. Fifty microliters of ONE-glo luciferase assay reagent was added to each well. The plates were shaken gently for 3 min at room temperature and luminescence was measured on a Victor³ V 1420 multilabel counter (Perkin Elmer) with a 1 second read time using a 700 nm cut-off filter. The $EC_{50}$ values were calculated from dose response curves from the resulting best-fit equations determined by Microsoft Excel and XLfit 4.1 software. When screening at two fixed concentrations, the results were expressed as % inhibition at 1 µM and 10 µM.

For cytotoxicity evaluation, Zluc cells were treated with compound as described herein, and cell viability was monitored using the CellTiter-Blue Cell Viability Assay (Promega) by adding 20 µL of the assay solution to each well. The plates were then incubated at 37° C./5% $CO_2$ for at least 3 hours. Fluorescence was detected in plates using excitation and emission wavelengths of 560 and 590 nm, respectively, in a Victor³ V 1420 multilabel counter (Perkin Elmer) and $CC_{50}$ values were determined using Microsoft Excel and XLfit 4.1 software.

Compounds presented in Table 2 below were assayed according to the replicon assay described herein.

TABLE 2

HCV Replicon Activity

| Compound Reference | HCV Replicon $EC_{50}$ | $CC_{50}$ | Compound Reference | HCV Replicon $EC_{50}$ | $CC_{50}$ |
|---|---|---|---|---|---|
| Compound 17ii Diastereomer 1 | ++ | + | Compound 17ii Diastereomer 2 | ++ | + |
| Compound 21ii Mixture of P-Diastereoisomers | + | + | | | |
| Compound 21ii Diastereomer 1 | + | + | Compound 21ii Diastereomer 2 | + | + |
| Compound 37 Diastereomer 1 | ++ | + | Compound 37 Diastereomer 2 | ++ | + |
| Compound 40i Diastereomer 1 | + | + | | | |
| Compound 40ii Diastereomer 1 | ++ | + | Compound 40ii Diastereomer 2 | ++++ | + |
| Compound 42ii Single Diastereoisomer | ++++ | + | | | |
| Compound 43ii Diastereomer 1 | +++ | + | Compound 43ii Diastereomer 2 | +++ | + |
| Compound 46 Single Diastereoisomer | ++++ | + | Compound 51 Mixture of P-Diastereoisomers | +++ | + |
| Compound 54 Single Diastereoisomer | ++ | + | Compound 56ii Diastereomer 1 | + | + |
| Compound 60 Diastereomer 1 | + | + | | | |
| Compound 61 Diastereomer 1 | ++++ | + | Compound 61 Diastereomer 2 | ++++ | + |
| Compound 70 Single Diastereomer | ++++ | + | Compound 72 Mixture of P-Diastereoisomers | + | + |
| Compound 72 Diastereomer 1 | + | + | Compound 72 Diastereomer 2 | + | + |
| Compound 77ii Diastereoisomer 1 | ++ | + | Compound 77ii Diastereoisomer 2 | +++ | + |
| Compound 79ii | +++ | + | Compound 201 Single Diastereomer | ++++ | + |
| Compound 93 Diastereoisomer 1 | ++ | + | Compound 93 Diastereoisomer 2 | +++ | + |
| Compound 95 Diastereoisomer 1 | +++ | + | Compound 95 Diastereoisomer 2 | +++ | + |
| Compound 202i Diastereomer 1 | ++ | + | Compound 202i Diastereomer 2 | +++ | + |
| Compound 202ii Diastereomer 1 | ++++ | + | Compound 202ii Diastereomer 2 | ++++ | + |
| Compound 203ii Diastereomer 1 | +++ | + | Compound 203ii Diastereomer 2 | +++ | + |
| Compound 204ii Diastereomer 1 | ++ | + | Compound 204ii Diastereomer 2 | +++ | + |
| Compound 205i Diastereomer 1 | ++ | + | Compound 205i Diastereomer 2 | +++ | + |
| Compound 207ii Diastereomer 1 | + | + | Compound 207ii Diastereomer 2 | + | + |
| Compound 208ii Diastereomer 1 | + | + | Compound 208ii Diastereomer 2 | + | + |
| Compound 301 | + | + | Compound 302 | + | + |
| Compound 303 | + | + | Compound 304 | + | + |
| Compound 305 | + | + | Compound 306 | + | + |

$EC_{50}$ is provided as follows:
++++ ≤ 250 nM, 250 nM < +++ ≤ 1 µM, 1 µM < ++ ≤ 10 µM, and + > 10 µM
$CC_{50}$ is provided as follows:
++ ≤ 50 µM, + > 50 µM Example 4

Stability Assays

Abbreviations:

HLM=Human liver microsomes; HIM=Human intestinal microsomes; WB_H=Human whole blood; SGF=Simulated gastric fluid; SIF=Simulated intestinal fluid.

Stability in Simulated Gastric and Intestinal Fluids: Simulated gastric and intestinal fluids containing pepsin and pancreatin respectively were prepared according to the U.S. Pharmacopoeia USP291 procedure(www.pharmacopeia.cn/v29240/usp29nf24s0_ris1s126.html). Each test compound (final concentration 100 µM) was incubated in duplicate in the appropriate fluid for 2 hours at 37° C. The samples were quenched with 200 µA cold acetonitrile, vortexed for 30 seconds and then centrifuged at 16100×g for 10 min. The supernatants were analyzed by HPLC on a C-18 column with UV detection at 252 nm. The time zero samples were prepared by adding SGF or SIF fluid to the quenching solvent followed by the test compound. Stability of the compound was determined by peak area of the test compound after incubation and calculated as percent of the peak area observed at time zero. Results are provided in Table 3 below.

Stability in Fresh Whole Blood:

Stability of the test compounds was determined in fresh human whole blood with $K_2EDTA$ as the anticoagulant (stored refrigerated at 2-8° C. and used within 7 days of receipt). The experiment was conducted with three replicates for each time point. Whole blood, pre-incubated at 37° C. for 10-15 minutes, was fortified with a solution of test compound for a final concentration of 0.5 μM and mixed for 30 sec. At intervals (0, 0.5, 1 and 2 hr), three 50-4 aliquots were combined with 200 μL (each) of an ice-cold solution of the internal standard (carbutamide 500 ng/mL in acetonitrile). The samples were vortexed for 30 sec and then centrifuged at 16100×g for 5 min. The supernatant was analyzed by LC-MS/MS. The MS peak area ratio of the test compound versus the internal standard was calculated and percent unchanged test compound was calculated for each time point using this ratio. Results are provided in Table 3 below.

Stability in Liver and Intestinal Microsomes:

Stability of test compounds were determined in human liver and intestinal microsomes in duplicate for each matrix. Pooled liver and intestinal microsomal proteins (1.0 mg/mL), suspended in incubation buffer (100 mM potassium phosphate, pH 7.4, 5 mM $MgCl_2$, and 0.1 mM EDTA), were preincubated for 5 min at 37° C. with 10 μM of a test compound from a 10 mM stock solution in DMSO (final DMSO concentration was 0.1%); the reaction was initiated by the addition of NADPH (3 mM final concentration). At specific times (0 and 60 min), 0.1 mL samples were taken and the reaction terminated by the addition of 4 volumes of stop solution (acetonitrile with 500 ng/mL carbutamide as an internal standard). The samples were vortexed for 30 sec and then centrifuged at 16000×g for 10 min. 100 μL of supernatants were transferred to 96 deep-well plates preloaded with 100 μL distilled water and analyzed after mixing by LC-MS/MS. The MS peak area ratio of the test compound versus the internal standard was calculated and percent unchanged test compound over 60 minutes was calculated using this ratio. Results expressed as percent remaining are shown in Table 3.

well plates for 24, 48 and 72 hr treatment, respectively. Plated cells were incubated overnight at 37° C. in an incubator.

The following morning test compound was diluted to 20 μM from a stock solution in DMSO in fresh culture medium pre-warmed to 37° C. and 1 mL of the solution/well was added to cells. A final medium volume per well was 2.0 mL, test compound concentration in well was 10 μM and final DMSO concentration was 0.1%.

After 24, 48 or 72 hr, the medium was carefully removed and cell monolayers were washed twice with 2 mL ice-cold PBS per well. Following the last wash, all PBS was carefully removed and 1.0 mL of extraction solution (ice-cold 70% methanol) added. The plate was tightly covered with Parafilm, plastic plate cover and Parafilm again and an intracellular content was extracted at −20° C. for 24 hr.

After 24 hr the extracts were transferred into polypropylene microfuge tubes and dry on a refrigerated centrivap concentrator. Dry residues were reconstituted in 250 μL of HPLC-grade water and centrifuged at 16,000×g for 10 min. Aliquots (100 μL each) of the supernatants were transferred into a 96 well plate and internal standard (4 ng/mL final concentration) was added as the internal standard (IS) for LC-MS/MS analysis.

Abbreviations:

FHH=fresh human hepatocytes; Ms=Mouse; MsH=fresh mouse hepatocyte.

Assay for the Release of Active Metabolite in Primary Hepatocytes:

Plates of fresh human and mouse hepatocytes were obtained on ice. The medium was removed and replaced with hepatocyte culture medium (William's E supplemented with penicillin-streptomycin, 1% L-glutamine, 1% insulin-transferrin-selenium and 0.1 μM Dexamethasone (Invitrogen) or with Invitro GRO HI medium complemented with Torpedo antibiotics (Celsis)). Cells were left overnight in an incubator at 37° C. to acclimatize to culture and the medium.

Hepatocyte incubations were conducted at a final volume of 0.5 mL hepatocyte culture medium/well (0.8 million

TABLE 3

Stability (expressed as percent remaining)

| Test system | Compound 37 Diastereomer 2 | Compound 40ii Diastereomer 2 | Compound 40ii Diastereomer 1 | Compound 40i Diastereomer 1 | Compound 40i Diastereomer 2 |
|---|---|---|---|---|---|
| SGF | ++++ | ++++ | ND[a] | ND | ND |
| SIF | ++++ | + | ND | ND | ND |
| WB_Human (37° C.; 2 hr) | ND | ++++ | ND | ND | ND |
| HLM (1 hr) | ND | ++ | + | + | +++ |
| HIM (1 hr) | ND | ++++ | +++ | +++ | ++++ |

[a]ND = not determined

Percent remaining is provided as follows: + ≤ 25% < ++ ≤ 50% < +++ ≤ 75% < ++++

Example 5

Metabolism Assays

Assay for the Release of Active Metabolite in Huh-7 Cells.

Huh-7 cells were plated in 1 mL culture medium (DMEM, containing glucose, L-glutamine and sodium pyruvate, 10% FBS, 100 IU/mL penicillin, 100 μg/mL streptomycin, 2 mM GlutaMAX, 1% MEM non-essential amino acids) at the concentration 0.8, 0.4 and 0.2 million cells per well on 6 cells/well for human and 0.5 million cells/well for mouse; 12 well plate no overlay, collagen coat). Culture medium from overnight incubation of cells was removed and replaced with fresh medium, pre-warmed to 37° C., containing 10 μM of test compound from a stock solution in DMSO (final DMSO concentration was 0.1%). At each specific time point, incubation medium was removed and cell monolayers were carefully washed two times with ice-cold PBS. Following the last wash, all PBS was carefully removed and 1.0 mL of extraction solution (ice-cold 70% methanol/30% water) added. Cells were scraped off and suspended in the extraction solution, transferred to 2 mL polypropylene microfuge tubes and intracellular contents extracted overnight at −20° C.

After the overnight treatment the cellular extracts were prepared by centrifugation at 16,000×g for 10 min to remove cellular debris. The remaining sample was then dried using a refrigerated centrivap concentrator. Dry extracts were reconstituted in 1000 μL of HPLC-grade water and centrifuged at 16,000×g for 10 min. Aliquots (100 μL each) of the supernatant were transferred into a 96 well plate and internal standard (4 ng/mL final concentration) was added as the internal standard (IS) for LC-MS/MS analysis.

The incubation time points were 6, 24 and 48 hours for human hepatocytes and 1, 4, 8, 12 and 24 hours for mouse hepatocytes. Results are provided in Table 4 below.

tiapride. For protein precipitation and extraction, each plasma sample (50 μL) was treated with 500 μL of 0.2% formic acid in acetonitrile and 20 μL of the internal standard working solution. After vortexing and centrifugation, 500 μL of the sample extracts were transferred to a new plate, dried under $N_2$ at ~28° C. and reconstituted with 75 μL of 0.2% FA in water. The extracts were chromatographed on an Aquasil C18 column using a gradient system of 0.2% formic acid in water and acetonitrile. The analytes were detected and quantified by tandem mass spectrometry in positive ion mode on an MDS Sciex API5000 equipped with a Turbo Ionspray® interface. The calibration range was 0.500 (LLOQ) to 200 ng/mL in mouse plasma.

Liver samples were analyzed for the active species nucleoside triphosphate by LC-MS/MS. The triphosphate

TABLE 4

Formation of Active Metabolite in Huh-7 cells and Hepatocytes

| Cells | Compound 37 Diastereomer 2 | Compound 40ii Diastereomer 2 | Compound 40ii Diastereomer 1 | Compound 40i Diastereomer 1 | Compound 40i Diastereomer 2 |
|---|---|---|---|---|---|
| Huh-7 TP $C_{max}$ (pmol/mill cells)[1] | ND[a] | ++++ | ++++ | ND | ND |
| Huh-7 TP (24 hr)[1] | ND | ++++ | ++ | ND | ND |
| Huh-7 TP (48 hr)[1] | ND | ++++ | +++ | ND | ND |
| Huh-7 TP (72 hr)[1] | ND | ++++ | ++++ | ND | ND |
| Huh-7 TP AUC (pmol.hr/mill cells)[2] | ND | ++++ | ++++ | ND | ND |
| FHH TP AUC (pmol.hr/mill cells)[2] | +++ | ++++ | ND | ND | ND |
| FHH TP $C_{max}$ (pmol/mill cells)[1] | ++ | ++++ | ND | ND | ND |
| FHH TP (6 hr)[1] | BLD[b] | ++++ | ND | ND | ND |
| FHH TP (24 hr)[1] | ++ | +++ | ND | ND | ND |
| FHH TP (48 hr)[1] | ++ | +++ | ND | ND | ND |
| MsH AUC (pmol.hr/mill cells)[2] | ++++ | ++++ | ND | ++++ | +++ |
| MsH $C_{max}$ (pmol/mill cells)[1] | ++++ | +++ | ND | ++++ | +++ |

[a]ND = not determined
[b]BLD = below limit of detection
[1]Single point concentration provided as follows: + ≤ 15 < ++ ≤ 50 < +++ ≤ 100 < ++++
[2]Integrated concentration provided as follows: + ≤ 150 < ++ ≤ 500 < +++ ≤ 1500 < ++++

Example 6

Pharmacokinetics of Plasma Nucleoside and Liver Triphosphate Following a Single Oral Dose in CD-1 Mice Abbreviations:
Ms=Mouse; TP=triphosphate.

A single oral dose of Compound 1 at 10 mg/kg in PEG 200 (dose volume 5 mL/kg) was administered to nine CD-1 male mice. Five untreated animals were used for the collection of control plasma and liver. Terminal plasma and liver samples were collected from three animals per time point at 4, 12 and 24 hours post dose. Liver specimens were collected from all animals immediately after the incision. Freezing forceps stored in liquid nitrogen were used to freeze the liver before excision.

Plasma samples were analyzed for nucleoside by LC-MS/MS. The internal standard (IS) was either 2′-MeG-D3 or levels were assayed by homogenizing (on ice) a known weight of mouse liver with 4× volume of 0.95 M trichloroacetic acid (TCA). Internal standard solution was added to the homogenate followed by neutralization with 20% ammonium hydroxide solution and addition of 500 μL 1% formic acid. The tissue samples were extracted by weak anion exchange solid phase extraction (SPE). Post extraction, the eluates were evaporated under nitrogen, followed by reconstitution before injection onto the LC-MS/MS system. The samples were chromatographed on a Luna $NH_2$ column using a gradient system of ammonium acetate (1 mM to 20 mM and pH 8.0 to pH 10.0) in water and acetonitrile (70:30). The analyte was detected and quantified by tandem mass spectrometry in positive ion mode on an API4000 equipped with a Turbo Ionspray® interface.

Results are provided in Table 5 below.

TABLE 5

Mouse plasma and liver pharmacokinetic parameters

| Compound | Ms Plasma nucleoside $C_{max}$ (pmol/mL at 1 μmol/kg)[1] | Ms Plasma nucleoside AUC (pmol · hr/mL at 1 μmol/kg)[2] | Ms Liver TP $C_{max}$ (pmol/g at 1 μmol/kg)[1] | Ms Liver TP AUC (pmol · hr/g at 1 μmol/kg)[2] |
|---|---|---|---|---|
| Compound 17ii Diastereomer 1 | ND | ND | BLQ | BLQ |
| Compound 17ii Diastereomer 2 | ND | ND | BLQ | BLQ |
| Compound 37 Diastereomer 1 | +++ | +++ | ++++ | ++++ |
| Compound 37 Diastereomer 2 | +++ | +++ | ++++ | ++++ |
| Compound 38ii Diastereomer 1 | +++ | +++ | + | + |
| Compound 38ii Diastereomer 2 | ++++ | +++ | ++ | +++ |
| Compound 40ii Diastereomer 1 | +++ | +++ | +++ | +++ |
| Compound 40ii Diastereomer 2 | +++ | +++ | ++ | +++ |
| Compound 40i Diastereomer 1 | +++ | +++ | ++++ | ++++ |
| Compound 40i Diastereomer 2 | +++ | +++ | ++++ | ++++ |
| Compound 54 Diastereomer 1 | +++ | +++ | ++ | + |
| Compound 54 Diastereomer 2 | ++ | +++ | + | + |
| Compound 61 Diastereomer 1 | ++++ | + | +++ | +++ |
| Compound 61 Diastereomer 2 | + | + | ++++ | +++ |
| Compound 70 Single Diastereomer | ++++ | ++++ | ++++ | ++++ |
| Compound 77ii Diastereomer 1 | + | + | ++++ | ++++ |
| Compound 77ii Diastereomer 2 | + | + | ++++ | ++++ |
| Compound 79ii Diastereomer 1 | + | + | +++ | +++ |
| Compound 79ii Diastereomer 2 | + | + | ++++ | ++++ |
| Compound 95i Diastereomer 1 | + | + | + | + |
| Compound 95i Diastereomer 2 | + | + | + | ++ |
| Compound 101 Diastereomer 1 | ND | ND | ++++ | ++++ |
| Compound 101 Diastereomer 2 | ND | ND | ++++ | ++++ |
| Compound 102i Diastereomer 1 | + | + | ++++ | ++++ |
| Compound 102i Diastereomer 2 | + | + | ++++ | ++++ |
| Compound 201 Single Diastereomer | +++ | +++ | ++++ | ++++ |
| Compound 202i Diastereomer 1 | ++++ | ++++ | ++++ | ++++ |
| Compound 202i Diastereomer 2 | ++++ | ++++ | ++++ | ++++ |
| Compound 202ii Diastereomer 1 | ++++ | ++++ | ++++ | +++ |
| Compound 202ii Diastereomer 2 | ++++ | ++++ | +++ | +++ |
| Compound 203ii Diastereomer 1 | +++ | +++ | +++ | +++ |
| Compound 203ii Diastereomer 2 | +++ | +++ | ++ | ++ |
| Compound 204ii Diastereomer 1 | +++ | +++ | ++ | ++ |
| Compound 204ii Diastereomer 2 | ++++ | ++++ | ++ | ++ |
| Compound 205i Diastereomer 1 | +++ | +++ | ++++ | ++++ |

TABLE 5-continued

Mouse plasma and liver pharmacokinetic parameters

| Compound | Ms Plasma nucleoside $C_{max}$ (pmol/mL at 1 μmol/kg)[1] | Ms Plasma nucleoside AUC (pmol · hr/mL at 1 μmol/kg)[2] | Ms Liver TP $C_{max}$ (pmol/g at 1 μmol/kg)[1] | Ms Liver TP AUC (pmol · hr/g at 1 μmol/kg)[2] |
|---|---|---|---|---|
| Compound 205i Diastereomer 2 | +++ | ++++ | ++++ | ++++ |
| Compound 206i Diastereomer 1 | +++ | +++ | ++++ | +++ |
| Compound 206i Diastereomer 2 | +++ | +++ | +++ | +++ |
| Compound 208ii Diastereomer 1 | ND | ND | BLQ | BLQ |
| Compound 208ii Diastereomer 2 | ND | ND | BLQ | BLQ |
| Compound 301 | +++ | +++ | BLQ | BLQ |

ND = Not determined;
BLQ = below limit of quantitation.
[1]Single point concentration provided as follows: + ≤ 15 < ++ ≤ 50 < +++ ≤ 100 < ++++
[2]Integrated concentration provided as follows: + ≤ 150 < ++ ≤ 500 < +++ ≤ 1500 < ++++

Example 7

Pharmacokinetics of Liver Triphosphate and Plasma Prodrug and Nucleoside Following a Single Oral Dose in Cynomolgus Monkeys Abbreviations:
Mo=Monkey; TP=triphosphate; AUC=area under the concentration curve.

For each compound, a single oral dose at 10 mg/kg in PEG 200 (dose volume 3 mL/kg) was administered to cynomolgus monkeys. Untreated animals were used for the collection of control liver. Plasma samples were collected at 0.5, 1, 2, 4, 6, 8, 12 and 24 hours for compound 37, diastereomer 2. Terminal liver samples were collected from three animals per time point at 6, 12 and 24 hours post dose for compound 37, diastereomer 2 and at 6 hours post dose for compound 44, diastereomer 2. Liver specimens were collected from all animals immediately after the incision. Freezing forceps stored in liquid nitrogen were used to freeze the liver before excision.

Plasma samples were analyzed for the prodrug and nucleoside by LC-MS/MS. For protein precipitation and extraction, each plasma sample (50 μL) was treated with 500 μL of 0.2% formic acid in acetonitrile and 20 μL of an appropriate internal standard working solution. After vortexing and centrifugation, 5004 of the sample extracts were transferred to a new plate, dried under $N_2$ at ~28° C. and reconstituted with 75 μL of 0.2% FA in water. The extracts were chromatographed on an Aquasil C18 column using a gradient system of 0.2% formic acid in water and acetonitrile. The analytes were detected and quantified by tandem mass spectrometry in positive ion mode on an MDS Sciex API4000 equipped with a Turbo Ionspray® interface.

Liver samples were analyzed for the relevant nucleoside triphosphate by LC-MS/MS. The triphosphate levels were assayed by homogenizing (on ice) a known weight of liver with 4× volume of 0.95 M trichloroacetic acid (TCA). Appropriate internal standard solution was added to the homogenate followed by neutralization with 20% ammonium hydroxide solution and addition of 500 μL 1% formic acid. The tissue samples were extracted by weak anion exchange solid phase extraction (SPE). Post extraction, the eluates were evaporated under nitrogen, followed by reconstitution before injection onto the LC-MS/MS system. The samples were chromatographed on a Luna $NH_2$ column using a gradient system of ammonium acetate (1 mM to 20 mM and pH 8.0 to pH 10.0) in water and acetonitrile (70:30). The analyte was detected and quantified by tandem mass spectrometry in positive ion mode on an API4000 equipped with a Turbo Ionspray® interface. Results are provided in Table 6 below.

TABLE 6

Pharmacokinetics of the prodrug and nucleoside in plasma and triphosphate in liver of Cynomolgus monkeys

| Compound | Compound 37 Diastereomer 2 | Compound 40ii Diastereomer 2 | Compound 40i Diastereomer 1 |
|---|---|---|---|
| Dose (mg/kg) | 10 | 10 | 10 |
| Dose-normalized parameters[a] | | | |
| Plasma prodrug | | | |
| $C_{max}$ (pmol/mL)[1] | ++++ | ND[b] | + |
| $T_{max}$ (hr) | 4 | ND | 2 |
| $AUC_{0-24}$ (pmol · hr/mL)[2] | ++++ | ND | + |
| Plasma nucleoside | | | |
| $C_{max}$ (pmol/mL)[1] | +++ | ND | ++ |
| $T_{max}$ (hr) | 4 | ND | 6 |
| $AUC_{0-24}$ (pmol · hr/mL)[2] | +++ | ND | ++ |
| Nucleoside triphosphate in Liver | | | |
| $C_6$ (pmol/g)[c,1] | ++++ | ++++ | ++++ |
| $C_{max}$ (pmol/g)[1] | ++++ | ND | ++++ |
| $T_{max}$ (hr) | 12 | ND | 6 |
| $AUC_{0-24}$ (pmol · hr/g)[2] | ++++ | ND | ++++ |

[a]The $C_{max}$, $C_6$ and $AUC_{0-24}$ data are normalized to 1 μmol/kg dose
[b]ND = not determined
[c]Dose for $C_6$ determination was 10 mg/kg
[1]Singlepoint concentration provided as follows: + ≤ 15 < ++ ≤ 50 < +++ ≤ 100 < ++++
[2]Integrated concentration provided as follows: + ≤ 150 < ++ ≤ 500 < +++ ≤ 1500 < ++++

Example 8

Effect of CES1 Overexpression on Replicon Activity of Compound 40ia

Introduction

In this example, the effect of transient CES1 overexpression in Huh-7 cells on in vitro anti-HCV activity of compound 40ia, which is cleaved by CES1, was evaluated in an HCV replicon assay. The HCV NS5B RNA-dependent RNA polymerase is essential for the viral life cycle and thus, is a target for antiviral therapy. The active site of NS5B is well conserved among the six genotypes of HCV and therefore, nucleos(t)ide analogs can act pan-genotypically. Furthermore, nucleotide inhibitors are typically not cross-resistant to other classes of direct acting antivirals and can have a higher barrier to resistance compared to non-nucleoside, protease and non-structural protein 5A (NS5A) inhibitors of HCV, making this class of HCV antivirals useful in a combination HCV antiviral therapy.

Nucleoside analogs are typically competitive inhibitors of endogenous nucleosides and may act through chain termination upon incorporation into the nascent HCV RNA chain during replication. (Eldrup, et al. 2004, Structure-Activity Relationship of Purine Ribonucleosides for Inhibition of Hepatitis C Virus RNA-Dependent RNA Polymerase. J. Med. Chem. 47: 2283-2295). However, upon cell entry a nucleoside analog must first be phosphorylated to the active triphosphate species. (Gardelli, et al 2009, Phosphoramidate prodrugs of 2'-C-methylcytidine for therapy of hepatitis C virus infection. J. Med. Chem. 52:5394-5407; Stein and Moore, 2001, Phosphorylation of nucleoside analog antiretrovirals: a review for clinicians. Pharmacotherapy 21:11-34; Tomassini, et al. 2005, Inhibitory effect of 2'-substituted nucleosides on hepatitis C virus replication correlates with metabolic properties in replicon cells. Antimicrob. Agents Chemother. 49:2050-2058; Murakami, et al 2007, Mechanism of activation of β-D-2'-deoxy-2'-fluoro-2'-C-methyl-cytidine and inhibition of hepatitis C virus NS5B RNA polymerase. Antimicrob. Agents Chemother. 51:503-509). A barrier to first generation nucleoside inhibitors was the often inefficient conversion of the nucleoside to a nucleotide monophosphate (NMP) by cellular kinases. (Gardelli, et al 2009, Phosphoramidate prodrugs of 2'-C-methylcytidine for therapy of hepatitis C virus infection. J. Med. Chem. 52:5394-5407; Stein and Moore, 2001, Phosphorylation of nucleoside analog antiretrovirals: a review for clinicians. Pharmacotherapy 21:11-34; Murakami, et al 2007, Mechanism of activation of β-D-2'-deoxy-2'-fluoro-2'-C-methyl-cytidine and inhibition of hepatitis C virus NS5B RNA polymerase. Antimicrob. Agents Chemother. 51:503-509).

Second generation nucleoside analogs have been designed as liver-targeted nucleotide prodrugs, which bypass the rate-limiting NMP conversion to active species by delivering the nucleoside as a monophosphate prodrug. Like sofosbuvir (Gilead Sciences, formerly PSI-7977 and GS-7977), compound 40ia is a pyrimidine nucleotide prodrug that acts by inhibition of the HCV NS5B RNA-dependent RNA polymerase through a 2' modified UTP metabolite. The chemical structure of sofosbuvir is provided below:

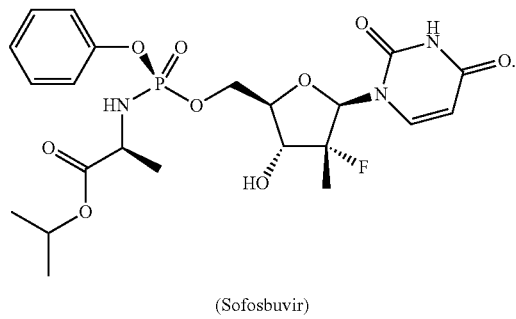 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

(Sofosbuvir)

The intracellular metabolism (anabolism) of nucleotide analogs is critical to their antiviral activity. A first step in the metabolism of nucleotide prodrugs is the removal of the prodrug moiety by cellular enzymes followed by the activation of the nucleoside monophosphate analog by host cell kinases for the sequential phosphorylation of the parent nucleos(t)ide analog to the 5'-triphosphate form, the biologically active metabolite. Removal of the prodrug moiety often involves sequential or independent work of different cellular enzymes.

The first step of sofosbuvir activation includes hydrolysis of the carboxyl ester by cathepsin A (CatA) and/or carboxylesterase 1 (CES1). (Saboulard et al, 2009, Characterization of the Activation Pathway of Phosphoramidate Triester Prodrugs of Stavudine and Zidovudine. Molecular Pharmacology. 56:693-704; Murakami et al, 2010, Mechanism of Activation of PSI-7851 and Its Diastereoisomer PSI-7977, JBC, 285(45):34337-34347; Sofia et al, 2010, Discovery of PSI-35366, a novel purine nucleotide prodrug for the treatment of hepatitis C virus. J Med. Chem. 53:7202-7218). Since CES1 is reported to be under-expressed in Huh-7 replicon cells, CatA appears to be the major enzyme that hydrolyzes sofosbuvir in these cells. (Murakami et al, 2010, Mechanism of Activation of PSI-7851 and Its Diastereoisomer PSI-7977, JBC, 285(45):34337-34347).

Methods

An Huh-7-derived cell line (Zluc) that harbors an HCV genotype 1b replicon and a luciferase reporter gene was grown in Dulbecco's Modified Eagle Medium (DMEM) supplemented with 10% fetal bovine serum, 2 mM Gluta-MAX, 1% MEM nonessential amino acids, 100 IU/mL penicillin, 100 μg/mL streptomycin, and 0.5 mg/mL Geneticin® (G418). Zluc cells were transiently transfected with human CES1 (GenBank Accession No. NM_001025194) by employing a lipid/histone based transfection procedure. Expression of CES1 was confirmed by Western blot, 24- and 48-hours after transfection, using anti-CES1 and anti-FLAG® tag antibodies.

For dose response testing the cells were seeded in 96-well plates at $7.5 \times 10^3$ cells per well in a volume of 50 μA, and incubated at 37° C./5% $CO_2$. Drug solutions were prepared freshly in the culture medium as 2× stocks. Ten additional 5-fold dilutions were prepared from these stocks in DMEM without G418. At least three hours after cells were seeded, drug treatment was initiated by adding 50 μL of drug dilutions to the plates in duplicate. Final concentrations of drug ranged from 100 μM to 0.0000512 μM. Cells were then incubated at 37° C./5% $CO_2$. After 72 hours of incubation, the inhibition of HCV replication was measured by quantification of photons emitted after mono-oxygenation of 5'-fluoroluciferin to oxyfluoroluciferin by firefly luciferase. For this, media was removed from the plates via gentle tapping. Fifty microliters of ONE-glo luciferase assay reagent was added to each well. The plates were shaken gently for 3 min at room temperature and luminescence was measured on a Victor³ V 1420 multilabel counter (Perkin Elmer) with a 1 second read time using a 700 nm cut-off filter. The $EC_{50}$ values were calculated from dose response curves from the resulting best-fit equations determined by Microsoft Excel and XLfit 4.1 software.

For cytotoxicity evaluation, cells were treated with compounds as described herein, and cell viability was monitored using the CellTiter-Blue Cell Viability Assay (Promega) by adding 20 µL of the assay solution to each well. The plates were then incubated at 37° C./5% $CO_2$ for at least 3 hours. Fluorescence was detected in plates using excitation and emission wavelengths of 560 and 590 nm, respectively, in a Victor³ V 1420 multilabel counter (Perkin Elmer) and $CC_{50}$ values were determined using Microsoft Excel and XLfit 4.1 software.

Results

Results are provided in Table 7, below, for compounds assayed in the replicon assay described above. The results indicate that overexpression of CES1 in Huh-1 cells increases the activity of compound 40ia, which is cleaved by CES1. In contrast, the activity of IDX-184 (not cleaved by CES1) and the activity of sofosbuvir (cleaved by both CES1 and CatA) was not increased in cells overexpressing CES1.

TABLE 7

Effect of CES1 overexpression on activity of Compound 40ia

| Drug | N | Zluc | | Zluc + CES1 | | Fold Activity Increase |
| | | $EC_{50}$ (µM) | $CC_{50}$ (µM) | $EC_{50}$ (µM) | $CC_{50}$ (µM) | $EC_{50}$ (Zluc)/$EC_{50}$ (Zluc + CES1) |
| --- | --- | --- | --- | --- | --- | --- |
| Compound 40ia | 2 | + | ++ | ++++ | ++ | ++++ |
| Sofosbuvir [1] | 2 | +++ | ++ | +++ | ++ | + |
| IDX-184 [2] | 2 | ++++ | ++ | ++++ | ++ | + |

[1] Gilead Sciences, formerly PSI-7977 and GS-7977
[2] Idenix Pharmaceuticals
$EC_{50}$ is provided as follows:
++++ ≤ 250 nM < +++ ≤ 1 µM < ++ ≤ 10 µM < +
$CC_{50}$ is provided as follows:
+ ≤ 50 µM < ++
Fold Activity Increase is provided as follows:
+ ≤ 1 < ++ ≤ 10 < +++ ≤ 100 < ++++

All publications, patents, and patent applications cited in this specification are herein incorporated by reference as if each individual publication, patent, or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the claimed subject matter is limited solely by the scope of the following claims, including equivalents thereof.

What is claimed is:

1. A compound according to Formula 2001:

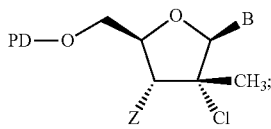

(2001)

or a pharmaceutically acceptable salt, solvate, tautomeric form or polymorphic form thereof, wherein:

B is

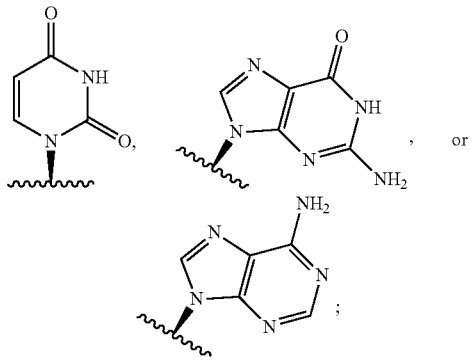

and

PD is monophosphate, diphosphate, or triphosphate; and Z is —OH; or

PD is

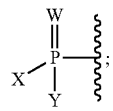

W is O; Z and Y join to form a six-membered heterocyclic ring wherein Z and Y together represent a single divalent —O—; and X is an N-linked amino acid ester.

2. The compound of claim 1 according to Formula II:

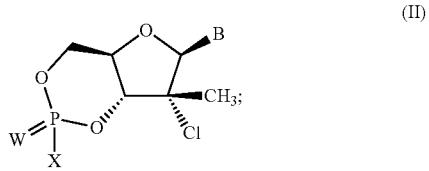

(II)

wherein X is an N-linked D-amino acid ester; or a pharmaceutically acceptable salt, solvate, tautomeric form or polymorphic form thereof.

3. The compound of claim 2 wherein each X is independently an N-linked D-alanine ester.

4. The compound of claim 2, wherein said compound is according to one of the following the structures:

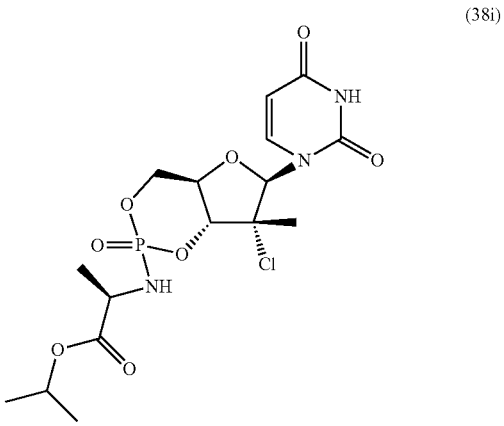

(38i)

(38ia)
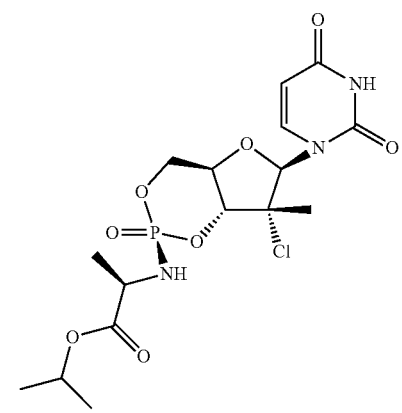
(38ib)
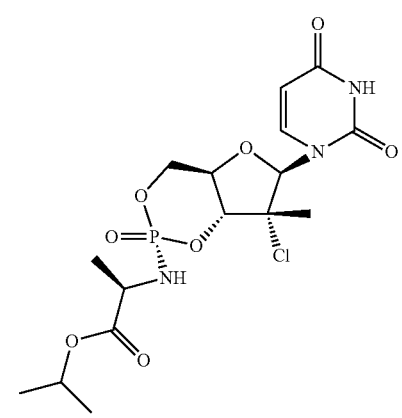
(77i)
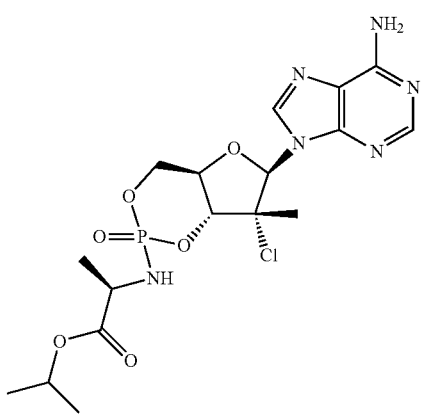
(77ia)
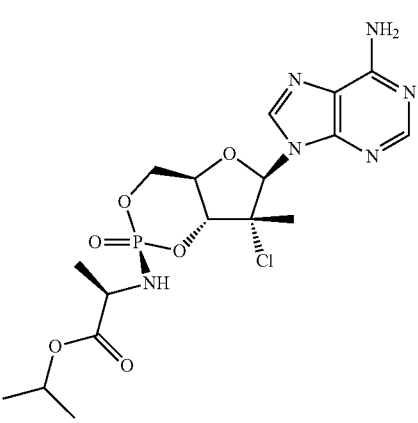
(77ib)
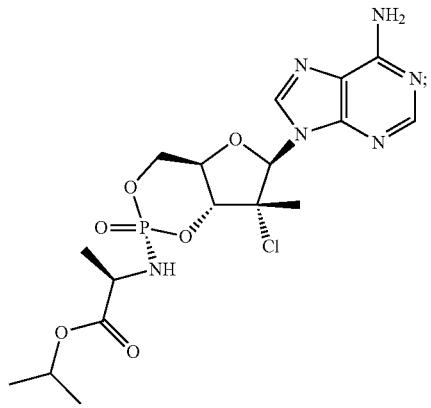
or a pharmaceutically acceptable salt, solvate, tautomeric form or polymorphic form thereof.
5. The compound according to claim 4, wherein said compound is selected from the group consisting of:
(38i)
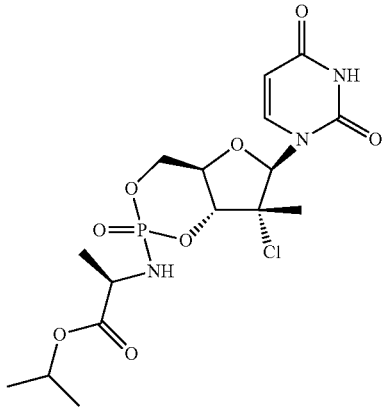
(38ia)
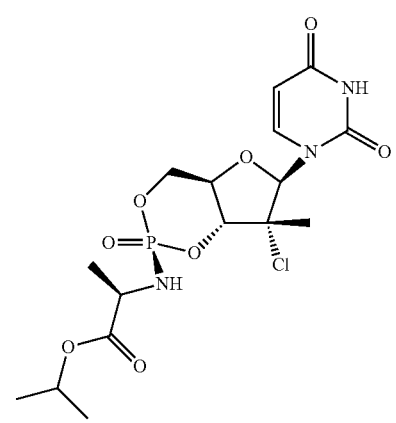

(38ib)
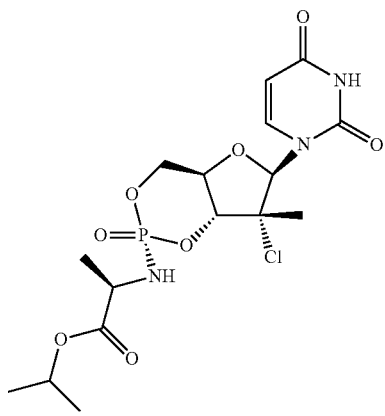

(77ib)
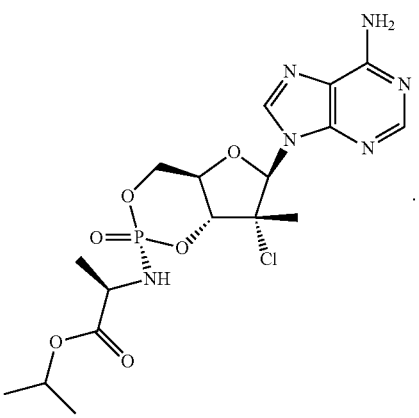

6. The compound of claim 1 according to Formula (2001) wherein PD is monophosphate, diphosphate, or triphosphate; or a pharmaceutically acceptable salt, solvate, tautomeric form or polymorphic form thereof.

7. The compound of claim 1 which is:

(77i)
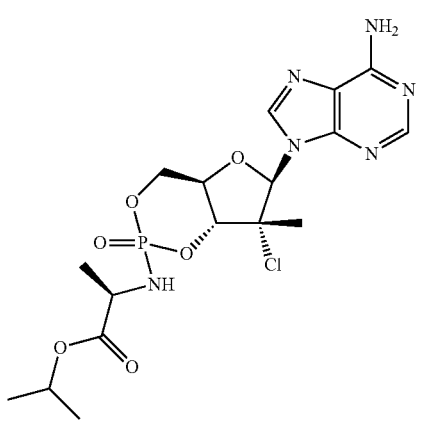

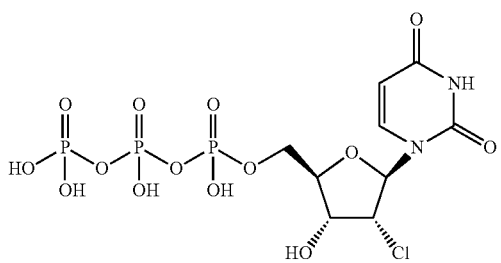 [SMILES: O=c1ccn([C@@H]2O[C@H](COP(=O)(O)OP(=O)(O)OP(=O)(O)O)[C@@H](O)[C@H]2Cl)c(=O)[nH]1]

(77ia)
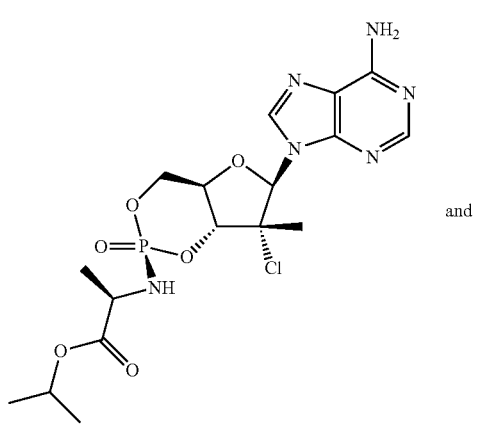 and or a pharmaceutically acceptable salt, solvate, tautomeric form or polymorphic form thereof.

8. A pharmaceutical composition comprising the compound of claim 1, or a pharmaceutically acceptable salt, solvate, tautomeric form or polymorphic form thereof, wherein:

PD is

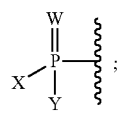;

and a pharmaceutically acceptable excipient, carrier or diluent.

9. The pharmaceutical composition of claim 8, wherein said compound is 281
(38i)
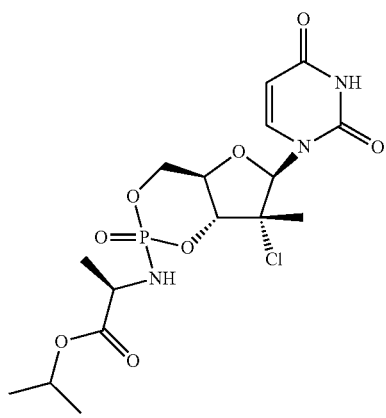
(38ia)
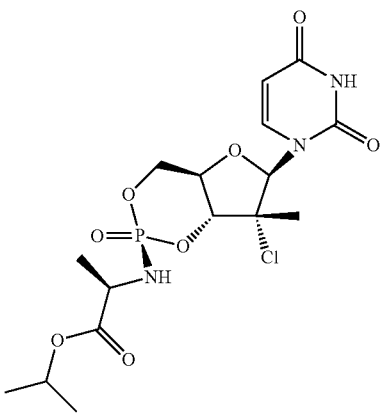
(38ib)
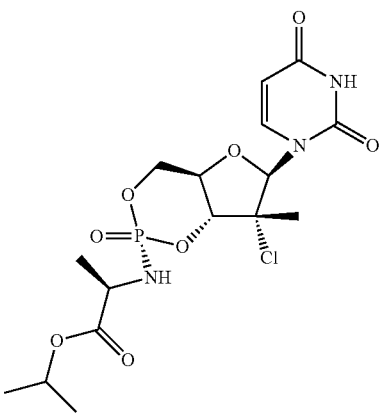
(77i)
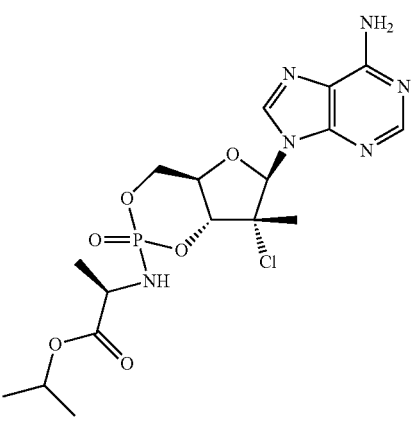
282
-continued
(77ia)
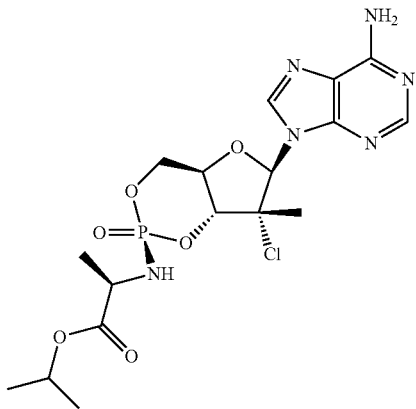
or
(77ib)
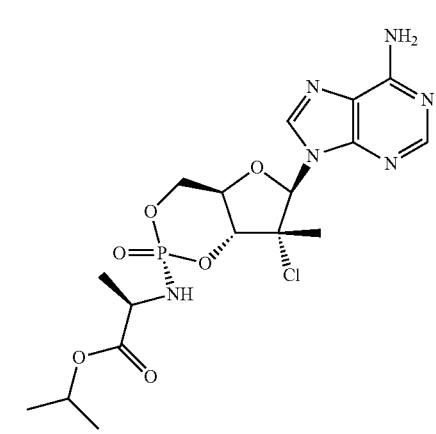
or a pharmaceutically acceptable salt, solvate, tautomeric form or polymorphic form thereof.
10. The pharmaceutical composition of claim 9, wherein said compound is:
(38i)
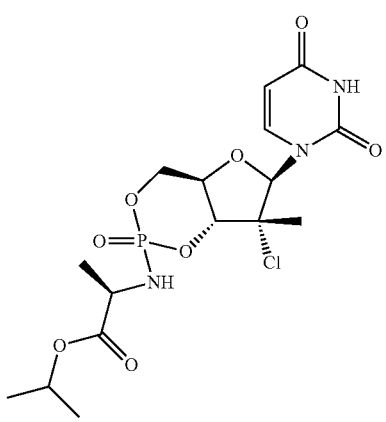

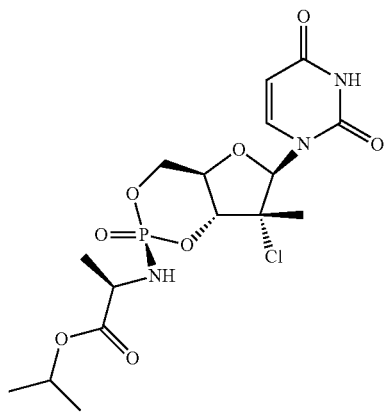
(38ia)
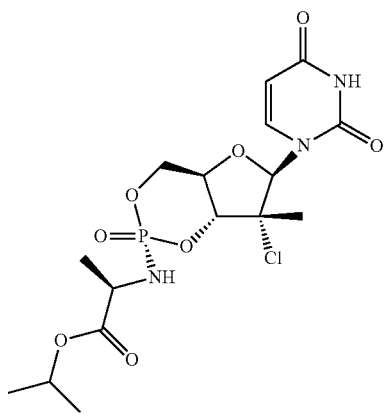
(38ib)
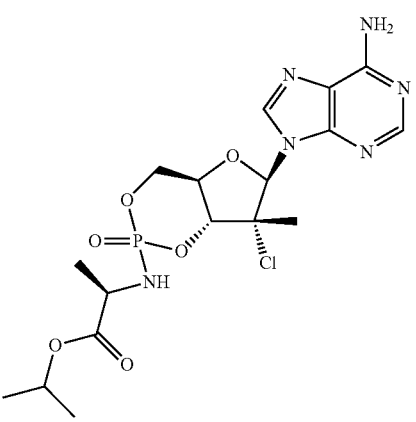
(77i)
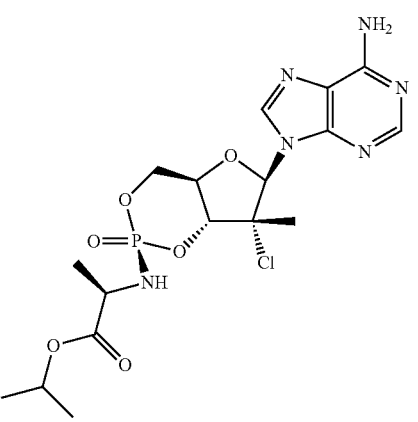
(77ia)
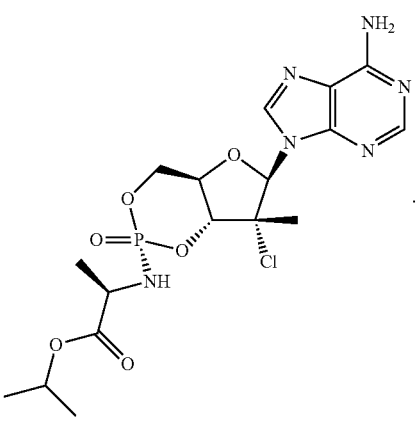
(77ib)
11. The pharmaceutical composition according to claim 8, wherein said compound is selected from the group consisting of:
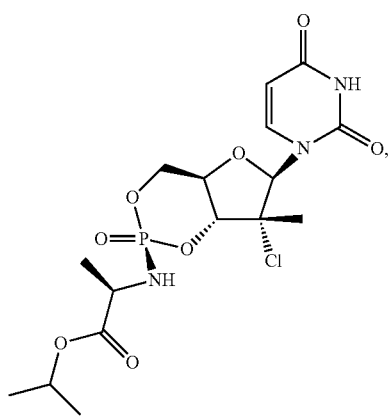
or -continued

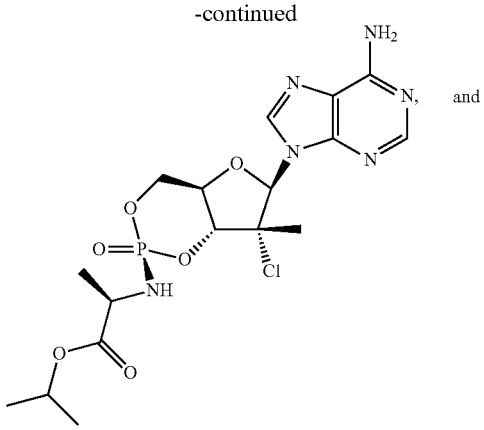
and

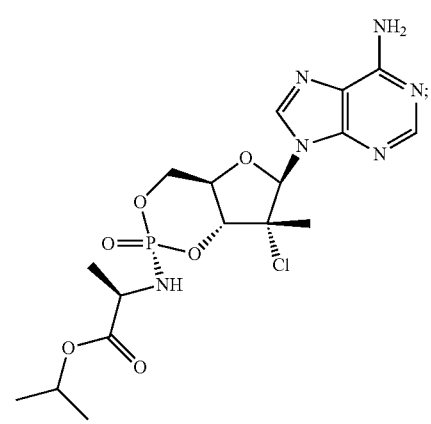

or a pharmaceutically acceptable salt, solvate, tautomeric form or polymorphic form thereof, said compound is a designated enantiomer and said composition is substantially free of stereoisomers of said designated enantiomer.

12. The pharmaceutical composition according to claim 11, wherein said compound is a designated enantiomer selected from the group consisting of:

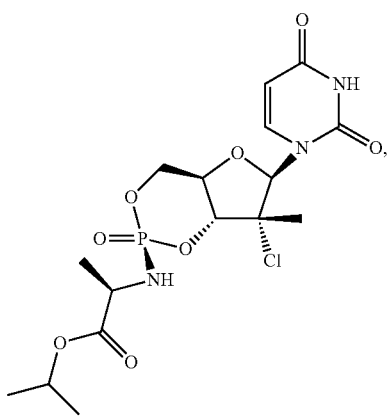

-continued

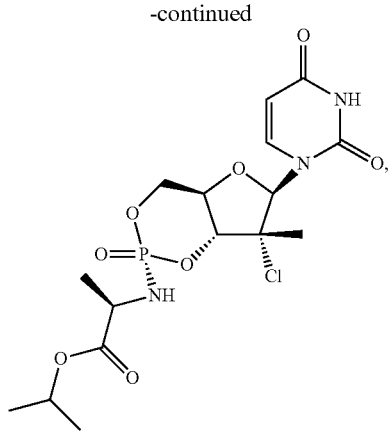

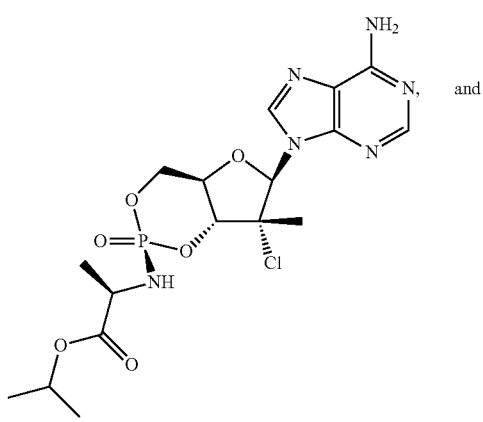
and

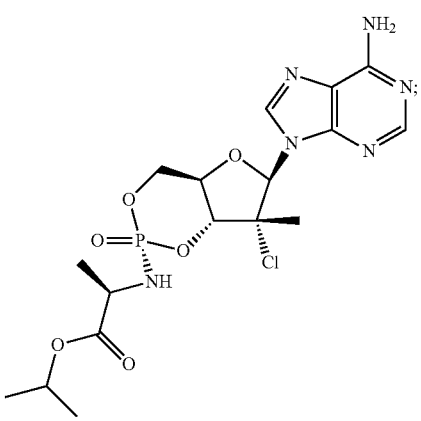

and said composition is substantially free of stereoisomers of said designated enantiomer.

13. A method of treating an hepatitis C virus (HCV) in a human infected with an HCV, comprising administering to the human an effective amount of the compound of claim 1.

14. The method of claim 13 where said compound is according to one of the following structures:

(38i)
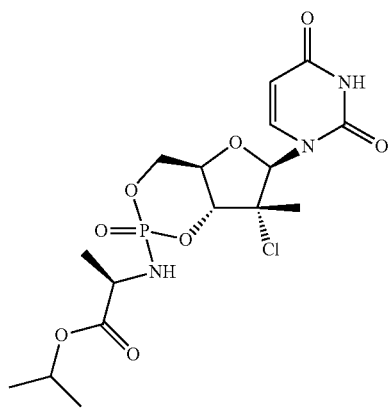
(38ia)
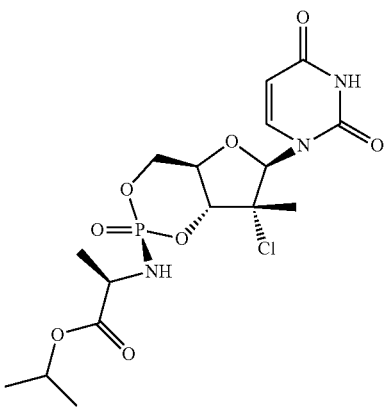
(38ib)
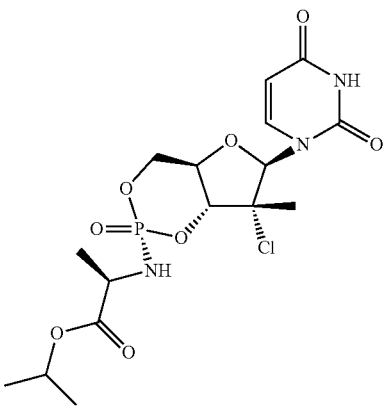
(77i)
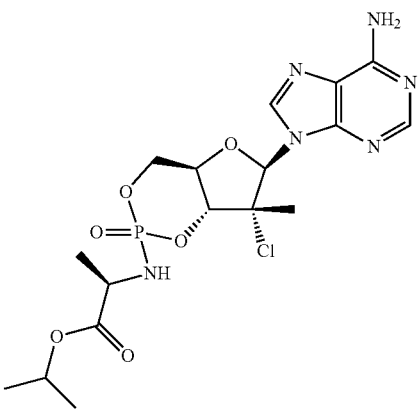
(77ia)
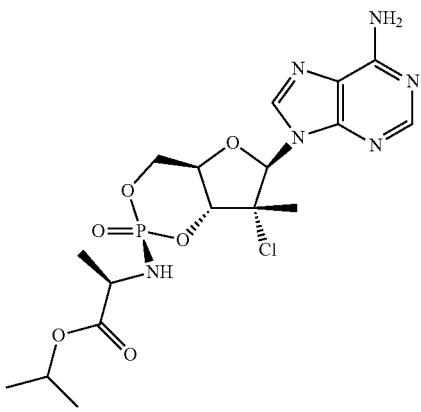
(77ib)
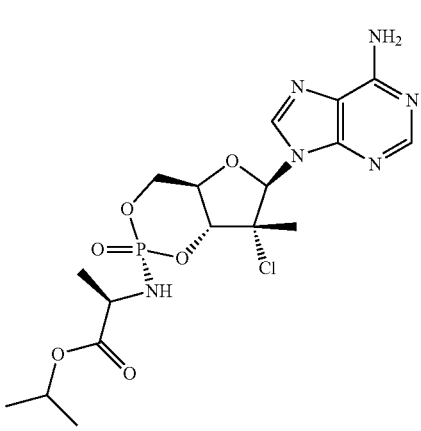
or a pharmaceutically acceptable salt, solvate, tautomeric form or polymorphic form thereof.
15. The method according to claim 14, wherein said compound is according to one of the following structures:
(38i)
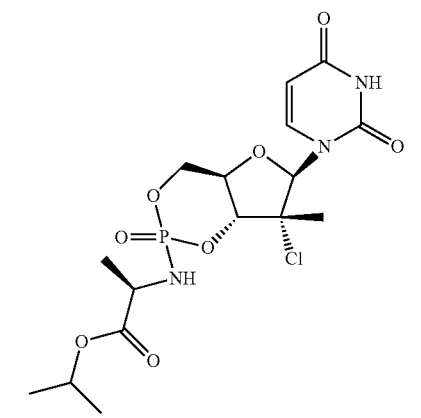

289
-continued (38ia)
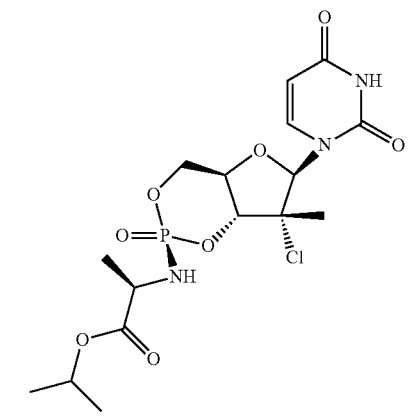

(38ib)
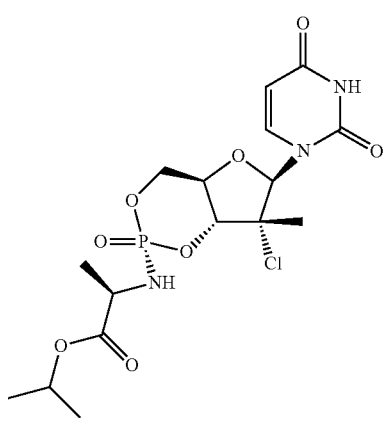

(77i)
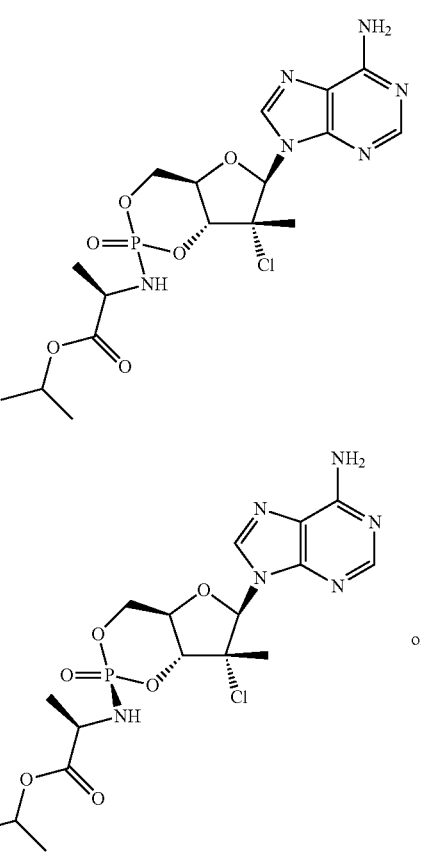

(77ia)

290
-continued (77ib)
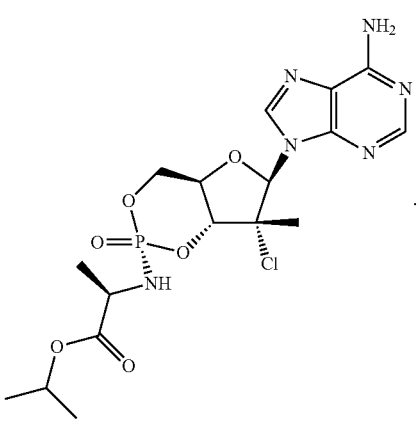

16. The method of claim 13, wherein said compound is

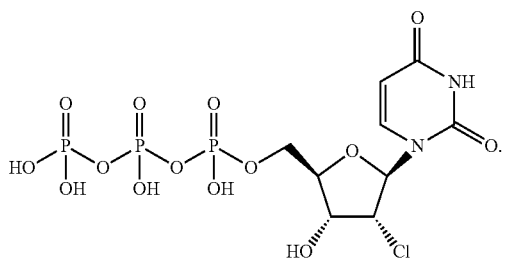 [SMILES: O=c1ccn([C@@H]2O[C@H](COP(=O)(O)OP(=O)(O)OP(=O)(O)O)[C@@H](O)[C@H]2Cl)c(=O)[nH]1]

17. The method of claim 13, wherein the compound is administered in combination or alternation with a second anti-viral agent selected from the group consisting of an interferon, a nucleotide analogue, a polymerase inhibitor, an NS3 protease inhibitor, an NS5A inhibitor, an entry inhibitor, a non-nucleoside polymerase inhibitor, a cyclosporine immune inhibitor, an NS4A antagonist, an NS4B-RNA binding inhibitor, a locked nucleic acid mRNA inhibitor, and a cyclophilin inhibitor, or a combination thereof.

18. A compound according to Formula III:

(III)
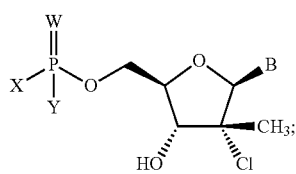

or a pharmaceutically acceptable salt, solvate, tautomeric form or polymorphic form thereof;

wherein B is uracil, adenine or guanine;

Y is $OR^1$;

$R^1$ is phenyl;

X is an N-linked amino acid ester; and

W is O.

19. The compound according to claim 18, wherein said compound is according to the structure:

or

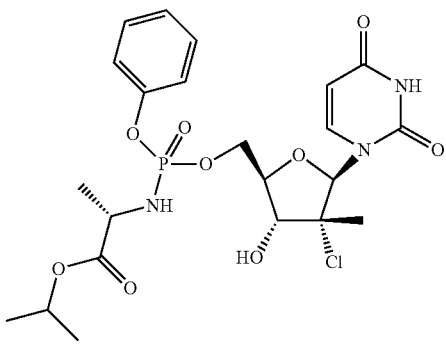 [SMILES: CC(C)OC(=O)[C@H](C)NP(=O)(OC[C@H]1O[C@@H](n2ccc(=O)[nH]c2=O)[C@](C)(Cl)[C@@H]1O)Oc1ccccc1]

or a pharmaceutically acceptable salt, solvate, tautomeric form or polymorphic form thereof.

20. The compound according to claim 19, wherein said compound is according to the structure:

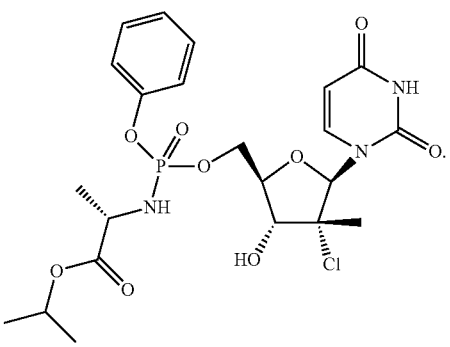 [SMILES: CC(C)OC(=O)[C@H](C)NP(=O)(OC[C@H]1O[C@@H](n2ccc(=O)[nH]c2=O)[C@](C)(Cl)[C@@H]1O)Oc1ccccc1]

21. The compound according to claim 19, wherein said compound is:

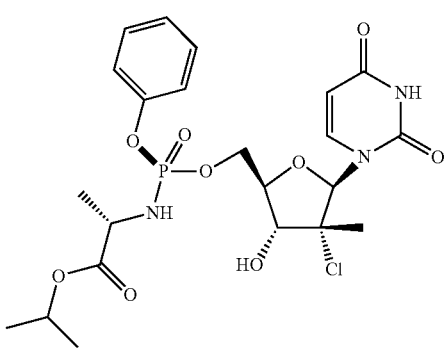 [SMILES: CC(C)OC(=O)[C@H](C)N[P@](=O)(OC[C@H]1O[C@@H](n2ccc(=O)[nH]c2=O)[C@](C)(Cl)[C@@H]1O)Oc1ccccc1]

or a pharmaceutically acceptable salt, solvate, tautomeric form or polymorphic form thereof.

22. The compound according to claim 21, wherein said compound is:

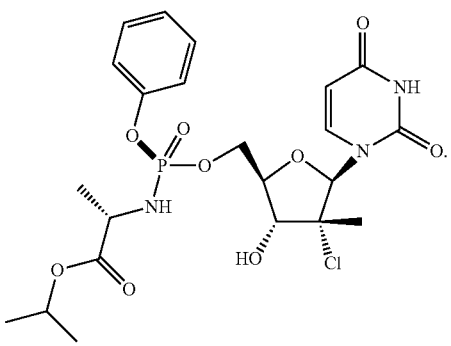 [SMILES: CC(C)OC(=O)[C@H](C)N[P@](=O)(OC[C@H]1O[C@@H](n2ccc(=O)[nH]c2=O)[C@](C)(Cl)[C@@H]1O)Oc1ccccc1]

23. The compound according to claim 18, wherein said compound is:

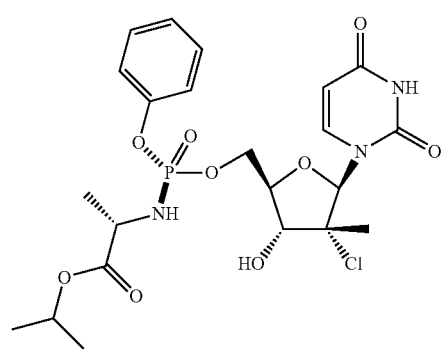 [SMILES: CC(C)OC(=O)[C@H](C)N[P@@](=O)(OC[C@H]1O[C@@H](n2ccc(=O)[nH]c2=O)[C@](C)(Cl)[C@@H]1O)Oc1ccccc1]

or a pharmaceutically acceptable salt, solvate, tautomeric form or polymorphic form thereof.

24. The compound of claim 23, wherein said compound is:

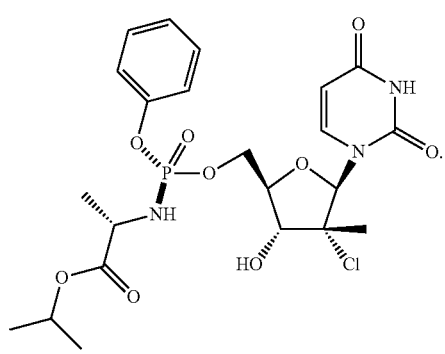 [SMILES: CC(C)OC(=O)[C@H](C)N[P@@](=O)(OC[C@H]1O[C@@H](n2ccc(=O)[nH]c2=O)[C@](C)(Cl)[C@@H]1O)Oc1ccccc1]

25. The compound according to claim 18, wherein said compound is according to the structure:

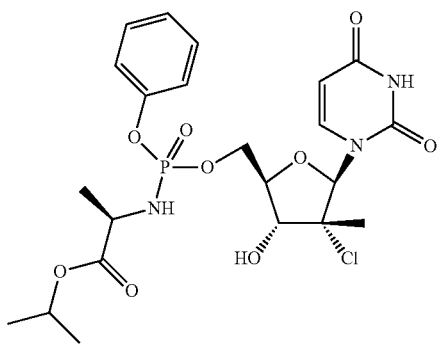 [SMILES: CC(C)OC(=O)[C@@H](C)NP(=O)(OC[C@H]1O[C@@H](n2ccc(=O)[nH]c2=O)[C@](C)(Cl)[C@@H]1O)Oc1ccccc1]

or a pharmaceutically acceptable salt, solvate, tautomeric form or polymorphic form thereof.

26. The compound according to claim 25, wherein said compound is according to the structure:

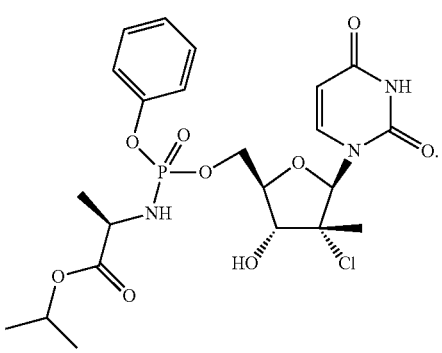 [SMILES: CC(C)OC(=O)[C@@H](C)NP(=O)(OC[C@H]1O[C@@H](n2ccc(=O)[nH]c2=O)[C@](C)(Cl)[C@@H]1O)Oc1ccccc1]

27. The compound according to claim 18, wherein said compound is:

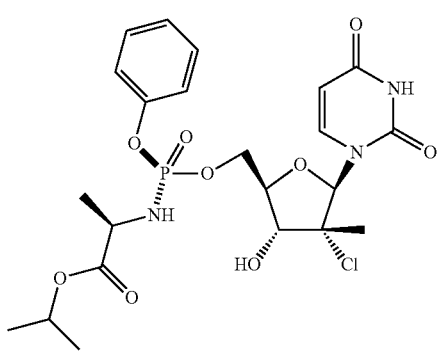 [SMILES: CC(C)OC(=O)[C@@H](C)N[P@](=O)(OC[C@H]1O[C@@H](n2ccc(=O)[nH]c2=O)[C@](C)(Cl)[C@@H]1O)Oc1ccccc1]

or a pharmaceutically acceptable salt, solvate, tautomeric form or polymorphic form thereof.

28. The compound according to claim 27, wherein said compound is:

29. The compound according to claim 18, wherein said compound is:

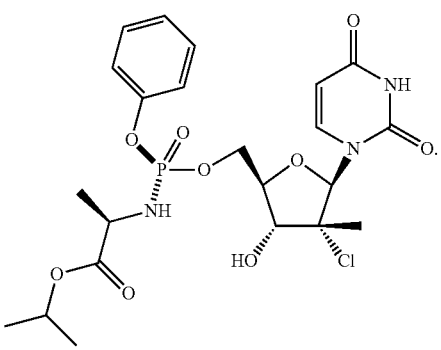 [SMILES: CC(C)OC(=O)[C@@H](C)N[P@](=O)(OC[C@H]1O[C@@H](n2ccc(=O)[nH]c2=O)[C@](C)(Cl)[C@@H]1O)Oc1ccccc1]

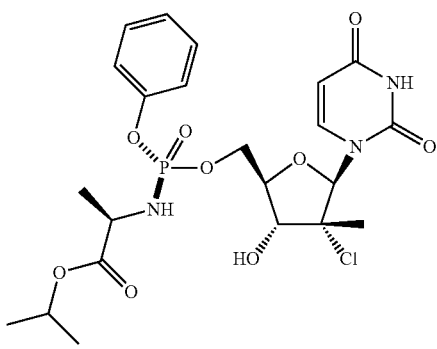 [SMILES: CC(C)OC(=O)[C@@H](C)N[P@@](=O)(OC[C@H]1O[C@@H](n2ccc(=O)[nH]c2=O)[C@](C)(Cl)[C@@H]1O)Oc1ccccc1]

or a pharmaceutically acceptable salt, solvate, tautomeric form or polymorphic form thereof.

30. The compound of claim 29, wherein said compound is:

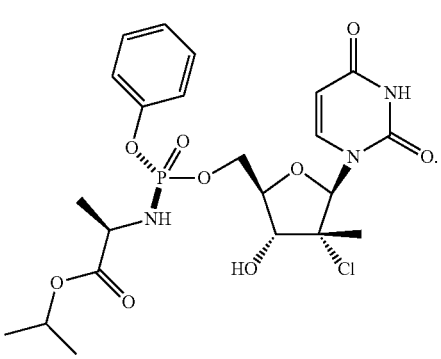 [SMILES: CC(C)OC(=O)[C@@H](C)N[P@@](=O)(OC[C@H]1O[C@@H](n2ccc(=O)[nH]c2=O)[C@](C)(Cl)[C@@H]1O)Oc1ccccc1]

31. The pharmaceutical composition according to claim 30, wherein said compound is a designated enantiomer, and said composition is substantially free of other stereoisomers of said compound.

32. A nucleoside composition comprising a compound selected from the group consisting of:

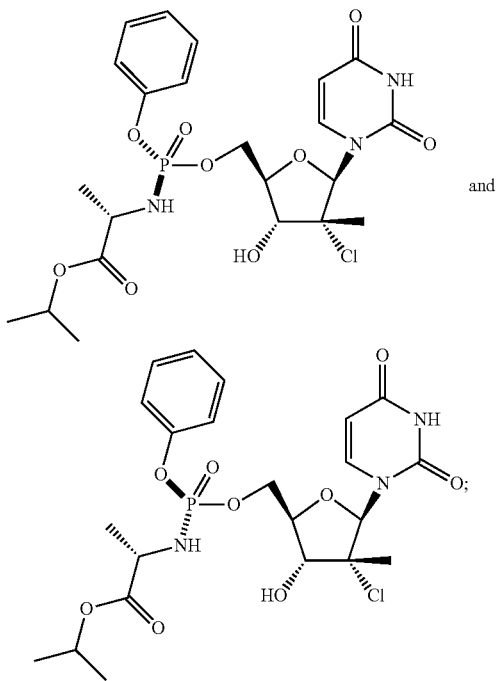

wherein said compound is a designated enantiomer and said composition is substantially free of other stereoisomers of said compound.

33. A nucleoside composition comprising a compound selected from the group consisting of:

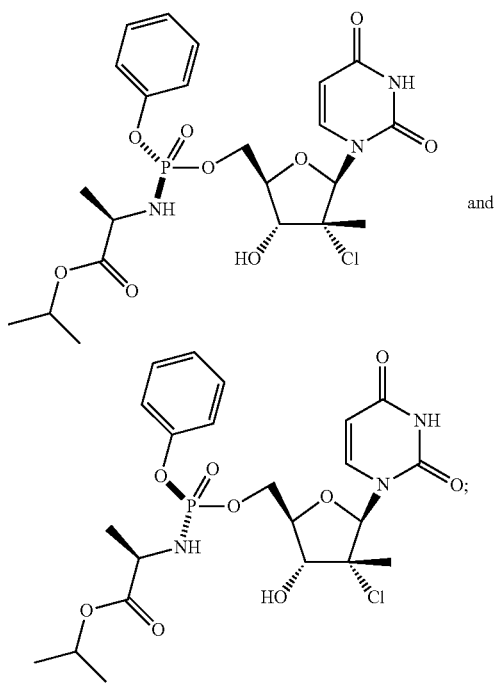

wherein said compound is a designated enantiomer and said composition is substantially free of other stereoisomers of said compound.

34. A pharmaceutical composition comprising a compound according to the structure:

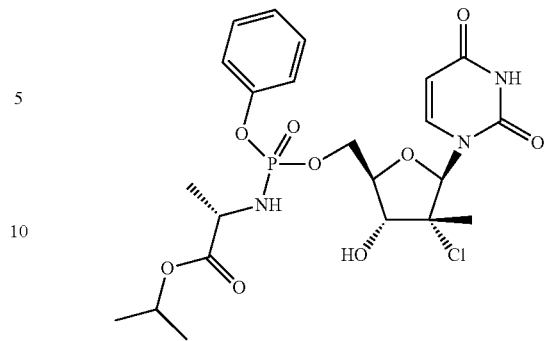

or a pharmaceutically acceptable salt, solvate, tautomeric form or polymorphic form thereof; and a pharmaceutically acceptable carrier.

35. The pharmaceutical composition according to claim 34, wherein said compound is according to the structure:

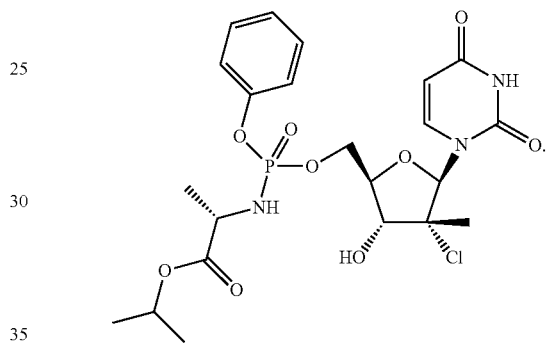

36. The pharmaceutical composition according to claim 34, wherein said compound is:

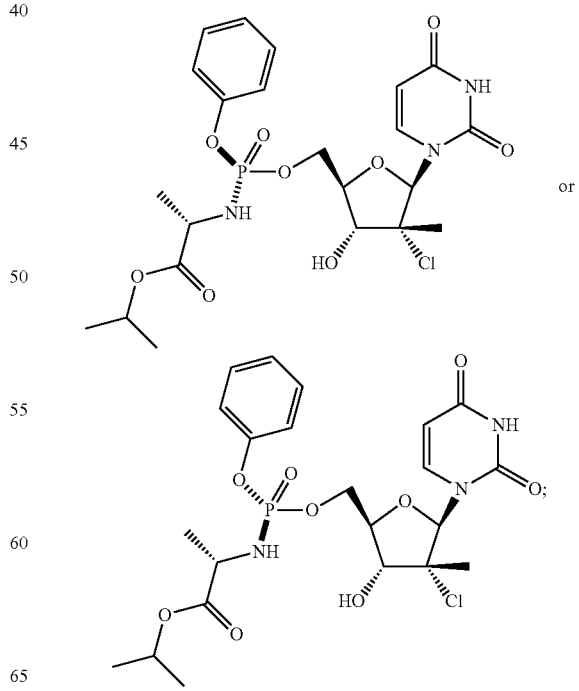

or a pharmaceutically acceptable salt, solvate, tautomeric form or polymorphic form thereof.

37. The pharmaceutical composition according to claim 36, wherein said compound is:

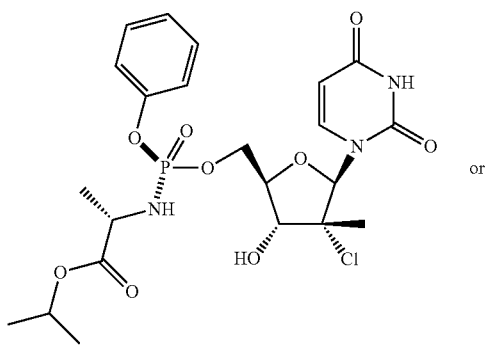

or

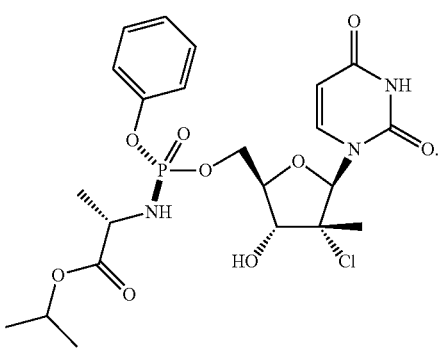

or a pharmaceutically acceptable salt, solvate, tautomeric form or polymorphic form thereof.

38. A pharmaceutical composition comprising a compound according to the structure:

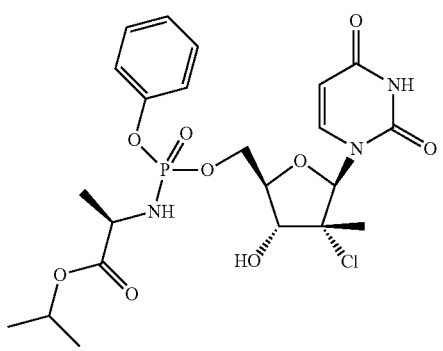 [SMILES: CC(C)OC(=O)[C@@H](C)NP(=O)(OC[C@H]1O[C@@H](n2ccc(=O)[nH]c2=O)[C@](C)(Cl)[C@@H]1O)Oc1ccccc1]

or a pharmaceutically acceptable salt, solvate, tautomeric form or polymorphic form thereof.

39. The pharmaceutical composition according to claim 38, wherein said compound is according to the structure:

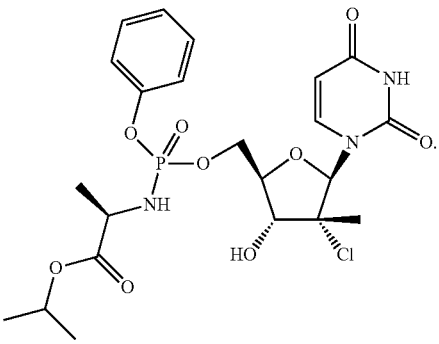 [SMILES: CC(C)OC(=O)[C@@H](C)NP(=O)(OC[C@H]1O[C@@H](n2ccc(=O)[nH]c2=O)[C@](C)(Cl)[C@@H]1O)Oc1ccccc1]

40. The pharmaceutical composition according to claim 38, wherein said compound is:

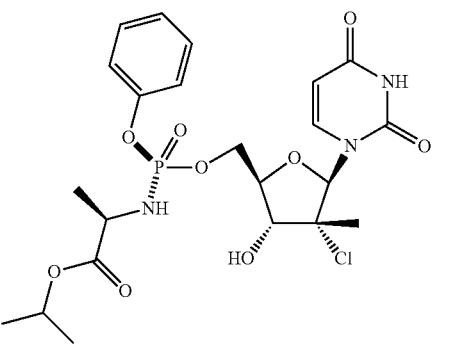

or or a pharmaceutically acceptable salt, solvate, tautomeric form or polymorphic form thereof.

41. The pharmaceutical composition according to claim 40, wherein said compound is:

or

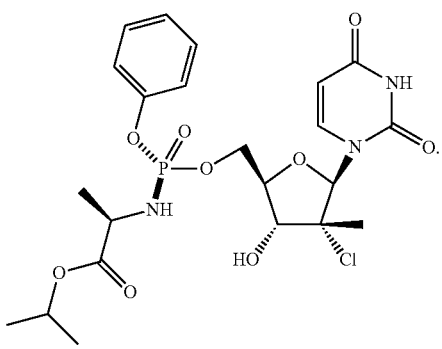

42. The pharmaceutical composition according to claim 41, wherein said compound is a designated enantiomer, and said composition is substantially free of other stereoisomers of said compound.

43. A method of treating an hepatitis C virus (HCV) in a human infected with a an HCV, comprising administering to the human an effective amount of a compound according to the structure:

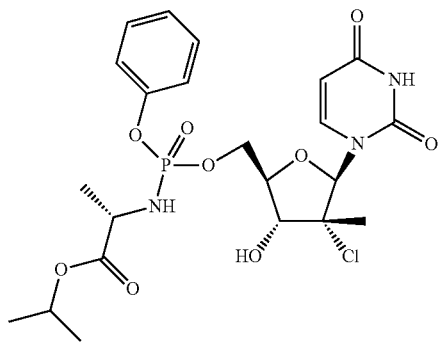 [SMILES: CC(C)OC(=O)[C@H](C)NP(=O)(OC[C@H]1O[C@@H](n2ccc(=O)[nH]c2=O)[C@](C)(Cl)[C@@H]1O)Oc1ccccc1]

or a pharmaceutically acceptable salt, solvate, tautomeric form or polymorphic form thereof.

44. The method according to claim 43, wherein said compound is according to the structure:

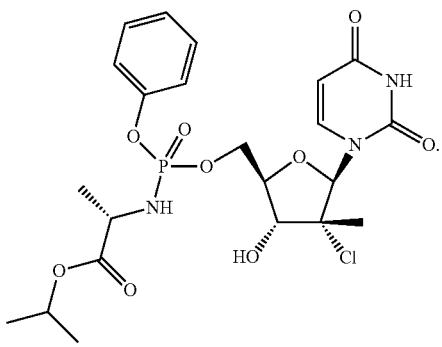 [SMILES: CC(C)OC(=O)[C@H](C)NP(=O)(OC[C@H]1O[C@@H](n2ccc(=O)[nH]c2=O)[C@](C)(Cl)[C@@H]1O)Oc1ccccc1]

45. The method according to claim 43, wherein said compound is:

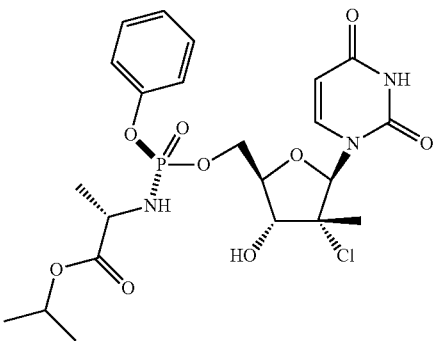 [SMILES: CC(C)OC(=O)[C@H](C)N[P@](=O)(OC[C@H]1O[C@@H](n2ccc(=O)[nH]c2=O)[C@](C)(Cl)[C@@H]1O)Oc1ccccc1]

or a pharmaceutically acceptable salt, solvate, tautomeric form or polymorphic form thereof.

46. The method according to claim 45, wherein said compound is:

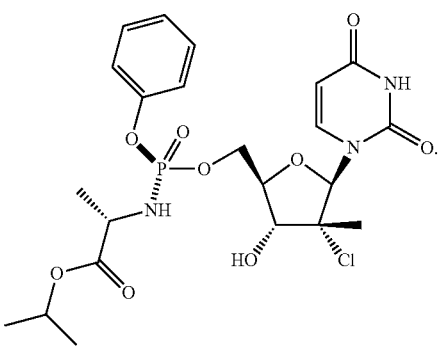 [SMILES: CC(C)OC(=O)[C@H](C)N[P@](=O)(OC[C@H]1O[C@@H](n2ccc(=O)[nH]c2=O)[C@](C)(Cl)[C@@H]1O)Oc1ccccc1]

47. The method according to claim 43, wherein said compound is:

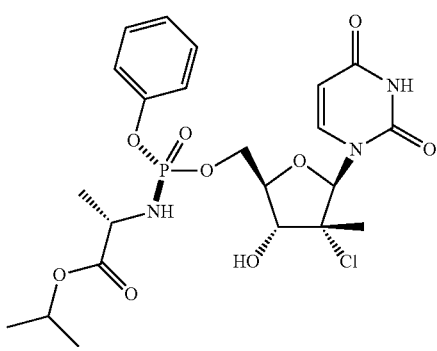 [SMILES: CC(C)OC(=O)[C@H](C)N[P@@](=O)(OC[C@H]1O[C@@H](n2ccc(=O)[nH]c2=O)[C@](C)(Cl)[C@@H]1O)Oc1ccccc1]

or a pharmaceutically acceptable salt, solvate, tautomeric form or polymorphic form thereof.

48. The method according to claim 47, wherein said compound is:

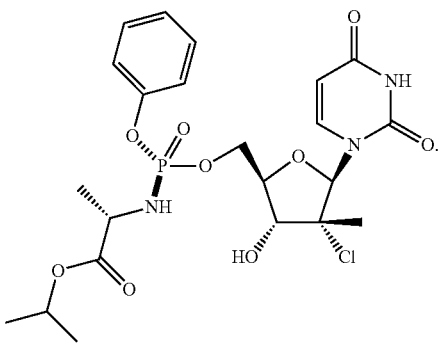 [SMILES: CC(C)OC(=O)[C@H](C)N[P@@](=O)(OC[C@H]1O[C@@H](n2ccc(=O)[nH]c2=O)[C@](C)(Cl)[C@@H]1O)Oc1ccccc1]

49. The method of claim 43, wherein the compound is administered in combination with or in alternation with a second anti-viral agent selected from the group consisting of an interferon, a nucleotide analogue, a polymerase inhibitor, an NS3 protease inhibitor, an NS5A inhibitor, an entry inhibitor, a non-nucleoside polymerase inhibitor, a cyclosporine immune inhibitor, an NS4A antagonist, an NS4B-RNA binding inhibitor, a locked nucleic acid mRNA inhibitor, a cyclophilin inhibitor, and combinations thereof.

50. The method of claim 49, wherein said second anti-viral agent is an NS3 protease inhibitor.

51. The method of claim 49, wherein said second anti-viral agent is an NS5A inhibitor.

52. A method of treating an hepatitis C virus (HCV) in a human infected with a an HCV, comprising administering to the human an effective amount of a compound according to the structure:

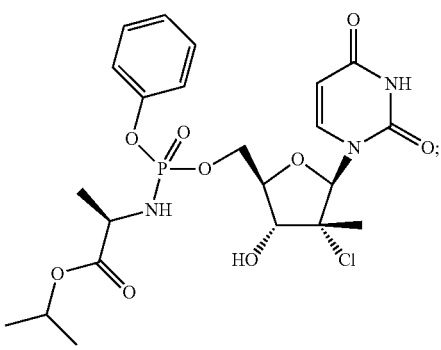 [SMILES: CC(C)OC(=O)[C@@H](C)NP(=O)(OC[C@H]1O[C@@H](n2ccc(=O)[nH]c2=O)[C@](C)(Cl)[C@@H]1O)Oc1ccccc1]

or a pharmaceutically acceptable salt, solvate, tautomeric form or polymorphic form thereof.

53. The method according to claim 52, wherein said compound is according to the structure:

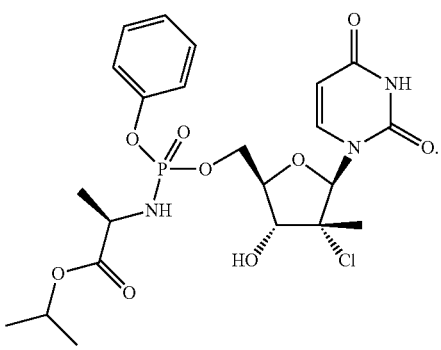 [SMILES: CC(C)OC(=O)[C@@H](C)NP(=O)(OC[C@H]1O[C@@H](n2ccc(=O)[nH]c2=O)[C@](C)(Cl)[C@@H]1O)Oc1ccccc1]

54. The method according to claim 52, wherein said compound is:

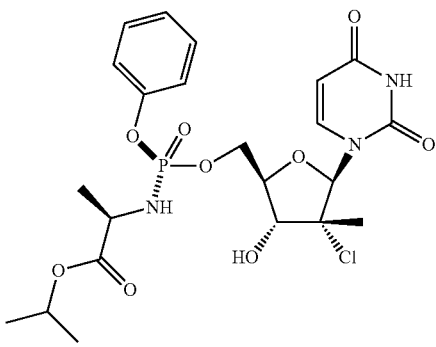 [SMILES: CC(C)OC(=O)[C@@H](C)N[P@](=O)(OC[C@H]1O[C@@H](n2ccc(=O)[nH]c2=O)[C@](C)(Cl)[C@@H]1O)Oc1ccccc1]

or a pharmaceutically acceptable salt, solvate, tautomeric form or polymorphic form thereof.

55. The method according to claim 54, wherein said compound is:

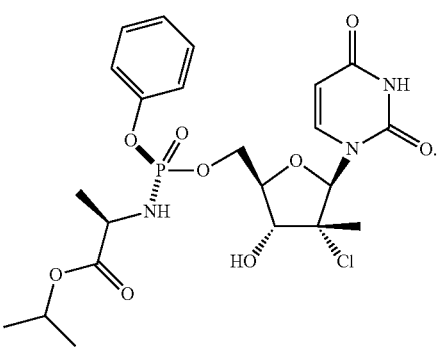

56. The method according to claim 52, wherein said compound is:

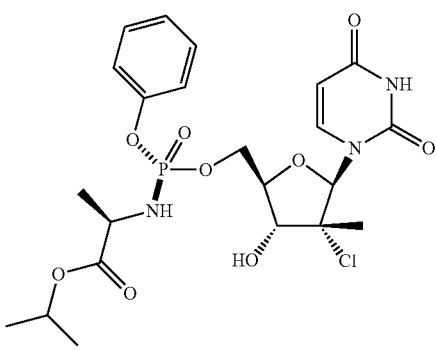 [SMILES: CC(C)OC(=O)[C@@H](C)N[P@@](=O)(OC[C@H]1O[C@@H](n2ccc(=O)[nH]c2=O)[C@](C)(Cl)[C@@H]1O)Oc1ccccc1]

or a pharmaceutically acceptable salt, solvate, tautomeric form or polymorphic form thereof.

57. The method according to claim 56, wherein said compound is:

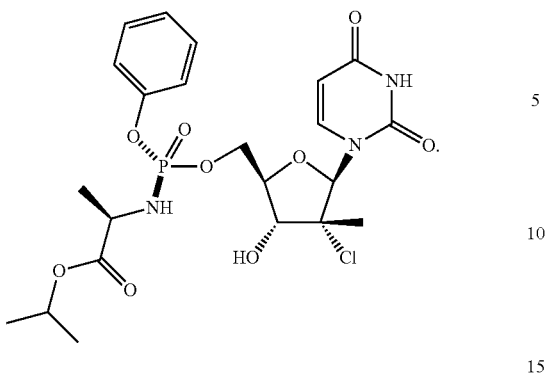

58. The method of claim 52, wherein the compound is administered in combination with or in alternation with a second anti-viral agent selected from the group consisting of an interferon, a nucleotide analogue, a polymerase inhibitor, an NS3 protease inhibitor, an NS5A inhibitor, an entry inhibitor, a non-nucleoside polymerase inhibitor, a cyclosporine immune inhibitor, an NS4A antagonist, an NS4B-RNA binding inhibitor, a locked nucleic acid mRNA inhibitor, a cyclophilin inhibitor, and combinations thereof.

59. The method of claim 58, wherein said second anti-viral agent is an NS3 protease inhibitor.

60. The method of claim 58, wherein said second anti-viral agent is an NS5A inhibitor.

* * * * *